(12) United States Patent
Gerstenberger et al.

(10) Patent No.: US 11,708,360 B2
(45) Date of Patent: *Jul. 25, 2023

(54) N-SUBSTITUTED-DIOXOCYCLOBUTENYLAMINO-3-HYDROXY-PICOLINAMIDES USEFUL AS CCR6 INHIBITORS

(71) Applicant: Pfizer Inc., New York, NY (US)

(72) Inventors: Brian Stephen Gerstenberger, Cambridge, MA (US); Andrew Christopher Flick, Carlsbad, CA (US); Daniel Wei-Shung Kung, Salem, CT (US); Vincent Michael Lombardo, Carmel, IN (US); James John Mousseau, Norwich, CT (US); Philippe Marcel Nuhant, Dorchester, MA (US); Ralph Pelton Robinson, Jr., Gales Ferry, CT (US); Daniel Copley Schmitt, Westerly, RI (US); Mark Edward Schnute, Acton, MA (US); Atli Thorarensen, Stow, MA (US); John Isidro Trujillo, Ledyard, CT (US); Rayomand Jal Unwalla, Bedford, MA (US); Huixian Wu, East Lyme, CT (US)

(73) Assignee: Pfizer Inc., New York, NY (US)

( * ) Notice: Subject to any disclaimer, the term of this patent is extended or adjusted under 35 U.S.C. 154(b) by 55 days.

This patent is subject to a terminal disclaimer.

(21) Appl. No.: 17/192,968

(22) Filed: Mar. 5, 2021

(65) Prior Publication Data

US 2021/0206757 A1 Jul. 8, 2021

Related U.S. Application Data

(63) Continuation of application No. 16/576,997, filed on Sep. 20, 2019, now Pat. No. 10,975,065.

(Continued)

(51) Int. Cl.
*C07D 413/14* (2006.01)
*A61P 29/00* (2006.01)
(Continued)

(52) U.S. Cl.
CPC ............ *C07D 413/14* (2013.01); *A61P 29/00* (2018.01); *C07D 401/12* (2013.01);
(Continued)

(58) Field of Classification Search
CPC .. C07D 413/14; C07D 401/12; C07D 401/14; C07D 405/14; C07D 413/12;
(Continued)

(56) References Cited

U.S. PATENT DOCUMENTS 5,466,712 A  11/1995  Butera et al.
6,495,576 B2  12/2002  Kort et al.
(Continued)

FOREIGN PATENT DOCUMENTS

CN  103958505  7/2014
WO  1995014005  5/1995
(Continued)

OTHER PUBLICATIONS

Buhl, Timo, et al., "Molecular and Morphological Characterization of Inflammatory Infiltrate in Rosacea Reveals Activation of Th1/Th17 Pathways", Journal of Investigative Dermatology, 2015, pp. 2198-2208, 135(9).

(Continued)

*Primary Examiner* — Taylor V Oh
(74) *Attorney, Agent, or Firm* — Young-In Julia Oh

(57) ABSTRACT

The present invention relates to N-substituted-dioxocyclobutenylamino-3-hydroxy-picolinamide compounds of Formulae (IA and 1B)

(Continued)

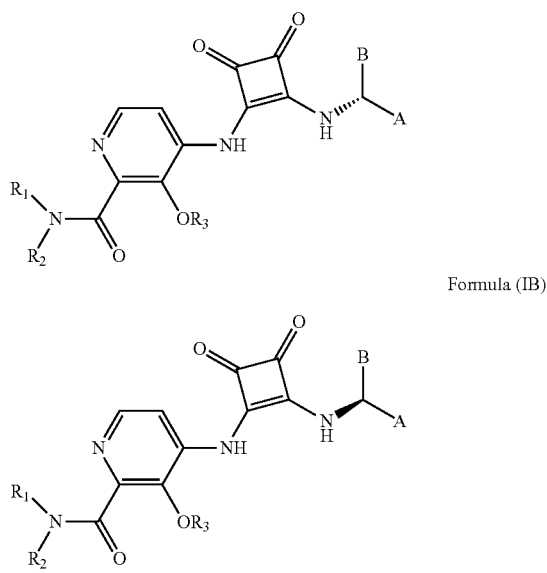

Formula (IA)

Formula (IB)

or a pharmaceutically acceptable salt or hydrate thereof, that inhibit CC chemokine receptor 6 (CCR6), pharmaceutical compositions containing these compounds, and the use of these compounds for treating or preventing diseases, conditions, or disorders ameliorated by inhibition of CCR6.

16 Claims, 12 Drawing Sheets

Related U.S. Application Data

(60) Provisional application No. 62/734,486, filed on Sep. 21, 2018.

(51) Int. Cl.

| | | |
|---|---|---|
| *C07D 401/12* | (2006.01) | |
| *C07D 401/14* | (2006.01) | |
| *C07D 405/14* | (2006.01) | |
| *C07D 413/12* | (2006.01) | |
| *C07D 417/12* | (2006.01) | |
| *C07D 417/14* | (2006.01) | |
| *C07F 9/6558* | (2006.01) | |

(52) U.S. Cl.
CPC ......... *C07D 401/14* (2013.01); *C07D 405/14* (2013.01); *C07D 413/12* (2013.01); *C07D 417/12* (2013.01); *C07D 417/14* (2013.01); *C07F 9/65583* (2013.01)

(58) Field of Classification Search
CPC .. C07D 417/12; C07D 417/14; C07D 413/08; C07D 417/08; C07D 401/08; A61P 29/00; A61P 37/00; C07F 9/65583; A61K 31/4439; A61K 31/496; C07B 2200/13
USPC ...................................................... 514/236.5
See application file for complete search history.

(56) References Cited

U.S. PATENT DOCUMENTS

| | | | |
|---|---|---|---|
| 7,566,718 B2 | 7/2009 | Wong et al. | |
| 7,956,185 B2 | 6/2011 | Diebold et al. | |
| 8,242,139 B2 | 8/2012 | Judd et al. | |
| 8,501,782 B2 | 8/2013 | Gardner et al. | |
| 8,785,440 B2 | 7/2014 | Bui et al. | |
| 10,975,065 B2* | 4/2021 | Gerstenberger | ..... C07D 401/08 |
| 2014/0296254 A1 | 10/2014 | Musicki et al. | |
| 2014/0309208 A1 | 10/2014 | Musicki et al. | |
| 2015/0087675 A1 | 3/2015 | Musicki et al. | |
| 2017/0144996 A1 | 5/2017 | Chen et al. | |
| 2017/0144997 A1 | 5/2017 | Chen et al. | |
| 2017/0349575 A1 | 12/2017 | Musicki et al. | |
| 2018/0177808 A1 | 6/2018 | Zebala et al. | |

FOREIGN PATENT DOCUMENTS

| | | |
|---|---|---|
| WO | 1996014300 | 5/1996 |
| WO | 1996015103 | 5/1996 |
| WO | 2002083624 | 10/2002 |
| WO | 2003080053 | 10/2003 |
| WO | 2007115071 | 10/2007 |
| WO | 2008005570 | 1/2008 |
| WO | 2008148790 | 12/2008 |
| WO | 2009005802 | 1/2009 |
| WO | 2009012375 | 1/2009 |
| WO | 2009015166 | 1/2009 |
| WO | 2009073683 | 6/2009 |
| WO | 2010015613 | 2/2010 |
| WO | 2010063802 | 6/2010 |
| WO | 2012080456 | 6/2010 |
| WO | 2012080457 | 6/2010 |
| WO | 2010131145 | 11/2010 |
| WO | 2010131146 | 11/2010 |
| WO | 2010131147 | 11/2010 |
| WO | 2011058027 | 5/2011 |
| WO | 2012001076 | 1/2012 |
| WO | 2013033068 | 3/2013 |
| WO | 2013061005 | 5/2013 |
| WO | 2013174947 | 11/2013 |
| WO | 2014097151 | 6/2014 |
| WO | 2014116772 | 7/2014 |
| WO | 2014149164 | 9/2014 |
| WO | 2016102877 | 6/2016 |

OTHER PUBLICATIONS

Hui, Jin, et al., "L-Proline Derived Bifunctional Organocatalysts: Enantioselective Michael Addition of Dithiomalonates to trans-β-Nitroolefins" Journal of Organic Chemistry, 2016, pp. 3263-3274, 81(8).
Taiwan Patent Application No. 108134010, filed Sep. 20, 2019, Search Report, 1 page.

* cited by examiner

N-SUBSTITUTED-DIOXOCYCLOBUTENYLAMINO-3-HYDROXY-PICOLINAMIDES USEFUL AS CCR6 INHIBITORS

CROSS REFERENCE TO PRIOR APPLICATIONS

This application is a Continuation of application Ser. No. 16/576,997, filed Sep. 20, 2019 which claims the benefit of U.S. Provisional Application Ser. No. 62/734,486, filed Sep. 21, 2018, under 35 USC 119(e), the disclosures of which are hereby incorporated in their entirety.

FIELD OF THE INVENTION

The present invention relates to N-substituted-dioxocyclobutenylamino-3-hydroxy-picolinamide compounds that inhibit CC chemokine receptor 6 (CCR6), pharmaceutical compositions containing these compounds, and the use of these compounds for treating or preventing diseases, conditions, or disorders ameliorated by inhibition of CCR6.

BACKGROUND OF THE INVENTION

Chemokine receptors are a large subfamily of cell surface seven transmembrane proteins. They can be divided by function into two main groups: G protein-coupled chemokine receptors, which mediate leukocyte trafficking, and "atypical chemokine receptors", which may signal through non-G protein-coupled mechanisms and act as chemokine scavengers to downregulate inflammation or shape chemokine gradients [Bachelerie, 2014; Murphy, 2002]. Chemokines, the natural ligands for chemokine receptors are low-molecular-weight proteins that stimulate recruitment of leukocytes. Based on the presence and the relative position of the NH2-terminal Cys residues, chemokines are structurally grouped into the CC, CXC, CX3C and C chemokines [White, 2013]. In humans, chemokines and chemokine receptors form a pharmacologically complex system. In many cases, recognition of a single chemokine by different receptors, as well as binding of different chemokines to the same receptor, leads to different signaling and trafficking responses [Kufareva, 2016]. Physiologically, members of the chemokine family induce recruitment of well-defined leukocyte subsets and play an important role in development, immunity and autoimmune diseases.

CC chemokine receptor 6 (CCR6) is expressed on a variety of key immune cells including immature dendritic cells, B cells, memory T cells (including all Th17 cells), neutrophils, and a subset of Tregs. CCR6 is the only known receptor for chemokine CCL20 (alternatively named LARC or MIP-3a). CCL20 is produced by synoviocytes, colonic epithelial cells, various skin cells (e.g., keratinocytes and dermal fibroblasts), and alveolar epithelial cells. The ligand-receptor pair CCL20-CCR6 is responsible for the migration of immature dendritic cells and effector/memory T-cells to the skin and mucosal surfaces under homeostatic and inflammatory conditions, as well as in autoimmune diseases such as psoriasis and inflammatory bowel diseases. [Liao, 1999; Schutyser, 2003].

CCL20 is an inducible chemokine that is highly upregulated in inflammatory lesions in various autoimmune diseases including psoriasis, ulcerative colitis, Crohn's disease, psoriatic arthritis and rheumatoid arthritis. Increased amounts of CCR6 positive T cells and dendritic cells were found in lesions co-localizing with CCL20 expression. These T cell-dendritic cell clusters maintained by CCR6-CCL20 interaction are crucial for disease initiation and maintenance. In mice, both CCR6 knock-out and neutralizing anti-CCL20 antibody were protective in an IL-23 induced skin inflammation model, suggesting that blocking CCR6-CCL20 mediated immune cell recruitment presents an attractive mechanism for novel small molecule therapy in autoimmune and inflammatory diseases. [Homey, 2000; Kim, 2014; Kwon, 2002; Shen, 2010].

C-X-C chemokine receptor type 1 (CXCR1) and C-X-C chemokine receptor type 2 (CXCR2) are chemokine receptors expressed on neutrophils. Both receptors bind the chemokine IL-8 (CXCL8) with high affinity. In contrast, CXCL1 (GRO alpha) and CXCL2 (GRO beta) are specific ligands for CXCR2 with 90% sequence homology. In clinical studies, CXCR1/2 dual antagonists such as Navarixin have shown a reversible decline in the absolute neutrophil count in patients [Hastrup, 2015]. Patients with reduced neutrophil counts may be subject to increased risk of infections. Therefore, CCR6 antagonists with reduced potency for antagonism of the CXCR2 receptor may offer an improved safety profile compared to non-discriminating antagonists. Human genetic evidence and knock-out studies in mice suggest the egress of neutrophils from the bone marrow is dependent on CXCR2 function and mediated by CXCR2 specific ligands CXCL1 (GRO alpha) and CXCL2 (GRO beta) [Auer, 2014; Eash, 2010]. Thus to understand the pharmacology of CXCR2 inhibitors on bone marrow neutrophil mobilization, it is important to use the relevant CXCR2 ligand (CXCL1 or CXCL2) in a primary human neutrophil assay system.

Auer, P. L. et. al. *Nature Genetics* (2014) 46, 629-634.
Bachelerie, F. et. al. *Pharmacol. Rev.* (2014) 66, 1-79.
Eash, K. J. et. al. *J. Clin. Invest.* (2010) 120, 2423-2431.
Hastrup, N. et. al. *Cytokine* (2015) 72, 197-203.
Homey, B. et. al. *J. Immunol.* (2000) 164, 6621-6632.
Kim, T.-G. et. al. *J. Invest. Dermatol.* (2014) 134, 1462-1465.
Kufareva, I. *Curr. Opin. Pharmacol.* (2016) 30, 27-37.
Kwon, J. H. et. al. *Gut* (2002) 51, 818-826.
Liao, F. et. al. *J. Immunol.* (1999) 162, 186-194.
Murphy, P. M. *Pharmacol. Rev.* (2002) 54, 227-229.
Schutyser, E.; Struyf, S.; Van Damme, J. *Cytokine Growth Factor Rev.* (2003) 14, 409-426.
Shen, H.; Goodall, J. C.; Gaston, J. S. H. *J. Rheumatol.* (2010) 37, 2096-2099.
White, G. E.; Iqbal, A. J.; Greaves, D. R. *Pharmacol. Rev.* (2013) 65, 47-89.

SUMMARY OF THE INVENTION

The present invention provides compounds of Formulae (IA) and (IB) that inhibit CCR6 and are useful for treating or preventing disorders ameliorated by inhibition of CCR6 in humans

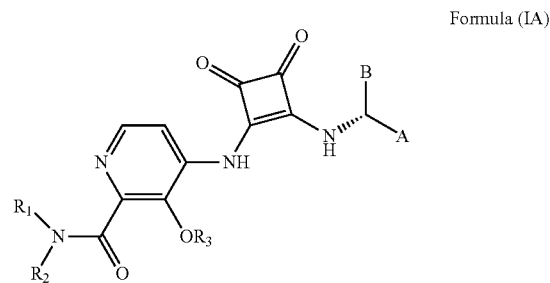

Formula (IA)

Formula (IB)

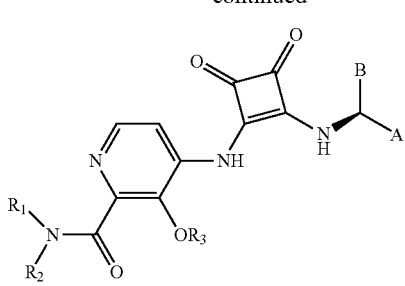

or a pharmaceutically acceptable salt or hydrate thereof, wherein $R_1$ and $R_2$ are independently H or $(C_1-C_6)$alkyl, or $R_1$ and $R_2$ taken together with the nitrogen atom to which they are attached form a 4-, 5-, or 6-membered heterocycle containing one N heteroatom and optionally 1 or 2 additional heteroatoms selected from the group consisting of O, N, and S, wherein the heterocycle is optionally substituted with 1, 2, or 3 $(C_1-C_4)$alkyl groups;

$R_3$ is H, $(C_1-C_6)$alkyl, $(C_1-C_4)$alkylcarbonyl, —C(═O)CH═CHCO$_2$H, —SO$_2$NH$_2$, —CH$_2$OC(═O)(C$_1$-C$_4$)alkyl, —CH$_2$OP(═O)(OH)$_2$, or —C(═O)NR$_A$R$_B$, wherein the $(C_1-C_4)$alkylcarbonyl is optionally substituted with —CO$_2$H or —NH$_2$, wherein the —CH$_2$OC(═O)(C$_1$-C$_4$)alkyl is optionally substituted with —NH$_2$, and wherein $R_A$ and $R_B$ are independently H or $(C_1-C_6)$alkyl;

A is

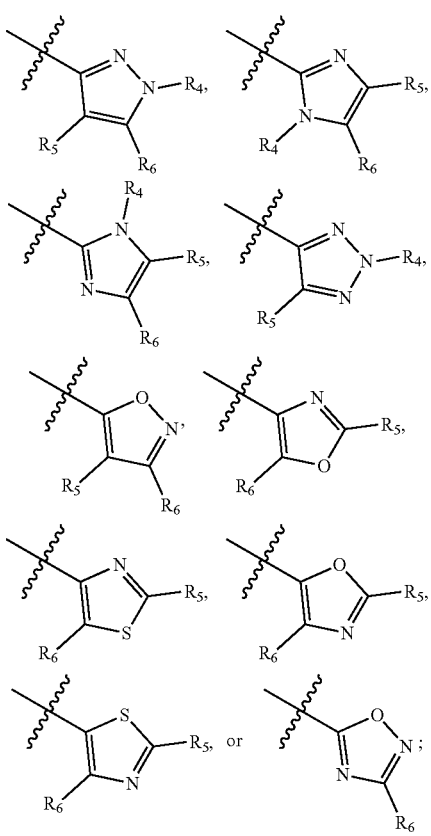

$R_4$ is H, $(C_1-C_4)$alkyl, $(C_3-C_4)$cycloalkyl, $(C_3-C_4)$cycloalkyl$(C_1-C_4)$alkyl, or halo$(C_1-C_4)$alkyl;

$R_5$ and $R_6$ are independently H, deuterium, $(C_2-C_4)$alkenyl, $(C_1-C_4)$alkoxy, $(C_1-C_4)$alkyl, $(C_1-C_4)$alkyl-d$_{1-9}$, $(C_3-C_4)$cycloalkyl, $(C_3-C_4)$cycloalkyl$(C_1-C_4)$alkyl, cyano, halogen, halo$(C_1-C_4)$alkoxy, halo$(C_1-C_4)$alkyl, or hydroxy$(C_1-C_4)$alkyl;

B is

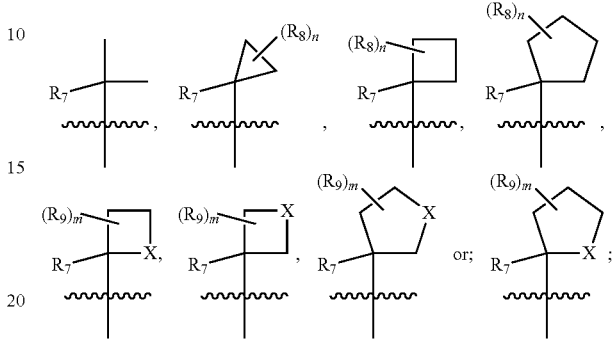

$R_7$ is —F, —CN, $(C_1-C_3)$alkyl, $(C_1-C_3)$alkyl-d$_{1-7}$, or halo$(C_1-C_3)$alkyl;

$R_8$ at each occurrence is independently deuterium, —F, —Cl, —Br, or —I, or two $R_8$s attached to the same carbon atom form a $(C_3-C_5)$cycloalkyl group;

n is 0, 1, 2, 3, or 4;

$R_9$ at each occurrence is independently deuterium, —F, —Cl, —Br, or —I, or two $R_9$s attached to the same carbon atom form a $(C_3-C_5)$cycloalkyl group;

m is 1, 2, 3, or 4; and

X is O, S, or NR$_C$, wherein R$_C$ is H or $(C_1-C_4)$alkyl.

In another embodiment, the present invention provides a method for treating or preventing diseases, conditions or disorders ameliorated by inhibition of CCR6 in a human comprising administering to the human, in need of such treatment, a therapeutically effective amount of a compound of Formula (IA), or a pharmaceutically acceptable salt or hydrate thereof.

In another embodiment, the present invention provides a method for treating or preventing diseases, conditions or disorders ameliorated by inhibition of CCR6 in a human comprising administering to the human, in need of such treatment, a therapeutically effective amount of a compound of Formula (IB), or a pharmaceutically acceptable salt or hydrate thereof.

In another embodiment, the present invention provides the use of a compound of Formula (IA), or a pharmaceutically acceptable salt or hydrate thereof, in the manufacture of a medicament for treating diseases, conditions or disorders ameliorated by inhibition of CCR6 in a human.

In another embodiment, the present invention provides the use of a compound of Formula (IB), or a pharmaceutically acceptable salt or hydrate thereof, in the manufacture of a medicament for treating diseases, conditions or disorders ameliorated by inhibition of CCR6 in a human.

In another embodiment, the present invention provides a compound of Formula (IA), or a pharmaceutically acceptable salt or hydrate thereof, for use as a medicament.

In another embodiment, the present invention provides a compound of Formula (IB), or a pharmaceutically acceptable salt or hydrate thereof, for use as a medicament.

In another embodiment, the present invention provides a compound of Formula (IA), or a pharmaceutically acceptable salt or hydrate thereof, for use in treating or preventing diseases, conditions or disorders ameliorated by inhibition of CCR6 in a human.

In another embodiment, the present invention provides a compound of Formula (IB), or a pharmaceutically acceptable salt or hydrate thereof, for use in treating or preventing diseases, conditions or disorders ameliorated by inhibition of CCR6 in a human.

In another embodiment, the present invention provides a pharmaceutical composition comprising a compound of Formula (IA), or a pharmaceutically acceptable salt or hydrate thereof, and at least one pharmaceutically acceptable excipient, diluent, or carrier. In another embodiment, the present invention provides a pharmaceutical composition comprising a compound of Formula (IB), or a pharmaceutically acceptable salt or hydrate thereof, and at least one pharmaceutically acceptable excipient, diluent, or carrier.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical composition comprising a compound of Formula (IA), or a pharmaceutically acceptable salt or hydrate thereof, and at least one pharmaceutically acceptable excipient, diluent, or carrier.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical composition comprising a compound of Formula (IB), or a pharmaceutically acceptable salt or hydrate thereof, and at least one pharmaceutically acceptable excipient, diluent, or carrier.

In another embodiment, the present invention provides the use of a pharmaceutical composition comprising a compound of Formula (IA), or a pharmaceutically acceptable salt or hydrate thereof, and at least one pharmaceutically acceptable excipient, diluent, or carrier, in the manufacture of a medicament for treating or preventing diseases, conditions or disorders ameliorated by inhibition of CCR6 in a human.

In another embodiment, the present invention provides the use of a pharmaceutical composition comprising a compound of Formula (IB), or a pharmaceutically acceptable salt or hydrate thereof, and at least one pharmaceutically acceptable excipient, diluent, or carrier, in the manufacture of a medicament for treating or preventing diseases, conditions or disorders ameliorated by inhibition of CCR6 in a human.

In another embodiment, the present invention provides a pharmaceutical combination comprising a compound of Formula (IA), or a pharmaceutically acceptable salt or hydrate thereof, and at least one anti-inflammatory agent.

In another embodiment, the present invention provides a pharmaceutical combination comprising a compound of Formula (IB), or a pharmaceutically acceptable salt or hydrate thereof, and at least one anti-inflammatory agent.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical combination comprising a compound of Formula (IA), or a pharmaceutically acceptable salt or hydrate thereof, and at least one anti-inflammatory agent.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical combination comprising a compound of Formula (IB), or a pharmaceutically acceptable salt or hydrate thereof, and at least one anti-inflammatory agent.

In another embodiment, the present invention provides the use of a pharmaceutical combination comprising a compound of Formula (IA), or a pharmaceutically acceptable salt or hydrate thereof, and at least one anti-inflammatory agent, in the manufacture of a medicament for treating or preventing diseases, conditions or disorders ameliorated by inhibition of CCR6 in a human.

In another embodiment, the present invention provides the use of a pharmaceutical combination comprising a compound of Formula (IB), or a pharmaceutically acceptable salt or hydrate thereof, and at least one anti-inflammatory agent, in the manufacture of a medicament for treating or preventing diseases, conditions or disorders ameliorated by inhibition of CCR6 in a human.

DETAILED DESCRIPTION

Figure 1:
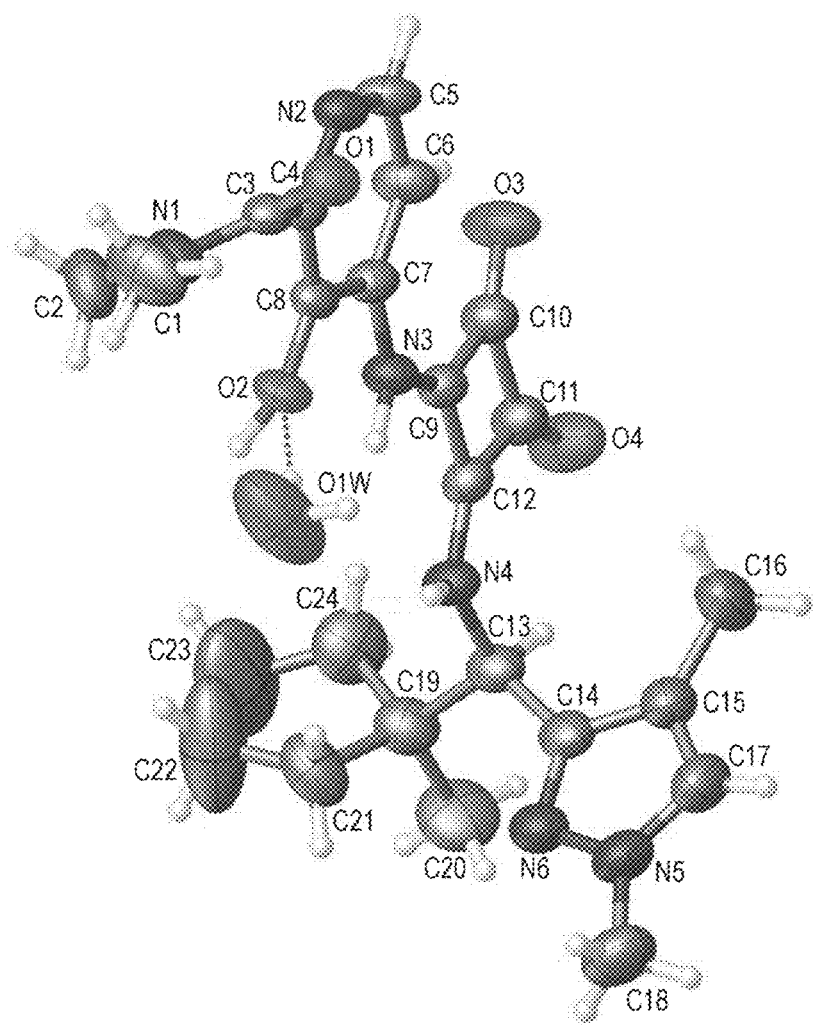
FIG. 1 is an X-ray structure (ORTEP drawing) of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides compounds of Formulae (IA) and (IB)

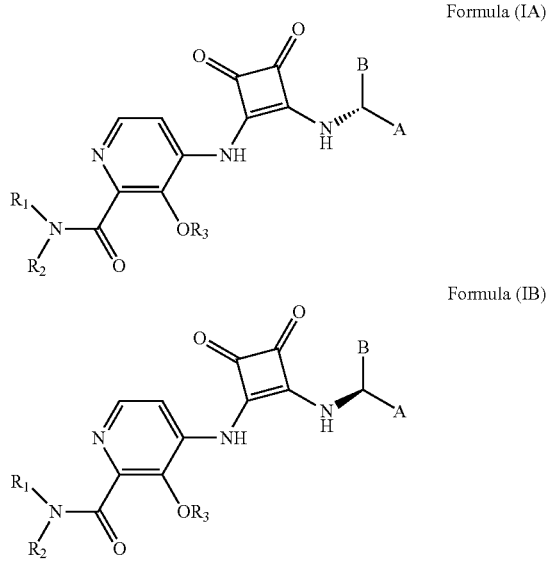

Formula (IA)

Formula (IB)

or a pharmaceutically acceptable salt or hydrate thereof, wherein $R_1$ and $R_2$ are independently $(C_1-C_6)$alkyl or $R_1$ and $R_2$ taken together with the nitrogen atom to which they are attached form a 4-, 5-, or 6-membered heterocycle containing one N heteroatom and optionally 1 or 2 additional heteroatoms selected from the group consisting of O, N, and S, optionally substituted with $(C_1-C_4)$alkyl; $R_3$ is H, $(C_1-C_6)$alkyl, $(C_1-C_4)$alkylcarbonyl, —C(=O)CH=CHCO$_2$H, —SO$_2$NH$_2$, —CH$_2$OC(=O)(C_1-C_4)alkyl, —CH$_2$OP(=O)(OH)$_2$, or —C(=O)NR$_A$R$_B$, wherein the $(C_1-C_4)$alkylcarbonyl is optionally substituted with —CO$_2$H or —NH$_2$, wherein the —CH$_2$OC(=O)(C_1-C_4)alkyl is optionally substituted with —NH$_2$, and wherein $R_A$ and $R_B$ are independently H or $(C_1-C_6)$alkyl; A is

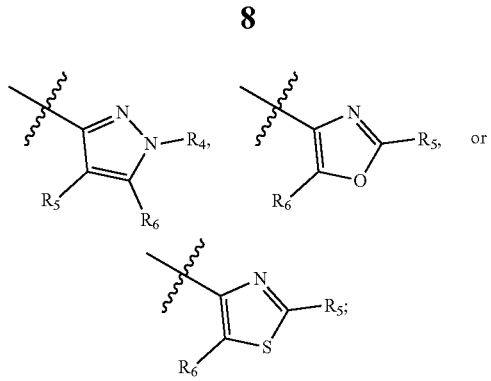

$R_4$ is $(C_1-C_4)$alkyl; $R_5$ and $R_6$ are independently H, deuterium, $(C_1-C_4)$alkoxy, $(C_1-C_4)$alkyl, $(C_1-C_4)$alkyl-d$_{1-}$, $(C_3-C_4)$cycloalkyl, cyano, halogen, halo$(C_1-C_4)$alkoxy, halo$(C_1-C_4)$alkyl, or hydroxy$(C_1-C_4)$alkyl; B is

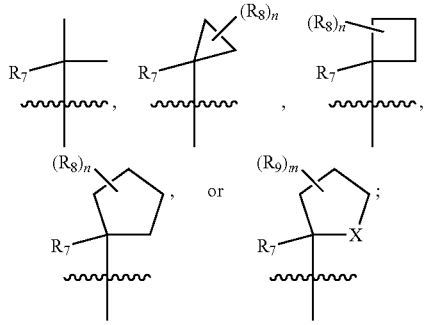

$R_7$ is $(C_1-C_3)$alkyl or $C_1-C_3$)alkyl-d$_{1-7}$; $R_8$ is deuterium or two $R_8$s attached to the same carbon atom form a $(C_3-C_5)$ cycloalkyl group; n is 0 or 2; $R_9$ at each occurrence is F; m is 1, 2, 3, or 4; and X is O.

In another embodiment, the present invention provides compounds of Formula (IA) and (IB), or a pharmaceutically acceptable salt or hydrate thereof, wherein $R_1$ and $R_2$ are independently $(C_1-C_6)$alkyl or $R_1$ and $R_2$ taken together with the nitrogen atom to which they are attached form a 4-, 5-, or 6-membered heterocycle containing one N heteroatom and optionally 1 or 2 additional heteroatoms selected from the group consisting of O, N, and S, optionally substituted with $(C_1-C_4)$alkyl; $R_3$ is H; A is

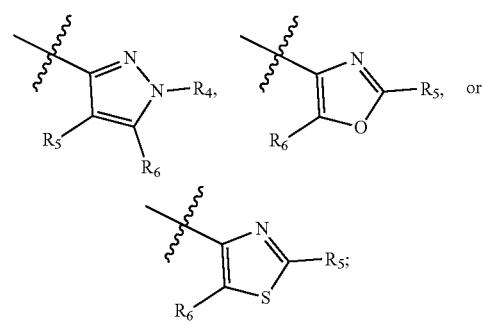

$R_4$ is $(C_1-C_4)$alkyl; $R_5$ and $R_6$ are independently H, deuterium, $(C_1-C_4)$alkoxy, $(C_1-C_4)$alkyl, $(C_1-C_4)$alkyl-d$_{1-9}$, $(C_3-C_4)$cycloalkyl, cyano, halogen, halo$(C_1-C_4)$alkoxy, halo$(C_1-C_4)$alkyl, or hydroxy$(C_1-C_4)$alkyl; B is

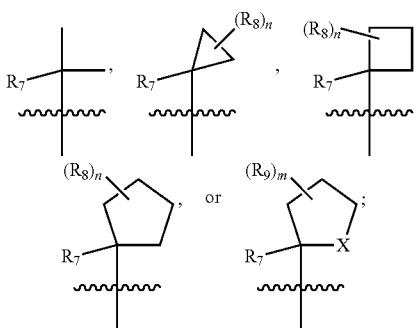

or $R_7$ is $(C_1$-$C_3)$alkyl or $C_1$-$C_3$)alkyl-$d_{1-7}$; $R_8$ is deuterium or two $R_8$s attached to the same carbon atom form a $(C_3$-$C_5)$ cycloalkyl group; n is 0 or 2; $R_9$ at each occurrence is F; m is 2; and X is O.

In another embodiment, the present invention provides compounds of Formula (IA) and (IB), or a pharmaceutically acceptable salt or hydrate thereof, wherein $R_1$ and $R_2$ are independently methyl, ethyl, or isopropyl, or $R_1$ and $R_2$ taken together with the nitrogen atom to which they are attached form morpholine or piperazine wherein the piperazine is substituted with methyl; $R_3$ is H; A is

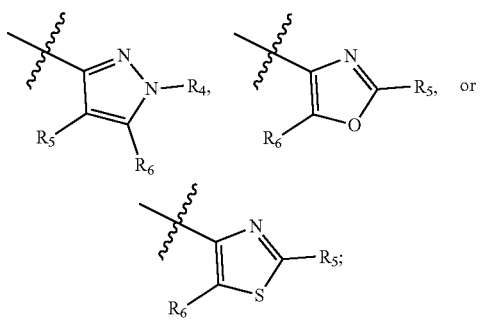

$R_4$ is methyl; $R_5$ is methyl, methyl-$d_3$, ethyl, methoxy, Cl, difluoromethoxy, cyano, cyclopropyl, or hydroxymethyl; $R_6$ is H or methyl; B is

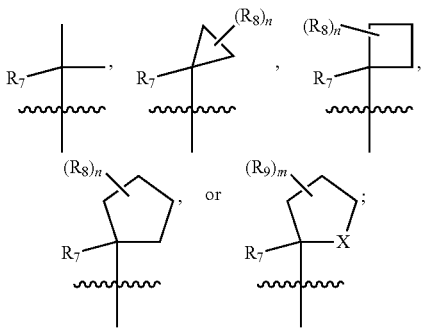

$R_7$ is methyl; $R_8$ is deuterium or two $R_8$s attached to the same carbon atom form cyclopropyl; n is 0 or 2; $R_9$ at each occurrence is F; m is 2; and X is O.

In another embodiment, the present invention provides compounds of Formula (IA) and (IB), or a pharmaceutically acceptable salt or hydrate thereof, wherein $R_1$ is methyl; $R_2$ is methyl, ethyl, or isopropyl; $R_3$ is H; A is

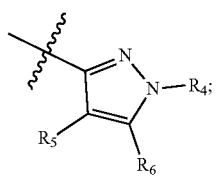

$R_4$ is methyl; $R_5$ is methyl, methyl-$d_3$, ethyl, methoxy, Cl, difluoromethoxy, cyano, or cyclopropyl; $R_6$ is H; B is

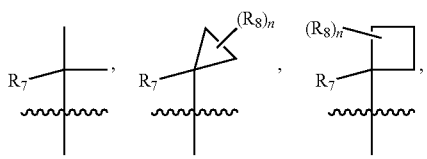

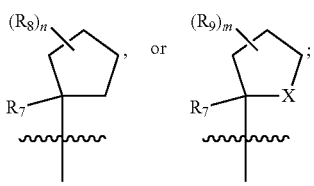

$R_7$ is methyl; $R_8$ is deuterium or two $R_8$s attached to the same carbon atom form cyclopropyl; n is 0 or 2; $R_9$ at each occurrence is F; m is 2; and X is O.

In another embodiment, the present invention provides compounds of Formula (IA) and (IB), or a pharmaceutically acceptable salt or hydrate thereof, wherein $R_1$ is methyl; $R_2$ is methyl, ethyl, or isopropyl; $R_3$ is H; A is

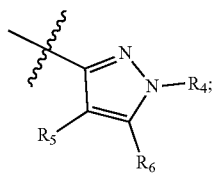

$R_4$ is methyl; $R_5$ is methyl, ethyl, methoxy, Cl, difluoromethoxy, cyano, or cyclopropyl; $R_6$ is H; B is

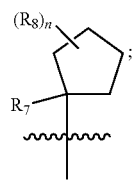

$R_7$ is methyl; and n is 0.

In another embodiment, the present invention provides compounds of Formula (IIA)

Formula (IIA)

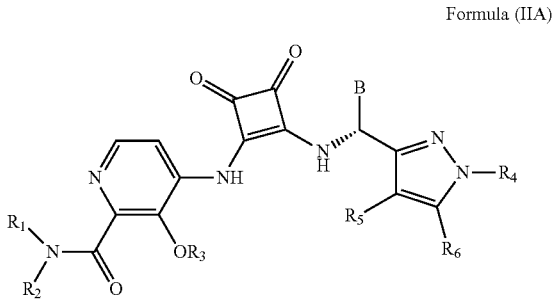

or a pharmaceutically acceptable salt or hydrate thereof, wherein $R_1$ and $R_2$ are independently $(C_1-C_6)$alkyl or $R_1$ and $R_2$ taken together with the nitrogen atom to which they are attached form a 4-, 5-, or 6-membered heterocycle containing one N heteroatom and optionally 1 or 2 additional heteroatoms selected from the group consisting of O, N, and S, optionally substituted with $(C_1-C_4)$alkyl; $R_3$ is H, $(C_1-C_6)$alkyl, $(C_1-C_4)$alkylcarbonyl, —C(=O)CH=CHCO$_2$H, —SO$_2$NH$_2$, —CH$_2$OC(=O)(C$_1$-C$_4$)alkyl, —CH$_2$OP(=O)(OH)$_2$, or —C(=O)NR$_A$R$_B$, wherein the $(C_1-C_4)$alkylcarbonyl is optionally substituted with —CO$_2$H or —NH$_2$, wherein the —CH$_2$OC(=O)(C$_1$-C$_4$)alkyl is optionally substituted with —NH$_2$, and wherein $R_A$ and $R_B$ are independently H or $(C_1-C_6)$alkyl; $R_4$ is $(C_1-C_4)$alkyl; $R_5$ and $R_6$ are independently H, deuterium, $(C_1-C_4)$alkoxy, $(C_1-C_4)$alkyl, $(C_1-C_4)$alkyl-d$_{1-9}$, $(C_3-C_4)$cycloalkyl, cyano, halogen, halo$(C_1-C_4)$alkoxy, or halo$(C_1-C_4)$alkyl; B is

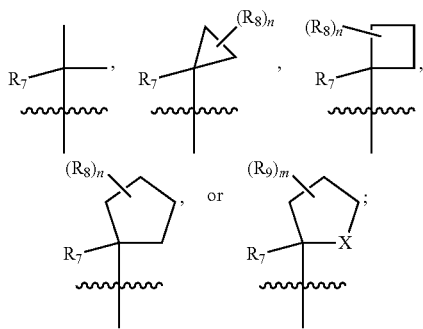

$R_7$ is $(C_1-C_3)$alkyl or $C_1-C_3$)alkyl-d$_{1-7}$; $R_8$ is deuterium or two $R_8$s attached to the same carbon atom form a $(C_3-C_5)$ cycloalkyl group; n is 0 or 2; $R_9$ at each occurrence is F; m is 2; and X is O.

In another embodiment, the present invention provides compounds of Formula (IIA), or a pharmaceutically acceptable salt or hydrate thereof, wherein $R_1$ is methyl; $R_2$ is methyl, ethyl, or isopropyl; $R_3$ is H; $R_4$ is methyl; $R_5$ is methyl, ethyl, methoxy, Cl, difluoromethoxy, cyano, or cyclopropyl; $R_6$ is H; B is

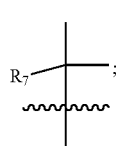

$R_7$ is methyl.

In another embodiment, the present invention provides compounds of Formula (IIA), or a pharmaceutically acceptable salt or hydrate thereof, wherein $R_1$ and $R_2$ taken together with the nitrogen atom to which they are attached form morpholine or 4-methylpiperazine; $R_3$ is H; $R_4$ is methyl; $R_5$ is methyl, ethyl, methoxy, Cl, difluoromethoxy, cyano, or cyclopropyl; $R_6$ is H; B is

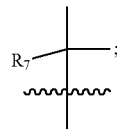

$R_7$ is methyl.

In another embodiment, the present invention provides compounds of Formula (IIA), or a pharmaceutically acceptable salt or hydrate thereof, wherein $R_1$ is methyl; $R_2$ is methyl, ethyl, or isopropyl; $R_3$ is H; $R_4$ is methyl; $R_5$ is methyl, ethyl, methoxy, Cl, difluoromethoxy, cyano, or cyclopropyl; $R_6$ is H; B is

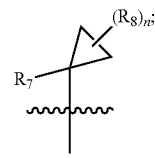

$R_7$ is methyl; and n is 0.

In another embodiment, the present invention provides compounds of Formula (IIA), or a pharmaceutically acceptable salt or hydrate thereof, wherein $R_1$ and $R_2$ taken together with the nitrogen atom to which they are attached form morpholine or 4-methylpiperazine; $R_3$ is H; $R_4$ is methyl; $R_5$ is methyl, methyl-d$_3$, ethyl, methoxy, Cl, difluoromethoxy, cyano, or cyclopropyl; $R_6$ is H; B is

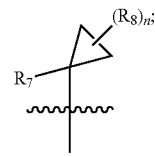

$R_7$ is methyl; and n is 0.

In another embodiment, the present invention provides compounds of Formula (IIA), or a pharmaceutically acceptable salt or hydrate thereof, wherein $R_1$ is methyl; $R_2$ is methyl, ethyl, or isopropyl; $R_3$ is H; $R_4$ is methyl; $R_5$ is methyl, methyl-d$_3$, ethyl, methoxy, Cl, difluoromethoxy, cyano, or cyclopropyl; $R_6$ is H; B is

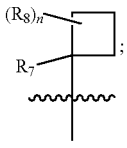

$R_7$ is methyl; two $R_8$s attached to the same carbon atom form cyclopropyl; and n is 0 or 2.

In another embodiment, the present invention provides compounds of Formula (IIA), or a pharmaceutically acceptable salt or hydrate thereof, wherein $R_1$ and $R_2$ taken together with the nitrogen atom to which they are attached form morpholine or 4-methylpiperazine; $R_3$ is H; $R_4$ is methyl; $R_5$ is methyl, ethyl, methoxy, Cl, difluoromethoxy, cyano, or cyclopropyl; $R_6$ is H; B is

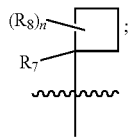

$R_7$ is methyl; two $R_8$s attached to the same carbon atom form cyclopropyl; and n is 0 or 2.

In another embodiment, the present invention provides compounds of Formula (IIA), or a pharmaceutically acceptable salt or hydrate thereof, wherein $R_1$ is methyl; $R_2$ is methyl, ethyl, or isopropyl; $R_3$ is H; $R_4$ is methyl; $R_5$ is methyl, methyl-d$_3$, ethyl, methoxy, Cl, difluoromethoxy, cyano, or cyclopropyl; $R_6$ is H; B is

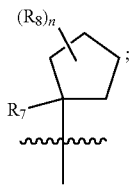

$R_7$ is methyl; $R_8$ is deuterium; and n is 0 or 2.

In another embodiment, the present invention provides compounds of Formula (IIA), or a pharmaceutically acceptable salt or hydrate thereof, wherein $R_1$ and $R_2$ taken together with the nitrogen atom to which they are attached form morpholine or 4-methylpiperazine; $R_3$ is H; $R_4$ is methyl; $R_5$ is methyl, ethyl, methoxy, Cl, difluoromethoxy, cyano, or cyclopropyl; $R_6$ is H; B is

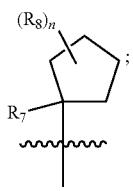

$R_7$ is methyl; and n is 0.

In another embodiment, the present invention provides compounds of Formula (IIA), or a pharmaceutically acceptable salt or hydrate thereof, wherein $R_1$ is methyl; $R_2$ is methyl, ethyl, or isopropyl; $R_3$ is H; $R_4$ is methyl; $R_5$ is methyl, ethyl, methoxy, Cl, difluoromethoxy, cyano, or cyclopropyl; $R_6$ is H; B is

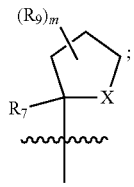

$R_7$ is methyl; $R_9$ is F; m is 2; and X is O.

In another embodiment, the present invention provides compounds of Formula (IIA), or a pharmaceutically acceptable salt or hydrate thereof, wherein $R_1$ and $R_2$ taken together with the nitrogen atom to which they are attached form morpholine or 4-methylpiperazine; $R_3$ is H; $R_4$ is methyl; $R_5$ is methyl, ethyl, methoxy, Cl, difluoromethoxy, cyano, or cyclopropyl; $R_6$ is H; B is

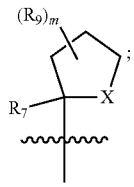

$R_7$ is methyl; $R_9$ is F; m is 2; and X is O.

In another embodiment the compound of Formula (IIA) is (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof.

In another embodiment the compound of Formula (IIA) is (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide.

In another embodiment, the present invention provides a compound of Formula (IIA), or a pharmaceutically acceptable salt or hydrate thereof, for use as a medicament.

In another embodiment, the present invention provides a compound of Formula (IIA), or a pharmaceutically acceptable salt or hydrate thereof, for use in treating or preventing diseases, conditions or disorders ameliorated by inhibition of CCR6 in a human.

In another embodiment, the present invention provides a method for treating or preventing diseases, conditions or disorders ameliorated by inhibition of CCR6 in a human comprising administering to the human, in need of such treatment, a therapeutically effective amount of a compound of Formula (IIA), or a pharmaceutically acceptable salt or hydrate thereof.

In another embodiment, the present invention provides a method for treating or preventing diseases, conditions or disorders ameliorated by inhibition of T cell chemotaxis in a human comprising administering to the human, in need of such treatment, a therapeutically effective amount of a compound of Formula (IIA), or a pharmaceutically acceptable salt or hydrate thereof.

In another embodiment, the present invention provides a method for treating or preventing inflammatory diseases, conditions or disorders in a human comprising administering to the human, in need of such treatment, a therapeutically effective amount of a compound of Formula (IIA), or a pharmaceutically acceptable salt or hydrate thereof.

In another embodiment, the present invention provides a method for treating or preventing autoimmune diseases, conditions or disorders in a human comprising administering to the human, in need of such treatment, a therapeutically effective amount of a compound of Formula (IIA), or a pharmaceutically acceptable salt or hydrate thereof.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a compound of Formula (IIA), or a pharmaceutically acceptable salt or hydrate thereof.

In another embodiment, the present invention provides a method for treating or preventing rheumatoid arthritis in a human comprising administering to the human, in need of such treatment, a therapeutically effective amount of (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof.

In another embodiment, the present invention provides a method for treating or preventing rheumatoid arthritis in a human comprising administering to the human, in need of such treatment, a therapeutically effective amount of a prodrug of (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide.

In another embodiment, the present invention provides the use of a compound of Formula (IIA), or a pharmaceutically acceptable salt or hydrate thereof, in the manufacture of a medicament for treating diseases, conditions or disorders ameliorated by inhibition of CCR6 in a human.

In another embodiment, the present invention provides the use of a compound of Formula (IIA), or a pharmaceutically acceptable salt or hydrate thereof, in the manufacture of a medicament for treating diseases, conditions or disorders ameliorated by inhibition of T cell chemotaxis in a human.

In another embodiment, the present invention provides the use of a compound of Formula (IIA), or a pharmaceutically acceptable salt or hydrate thereof, in the manufacture of a medicament for treating an inflammatory disease, condition, or disorder in a human.

In another embodiment, the present invention provides the use of a compound of Formula (IIA), or a pharmaceutically acceptable salt or hydrate thereof, in the manufacture of a medicament for treating an autoimmune disease, condition, or disorder in a human.

In another embodiment, the present invention provides the use of a compound of Formula (IIA), or a pharmaceutically acceptable salt or hydrate thereof, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, in the manufacture of a medicament for treating rheumatoid arthritis in a human.

In another embodiment, the present invention provides the use of a prodrug of (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, in the manufacture of a medicament for treating rheumatoid arthritis in a human.

In another embodiment, the present invention provides a pharmaceutical composition comprising a compound of Formula (IIA), or a pharmaceutically acceptable salt or hydrate thereof, and at least one pharmaceutically acceptable excipient, diluent, or carrier.

In another embodiment, the present invention provides a pharmaceutical composition comprising (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier.

In another embodiment, the present invention provides a pharmaceutical composition comprising a prodrug of (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical composition comprising a compound of Formula (IIA), or a pharmaceutically acceptable salt or hydrate thereof, and at least one pharmaceutically acceptable excipient, diluent, or carrier.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical composition comprising a compound of Formula (IIA), or a pharmaceutically acceptable salt or hydrate thereof, and at least one pharmaceutically acceptable excipient, diluent, or carrier.

In another embodiment, the present invention provides a method for treating or preventing an inflammatory disease, condition, or disorder in a human comprising administering to the human, in need of such treatment, a therapeutically effective amount of a pharmaceutical composition comprising a compound of Formula (IIA), or a pharmaceutically acceptable salt or hydrate thereof, and at least one pharmaceutically acceptable excipient, diluent, or carrier.

In another embodiment, the present invention provides a method for treating or preventing an autoimmune disease, condition, or disorder in a human comprising administering to the human, in need of such treatment, a therapeutically effective amount of a pharmaceutical composition comprising a compound of Formula (IIA), or a pharmaceutically acceptable salt or hydrate thereof, and at least one pharmaceutically acceptable excipient, diluent, or carrier.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical composition comprising a compound of Formula (IIA), or a pharmaceutically acceptable salt or hydrate thereof, and at least one pharmaceutically acceptable excipient, diluent, or carrier.

In another embodiment, the present invention provides a method for treating or preventing rheumatoid arthritis in a human comprising administering to the human, in need of such treatment, a therapeutically effective amount of a pharmaceutical composition comprising (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier.

In another embodiment, the present invention provides a method for treating or preventing rheumatoid arthritis in a human comprising administering to the human, in need of such treatment, a therapeutically effective amount of a pharmaceutical composition comprising a prodrug of (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier.

In another embodiment, the present invention provides the use of a pharmaceutical composition comprising a compound of Formula (IIA), or a pharmaceutically acceptable salt or hydrate thereof, and at least one pharmaceutically acceptable excipient, diluent, or carrier, in the manufacture of a medicament for treating diseases, conditions or disorders ameliorated by inhibition of CCR6 in a human.

In another embodiment, the present invention provides the use of a pharmaceutical composition comprising a compound of Formula (IIA), or a pharmaceutically acceptable salt or hydrate thereof, and at least one pharmaceutically acceptable excipient, diluent, or carrier, in the manufacture of a medicament for treating diseases, conditions or disorders ameliorated by inhibition of T cell chemotaxis in a human.

In another embodiment, the present invention provides the use of a pharmaceutical composition comprising a compound of Formula (IIA), or a pharmaceutically acceptable salt or hydrate thereof, and at least one pharmaceutically acceptable excipient, diluent, or carrier, in the manufacture of a medicament for treating an inflammatory disease, condition, or disorder in a human.

In another embodiment, the present invention provides the use of a pharmaceutical composition comprising a compound of Formula (IIA), or a pharmaceutically acceptable salt or hydrate thereof, and at least one pharmaceutically acceptable excipient, diluent, or carrier, in the manufacture of a medicament for treating an autoimmune disease, condition, or disorder in a human.

In another embodiment, the present invention provides the use of a pharmaceutical composition comprising a compound of Formula (IIA), or a pharmaceutically acceptable salt or hydrate thereof, and at least one pharmaceutically acceptable excipient, diluent, or carrier, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of a pharmaceutical composition comprising (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier, in the manufacture of a medicament for treating rheumatoid arthritis in a human.

In another embodiment, the present invention provides the use of a pharmaceutical composition comprising a prodrug of (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier, in the manufacture of a medicament for treating rheumatoid arthritis in a human.

In another embodiment, the present invention provides a pharmaceutical combination comprising a compound of Formula (IIA), or a pharmaceutically acceptable salt or hydrate thereof, and at least one anti-inflammatory agent.

In another embodiment, the present invention provides a pharmaceutical combination comprising (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent.

In another embodiment, the present invention provides a pharmaceutical combination comprising a prodrug of (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical combination comprising a compound of Formula (IIA), or a pharmaceutically acceptable salt or hydrate thereof, and at least one anti-inflammatory agent.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical combination comprising a compound of Formula (IIA), or a pharmaceutically acceptable salt or hydrate thereof, and at least one anti-inflammatory agent.

In another embodiment, the present invention provides a method for treating or preventing an inflammatory disease, condition, or disorder in a human comprising administering to the human, in need of such treatment, a therapeutically effective amount of a pharmaceutical combination comprising a compound of Formula (IIA), or a pharmaceutically acceptable salt or hydrate thereof, and at least one anti-inflammatory agent.

In another embodiment, the present invention provides a method for treating or preventing an autoimmune disease, condition, or disorder in a human comprising administering to the human, in need of such treatment, a therapeutically effective amount of a pharmaceutical combination comprising a compound of Formula (IIA), or a pharmaceutically acceptable salt or hydrate thereof, and at least one anti-inflammatory agent.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical combination comprising a compound of Formula (IIA), or a pharmaceutically acceptable salt or hydrate thereof, and at least one anti-inflammatory agent.

In another embodiment, the present invention provides a method for treating or preventing rheumatoid arthritis in a human comprising administering to the human, in need of such treatment, a therapeutically effective amount of a pharmaceutical combination comprising (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent.

In another embodiment, the present invention provides a method for treating or preventing rheumatoid arthritis in a human comprising administering to the human, in need of such treatment, a therapeutically effective amount of a pharmaceutical combination comprising a prodrug of (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent.

In another embodiment, the present invention provides the use of a pharmaceutical combination comprising a compound of Formula (IIA), or a pharmaceutically acceptable salt or hydrate thereof, and at least one anti-inflammatory agent, in the manufacture of a medicament for treating diseases, conditions or disorders ameliorated by inhibition of CCR6 in a human.

In another embodiment, the present invention provides the use of a pharmaceutical combination comprising a compound of Formula (IIA), or a pharmaceutically acceptable salt or hydrate thereof, and at least one anti-inflammatory agent, in the manufacture of a medicament for treating diseases, conditions or disorders ameliorated by inhibition of T cell chemotaxis in a human.

In another embodiment, the present invention provides the use of a pharmaceutical combination comprising a compound of Formula (IIA), or a pharmaceutically acceptable salt or hydrate thereof, and at least one anti-inflammatory agent, in the manufacture of a medicament for treating an inflammatory disease, condition, or disorder in a human.

In another embodiment, the present invention provides the use of a pharmaceutical combination comprising a compound of Formula (IIA), or a pharmaceutically acceptable salt or hydrate thereof, and at least one anti-inflammatory agent, in the manufacture of a medicament for treating an autoimmune disease, condition, or disorder in a human.

In another embodiment, the present invention provides the use of a pharmaceutical combination comprising a compound of Formula (IIA), or a pharmaceutically acceptable salt or hydrate thereof, and at least one anti-inflammatory agent, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of a pharmaceutical combination comprising (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent, in the manufacture of a medicament for treating rheumatoid arthritis in a human.

In another embodiment, the present invention provides the use of a pharmaceutical combination comprising a prodrug of (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent, in the manufacture of a medicament for treating rheumatoid arthritis in a human.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising diffraction peaks 18.7±0.2, 19.1±0.2, and 20.2±0.2 degrees two theta.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising diffraction peaks 17.6±0.2, 18.4±0.2, 18.7±0.2, 19.1±0.2, and 20.2±±0.2 degrees two theta.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising diffraction peaks 11.4±0.2, 15.5±0.2, 17.6±0.2, 18.4±0.2, 18.7±0.2, 19.1±0.2, 20.2±0.2, and 24.3±0.2 degrees two theta.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising diffraction peaks 11.4±0.2, 12.4±0.2, 15.5±0.2, 17.6±0.2, 18.4±0.2, 18.7±0.2, 19.1±0.2, 20.2±0.2, 24.3±0.2, 26.8±0.2, and 30.5±0.2 degrees two theta.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising 3 to 10 diffraction peaks selected from the group consisting of 11.4±0.2, 12.4±0.2, 15.5±0.2, 17.6±0.2, 18.4±0.2, 18.7±0.2, 19.1±0.2, 20.2±0.2, 24.3±0.2, 26.8±±0.2, and 30.5±0.2 degrees two theta.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising 3 to 10 diffraction peaks listed in Table 7.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising the diffraction peaks listed in Table 7.

Figure 4:
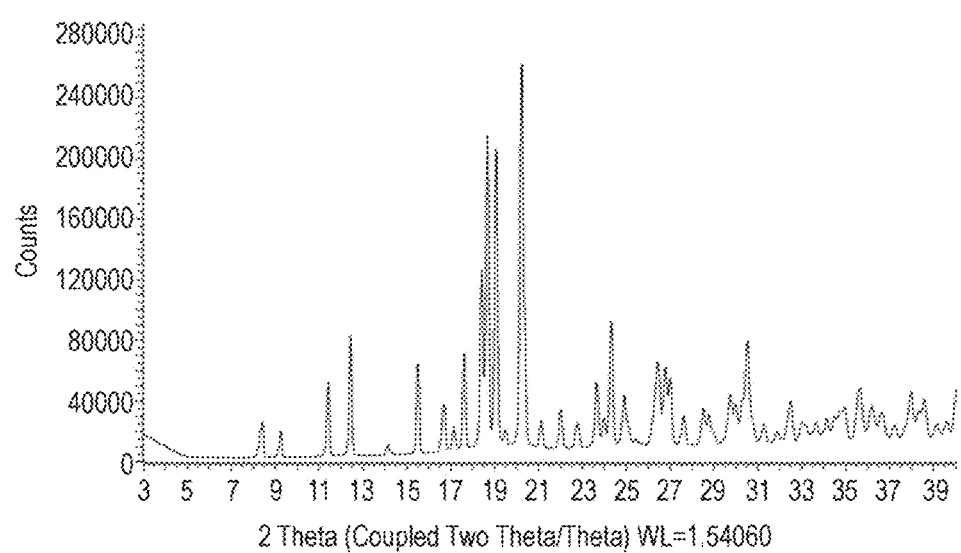
FIG. 4 is a powder X-ray diffraction analysis of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides crystalline (R)-4-((2-(((1,4-dimethyl-1H-pyrazol-3-yl)(1- methylcyclopentyl)methyl)amino)-3,4-dioxocyclobut-1-en-1-yl)amino)-3-hydroxy-N,N-dimethylpicolinamide monohydrate having an X-ray powder diffraction pattern as depicted in FIG. 4.

Figure 5:
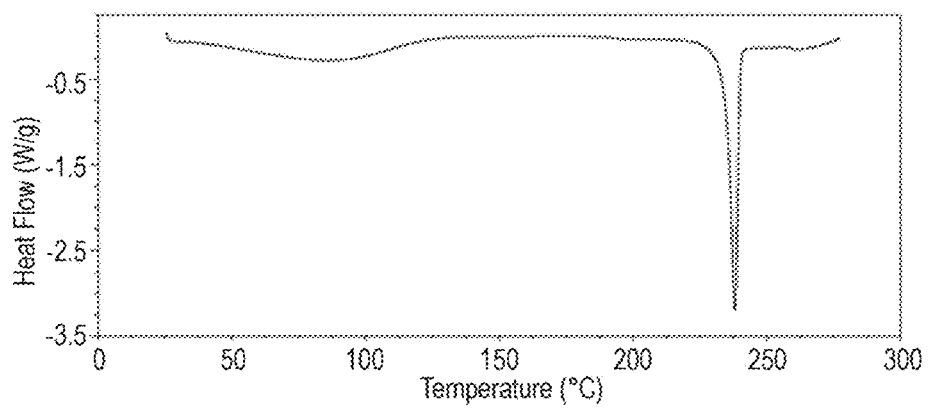
FIG. 5 is a differential scanning calorimeter analysis for crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having a differential scanning calorimeter analysis as depicted in FIG. 5.

Figure 6:
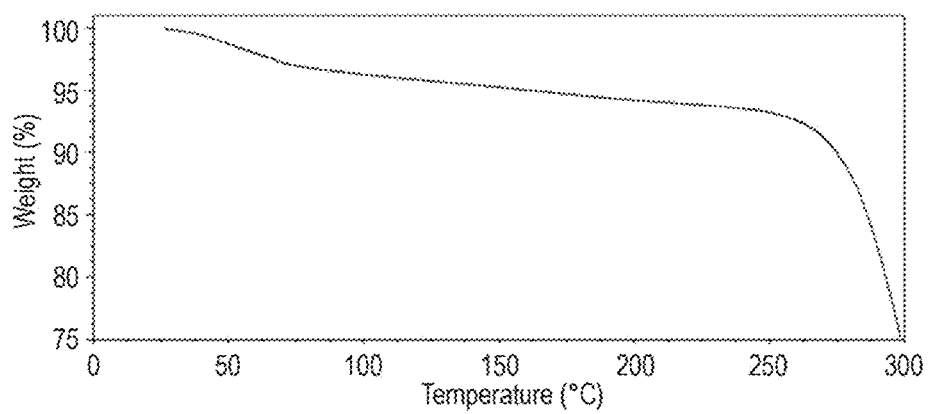
FIG. 6 is a thermogravimetric analysis for crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having a thermogravimetric analysis as depicted in FIG. 6.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate for use as a medicament.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate for use in treating or preventing diseases, conditions or disorders ameliorated by inhibition of CCR6 in a human.

In another embodiment, the present invention provides a method for treating or preventing diseases, conditions or disorders ameliorated by inhibition of CCR6 in a human comprising administering to the human, in need of such treatment, a therapeutically effective amount of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides a method for treating or preventing diseases, conditions or disorders ameliorated by inhibition of T cell chemotaxis in a human comprising administering to the human, in need of such treatment, a therapeutically effective amount of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides a method for treating or preventing inflammatory diseases, conditions or disorders in a human comprising administering to the human, in need of such treatment, a therapeutically effective amount of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides a method for treating or preventing autoimmune diseases, conditions or disorders in a human comprising administering to the human, in need of such treatment, a therapeutically effective amount of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides a method for treating or preventing rheumatoid arthritis in a human comprising administering to the human, in need of such treatment, a therapeutically effective amount of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating diseases, conditions or disorders ameliorated by inhibition of CCR6 in a human.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating diseases, conditions or disorders ameliorated by inhibition of T cell chemotaxis in a human.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating an inflammatory disease, condition, or disorder in a human.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating an autoimmune disease, condition, or disorder in a human.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating rheumatoid arthritis in a human.

In another embodiment, the present invention provides a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N, N-dimethylpicolinamide monohydrate, and at least one pharmaceutically acceptable excipient, diluent, or carrier.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides a method for treating or preventing an inflammatory disease, condition, or disorder in a human comprising administering to the human, in need of such treatment, a therapeutically effective amount of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides a method for treating or preventing an autoimmune disease, condition, or disorder in a human comprising administering to the human, in need of such treatment, a therapeutically effective amount of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides a method for treating or preventing rheumatoid arthritis in a human comprising administering to the human, in need of such treatment, a therapeutically effective amount of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating diseases, conditions or disorders ameliorated by inhibition of CCR6 in a human.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating diseases, conditions or disorders ameliorated by inhibition of T cell chemotaxis in a human.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating an inflammatory disease, condition, or disorder in a human.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating an autoimmune disease, condition, or disorder in a human.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating rheumatoid arthritis in a human.

In another embodiment, the present invention provides a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing an inflammatory disease, condition, or disorder in a human comprising administering to the human, in need of such treatment, a therapeutically effective amount of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing an autoimmune disease, condition, or disorder in a human comprising administering to the human, in need of such treatment, a therapeutically effective amount of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing rheumatoid arthritis in a human comprising administering to the human, in need of such treatment, a therapeutically effective amount of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating diseases, conditions or disorders ameliorated by inhibition of CCR6 in a human.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating diseases, conditions or disorders ameliorated by inhibition of T cell chemotaxis in a human.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating an inflammatory disease, condition, or disorder in a human.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating an autoimmune disease, condition, or disorder in a human.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating rheumatoid arthritis in a human.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate having an X-ray powder diffraction pattern comprising diffraction peaks 7.8±0.2, 10.3±0.2, and 10.7±0.2 degrees two theta.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate having an X-ray powder diffraction pattern comprising diffraction peaks 7.8±0.2, 10.3±0.2, 10.7±0.2, 15.5±0.2, and 18.4±0.2 degrees two theta.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate having an X-ray powder diffraction pattern comprising diffraction peaks 7.7±0.2, 7.8±0.2, 10.3±0.2, 10.7±0.2, 15.5±0.2, 17.0±0.2, 18.4±0.2, 20.8±0.2, and 21.0±0.2 degrees two theta.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate having an X-ray powder diffraction pattern comprising diffraction peaks 7.7±0.2, 7.8±0.2, 10.3±0.2, 10.7±0.2, 15.5±0.2, 17.0±0.2, 18.4±0.2, 20.5±0.2, 20.8±0.2, 21.0±0.2, 24.0±0.2, and 25.6±0.2, degrees two theta.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en- 1-yl)amino)-3-hydroxy-N,N-dimethylpicolinamide, 0.5 calcium salt, monohydrate having an X-ray powder diffraction pattern comprising diffraction peaks 7.7±0.2, 7.8±0.2, 10.3±0.2, 10.7±0.2, 11.9±0.2, 13.6±0.2, 15.5±0.2, 16.6±0.2, 17.0±0.2, 18.4±0.2, 20.5±0.2, 20.8±0.2, 21.0±0.2, 22.3±0.2, 24.0±0.2, 24.9±0.2, 25.6±0.2, 26.1±0.2, 31.3±0.2, and 31.4±0.2, degrees two theta.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate having an X-ray powder diffraction pattern comprising 3 to 10 diffraction peaks listed in Table 10.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate having an X-ray powder diffraction pattern comprising the diffraction peaks listed in Table 10.

Figure 12:
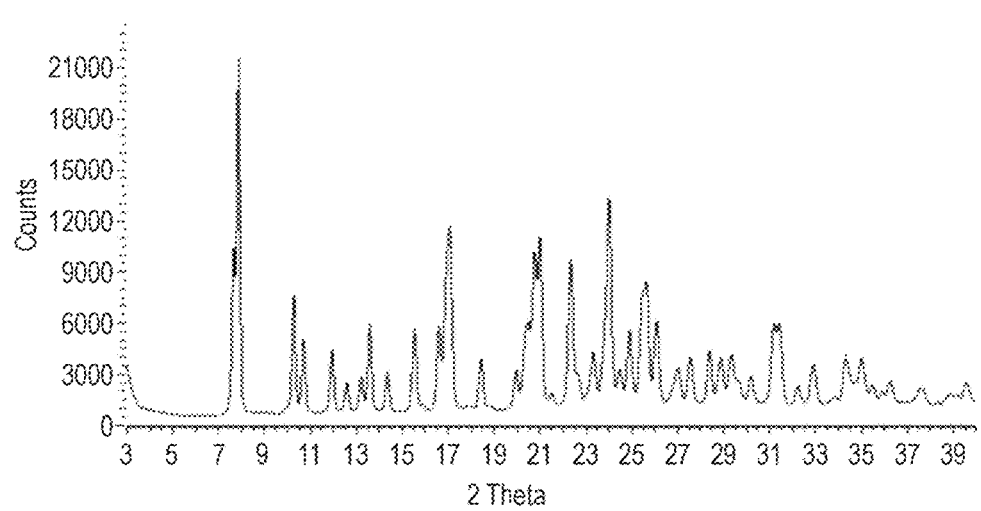
FIG. 12 is a powder X-ray diffraction analysis of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate having an X-ray powder diffraction pattern as depicted in FIG. 12.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate for use as a medicament.

In another embodiment, the present invention provides crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate for use in treating or preventing diseases, conditions or disorders ameliorated by inhibition of CCR6 in a human.

In another embodiment, the present invention provides a method for treating or preventing diseases, conditions or disorders ameliorated by inhibition of CCR6 in a human comprising administering to the human, in need of such treatment, a therapeutically effective amount of crystalline ((R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate.

In another embodiment, the present invention provides a method for treating or preventing diseases, conditions or disorders ameliorated by inhibition of T cell chemotaxis in a human comprising administering to the human, in need of such treatment, a therapeutically effective amount of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate.

In another embodiment, the present invention provides a method for treating or preventing inflammatory diseases, conditions or disorders in a human comprising administering to the human, in need of such treatment, a therapeutically effective amount of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate.

In another embodiment, the present invention provides a method for treating or preventing autoimmune diseases, conditions or disorders in a human comprising administering to the human, in need of such treatment, a therapeutically effective amount of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate.

In another embodiment, the present invention provides a method for treating or preventing rheumatoid arthritis in a human comprising administering to the human, in need of such treatment, a therapeutically effective amount of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, in the manufacture of a medicament for treating diseases, conditions or disorders ameliorated by inhibition of CCR6 in a human.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, in the manufacture of a medicament for treating diseases, conditions or disorders ameliorated by inhibition of T cell chemotaxis in a human.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, in the manufacture of a medicament for treating an inflammatory disease, condition, or disorder in a human.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, in the manufacture of a medicament for treating an autoimmune disease, condition, or disorder in a human.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, in the manufacture of a medicament for treating rheumatoid arthritis in a human.

In another embodiment, the present invention provides a pharmaceutical composition comprising crystalline (R)-4-

((2-(((1,4-dimethyl-1H-pyrazol-3-yl)(1-methylcyclopentyl) methyl)amino)-3,4-dioxocyclobut-1-en-1-yl)amino)-3-hydroxy-N,N-dimethylpicolinamide, 0.5 calcium salt, monohydrate, and at least one pharmaceutically acceptable excipient, diluent, or carrier.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one pharmaceutically acceptable excipient, diluent, or carrier.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical composition comprising crystalline (R)-4-((2-(((1,4-dimethyl-1H-pyrazol-3-yl)(1-methylcyclopentyl) methyl)amino)-3,4-dioxocyclobut-1-en-1-yl)amino)-3-hydroxy-N,N-dimethylpicolinamide, 0.5 calcium salt, monohydrate, and at least one pharmaceutically acceptable excipient, diluent, or carrier.

In another embodiment, the present invention provides a method for treating or preventing an inflammatory disease, condition, or disorder in a human comprising administering to the human, in need of such treatment, a therapeutically effective amount of a pharmaceutical composition comprising crystalline (R)-4-((2-(((1,4-dimethyl-1H-pyrazol-3-yl) (1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one pharmaceutically acceptable excipient, diluent, or carrier.

In another embodiment, the present invention provides a method for treating or preventing an autoimmune disease, condition, or disorder in a human comprising administering to the human, in need of such treatment, a therapeutically effective amount of a pharmaceutical composition comprising crystalline (R)-4-((2-(((1,4-dimethyl-1H-pyrazol-3-yl) (1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one pharmaceutically acceptable excipient, diluent, or carrier.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one pharmaceutically acceptable excipient, diluent, or carrier.

In another embodiment, the present invention provides a method for treating or preventing rheumatoid arthritis in a human comprising administering to the human, in need of such treatment, a therapeutically effective amount of a pharmaceutical composition comprising crystalline (R)-4-((2-(((1,4-dimethyl-1H-pyrazol-3-yl)(1-methylcyclopentyl) methyl)amino)-3,4-dioxocyclobut-1-en-1-yl)amino)-3-hydroxy-N,N-dimethylpicolinamide, 0.5 calcium salt, monohydrate, and at least one pharmaceutically acceptable excipient, diluent, or carrier.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl) amino)-3-hydroxy-N,N-dimethylpicolinamide, 0.5 calcium salt, monohydrate, and at least one pharmaceutically acceptable excipient, diluent, or carrier, in the manufacture of a medicament for treating diseases, conditions or disorders ameliorated by inhibition of CCR6 in a human.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl) amino)-3-hydroxy-N,N-dimethylpicolinamide, 0.5 calcium salt, monohydrate, and at least one pharmaceutically acceptable excipient, diluent, or carrier, in the manufacture of a medicament for treating diseases, conditions or disorders ameliorated by inhibition of T cell chemotaxis in a human.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl) amino)-3-hydroxy-N,N-dimethylpicolinamide, 0.5 calcium salt, monohydrate, and at least one pharmaceutically acceptable excipient, diluent, or carrier, in the manufacture of a medicament for treating an inflammatory disease, condition, or disorder in a human.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl) amino)-3-hydroxy-N,N-dimethylpicolinamide, 0.5 calcium salt, monohydrate, and at least one pharmaceutically acceptable excipient, diluent, or carrier, in the manufacture of a medicament for treating an autoimmune disease, condition, or disorder in a human.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl) amino)-3-hydroxy-N,N-dimethylpicolinamide, 0.5 calcium salt, monohydrate, and at least one pharmaceutically acceptable excipient, diluent, or carrier, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of a pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl) amino)-3-hydroxy-N,N-dimethylpicolinamide, 0.5 calcium salt, monohydrate, and at least one pharmaceutically acceptable excipient, diluent, or carrier, in the manufacture of a medicament for treating rheumatoid arthritis in a human.

In another embodiment, the present invention provides a pharmaceutical combination comprising crystalline (R)-4-((2-(((1,4-dimethyl-1H-pyrazol-3-yl)(1-methylcyclopentyl) methyl)amino)-3,4-dioxocyclobut-1-en-1-yl)amino)-3-hydroxy-N,N-dimethylpicolinamide, 0.5 calcium salt, monohydrate, and at least one anti-inflammatory agent.

In another embodiment, the present invention provides a pharmaceutical combination comprising crystalline (R)-4-((2-(((1,4-dimethyl-1H-pyrazol-3-yl)(1-methylcyclopentyl) methyl)amino)-3,4-dioxocyclobut-1-en-1-yl)amino)-3-hydroxy-N,N-dimethylpicolinamide, 0.5 calcium salt, monohydrate, and at least one anti-inflammatory agent.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical combination comprising crystalline (R)-4-((2-(((1, 4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent.

In another embodiment, the present invention provides a method for treating or preventing an inflammatory disease, condition, or disorder in a human comprising administering to the human, in need of such treatment, a therapeutically effective amount of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent.

In another embodiment, the present invention provides a method for treating or preventing an autoimmune disease, condition, or disorder in a human comprising administering to the human, in need of such treatment, a therapeutically effective amount of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent.

In another embodiment, the present invention provides a method for treating or preventing rheumatoid arthritis in a human comprising administering to the human, in need of such treatment, a therapeutically effective amount of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent, in the manufacture of a medicament for treating diseases, conditions or disorders ameliorated by inhibition of CCR6 in a human.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent, in the manufacture of a medicament for treating diseases, conditions or disorders ameliorated by inhibition of T cell chemotaxis in a human.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent, in the manufacture of a medicament for treating an inflammatory disease, condition, or disorder in a human.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent, in the manufacture of a medicament for treating an autoimmune disease, condition, or disorder in a human.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of a pharmaceutical combination comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate, and at least one anti-inflammatory agent, in the manufacture of a medicament for treating rheumatoid arthritis in a human.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising diffraction peaks 18.5±0.2, 18.8±0.2, and 19.2±0.2 degrees two theta.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising diffraction peaks 8.4±0.2, 11.5±0.2, 12.5±0.2, 18.5±0.2, 18.8±0.2, and 19.2±0.2 degrees two theta.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising diffraction peaks 8.4±0.2, 9.3±0.2, 11.5±0.2, 12.5±0.2, 18.5±0.2, 18.8±0.2, 19.2±0.2, and 20.4±0.2 degrees two theta.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising 3 to 10 diffraction peaks selected from the group consisting of 8.4±0.2, 9.3±0.2, 11.5±0.2, 12.5±0.2, 18.5±0.2, 18.8±0.2, 19.2±0.2, 20.4±0.2, 24.5±0.2, 25.1±0.2, and 26.7±0.2 degrees two theta.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising 3 to 10 diffraction peaks listed in Table 8.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising the diffraction peaks listed in Table 8.

Figure 7:
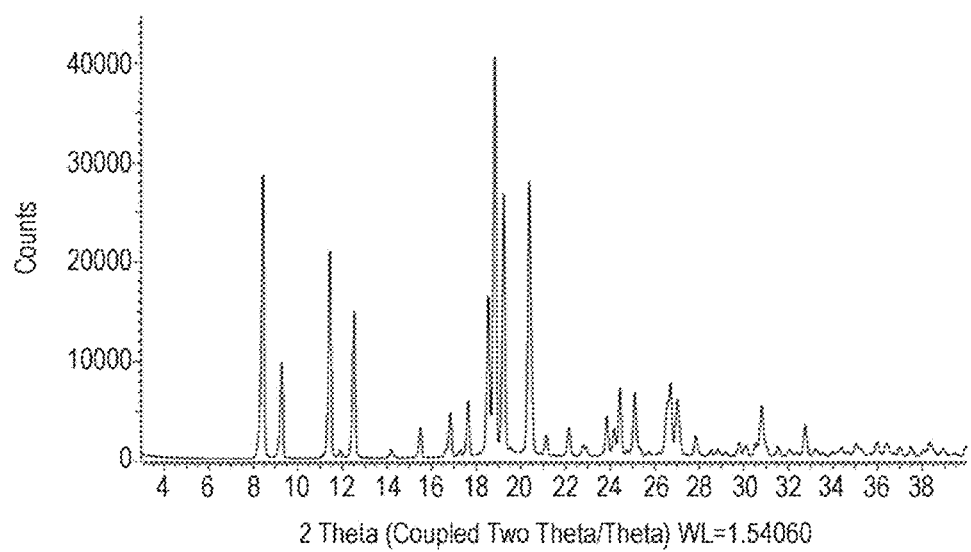
FIG. 7 is a powder X-ray diffraction analysis of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern as depicted in FIG. 7.

Figure 8:
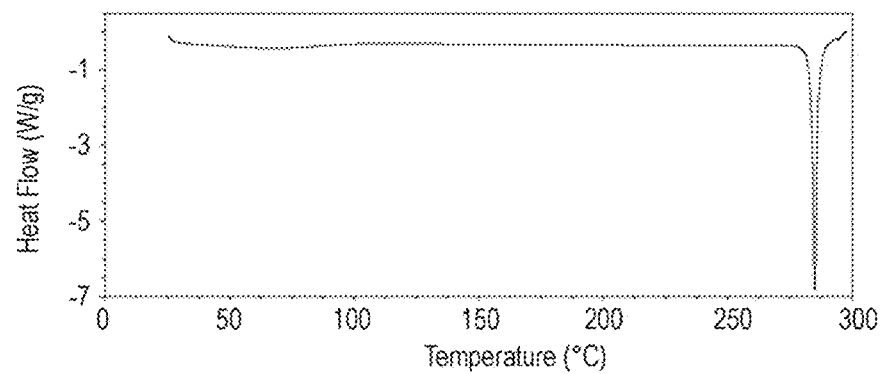
FIG. 8 is a differential scanning calorimeter analysis for crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having a differential scanning calorimeter analysis as depicted in FIG. 8.

Figure 9:
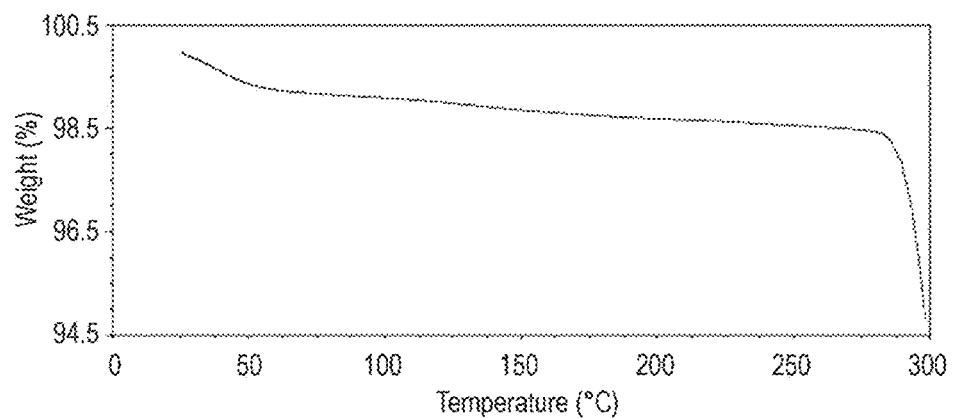
FIG. 9 is a thermogravimetric analysis for crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having a thermogravimetric analysis as depicted in FIG. 9.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate for use as a medicament.

In another embodiment, the present invention provides crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate for use in treating or preventing diseases, conditions or disorders ameliorated by inhibition of CCR6 in a human.

In another embodiment, the present invention provides a method for treating or preventing diseases, conditions or disorders ameliorated by inhibition of CCR6 in a human comprising administering to the human, in need of such treatment, a therapeutically effective amount of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides a method for treating or preventing diseases, conditions or disorders ameliorated by inhibition of T cell chemotaxis in a human comprising administering to the human, in need of such treatment, a therapeutically effective amount of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides a method for treating or preventing inflammatory diseases, conditions or disorders in a human comprising administering to the human, in need of such treatment, a therapeutically effective amount of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides a method for treating or preventing autoimmune diseases, conditions or disorders in a human comprising administering to the human, in need of such treatment, a therapeutically effective amount of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides a method for treating or preventing rheumatoid arthritis in a human comprising administering to the human, in need of such treatment, a therapeutically effective amount of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

In another embodiment, the present invention provides the use of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating diseases, conditions or disorders ameliorated by inhibition of CCR6 in a human.

In another embodiment, the present invention provides the use of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating diseases, conditions or disorders ameliorated by inhibition of T cell chemotaxis in a human.

In another embodiment, the present invention provides the use of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating an inflammatory disease, condition, or disorder in a human.

In another embodiment, the present invention provides the use of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating an autoimmune disease, condition, or disorder in a human.

In another embodiment, the present invention provides the use of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, in the manufacture of a medicament for treating rheumatoid arthritis in a human.

In another embodiment, the present invention provides a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides a method for treating or preventing an inflammatory disease, condition, or disorder in a human comprising administering to the human, in need of such treatment, a therapeutically effective amount of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides a method for treating or preventing an autoimmune disease, condition, or disorder in a human comprising administering to the human, in need of such treatment, a therapeutically effective amount of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides a method for treating or preventing rheumatoid arthritis in a human comprising administering to the human, in need of such treatment, a therapeutically effective amount of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

In another embodiment, the present invention provides the use of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating diseases, conditions or disorders ameliorated by inhibition of CCR6 in a human.

In another embodiment, the present invention provides the use of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating diseases, conditions or disorders ameliorated by inhibition of T cell chemotaxis in a human.

In another embodiment, the present invention provides the use of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating an inflammatory disease, condition, or disorder in a human.

In another embodiment, the present invention provides the use of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating an autoimmune disease, condition, or disorder in a human.

In another embodiment, the present invention provides the use of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of a pharmaceutical composition comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier, in the manufacture of a medicament for treating rheumatoid arthritis in a human.

In another embodiment, the present invention provides a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing an inflammatory disease, condition, or disorder in a human comprising administering to the human, in need of such treatment, a therapeutically effective amount of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing an autoimmune disease, condition, or disorder in a human comprising administering to the human, in need of such treatment, a therapeutically effective amount of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides a method for treating or preventing rheumatoid arthritis in a human comprising administering to the human, in need of such treatment, a therapeutically effective amount of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent.

In another embodiment, the present invention provides the use of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating diseases, conditions or disorders ameliorated by inhibition of CCR6 in a human.

In another embodiment, the present invention provides the use of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating diseases, conditions or disorders ameliorated by inhibition of T cell chemotaxis in a human.

In another embodiment, the present invention provides the use of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating an inflammatory disease, condition, or disorder in a human.

In another embodiment, the present invention provides the use of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating an autoimmune disease, condition, or disorder in a human.

In another embodiment, the present invention provides the use of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of a pharmaceutical combination comprising crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one anti-inflammatory agent, in the manufacture of a medicament for treating rheumatoid arthritis in a human.

In another embodiment, the present invention provides compounds of Formula (IIB)

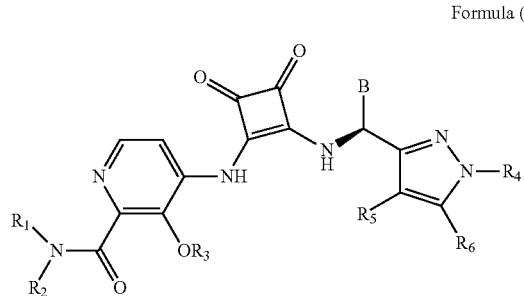

Formula (IIB)

or a pharmaceutically acceptable salt or hydrate thereof, wherein $R_1$ and $R_2$ are independently $(C_1-C_6)$alkyl or $R_1$ and $R_2$ taken together with the nitrogen atom to which they are attached form a 4-, 5-, or 6-membered heterocycle containing one N heteroatom and optionally 1 or 2 additional heteroatoms selected from the group consisting of O, N, and S, optionally substituted with $(C_1-C_4)$alkyl; $R_3$ is H, $(C_1-C_6)$alkyl, $(C_1-C_4)$alkylcarbonyl, —C(=O)CH=CHCO$_2$H, —SO$_2$NH$_2$, —CH$_2$OC(=O)(C$_1$-C$_4$)alkyl, —CH$_2$OP(=O)(OH)$_2$, or —C(=O)NR$_A$R$_B$, wherein the $(C_1-C_4)$alkylcarbonyl is optionally substituted with —CO$_2$H or —NH$_2$, wherein the —CH$_2$OC(=O)(C$_1$-C$_4$)alkyl is optionally substituted with —NH$_2$, and wherein $R_A$ and $R_B$ are independently H or $(C_1-C_6)$alkyl; $R_4$ is $(C_1-C_4)$alkyl; $R_5$ and $R_6$ are independently H, deuterium, $(C_1-C_4)$alkoxy, $(C_1-C_4)$alkyl, $(C_1-C_4)$alkyl-d$_{1-9}$, $(C_3-C_4)$cycloalkyl, cyano, halogen, halo$(C_1-C_4)$alkoxy, or halo$(C_1-C_4)$alkyl; B is

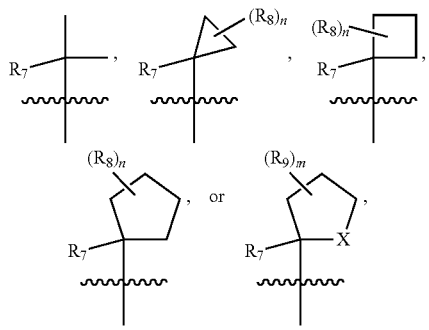

$R_7$ is $(C_1-C_3)$alkyl or $C_1-C_3$)alkyl-d$_{1-7}$; $R_8$ is deuterium or two $R_8$s attached to the same carbon atom form a $(C_3-C_5)$ cycloalkyl group; n is 0 or 2; $R_9$ at each occurrence is F; m is 2; and X is O.

In another embodiment, the present invention provides compounds of Formula (IB), or a pharmaceutically acceptable salt or hydrate thereof, wherein $R_1$ is methyl; $R_2$ is methyl, ethyl, or isopropyl; $R_3$ is H; $R_4$ is methyl; $R_5$ is methyl, ethyl, methoxy, Cl, difluoromethoxy, cyano, or cyclopropyl; $R_6$ is H; B is

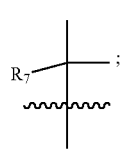

$R_7$ is methyl.

In another embodiment, the present invention provides compounds of Formula (IB), or a pharmaceutically acceptable salt or hydrate thereof, wherein $R_1$ and $R_2$ taken together with the nitrogen atom to which they are attached form morpholine or 4-methylpiperazine; $R_3$ is H; $R_4$ is methyl; $R_5$ is methyl, ethyl, methoxy, Cl, difluoromethoxy, cyano, or cyclopropyl; $R_6$ is H; B is

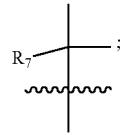

$R_7$ is methyl.

In another embodiment, the present invention provides compounds of Formula (IB), or a pharmaceutically acceptable salt or hydrate thereof, wherein $R_1$ is methyl; $R_2$ is methyl, ethyl, or isopropyl; $R_3$ is H; $R_4$ is methyl; $R_5$ is methyl, ethyl, methoxy, Cl, difluoromethoxy, cyano, or cyclopropyl; $R_6$ is H; B is

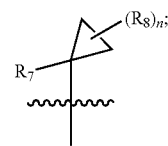

$R_7$ is methyl; and n is 0.

In another embodiment, the present invention provides compounds of Formula (IB), or a pharmaceutically acceptable salt or hydrate thereof, wherein $R_1$ and $R_2$ taken together with the nitrogen atom to which they are attached form morpholine or 4-methylpiperazine; $R_3$ is H; $R_4$ is methyl; $R_5$ is methyl, methyl-d$_3$, ethyl, methoxy, Cl, difluoromethoxy, cyano, or cyclopropyl; $R_6$ is H; B is

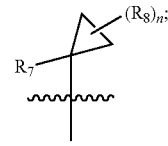

$R_7$ is methyl; and n is 0.

In another embodiment, the present invention provides compounds of Formula (I), or a pharmaceutically acceptable salt or hydrate thereof, wherein $R_1$ is methyl; $R_2$ is methyl, ethyl, or isopropyl; $R_3$ is H; $R_4$ is methyl; $R_5$ is methyl, methyl-d$_3$, ethyl, methoxy, Cl, difluoromethoxy, cyano, or cyclopropyl; $R_6$ is H; B is

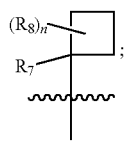

$R_7$ is methyl; two $R_8$s attached to the same carbon atom form cyclopropyl; and n is 0 or 2.

In another embodiment, the present invention provides compounds of Formula (I), or a pharmaceutically acceptable salt or hydrate thereof, wherein $R_1$ and $R_2$ taken together with the nitrogen atom to which they are attached form morpholine or 4-methylpiperazine; $R_3$ is H; $R_4$ is methyl; $R_5$ is methyl, ethyl, methoxy, Cl, difluoromethoxy, cyano, or cyclopropyl; $R_6$ is H; B is

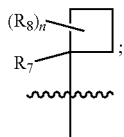

$R_7$ is methyl; two $R_8$s attached to the same carbon atom form cyclopropyl; and n is 0 or 2.

In another embodiment, the present invention provides compounds of Formula (IB), or a pharmaceutically acceptable salt or hydrate thereof, wherein $R_1$ is methyl; $R_2$ is methyl, ethyl, or isopropyl; $R_3$ is H; $R_4$ is methyl; $R_5$ is methyl, methyl-ds, ethyl, methoxy, Cl, difluoromethoxy, cyano, or cyclopropyl; $R_6$ is H; B is

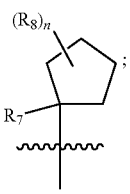

$R_7$ is methyl; $R_8$ is deuterium; and n is 0 or 2.

In another embodiment, the present invention provides compounds of Formula (IB), or a pharmaceutically acceptable salt or hydrate thereof, wherein $R_1$ and $R_2$ taken together with the nitrogen atom to which they are attached form morpholine or 4-methylpiperazine; $R_3$ is H; $R_4$ is methyl; $R_5$ is methyl, ethyl, methoxy, Cl, difluoromethoxy, cyano, or cyclopropyl; $R_6$ is H; B is

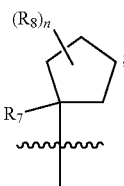

$R_7$ is methyl; and n is 0.

In another embodiment, the present invention provides compounds of Formula (IB), or a pharmaceutically acceptable salt or hydrate thereof, wherein $R_1$ is methyl; $R_2$ is methyl, ethyl, or isopropyl; $R_3$ is H; $R_4$ is methyl; $R_5$ is methyl, ethyl, methoxy, Cl, difluoromethoxy, cyano, or cyclopropyl; $R_6$ is H; B is

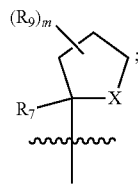

$R_7$ is methyl; $R_9$ is F; m is 2; and X is O.

In another embodiment, the present invention provides compounds of Formula (I), or a pharmaceutically acceptable salt or hydrate thereof, wherein $R_1$ and $R_2$ taken together with the nitrogen atom to which they are attached form morpholine or 4-methylpiperazine; $R_3$ is H; $R_4$ is methyl; $R_5$ is methyl, ethyl, methoxy, Cl, difluoromethoxy, cyano, or cyclopropyl; $R_6$ is H; B is

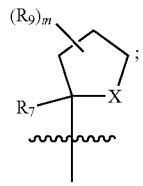

$R_7$ is methyl; $R_9$ is F; m is 2; and X is O.

In another embodiment the compound of Formula (IIA) is (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof.

In another embodiment the compound of Formula (IIA) is (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide.

In another embodiment, the present invention provides a compound of Formula (II), or a pharmaceutically acceptable salt or hydrate thereof, for use as a medicament.

In another embodiment, the present invention provides a compound of Formula (II), or a pharmaceutically acceptable salt or hydrate thereof, for use in treating or preventing diseases, conditions or disorders ameliorated by inhibition of CCR6 in a human.

In another embodiment, the present invention provides a method for treating or preventing diseases, conditions or disorders ameliorated by inhibition of CCR6 in a human comprising administering to the human, in need of such treatment, a therapeutically effective amount of a compound of Formula (IIB), or a pharmaceutically acceptable salt or hydrate thereof.

In another embodiment, the present invention provides a method for treating or preventing diseases, conditions or disorders ameliorated by inhibition of T cell chemotaxis in a human comprising administering to the human, in need of such treatment, a therapeutically effective amount of a compound of Formula (IIB), or a pharmaceutically acceptable salt or hydrate thereof.

In another embodiment, the present invention provides a method for treating or preventing inflammatory diseases, conditions or disorders in a human comprising administering to the human, in need of such treatment, a therapeutically effective amount of a compound of Formula (IIB), or a pharmaceutically acceptable salt or hydrate thereof.

In another embodiment, the present invention provides a method for treating or preventing autoimmune diseases, conditions or disorders in a human comprising administering to the human, in need of such treatment, a therapeutically effective amount of a compound of Formula (IIB), or a pharmaceutically acceptable salt or hydrate thereof.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a compound of Formula (IIB), or a pharmaceutically acceptable salt or hydrate thereof.

In another embodiment, the present invention provides a method for treating or preventing rheumatoid arthritis in a human comprising administering to the human, in need of such treatment, a therapeutically effective amount of a compound of (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof.

In another embodiment, the present invention provides a method for treating or preventing rheumatoid arthritis in a human comprising administering to the human, in need of such treatment, a therapeutically effective amount of a compound of a prodrug of (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide.

In another embodiment, the present invention provides the use of a compound of Formula (IIB), or a pharmaceutically acceptable salt or hydrate thereof, in the manufacture of a medicament for treating diseases, conditions or disorders ameliorated by inhibition of CCR6 in a human.

In another embodiment, the present invention provides the use of a compound of Formula (IIB), or a pharmaceutically acceptable salt or hydrate thereof, in the manufacture of a medicament for treating diseases, conditions or disorders ameliorated by inhibition of T cell chemotaxis in a human.

In another embodiment, the present invention provides the use of a compound of Formula (IIB), or a pharmaceutically acceptable salt or hydrate thereof, in the manufacture of a medicament for treating an inflammatory disease, condition, or disorder in a human.

In another embodiment, the present invention provides the use of a compound of Formula (IIB), or a pharmaceutically acceptable salt or hydrate thereof, in the manufacture of a medicament for treating an autoimmune disease, condition, or disorder in a human.

In another embodiment, the present invention provides the use of a compound of Formula (IIB), or a pharmaceutically acceptable salt or hydrate thereof, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, in the manufacture of a medicament for treating rheumatoid arthritis in a human.

In another embodiment, the present invention provides the use of a prodrug of (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, in the manufacture of a medicament for treating rheumatoid arthritis in a human.

In another embodiment, the present invention provides a pharmaceutical composition comprising a compound of Formula (IIB), or a pharmaceutically acceptable salt or hydrate thereof, and at least one pharmaceutically acceptable excipient, diluent, or carrier.

In another embodiment, the present invention provides a pharmaceutical composition comprising (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier.

In another embodiment, the present invention provides a pharmaceutical composition comprising a prodrug of (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical composition comprising a compound of Formula (II), or a pharmaceutically acceptable salt or hydrate thereof, and at least one pharmaceutically acceptable excipient, diluent, or carrier.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical composition comprising a compound of Formula (IIB), or a pharmaceutically acceptable salt or hydrate thereof, and at least one pharmaceutically acceptable excipient, diluent, or carrier.

In another embodiment, the present invention provides a method for treating or preventing an inflammatory disease, condition, or disorder in a human comprising administering to the human, in need of such treatment, a therapeutically effective amount of a pharmaceutical composition comprising a compound of Formula (IIB), or a pharmaceutically acceptable salt or hydrate thereof, and at least one pharmaceutically acceptable excipient, diluent, or carrier.

In another embodiment, the present invention provides a method for treating or preventing an autoimmune disease, condition, or disorder in a human comprising administering to the human, in need of such treatment, a therapeutically effective amount of a pharmaceutical composition comprising a compound of Formula (IIB), or a pharmaceutically acceptable salt or hydrate thereof, and at least one pharmaceutically acceptable excipient, diluent, or carrier.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical composition comprising a compound of Formula (IIB), or a pharmaceutically acceptable salt or hydrate thereof, and at least one pharmaceutically acceptable excipient, diluent, or carrier.

In another embodiment, the present invention provides a method for treating or preventing rheumatoid arthritis in a human comprising administering to the human, in need of such treatment, a therapeutically effective amount of a pharmaceutical composition comprising (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier.

In another embodiment, the present invention provides a method for treating or preventing rheumatoid arthritis in a human comprising administering to the human, in need of such treatment, a therapeutically effective amount of a pharmaceutical composition comprising a prodrug of (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier.

In another embodiment, the present invention provides the use of a pharmaceutical composition comprising a compound of Formula (IIB), or a pharmaceutically acceptable salt or hydrate thereof, and at least one pharmaceutically acceptable excipient, diluent, or carrier, in the manufacture of a medicament for treating diseases, conditions or disorders ameliorated by inhibition of CCR6 in a human.

In another embodiment, the present invention provides the use of a pharmaceutical composition comprising a compound of Formula (IIB), or a pharmaceutically acceptable salt or hydrate thereof, and at least one pharmaceutically acceptable excipient, diluent, or carrier, in the manufacture of a medicament for treating diseases, conditions or disorders ameliorated by inhibition of T cell chemotaxis in a human.

In another embodiment, the present invention provides the use of a pharmaceutical composition comprising a compound of Formula (IIB), or a pharmaceutically acceptable salt or hydrate thereof, and at least one pharmaceutically acceptable excipient, diluent, or carrier, in the manufacture of a medicament for treating an inflammatory disease, condition, or disorder in a human.

In another embodiment, the present invention provides the use of a pharmaceutical composition comprising a compound of Formula (IIB), or a pharmaceutically acceptable salt or hydrate thereof, and at least one pharmaceutically acceptable excipient, diluent, or carrier, in the manufacture of a medicament for treating an autoimmune disease, condition, or disorder in a human.

In another embodiment, the present invention provides the use of a pharmaceutical composition comprising a compound of Formula (IIB), or a pharmaceutically acceptable salt or hydrate thereof, and at least one pharmaceutically acceptable excipient, diluent, or carrier, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of a pharmaceutical composition comprising (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier, in the manufacture of a medicament for treating rheumatoid arthritis in a human.

In another embodiment, the present invention provides the use of a pharmaceutical composition comprising a prodrug of (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one pharmaceutically acceptable excipient, diluent, or carrier, in the manufacture of a medicament for treating rheumatoid arthritis in a human.

In another embodiment, the present invention provides a pharmaceutical combination comprising a compound of Formula (IIB), or a pharmaceutically acceptable salt or hydrate thereof, and at least one anti-inflammatory agent.

In another embodiment, the present invention provides a pharmaceutical combination comprising (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent.

In another embodiment, the present invention provides a pharmaceutical combination comprising a prodrug of (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical combination comprising a compound of Formula (II), or a pharmaceutically acceptable salt or hydrate thereof, and at least one anti-inflammatory agent.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical combination comprising a compound of Formula (II), or a pharmaceutically acceptable salt or hydrate thereof, and at least one anti-inflammatory agent.

In another embodiment, the present invention provides a method for treating or preventing an inflammatory disease, condition, or disorder in a human comprising administering to the human, in need of such treatment, a therapeutically effective amount of a pharmaceutical combination comprising a compound of Formula (IIB), or a pharmaceutically acceptable salt or hydrate thereof, and at least one anti-inflammatory agent.

In another embodiment, the present invention provides a method for treating or preventing an autoimmune disease, condition, or disorder in a human comprising administering to the human, in need of such treatment, a therapeutically effective amount of a pharmaceutical combination comprising a compound of Formula (IIB), or a pharmaceutically acceptable salt or hydrate thereof, and at least one anti-inflammatory agent.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical combination comprising a compound of Formula (IIB), or a pharmaceutically acceptable salt or hydrate thereof, and at least one anti-inflammatory agent.

In another embodiment, the present invention provides a method for treating or preventing rheumatoid arthritis in a human comprising administering to the human, in need of such treatment, a therapeutically effective amount of a pharmaceutical combination comprising (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent.

In another embodiment, the present invention provides a method for treating or preventing rheumatoid arthritis in a human comprising administering to the human, in need of such treatment, a therapeutically effective amount of a pharmaceutical combination comprising a prodrug of (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent.

In another embodiment, the present invention provides the use of a pharmaceutical combination comprising a compound of Formula (IIB), or a pharmaceutically acceptable salt or hydrate thereof, and at least one anti-inflammatory agent, in the manufacture of a medicament for treating diseases, conditions or disorders ameliorated by inhibition of CCR6 in a human.

In another embodiment, the present invention provides the use of a pharmaceutical combination comprising a compound of Formula (IIB), or a pharmaceutically acceptable salt or hydrate thereof, and at least one anti-inflammatory agent, in the manufacture of a medicament for treating diseases, conditions or disorders ameliorated by inhibition of T cell chemotaxis in a human.

In another embodiment, the present invention provides the use of a pharmaceutical combination comprising a compound of Formula (IIB), or a pharmaceutically acceptable salt or hydrate thereof, and at least one anti-inflammatory agent, in the manufacture of a medicament for treating an inflammatory disease, condition, or disorder in a human.

In another embodiment, the present invention provides the use of a pharmaceutical combination comprising a compound of Formula (IIB), or a pharmaceutically acceptable salt or hydrate thereof, and at least one anti-inflammatory agent, in the manufacture of a medicament for treating an autoimmune disease, condition, or disorder in a human.

In another embodiment, the present invention provides the use of a pharmaceutical combination comprising a compound of Formula (IIB), or a pharmaceutically acceptable salt or hydrate thereof, and at least one anti-inflammatory agent, in the manufacture of a medicament for treating psoriasis, ulcerative colitis, Crohn's disease, inflammatory bowel disease, psoriatic arthritis, or rheumatoid arthritis in a human.

In another embodiment, the present invention provides the use of a pharmaceutical combination comprising (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent, in the manufacture of a medicament for treating rheumatoid arthritis in a human.

In another embodiment, the present invention provides the use of a pharmaceutical combination comprising a prodrug of (S)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, or a pharmaceutically acceptable salt or hydrate thereof, and at least one anti-inflammatory agent, in the manufacture of a medicament for treating rheumatoid arthritis in a human.

In another embodiment, the present invention provides compounds of Formula (IIIA)

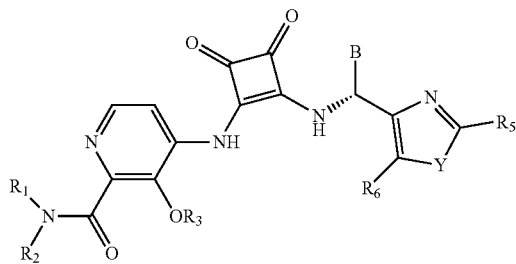

Formula (IIIA)

or a pharmaceutically acceptable salt or hydrate thereof, wherein Y is O or S; $R_1$ and $R_2$ are independently $(C_1-C_5)$ alkyl or $R_1$ and $R_2$ taken together with the nitrogen atom to which they are attached form a 4-, 5-, or 6-membered heterocycle containing one N heteroatom and optionally 1 or 2 additional heteroatoms selected from the group consisting of O, N, and S, optionally substituted with $(C_1-C_4)$alkyl; $R_3$ is H, $(C_1-C_6)$alkyl, $(C_1-C_4)$alkylcarbonyl, —C(=O)CH=CHCO$_2$H, —SO$_2$NH$_2$, —CH$_2$OC(=O)$(C_1-C_4)$alkyl, —CH$_2$OP(=O)(OH)$_2$, or —C(=O)NR$_A$R$_B$, wherein the $(C_1-C_4)$alkylcarbonyl is optionally substituted with —CO$_2$H or —NH$_2$, wherein the —CH$_2$OC(=O)$(C_1-C_4)$alkyl is optionally substituted with —NH$_2$, and wherein $R_A$ and $R_B$ are independently H or $(C_1-C_6)$alkyl; $R_5$ and $R_6$ are independently H, deuterium, $(C_1-C_4)$alkoxy, $(C_1-C_4)$alkyl, $(C_1-C_4)$alkyl-$d_{1-9}$, $(C_3-C_4)$cycloalkyl, cyano, halogen, halo$(C_1-C_4)$alkoxy, or halo$(C_1-C_4)$alkyl; B is

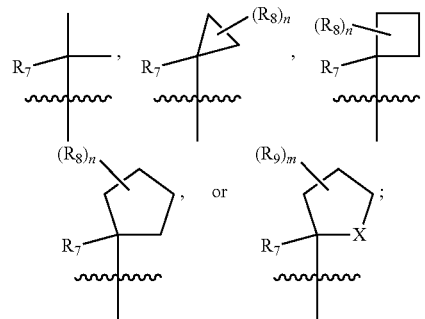

$R_7$ is $(C_1-C_3)$alkyl or $(C_1-C_3)$alkyl-$d_{1-7}$; $R_8$ is deuterium or two $R_8$s attached to the same carbon atom form a $(C_3-C_5)$ cycloalkyl group; n is 0 or 2; $R_9$ at each occurrence is F; m is 2; and X is O.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ and $R_6$ are independently methyl, ethyl, methoxy, Cl, difluoromethoxy, cyano, cyclopropyl, or hydroxymethyl; B is

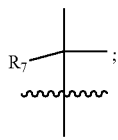

$R_7$ is methyl.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ is methyl, ethyl, methoxy, Cl, difluoromethoxy, cyano, cyclopropyl, or hydroxymethyl; $R_6$ is methyl or methoxy; B is

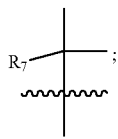

$R_7$ is methyl.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ is methyl or hydroxymethyl; $R_6$ is methyl or methoxy; B is

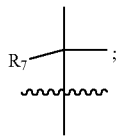

$R_7$ is methyl.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ and $R_6$ are independently methyl, ethyl, methoxy, Cl, difluoromethoxy, cyano, cyclopropyl, or hydroxymethyl; B is

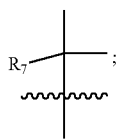

$R_7$ is methyl.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl, ethyl, methoxy, Cl, difluoromethoxy, cyano, cyclopropyl, or hydroxymethyl; $R_6$ is methyl or methoxy; B is

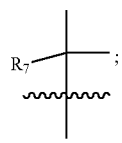

$R_7$ is methyl.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl or hydroxymethyl; $R_6$ is methyl or methoxy; B is

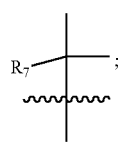

$R_7$ is methyl.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ and $R_6$ are independently methyl, ethyl, methoxy, Cl, difluoromethoxy, cyano, cyclopropyl, or hydroxymethyl; B is

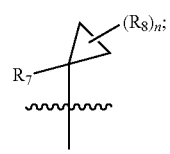

$R_7$ is methyl; and n is 0.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ is methyl, ethyl, methoxy, Cl, difluoromethoxy, cyano, cyclopropyl, or hydroxymethyl; $R_6$ is methyl or methoxy; B is

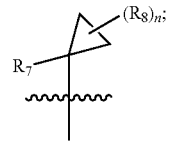

$R_7$ is methyl; and n is 0.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ is methyl or hydroxymethyl; $R_6$ is methyl or methoxy; B is

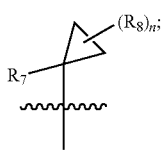

$R_7$ is methyl; and n is 0.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ and $R_6$ are independently methyl, ethyl, methoxy, Cl, difluoromethoxy, cyano, cyclopropyl, or hydroxymethyl; B is

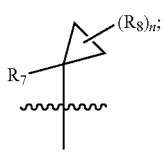

$R_7$ is methyl; and n is 0.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl, ethyl, methoxy, Cl, difluoromethoxy, cyano, cyclopropyl, or hydroxymethyl; $R_6$ is methyl or methoxy; B is

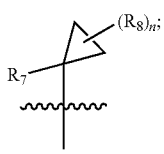

$R_7$ is methyl; and n is 0.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl or hydroxymethyl; $R_6$ is methyl or methoxy; B is

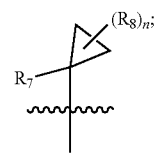

$R_7$ is methyl; and n is 0.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ and $R_6$ are independently methyl, ethyl, methoxy, Cl, difluoromethoxy, cyano, cyclopropyl, or hydroxymethyl; B is

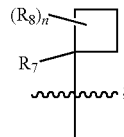

$R_7$ is methyl; two $R_8$s attached to the same carbon atom form cyclopropyl; and n is 0 or 2.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ is methyl, ethyl, methoxy, Cl, difluoromethoxy, cyano, cyclopropyl, or hydroxymethyl; $R_6$ is methyl or methoxy; B is

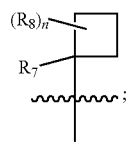

$R_7$ is methyl; two $R_8$s attached to the same carbon atom form cyclopropyl; and n is 0 or 2.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ is methyl or hydroxymethyl; $R_6$ is methyl or methoxy; B is

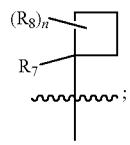

$R_7$ is methyl; two $R_8$s attached to the same carbon atom form cyclopropyl; and n is 0 or 2.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ and $R_6$ are independently methyl, ethyl, methoxy, Cl, difluoromethoxy, cyano, cyclopropyl, or hydroxymethyl; B is

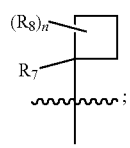

$R_7$ is methyl; two $R_8$s attached to the same carbon atom form cyclopropyl; and n is 0 or 2.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl, ethyl, methoxy, Cl, difluoromethoxy, cyano, cyclopropyl, or hydroxymethyl; $R_6$ is methyl or methoxy; B is

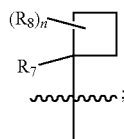

$R_7$ is methyl; two $R_8$s attached to the same carbon atom form cyclopropyl; and n is 0 or 2.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl or hydroxymethyl; $R_6$ is methyl or methoxy; B is

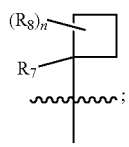

$R_7$ is methyl; two $R_8$s attached to the same carbon atom form cyclopropyl; and n is 0 or 2.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ and $R_6$ are independently methyl, ethyl, methoxy, Cl, difluoromethoxy, cyano, cyclopropyl, or hydroxymethyl; B is

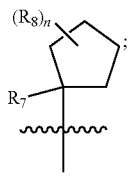

$R_7$ is methyl; and n is 0.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ is methyl, ethyl, methoxy, Cl, difluoromethoxy, cyano, cyclopropyl, or hydroxymethyl; $R_6$ is methyl or methoxy; B is

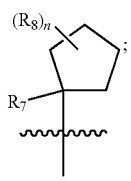

$R_7$ is methyl; and n is 0.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ is methyl or hydroxymethyl; $R_6$ is methyl or methoxy; B is

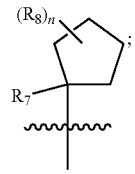

$R_7$ is methyl; and n is 0.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ and $R_6$ are independently methyl, ethyl, methoxy, Cl, difluoromethoxy, cyano, cyclopropyl, or hydroxymethyl; B is

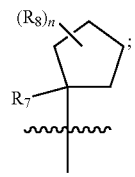

$R_7$ is methyl; and n is 0.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl, ethyl, methoxy, Cl, difluoromethoxy, cyano, cyclopropyl, or hydroxymethyl; $R_6$ is methyl or methoxy; B is

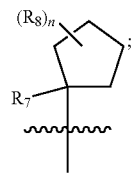

$R_7$ is methyl; and n is 0.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl or hydroxymethyl; $R_6$ is methyl or methoxy; B is

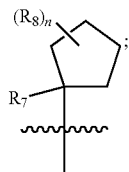

$R_7$ is methyl; and n is 0.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ and $R_6$ are independently methyl, ethyl, methoxy, Cl, difluoromethoxy, cyano, cyclopropyl, or hydroxymethyl; B is

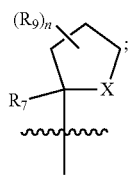

$R_7$ is methyl; $R_9$ is F; m is 2; and X is O.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ is methyl, ethyl, methoxy, Cl, difluoromethoxy, cyano, cyclopropyl, or hydroxymethyl; $R_6$ is methyl or methoxy; B is

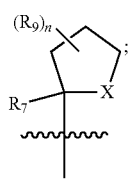

$R_7$ is methyl; $R_9$ is F; m is 2; and X is O.

In another embodiment, the present invention provides compounds of Formula (IIIA), or a pharmaceutically acceptable salt or hydrate thereof, wherein Y is O or S; $R_1$ is methyl; $R_2$ is methyl, ethyl, or isopropyl; $R_3$ is H; $R_5$ is methyl or hydroxymethyl; $R_6$ is methyl or methoxy; B is

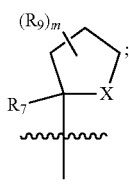

$R_7$ is methyl; $R_9$ is F; m is 2; and X is O.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ and $R_6$ are independently methyl, ethyl, methoxy, Cl, difluoromethoxy, cyano, cyclopropyl, or hydroxymethyl; B is

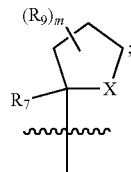

$R_7$ is methyl; $R_9$ is F; m is 2; and X is O.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl, ethyl, methoxy, Cl, difluoromethoxy, cyano, cyclopropyl, or hydroxymethyl; $R_6$ is methyl or methoxy; B is

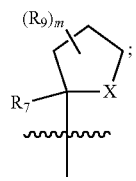

$R_7$ is methyl; $R_9$ is F; m is 2; and X is O.

In another embodiment, the present invention provides compounds of Formula (IIIA), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl or hydroxymethyl; $R_6$ is methyl or methoxy; B is

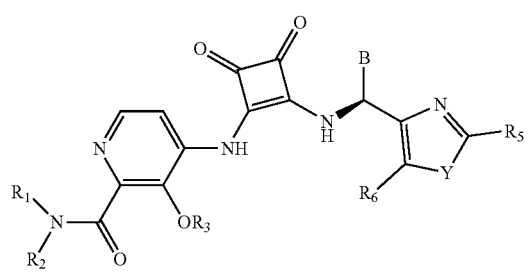

$R_7$ is methyl; $R_9$ is F; m is 2; and X is O.

In another embodiment, the present invention provides compounds of Formula (IIIB)

Formula (IIIB)

or a pharmaceutically acceptable salt or hydrate thereof, wherein Y is O or S; $R_1$ and $R_2$ are independently $(C_1$-$C_5)$ alkyl or $R_1$ and $R_2$ taken together with the nitrogen atom to which they are attached form a 4-, 5-, or 6-membered heterocycle containing one N heteroatom and optionally 1 or 2 additional heteroatoms selected from the group consisting of O, N, and S, optionally substituted with $(C_1-C_4)$alkyl; $R_3$ is H, $(C_1-C_6)$alkyl, $(C_1-C_4)$alkylcarbonyl, $—C(=O)$ $CH=CHCO_2H$, $—SO_2NH_2$, $—CH_2OC(=O)(C_1-C_4)$alkyl, $—CH_2OP(=O)(OH)_2$, or $—C(=O)NR_AR_B$, wherein the $(C_1-C_4)$alkylcarbonyl is optionally substituted with $—CO_2H$ or $—NH_2$, wherein the $—CH_2OC(=O)(C_1-C_4)$alkyl is optionally substituted with $—NH_2$, and wherein $R_A$ and $R_B$ are independently H or $(C_1-C_6)$alkyl; $R_5$ and $R_6$ are independently H, deuterium, $(C_1-C_4)$alkoxy, $(C_1-C_4)$alkyl, $(C_1-C_4)$alkyl-$d_{1-9}$, $(C_3-C_4)$cycloalkyl, cyano, halogen, halo$(C_1-C_4)$alkoxy, or halo$(C_1-C_4)$alkyl; B is

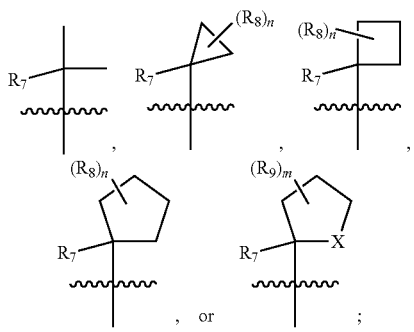

$R_7$ is $(C_1-C_3)$alkyl or $(C_1-C_3)$alkyl-$d_{1-7}$; $R_8$ is deuterium or two $R_8$s attached to the same carbon atom form a $(C_3-C_5)$ cycloalkyl group; n is 0 or 2; $R_9$ at each occurrence is F; m is 2; and X is O.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ and $R_6$ are independently methyl, ethyl, methoxy, Cl, difluoromethoxy, cyano, cyclopropyl, or hydroxymethyl; B is

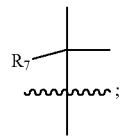

$R_7$ is methyl.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ is methyl, ethyl, methoxy, Cl, difluoromethoxy, cyano, cyclopropyl, or hydroxymethyl; $R_6$ is methyl or methoxy; B is

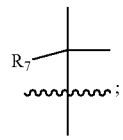

$R_7$ is methyl.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ is methyl or hydroxymethyl; $R_6$ is methyl or methoxy; B is

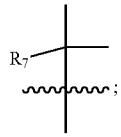

$R_7$ is methyl.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ and $R_6$ are independently methyl, ethyl, methoxy, Cl, difluoromethoxy, cyano, cyclopropyl, or hydroxymethyl; B is

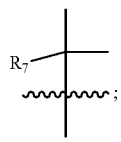

$R_7$ is methyl.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl, ethyl, methoxy, Cl, difluoromethoxy, cyano, cyclopropyl, or hydroxymethyl; $R_6$ is methyl or methoxy; B is

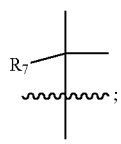

$R_7$ is methyl.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl or hydroxymethyl; $R_6$ is methyl or methoxy; B is

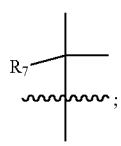

$R_7$ is methyl.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ and $R_6$ are independently methyl, ethyl, methoxy, Cl, difluoromethoxy, cyano, cyclopropyl, or hydroxymethyl; B is

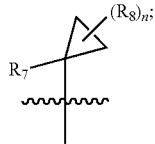

$R_7$ is methyl; and n is 0.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ is methyl, ethyl, methoxy, Cl, difluoromethoxy, cyano, cyclopropyl, or hydroxymethyl; $R_6$ is methyl or methoxy; B is

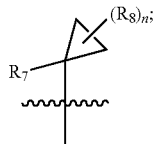

$R_7$ is methyl; and n is 0.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ is methyl or hydroxymethyl; $R_6$ is methyl or methoxy; B is

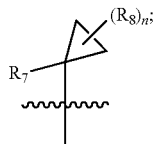

$R_7$ is methyl; and n is 0.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ and $R_6$ are independently methyl, ethyl, methoxy, Cl, difluoromethoxy, cyano, cyclopropyl, or hydroxymethyl; B is

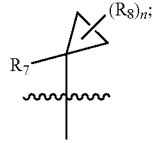

$R_7$ is methyl; and n is 0.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H;

$R_5$ is methyl, ethyl, methoxy, Cl, difluoromethoxy, cyano, cyclopropyl, or hydroxymethyl; $R_6$ is methyl or methoxy; B is

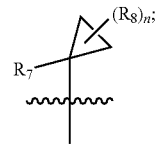

$R_7$ is methyl; and n is 0.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl or hydroxymethyl; $R_6$ is methyl or methoxy; B is

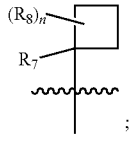

$R_7$ is methyl; and n is 0.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ and $R_6$ are independently methyl, ethyl, methoxy, Cl, difluoromethoxy, cyano, cyclopropyl, or hydroxymethyl; B is

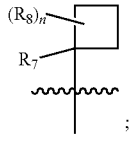

$R_7$ is methyl; two $R_8$s attached to the same carbon atom form cyclopropyl; and n is 0 or 2.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ is methyl, ethyl, methoxy, Cl, difluoromethoxy, cyano, cyclopropyl, or hydroxymethyl; $R_6$ is methyl or methoxy; B is

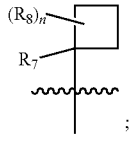

$R_7$ is methyl; two $R_8$s attached to the same carbon atom form cyclopropyl; and n is 0 or 2.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ is methyl or hydroxymethyl; $R_6$ is methyl or methoxy; B is

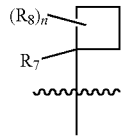
;

$R_7$ is methyl; two $R_8$s attached to the same carbon atom form cyclopropyl; and n is 0 or 2.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ and $R_6$ are independently methyl, ethyl, methoxy, Cl, difluoromethoxy, cyano, cyclopropyl, or hydroxymethyl; B is

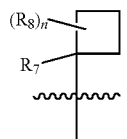
;

$R_7$ is methyl; two $R_8$s attached to the same carbon atom form cyclopropyl; and n is 0 or 2.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl, ethyl, methoxy, Cl, difluoromethoxy, cyano, cyclopropyl, or hydroxymethyl; $R_6$ is methyl or methoxy; B is

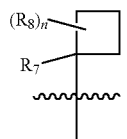
;

$R_7$ is methyl; two $R_8$s attached to the same carbon atom form cyclopropyl; and n is 0 or 2.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl or hydroxymethyl; $R_6$ is methyl or methoxy; B is

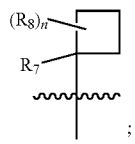
;

$R_7$ is methyl; two $R_8$s attached to the same carbon atom form cyclopropyl; and n is 0 or 2.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ and $R_6$ are independently methyl, ethyl, methoxy, Cl, difluoromethoxy, cyano, cyclopropyl, or hydroxymethyl; B is

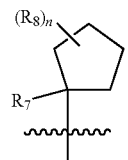
;

$R_7$ is methyl; and n is 0.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ is methyl, ethyl, methoxy, Cl, difluoromethoxy, cyano, cyclopropyl, or hydroxymethyl; $R_6$ is methyl or methoxy; B is

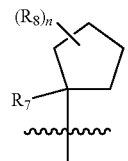
;

$R_7$ is methyl; and n is 0.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ is methyl or hydroxymethyl; $R_6$ is methyl or methoxy; B is

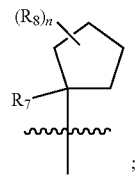
;

$R_7$ is methyl; and n is 0.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ and $R_6$ are independently methyl, ethyl, methoxy, Cl, difluoromethoxy, cyano, cyclopropyl, or hydroxymethyl; B is

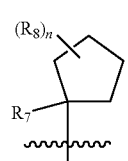
;

$R_7$ is methyl; and n is 0.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl, ethyl, methoxy, Cl, difluoromethoxy, cyano, cyclopropyl, or hydroxymethyl; $R_6$ is methyl or methoxy; B is

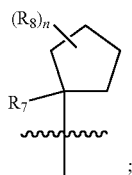

;

$R_7$ is methyl; and n is 0.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl or hydroxymethyl; $R_6$ is methyl or methoxy; B is

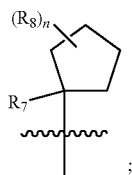

;

$R_7$ is methyl; and n is 0.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ and $R_6$ are independently methyl, ethyl, methoxy, Cl, difluoromethoxy, cyano, cyclopropyl, or hydroxymethyl; B is

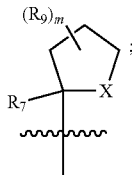

;

$R_7$ is methyl; $R_9$ is F; m is 2; and X is O.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ is methyl, ethyl, methoxy, Cl, difluoromethoxy, cyano, cyclopropyl, or hydroxymethyl; $R_6$ is methyl or methoxy; B is

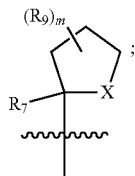

;

$R_7$ is methyl; $R_9$ is F; m is 2; and X is O.

In another embodiment, the present invention provides compounds of Formula (IIIB), or a pharmaceutically acceptable salt or hydrate thereof, wherein Y is O or S; $R_1$ is methyl; $R_2$ is methyl, ethyl, or isopropyl; $R_3$ is H; $R_5$ is methyl or hydroxymethyl; $R_6$ is methyl or methoxy; B is

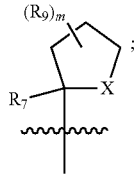

;

$R_7$ is methyl; $R_9$ is F; m is 2; and X is O.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ and $R_6$ are independently methyl, ethyl, methoxy, Cl, difluoromethoxy, cyano, cyclopropyl, or hydroxymethyl; B is

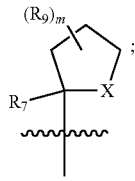

;

$R_7$ is methyl; $R_9$ is F; m is 2; and X is O.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl, ethyl, methoxy, Cl, difluoromethoxy, cyano, cyclopropyl, or hydroxymethyl; $R_6$ is methyl or methoxy; B is

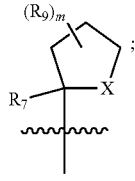

;

$R_7$ is methyl; $R_9$ is F; m is 2; and X is O.

In another embodiment, the present invention provides compounds of Formula (IIIB), or a pharmaceutically acceptable salt or hydrate thereof, wherein Y is O or S; $R_1$ and $R_2$ taken together with the nitrogen atom to which they are attached form morpholine or 4-methylpiperazine; $R_3$ is H; $R_5$ is methyl or hydroxymethyl; $R_6$ is methyl or methoxy; B is

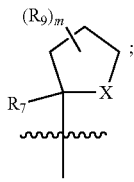

$R_7$ is methyl; $R_9$ is F; m is 2; and X is O.

In another embodiment, the present invention provides a compound of Formula (IIIA) or (IIIB), or a pharmaceutically acceptable salt or hydrate thereof, for use as a medicament.

In another embodiment, the present invention provides a compound of Formula (IIIA) or (IIIB), or a pharmaceutically acceptable salt or hydrate thereof, for use in treating or preventing diseases, conditions or disorders ameliorated by inhibition of CCR6 in a human.

In another embodiment, the present invention provides a method for treating or preventing diseases, conditions or disorders ameliorated by inhibition of CCR6 in a human comprising administering to the human, in need of such treatment, a therapeutically effective amount of a compound of Formula (IIIA) or (IIIB), or a pharmaceutically acceptable salt or hydrate thereof.

In another embodiment, the present invention provides a method for treating or preventing diseases, conditions or disorders ameliorated by inhibition of T cell chemotaxis in a human comprising administering to the human, in need of such treatment, a therapeutically effective amount of a compound of Formula (IIIA) or (IIIB), or a pharmaceutically acceptable salt or hydrate thereof.

In another embodiment, the present invention provides a method for treating or preventing inflammatory diseases, conditions or disorders in a human comprising administering to the human, in need of such treatment, a therapeutically effective amount of a compound of Formula (IIA) or (IIIB), or a pharmaceutically acceptable salt or hydrate thereof.

In another embodiment, the present invention provides a method for treating or preventing autoimmune diseases, conditions or disorders in a human comprising administering to the human, in need of such treatment, a therapeutically effective amount of a compound of Formula (IIA) or (IIIB), or a pharmaceutically acceptable salt or hydrate thereof.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a compound of Formula (IIIA) or (IIIB), or a pharmaceutically acceptable salt or hydrate thereof.

In another embodiment, the present invention provides the use of a compound of Formula (IIA) or (IIIB), or a pharmaceutically acceptable salt or hydrate thereof, in the manufacture of a medicament for treating diseases, conditions or disorders ameliorated by inhibition of CCR6 in a human.

In another embodiment, the present invention provides the use of a compound of Formula (IIA) or (IIIB), or a pharmaceutically acceptable salt or hydrate thereof, in the manufacture of a medicament for treating diseases, conditions or disorders ameliorated by inhibition of T cell chemotaxis in a human.

In another embodiment, the present invention provides the use of a compound of Formula (IIA) or (IIIB), or a pharmaceutically acceptable salt or hydrate thereof, in the manufacture of a medicament for treating an inflammatory disease, condition, or disorder in a human.

In another embodiment, the present invention provides the use of a compound of Formula (IIA) or (IIIB), or a pharmaceutically acceptable salt or hydrate thereof, in the manufacture of a medicament for treating an autoimmune disease, condition, or disorder in a human.

In another embodiment, the present invention provides the use of a compound of Formula (IIA) or (IIIB), or a pharmaceutically acceptable salt or hydrate thereof, in the manufacture of a medicament for treating psoriasis, ulcerative colitis, Crohn's disease, inflammatory bowel disease, psoriatic arthritis, or rheumatoid arthritis in a human.

In another embodiment, the present invention provides a pharmaceutical composition comprising a compound of Formula (IIA) or (IIIB), or a pharmaceutically acceptable salt or hydrate thereof, and at least one pharmaceutically acceptable excipient, diluent, or carrier.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical composition comprising a compound of Formula (IIIA) or (IIIB), or a pharmaceutically acceptable salt or hydrate thereof, and at least one pharmaceutically acceptable excipient, diluent, or carrier.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical composition comprising a compound of Formula (IIIA) or (IIIB), or a pharmaceutically acceptable salt or hydrate thereof, and at least one pharmaceutically acceptable excipient, diluent, or carrier.

In another embodiment, the present invention provides a method for treating or preventing an inflammatory disease, condition, or disorder in a human comprising administering to the human, in need of such treatment, a therapeutically effective amount of a pharmaceutical composition comprising a compound of Formula (IIIA) or (IIIB), or a pharmaceutically acceptable salt or hydrate thereof, and at least one pharmaceutically acceptable excipient, diluent, or carrier.

In another embodiment, the present invention provides a method for treating or preventing an autoimmune disease, condition, or disorder in a human comprising administering to the human, in need of such treatment, a therapeutically effective amount of a pharmaceutical composition comprising a compound of Formula (IIIA) or (IIIB), or a pharmaceutically acceptable salt or hydrate thereof, and at least one pharmaceutically acceptable excipient, diluent, or carrier.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical composition comprising a compound of Formula (IIIA) or (IIIB), or a pharmaceutically acceptable salt or hydrate thereof, and at least one pharmaceutically acceptable excipient, diluent, or carrier.

In another embodiment, the present invention provides the use of a pharmaceutical composition comprising a compound of Formula (IIIA) or (IIIB), or a pharmaceutically acceptable salt or hydrate thereof, and at least one pharmaceutically acceptable excipient, diluent, or carrier, in the manufacture of a medicament for treating diseases, conditions or disorders ameliorated by inhibition of CCR6 in a human.

In another embodiment, the present invention provides the use of a pharmaceutical composition comprising a compound of Formula (IIIA) or (IIIB), or a pharmaceutically acceptable salt or hydrate thereof, and at least one pharmaceutically acceptable excipient, diluent, or carrier, in the manufacture of a medicament for treating diseases, conditions or disorders ameliorated by inhibition of T cell chemotaxis in a human.

In another embodiment, the present invention provides the use of a pharmaceutical composition comprising a compound of Formula (IIIA) or (IIIB), or a pharmaceutically acceptable salt or hydrate thereof, and at least one pharmaceutically acceptable excipient, diluent, or carrier, in the manufacture of a medicament for treating an inflammatory disease, condition, or disorder in a human.

In another embodiment, the present invention provides the use of a pharmaceutical composition comprising a compound of Formula (IIIA) or (IIIB), or a pharmaceutically acceptable salt or hydrate thereof, and at least one pharmaceutically acceptable excipient, diluent, or carrier, in the manufacture of a medicament for treating an autoimmune disease, condition, or disorder in a human.

In another embodiment, the present invention provides the use of a pharmaceutical composition comprising a compound of Formula (IIIA) or (IIIB), or a pharmaceutically acceptable salt or hydrate thereof, and at least one pharmaceutically acceptable excipient, diluent, or carrier, in the manufacture of a medicament for treating psoriasis, ulcerative colitis, Crohn's disease, inflammatory bowel disease, psoriatic arthritis, or rheumatoid arthritis in a human.

In another embodiment, the present invention provides a pharmaceutical combination comprising a compound of Formula (IIIA) or (IIIB), or a pharmaceutically acceptable salt or hydrate thereof, and at least one anti-inflammatory agent.

In another embodiment, the present invention provides a method for treating or preventing diseases, conditions or disorders ameliorated by inhibition of CCR6 in a human comprising administering to the human, in need of such treatment, a therapeutically effective amount of a pharmaceutical combination comprising a compound of Formula (IIIA) or (IIIB), or a pharmaceutically acceptable salt or hydrate thereof, and at least one anti-inflammatory agent.

In another embodiment, the present invention provides a method for treating or preventing diseases, conditions or disorders ameliorated by inhibition of T cell chemotaxis in a human comprising administering to the human, in need of such treatment, a therapeutically effective amount of a pharmaceutical combination comprising a compound of Formula (IIIA) or (IIIB), or a pharmaceutically acceptable salt or hydrate thereof, and at least one anti-inflammatory agent.

In another embodiment, the present invention provides a method for treating or preventing an inflammatory disease, condition, or disorder in a human comprising administering to the human, in need of such treatment, a therapeutically effective amount of a pharmaceutical combination comprising a compound of Formula (IIIA) or (IIIB), or a pharmaceutically acceptable salt or hydrate thereof, and at least one anti-inflammatory agent.

In another embodiment, the present invention provides a method for treating or preventing an autoimmune disease, condition, or disorder in a human comprising administering to the human, in need of such treatment, a therapeutically effective amount of a pharmaceutical combination comprising a compound of Formula (IIIA) or (IIIB), or a pharmaceutically acceptable salt or hydrate thereof, and at least one anti-inflammatory agent.

In another embodiment, the present invention provides a method for treating or preventing psoriasis, ulcerative colitis, Crohn's disease, inflammatory bowel disease, psoriatic arthritis, or rheumatoid arthritis in a human comprising administering to the human, in need of such treatment, a therapeutically effective amount of a pharmaceutical combination comprising a compound of Formula (IIIA) or (IIIB), or a pharmaceutically acceptable salt or hydrate thereof, and at least one anti-inflammatory agent.

In another embodiment, the present invention provides the use of a pharmaceutical combination comprising a compound of Formula (IIIA) or (IIIB), or a pharmaceutically acceptable salt or hydrate thereof, and at least one anti-inflammatory agent, in the manufacture of a medicament for treating diseases, conditions or disorders ameliorated by inhibition of CCR6 in a human.

In another embodiment, the present invention provides the use of a pharmaceutical combination comprising a compound of Formula (IIIA) or (IIIB), or a pharmaceutically acceptable salt or hydrate thereof, and at least one anti-inflammatory agent, in the manufacture of a medicament for treating diseases, conditions or disorders ameliorated by inhibition of T cell chemotaxis in a human.

In another embodiment, the present invention provides the use of a pharmaceutical combination comprising a compound of Formula (IIIA) or (IIIB), or a pharmaceutically acceptable salt or hydrate thereof, and at least one anti-inflammatory agent, in the manufacture of a medicament for treating an inflammatory disease, condition, or disorder in a human.

In another embodiment, the present invention provides the use of a pharmaceutical combination comprising a compound of Formula (IIIA) or (IIIB), or a pharmaceutically acceptable salt or hydrate thereof, and at least one anti-inflammatory agent, in the manufacture of a medicament for treating an autoimmune disease, condition, or disorder in a human.

In another embodiment, the present invention provides the use of a pharmaceutical combination comprising a compound of Formula (IIIA) or (IIIB), or a pharmaceutically acceptable salt or hydrate thereof, and at least one anti-inflammatory agent, in the manufacture of a medicament for treating psoriasis, ulcerative colitis, Crohn's disease, inflammatory bowel disease, psoriatic arthritis, or rheumatoid arthritis in a human.

In another embodiment, the present invention provides a method for treating or preventing an immune disorder in a human comprising administering to the human, in need of such treatment, a therapeutically effective amount of a compound of Formula (IA), (IB), (IIA), (IIB), (IIIA), or (IIIB), or a pharmaceutically acceptable salt or hydrate thereof.

In another embodiment, the present invention provides a method for treating or preventing an autoimmune disorder in a human comprising administering to the human, in need of such treatment, a therapeutically effective amount of a compound of Formula (IA), (IB), (IIA), (IB), (IIA), or (IIIB), or a pharmaceutically acceptable salt or hydrate thereof.

In another embodiment, the present invention provides a method for treating or preventing a neurodegenerative or neuroinflammatory disorder in a human comprising administering to the human, in need of such treatment, a therapeutically effective amount of a compound of Formula (IA), (IB), (IIA), (IIB), (IIA), or (IIIB), or a pharmaceutically acceptable salt or hydrate thereof.

In another embodiment, the present invention provides a method for treating or preventing rheumatoid arthritis, juvenile arthritis, Still's disease, juvenile rheumatoid arthritis, systemic onset rheumatoid arthritis, pauciarticular rheumatoid arthritis, pauciarticular juvenile rheumatoid arthritis, polyarticular rheumatoid arthritis, enteropathic arthritis, juvenile Reiter's Syndrome, ankylosing spondylitis, juvenile ankylosing spondylitis, SEA Syndrome, reactive arthritis (reactive arthropathy), psoriatic arthropathy, juvenile enteropathic arthritis, polymyalgia rheumatica, enteropathic spondylitis, juvenile idiopathic arthritis (JIA), juvenile psoriatic arthritis, juvenile rheumatoid arthritis, systemic onset juvenile rheumatoid arthritis, giant cell arteritis, or secondary osteoarthritis from inflammatory diseases in a human comprising administering to the human, in need of such treatment, a therapeutically effective amount of a compound of Formula (IA), (IB), (IIA), (IIB), (IIA), or (IIIB), or a pharmaceutically acceptable salt or hydrate thereof.

In another embodiment, the present invention provides a method for treating or preventing lupus, systemic lupus erythematosus, juvenile systemic lupus erythematosus, lupus nephritis, Sjögren's syndrome, scleroderma (systemic sclerosis), Raynaud's phenomenonjuvenile scleroderma, polymyositis, dermatomyositis, polymyositis-dermatomyositis, mixed connective tissue disease, sarcoidosis, fibromyalgia, vasculitis microscopic polyangiitis, vasculitis, eosinophilic granulomatosis with polyangiitis (formerly known as Churg-Strauss syndrome), granulomatosis with polyangiitis (formerly known as Wegener's granulomatosis), polyarteritis nodosa, Henoch-Schönlein purpura, idiopathic thrombocytopenic thrombotic purpura, juvenile vasculitis, polyarteritis nodossa (also known as panarteritis nodosa, periarteritis nodosa, Kussmaul disease, Kussmaul-Maier disease or PAN), serum sickness, Myasthenia gravis, Takayasu's arteritis, Behçet's syndrome, Kawasaki's disease (mucocutaneous lymph node syndrome), Buerger's disease (thromboangiitis obliterans), Vogt-Koyanagi-Harada syndrome, Addison's disease, Hashimoto's thyroiditis, sclerosing cholangitis, membranous glomerulopathy, polymyositis, myositis, atherosclerosis, autoimmune hemolytic anemia, autoimmune orchitis, or Goodpasture's disease in a human comprising administering to the human, in need of such treatment, a therapeutically effective amount of a compound of Formula (IA), (IB), (IIA), (IIB), (IIIA), or (IIIB), or a pharmaceutically acceptable salt or hydrate thereof.

In another embodiment, the present invention provides a method for treating or preventing is inflammatory bowel diseases, Crohn's disease, ulcerative colitis, celiac sprue, celiac diseases, proctitis, eosinophilic gastroenteritis, autoimmune atrophic gastritis of pernicious anemia, or mastocytosis in a human comprising administering to the human, in need of such treatment, a therapeutically effective amount of a compound of Formula (IA), (IB), (IIA), (IIB), (IIA), or (IIIB), or a pharmaceutically acceptable salt or hydrate thereof.

In another embodiment, the present invention provides a method for treating or preventing psoriasis, atopic dermatitis, eczema dermatitis, dermatitis, pruritus, alopecia, autoimmune alopecia, vitiligo, epidermal hyperplasia, juvenile dermatomyositis, or dermatomyositis. In certain other embodiments, the psoriasis is plaque psoriasis, Guttate psoriasis, psoriatic epidermal hyperplasia, inverse psoriasis, pustular psoriasis, erythrodermic psoriasis in a human comprising administering to the human, in need of such treatment, a therapeutically effective amount of a compound of Formula (IA), (IB), (IIA), (IIB), (IIIA), or (IIIB), or a pharmaceutically acceptable salt or hydrate thereof.

In another embodiment, the present invention provides a method for treating or preventing non-alcoholic steatohepatitis, non-alcoholic fatty liver disease, autoimmune hepatitis, chronic aggressive hepatitis, or primary biliary sclerosis in a human comprising administering to the human, in need of such treatment, a therapeutically effective amount of a compound of Formula (IA), (IB), (IIA), (IIB), (IIA), or (IIIB), or a pharmaceutically acceptable salt or hydrate thereof.

In another embodiment, the present invention provides a method for treating or preventing multiple sclerosis, amyotropic lateral sclerosis, Guillain-Barre disease, autoimmune encephalomyelitis, Alzheimer's disease, major depressive disorder, traumatic brain injury, epilepsy, Parkinson's disease, or bipolar disorder in a human comprising administering to the human, in need of such treatment, a therapeutically effective amount of a compound of Formula (IA), (IB), (IIA), (IIB), (IIA), or (IIIB), or a pharmaceutically acceptable salt or hydrate thereof.

In another embodiment, the present invention provides a method for treating or preventing Graves' disease, noninfectious uveitis, dry eye syndrome, sympathetic ophthalmia, Cogan's syndrome, keratoconjunctivitis, vernal conjunctivitis, uveitis including uveitis associated with Behçet's disease and lens-induced uveitis, keratitis, herpetic keratitis, conical keratitis, corneal epithelial dystrophy, keratoleukoma, ocular premphigus, Mooren's ulcer, scleritis, keratoconjunctivitis sicca (dry eye), phlyctenule, iridocyclitis, sarcoidosis, endocrine ophthalmopathy, sympathetic ophthalmitis, allergic conjunctivitis, ocular neovascularization, or proliferative diabetic retinopathy in a human comprising administering to the human, in need of such treatment, a therapeutically effective amount of a compound of Formula (IA), (IB), (IIA), (IIB), (IIA), or (IIIB), or a pharmaceutically acceptable salt or hydrate thereof.

In another embodiment, the present invention provides a method for treating or preventing asthma, allergy, chronic obstructive pulmonary disease, or acute respiratory disease in a human comprising administering to the human, in need of such treatment, a therapeutically effective amount of a compound of Formula (IA), (IB), (IIA), (IIB), (IIIA), or (IIIB), or a pharmaceutically acceptable salt or hydrate thereof.

In another embodiment, the present invention provides a method for treating or preventing alimentary/gastrointestinal tract cancer, colon cancer, liver cancer, skin cancer including mast cell tumor and squamous cell carcinoma, breast and mammary cancer, ovarian cancer, prostate cancer, leukemia, diffuse large B cell lymphoma, cutaneous T-cell lymphoma, non-Hodgkin lymphoma, kidney cancer, lung cancer, muscle cancer, bone cancer, bladder cancer, brain cancer, melanoma including oral and metastatic melanoma, Kaposi's sarcoma, multiple myeloma, myeloproliferative disorders, glioblastoma, oligodendroglioma, pancreatic cancer, brain tumors, or gliomas including astrocytoma. In certain other embodiments, the leukemia is acute myeloid leukemia, T cell acute lymphoblastic leukemia, or adult T cell leukemia in a human comprising administering to the human, in need of such treatment, a therapeutically effective amount of a compound of Formula (IA), (IB), (IIA), (IIB), (IIIA), or (IIIB), or a pharmaceutically acceptable salt or hydrate thereof.

In another embodiment, the present invention provides a method for treating or preventing Type I diabetes mellitus, Type II diabetes mellitus, or Juvenile onset diabetes in a human comprising administering to the human, in need of such treatment, a therapeutically effective amount of a compound of Formula (IA), (IB), (IIA), (IIB), (IIIA), or (IIIB), or a pharmaceutically acceptable salt or hydrate thereof.

Definitions

As used throughout this specification and the appended claims, the following terms have the following meanings.

The term "$(C_2-C_4)$alkenyl" as used herein, means a straight or branched chain hydrocarbon containing from 2 to 4 carbons and containing one carbon-carbon double bond. Representative examples of $(C_2-C_4)$alkenyl include, but are not limited to, ethenyl, 2-propenyl, 2-methyl-2-propenyl, and 3-butenyl.

The term "$(C_1-C_4)$alkoxy" as used herein, means a $(C_1-C_4)$alkyl group, as defined herein, appended to the parent molecular moiety through an oxygen atom. Representative examples of $(C_1-C_4)$alkoxy include, but are not limited to, methoxy, ethoxy, propoxy, 2-propoxy, butoxy, and tert-butoxy.

The term "$(C_1-C_3)$alkyl" as used herein, means a straight or branched chain hydrocarbon containing from 1 to 3 carbon atoms. Representative examples of $(C_1-C_3)$alkyl include methyl, ethyl, n-propyl, and iso-propyl.

The term "$(C_1-C_3)$alkyl-$d_{1-7}$" as used herein, means a straight or branched chain hydrocarbon containing from 1 to 3 carbon atoms wherein one to seven of the hydrogens have been exchanged for deuterium ($^2$H or D). Representative examples of $(C_1-C_3)$alkyl-$d_{1-7}$ include methyl-$d_3$, ethyl-$d_5$, and ethyl-2,2,2-$d_3$.

The term "$(C_1-C_4)$alkyl" as used herein, means a straight or branched chain hydrocarbon containing from 1 to 4 carbon atoms. Representative examples of $(C_1-C_4)$alkyl include methyl, ethyl, n-propyl, iso-propyl, n-butyl, sec-butyl, iso-butyl, and tert-butyl.

The term "$(C_1-C_4)$alkyl-$d_1$" as used herein, means a straight or branched chain hydrocarbon containing from 1 to 4 carbon atoms wherein one to nine of the hydrogens have been exchanged for deuterium ($^2$H or D). Representative examples of $(C_1-C_4)$alkyl-$d_{1-9}$ include methyl-$d_3$, ethyl-$d_5$, and ethyl-2,2,2-$d_3$.

The term "$(C_1-C_6)$alkyl" as used herein, means a straight or branched chain hydrocarbon containing from 1 to 6 carbon atoms. Representative examples of $(C_1-C_6)$alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "$(C_1-C_4)$alkylcarbonyl" as used herein, means a $(C_1-C_4)$alkyl group, as defined herein, appended to the parent molecular moiety through a carbonyl group, as defined herein. Representative examples of $(C_1-C_4)$alkylcarbonyl include, but are not limited to, acetyl, 1-oxopropyl, and 2,2-dimethyl-1-oxopropyl.

The term "carbonyl" as used herein, means a —C(=O)— group.

The term "cyano" as used herein, means a —CN group.

The term "$(C_3-C_4)$cycloalkyl" as used herein, means a saturated cyclic hydrocarbon group containing from 3 to 4 carbons, examples of $(C_3-C_4)$cycloalkyl include cyclopropyl and cyclobutyl. The $(C_3-C_4)$cycoalkyl groups of the invention are optionally substituted with 1, 2, or 3 substituents that are independently $(C_1-C_4)$alkyl, CN, halogen, or OH.

The term "$(C_3-C_4)$cycloalkyl($C_1-C_4$)alkyl" as used herein, means a $(C_3-C_4)$cycloalkyl as defined herein, appended to the parent molecular moiety through a $(C_1-C_4)$ alkyl group, as defined herein. Representative examples of $(C_3-C_4)$cycloalkyl($C_1-C_4$)alkyl include cyclopropylmethyl, 2-cyclopropylethyl, 2-cyclopropylpropyl, 3-cyclopropylpropyl, cyclobutylmethyl, 2-cyclobutylethyl, 2-cyclobutylpropyl, and 3-cyclobutylpropyl.

The term "$(C_3-C_5)$cycloalkyl" as used herein, means a saturated cyclic hydrocarbon group containing from 3 to 5 carbons, examples of $(C_3-C_5)$cycloalkyl include cyclopropyl, cyclobutyl, and cyclopentyl. The $(C_3-C_5)$cycoalkyl groups of the invention are optionally substituted with 1, 2, or 3 substituents that are independently $(C_1-C_4)$alkyl, CN, halogen, or OH.

The term "halo" or "halogen" as used herein, means —Cl, —Br, —I or —F.

The term "halo($C_1-C_4$)alkoxy" as used herein, means at least one halogen, as defined herein, appended to the parent molecular moiety through a $(C_1-C_4)$alkoxy group, as defined herein. Representative examples of halo($C_1-C_4$)alkoxy include, but are not limited to, chloromethoxy, difluoromethoxy, 2-fluoroethoxy, trifluoromethoxy, and pentafluoroethoxy.

The term "halo($C_1-C_3$)alkyl" as used herein, means at least one halogen, as defined herein, appended to the parent molecular moiety through a $(C_1-C_3)$alkyl group, as defined herein. Representative examples of halo($C_1-C_3$)alkyl include, but are not limited to, chloromethyl, difluoromethyl, 2-fluoroethyl, trifluoromethyl, and pentafluoroethyl.

The term "halo($C_1-C_4$)alkyl" as used herein, means at least one halogen, as defined herein, appended to the parent molecular moiety through a $(C_1-C_4)$alkyl group, as defined herein. Representative examples of halo($C_1-C_4$)alkyl include, but are not limited to, chloromethyl, 2-fluoroethyl, trifluoromethyl, and pentafluoroethyl.

The term "heterocycle" or "heterocyclic" as used herein, means a 4, 5, or 6 membered ring containing one N heteroatom and optionally 1 or 2 additional heteroatoms selected from the group consisting of O, N, and S. Representative examples of heterocycle include, but are not limited to, azetidinyl, imidazolidinyl, morpholinyl, oxadiazolidinyl, oxazolidinyl, piperazinyl, piperidinyl, pyrazolidinyl, pyrrolidinyl, thiadiazolidinyl, thiazolidinyl, and thiomorpholinyl. The heterocycle groups of the invention are optionally substituted with 1, 2, or 3 $(C_1-C_4)$alkyl groups.

The term "hydroxy($C_1-C_4$)alkyl" as used herein, means at least one hydroxy group, as defined herein, is appended to the parent molecular moiety through a $(C_1-C_4)$alkyl group, as defined herein. Representative examples of hydroxy($C_1-C_4$)alkyl include, but are not limited to, hydroxymethyl, 2-hydroxyethyl, 3-hydroxypropyl, 2,4-dihydroxybutyl, and 2,3-dihydroxypropyl.

In another embodiment, the present invention provides pharmaceutical combinations for topical administration comprising a compound of Formula (IA), (IB), (IIA), (IIB), (IIIA), or (IIIB), or a pharmaceutically acceptable salt or hydrate thereof, in combination with another pharmaceutical agent for the treatment of the diseases, conditions and/or disorders described herein. Suitable pharmaceutical agents that may be used in combination with the compounds of the present invention for topical administration include, but are not limited to: a second compound of Formula (IA), (IB), (IIA), (IIB), (IIA), or (IIIB), or a pharmaceutically acceptable salt or hydrate thereof; a PDE4 isoenzyme inhibitor including, but not limited to, apremilast, roflumilast, rolipram, piclamilast, crisaborole, PF-07038124, PF-07091905, PF-07090414, PF-07062087, PF-07062077, and PF-07057566; a corticosteroid including, but not limited to, fluocinonide, desoximetasone, mometasone, triamcinolone, betamethasone, alclometasone, desonide, hydrocortisone, LEO-134310A and mapracorat; a calcineurin inhibitor including, but not limited to, tacrolimus, pimecrolimus and cyclosporine; a JAK inhibitor including, but not limited to, tofacitinib, JTE-052, baricitinib, upadacitinib, PF-04965842, PF-06651600 and PF-06700841; a TYK inhibitors including, but not limited to, PF-06826647 and BMS-986165; an ITK inhibitor including, but not limited to, JTE-051; a SYK inhibitor including, but not limited to, fostamatinib, cerdulatinib, entospletinib, TAK-659, ASN-002 and GS-9876; a tyrosine kinase inhibitor including, but not limited to, cerdulatinib; an IRAK4 inhibitor including, but not limited to, 1-(((2S,3S,4S)-3-ethyl-4-fluoro-5-oxopyrrolidin-2-yl)methoxy)-7-methoxyisoquinoline-6 carboxamide; an anti-inflammatory agent including, but not limited to, WBI-1001 and MRX-6; retinoic acid derivatives including, but not limited to, alitretinoin; a liver X receptor (LXR) selective agonist including, but not limited to, VTP-38543; a H4 receptor antagonists including, but not limited to, ZPL-389; a NKI receptor antagonists including, but not limited to, Aprepitant and Tradipitant; a CRTH2 receptor antagonists including, but not limited to, Fevipiprant and OC-459; a Chymase inhibitors including, but not limited to, SUN 13834; a GATA-3 inhibitors including, but not limited to, SB-011; and a RORC2 inverse agonist including, but not limited to, PF-06763809, ESR-114, VTP-43742, ARN6039, TAK-828, RTA-1701, BOS-172767, AUR-101 and JTE-451.

In another embodiment, the present invention provides pharmaceutical combinations for oral administration comprising a compound of Formula (IA), (IB), (IIA), (IIB), (IIIA), or (IIIB), or a pharmaceutically acceptable salt or hydrate thereof, in combination with another pharmaceutical agent for the treatment of the diseases, conditions and/or disorders described herein. Suitable pharmaceutical agents that may be used in combination with the compounds of the present invention for oral administration include, but are not limited to: a second compound of Formula (IA), (IB), (IIA), (IIB), (IIA), or (IIIB), or a pharmaceutically acceptable salt or hydrate thereof; oral anti-inflammatory agents including, but not limited to, aspirin, ibuprofen, naproxen, sulindac, indomethacin, mefenamate, droxicam, diclofenac, sulfinpyrazone, piroxicam, CELEBREX®, and pharmaceutically acceptable salts or prodrugs thereof; oral retinoic acid derivatives including, but not limited to, alitretinoin; oral liver X receptor (LXR) selective agonists including, but not limited to, VTP-38543; oral H4 receptor antagonists including, but not limited to, ZPL-389; oral NKI receptor antagonists including, but not limited to, Aprepitant and Tradipitant; oral CRTH2 receptor antagonists including, but not limited to, Fevipiprant and OC-459; oral Chymase inhibitors including, but not limited to, SUN 13834; oral GATA-3 inhibitors including, but not limited to, SB-011; oral RORC2 inverse agonists including, but not limited to, ESR-114, VTP-43742, ARN6039, TAK-828, RTA-1701, BOS-172767, AUR-101 and JTE-451; oral JAK inhibitors including, but not limited to, tofacitinib, JTE-052, baricitinib, upadacitinib, PF-04965842, PF-06651600, and PF-06700841; oral TYK inhibitors including, but not limited to, PF-06826647 and BMS-986165; oral ITK inhibitors including, but not limited to, JTE-051; oral SYK inhibitors including, but not limited to, fostamatinib, cerdulatinib, entospletinib, TAK-659, ASN-002 and GS-9876; oral S1P receptor modulators including, but not limited to, ozanimod and etrasimod; and oral IRAK4 inhibitors including, but not limited to, 1-(((2S,3S,4S)-3-ethyl-4-fluoro-5-oxopyrrolidin-2-yl)methoxy)-7-methoxyisoquinoline-6 carboxamide and BAY 1830839.

In another embodiment, the present invention provides pharmaceutical combinations for injectable administration comprising a compound of Formula (IA), (IB), (IIA), (IIB), (IIIA), or (IIIB), or a pharmaceutically acceptable salt or hydrate thereof, in combination with another pharmaceutical agent for the treatment of the diseases, conditions and/or disorders described herein. Suitable pharmaceutical agents that may be used in combination with the compounds of the present invention for injectable administration include, but are not limited to: TNFα inhibitors including, but not limited to, infliximab, adalimumab, golimumab, and certolizumab pegol; anti-MAdCAM including, but not limited to, SHP647; anti IL-12 P40 including, but not limited to, ustekinumab; anti-IL-23 P19 including, but not limited to, risankizumab, mirikizumab, brazikumab, guselkumab, and tidrakizumab; anti-IL-17 including, but not limited to, secukinumab, brodalumab and ixekizumab; integrin inhibitors including, but not limited to, natalizumab, vedolizumab and etrolizumab.

Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt, hydrate, ester or prodrug thereof according to the Formula (IA), (IB), (IIA), (IIB), (IIA), or (IIIB), another therapeutic agent or a pharmaceutically acceptable salt, hydrate, ester or prodrug thereof, and at least one pharmaceutically acceptable excipient or carrier.

The term "pharmaceutically acceptable salt" or "salt," as used herein, refers to salts that are well known in the art. For example, S. M Berge et al. describe pharmaceutically acceptable salts in detail in J. Pharmaceutical Sciences, 66:1-19 (1977) which is incorporated herein by reference. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, besylate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, and the like, metal salts such as sodium, potassium, magnesium or calcium salts or amino salts such as ammonium, triethylamine salts, and the like, all of which may be prepared according to conventional methods.

Basic addition salts can be prepared in situ during the final isolation and purification of compounds of this invention by reacting the hydroxy group at the 3-position of the N,N- dimethylpicolinamide moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

The present invention also includes pharmaceutically acceptable salts of the prodrugs of the compounds of the present invention. Representative examples include, but are not limited to, the compounds shown below wherein $R^+$ is lithium, sodium, potassium, ammonium, tetramethylammonium, tetraethylammonium, methylammonium, dimethylammonium, trimethylammonium, triethylammonium, diethylammonium, ethylammonium and the like, and wherein $R^{2+}$ is calcium, magnesium, aluminum, and the like.

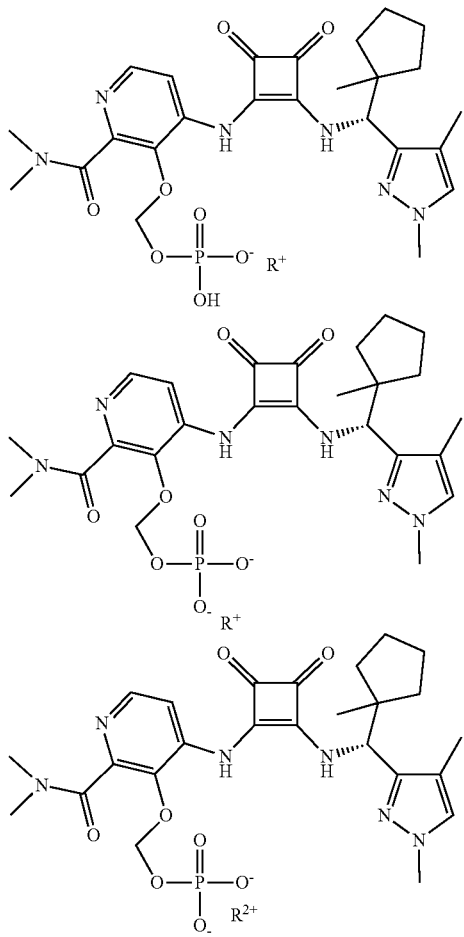

The compounds of the present invention may be isolated and used per se in the form of their pharmaceutically acceptable salts, including salts of a prodrug. In accordance with the present invention, compounds with multiple basic nitrogen atoms can form salts with varying number of equivalents ("eq.") of acid. Compounds with multiple acidic groups may form basic addition salts with varying numbers of equivalents ("eq.") of the basic addition molecule or positive counterion. It will be understood by practitioners that all such salts are within the scope of the present invention.

The present invention encompasses compounds of Formula (IA), (IB), (IIA), (IIB), (IIIA), or (IIIB), when prepared by synthetic processes or by metabolic processes. Preparation of the compounds of the invention by metabolic processes include those occurring in the human or animal body (in vivo) or processes occurring in vitro.

The present invention also contemplates pharmaceutically active metabolites formed by in vivo biotransformation of compounds of Formula (IA), (IB), (IIA), (IIB), (IIIA), or (IIIB). The term pharmaceutically active metabolite, as used herein, refers to a compound formed by the in vivo biotransformation of compounds of Formula (IA), (IB), (IIA), (IIB), (IIIA), or (IIIB). A thorough discussion of biotransformation is provided in (Goodman and Gilman's, The Pharmacological Basis of Therapeutics, seventh edition, MacMillan Publishing Company, New York, N.Y., (1985)).

When used in the above or other treatments, a therapeutically effective amount of one of the compounds of the present invention can be employed in pure form or, where such forms exist, in pharmaceutically acceptable salt, ester, amide, or prodrug form. Alternatively, the compound can be administered as a pharmaceutical composition containing the compound of interest in combination with one or more pharmaceutically acceptable carriers. The phrase "therapeutically effective amount" of the compound of the present invention means a sufficient amount of the compound to treat the diseases, conditions, or disorders indicated herein at a reasonable benefit/risk ratio applicable to any medical treatment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Pharmaceutical Compositions or Formulations

In another embodiment, the present invention provides pharmaceutical compositions, or formulations, comprising a therapeutically effective amount of a compound of the present invention and a pharmaceutically acceptable excipient, diluent or carrier. The pharmaceutical compositions, or formulations, of this invention may be administered to humans and other mammals topically, orally, parenterally, intracisternally, intravaginally, intraperitoneally, bucally, as an oral spray, as a nasal spray, rectally as a suppository, or in the form of a liposome.

A typical pharmaceutical composition or formulation is prepared by mixing a compound of the present invention and a carrier, diluent or excipient. Suitable carriers, diluents and excipients include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., for use in the preparing a medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The dissolution rate of poorly water-soluble compounds may be enhanced by the use of a spray-dried dispersion, such as those described by Takeuchi, H., et al. in "Enhancement of the dissolution rate of a poorly water-soluble drug (tolbutamide) by a spray-drying solvent deposition method and disintegrants" *J. Pharm. Pharmacol.*, 39, 769-773 (1987); and EP0901786 E1 (US2002/009494), incorporated herein by reference. The compound of the present invention is typically formulated into pharmaceutical dosage forms to provide an easily controllable dosage of the drug and to give the patient an elegant and easily handleable product.

The pharmaceutical composition, or formulation, for application may be packaged in a variety of ways depending upon the method used for administering the drug. Generally, an article for distribution includes a container having deposited therein the pharmaceutical formulation in an appropriate form. Suitable containers include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The term "pharmaceutically acceptable carrier" refers to carrier medium that provides the appropriate delivery of an effective amount of a active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Additional information concerning carriers can be found in Remington: The Science and Practice of Pharmacy, 21st Ed., Lippincott, Williams & Wilkins (2005) which is incorporated herein by reference. Further examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "pharmaceutically acceptable topical carrier" refers to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to an broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

Dosage forms for topical or transdermal administration of a compound of the present invention include ointments, pastes, creams, lotions, gels, powders, solutions, sprays, inhalants or patches. The active component is admixed under sterile conditions with a pharmaceutically acceptable carrier and any needed preservatives or buffers as may be required. Compounds that are volatile in may require admixture with special formulating agents or with special packaging materials to assure proper dosage delivery. In addition, compounds of the present invention that have poor human skin permeability may require one or more permeability enhancers whereas compounds rapidly absorbed through the skin may require formulation with absorption-retarding agents or barriers.

The ointments, pastes, creams, lotions, gels, powders, and solutions, for topical administration may contain, in addition to an active compound of the present invention, pharmaceutically acceptable excipients such as animal and vegetable fats, oils, waxes, paraffins, starch, tragacanth, cellulose derivatives, polyethylene glycols, silicones, bentonites, silicic acid, talc, zinc oxide, preservatives, antioxidants, fragrances, emulsifiers, dyes, inert fillers, anti-irritants, tackifiers, fragrances, opacifiers, antioxidants, gelling agents, stabilizers, surfactants, emollients, coloring agents, preservatives, buffering agents, permeation enhancers, or mixtures thereof. Topical excipients should not interfere with the effectiveness of the biological activity of the active agent and not be deleterious to the epithelial cells or their function.

The terms "permeability enhancer," or "permeation enhancer," relates to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal or human skin, nail, hair, claw or hoof using a diffusion cell apparatus. A diffusion cell is described by Merritt et al. Diffusion Apparatus for Skin Penetration, J of Controlled Release, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Solid dosage forms for oral administration include capsules, tablets, pills, powders, and granules. In such solid dosage forms, the active compound is mixed with at least one inert pharmaceutically acceptable carrier such as sodium citrate or calcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

The term "parenterally," as used herein, refers to modes of administration which include intravenous, intramuscular, intraperitoneal, intrasternal, subcutaneous, intraarticular injection and infusion. Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Pharmaceutical compositions, or formulations, for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Compounds of the present invention may also be administered in the form of liposomes. Liposomes are generally derived from phospholipids or other lipid substances and are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

Pharmaceutical compositions, or formulations, of the present invention may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

The pharmaceutical compositions, or formulations, of the invention may be suspensions. Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

The total daily dose of the compounds of this invention administered to a human or lower animal may range from about 0.0001 to about 15 mg/kg/day. For purposes of oral administration, more preferable doses can be in the range of from about 0.01 to about 5 mg/kg/day. For topical administration, more preferable doses can be in the range of 0.001 mg/kg/day to about 5 mg/kg/day. If desired, the effective daily dose can be divided into multiple doses for purposes of administration, e.g. two to four separate doses per day.

The pharmaceutical compositions also include solvates and hydrates of the compounds of the present invention. The term "solvate" refers to a molecular complex of a compound represented by Formula (IA), (IB), (IIA), (IIB), (IIIA), or (IIIB), including pharmaceutically acceptable salts or hydrates thereof, with one or more solvent molecules. Such solvent molecules are those commonly used in the pharmaceutical art, which are known to be innocuous to the recipient, e.g., water, ethanol, ethylene glycol, (S)-propylene glycol, (R)-propylene glycol, and the like, The term "hydrate" refers to the complex where the solvent molecule is water. The solvates and/or hydrates preferably exist in crystalline form. Other solvents may be used as intermediate solvates in the preparation of more desirable solvates. Intermediate solvents include, but are not limited to, methanol, methyl t-butyl ether, ethyl acetate, methyl acetate, 1,4-butyne-diol, and the like.

Compounds of the present invention may exist in more than one crystal form. Polymorphs of compounds of Formulae (IA), (IB), (IIA), (IIB), (IIA), or (IIIB), and salts thereof (including solvates and hydrates) form part of this invention and may be prepared by crystallization of a compound of the present invention under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of the present invention followed by gradual or fast cooling. The presence of polymorphs may be determined by solid probe nuclear magnetic resonance (NMR) spectroscopy, infrared (IR) spectroscopy, differential scanning calorimetry, powder X-ray diffraction or such other techniques.

This invention also includes isotopically-labeled compounds, which are identical to those described by Formula (IA), (IB), (IIA), (IIB), (IIA), and (IIIB) but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur and fluorine, such as $^{2}H$, $^{3}H$, $^{13}C$, $^{14}C$, $^{15}N$, $^{18}O$, $^{17}O$, $^{35}S$, $^{36}Cl$, $^{125}I$, $^{129}I$, and $^{18}F$ respectively. Certain isotopically-labeled compounds of the present invention, for example those into which radioactive isotopes such as $^{3}H$ and $^{14}C$ are incorporated, are useful in drug and/or substrate tissue distribution assays. Tritiated (i.e., $^{3}H$), and carbon-14 (i.e., $^{14}C$), isotopes are particularly preferred for their ease of preparation and detectability. Further, substitution with heavier isotopes such as deuterium (i.e., $^{2}H$), can afford certain therapeutic advantages resulting from greater metabolic stability, for example increased in vivo half-life or reduced dosage requirements and, hence, may be preferred in some circumstances. Isotopically labeled compounds of the present invention can generally be prepared by carrying out the procedures disclosed in the schemes and/or in the Examples below, by substituting a readily available isotopically labeled reagent for a non-isotopically labeled reagent.

In particular, the present invention includes deuterated compounds of Formula (IA), (IB), (IIA), (IIB), (IIA), and (IIIB). Any of the hydrogens contained on the compounds of the present invention may be exchanged for deuterium including the pyridine hydrogens as shown below.

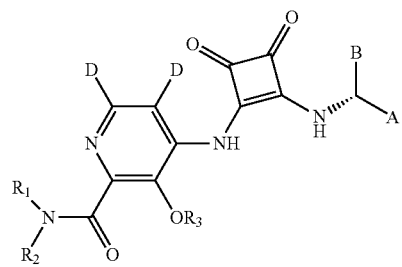

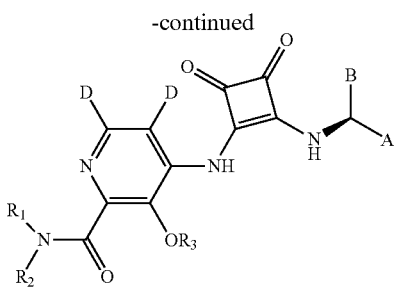

Representative examples of deuterated compounds of the present invention include, but are not limited to, Examples 39 and 40.

All of the recited U.S. patents and publications (including all technical bulletins referenced in the Examples) are incorporated herein by reference in their entireties.

The compounds of the present invention, or their pharmaceutically acceptable salts or hydrates thereof, may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books including Compendium of Organic Synthetic Methods, Vol. I-VI, published by Wiley-Interscience). Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

Compounds of the present invention may be prepared as a single enantiomer or as a mixture of individual enantiomers which includes racemic mixtures. Methods to obtain preferentially a single enantiomer from a mixture of individual enantiomers or a racemic mixture are well known to those ordinarily skilled in the art of organic chemistry. Such methods include but are not limited to preferential crystallization of diastereomeric salts (e.g. tartrate or camphor sulfonate), covalent derivatization by a chiral, non-racemic reagent followed by separation of the resulting diastereomers by common methods (e.g. crystallization, chromatographic separation, or distillation) and chemical reversion to scalemic compound, or high/medium-pressure liquid chromatography or supercritical fluid chromatography employing a chiral stationary phase.

These techniques may be performed on the final compounds of the invention or on any intermediates to compounds of the invention which bear a stereogenic center. Also, to facilitate separation by any of the methods described above, the compounds of the invention or any intermediates to the compounds of the invention which bear a stereogenic center may be transiently reacted with an achiral reagent, separated, and then reverted to scalemic compound by standard synthetic techniques.

Stereoisomers are designated (R) or (S), depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30. In particular, the stereochemistry at the point of attachment of the variables "A" and "B"

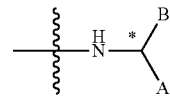

of Formulae (IA), (IB), (IIA), (IIB), (IIA), and (IIIB) may independently be either (R) or (S). The enantiomers of the present invention indicated by (R), (S), or * are substantially free of the other enantiomer. "Substantially free" means that the enantiomeric excess is greater than about 90%, preferably greater than about 95%, and more preferably greater than about 99%. Within the context of enantiomeric excess, the term "about" means±1.0%. The symbol * designates a chiral carbon atom as either (R) or (S) stereochemistry depending on the configuration of substituents around the chiral carbon atom.

Compounds of the present invention not designated (R), (S), or * may exist as racemates (i.e. 50% (R) and 50% (S)) or as a mixture of two enantiomers wherein one enantiomer is in excess. For example, enantiomeric mixtures may include the (R) enantiomer in 51% and the (S) enantiomer in 49% or vice versa or any combination of (R) and (S) other than the racemic mixture of 50% (R) and 50% (S). The present invention includes racemates and enantiomeric mixtures of the compounds of the present invention.

Compounds of the present invention may exist in different stable conformational forms which may be separable. Torsional asymmetry due to restricted rotation about an asymmetric single bond, for example because of steric hindrance or ring strain, may permit separation of different conformers. The compounds of the present invention further include each conformational isomer of compounds of Formula (IA), (IB), (IIA), (IIB), (IIIA), (IIIB), and mixtures thereof.

Tautomers may exist in the compounds of the present invention and are specifically included within the scope of the present invention. The term "tautomer," as used herein, means a proton shift from one atom of a molecule to another atom of the same molecule wherein two or more structurally distinct compounds are in equilibrium with each other. Compounds of the present invention may exist as tautomers. The present invention contemplates tautomers due to proton shifts from one atom to another atom of the same molecule generating two or more distinct compounds that are in equilibrium with each other. In particular, the bis(amino) cyclobut-3-ene-1,2-dione moiety contained within the compounds of the present invention may tautomerize as shown below and are included within the scope of the present invention.

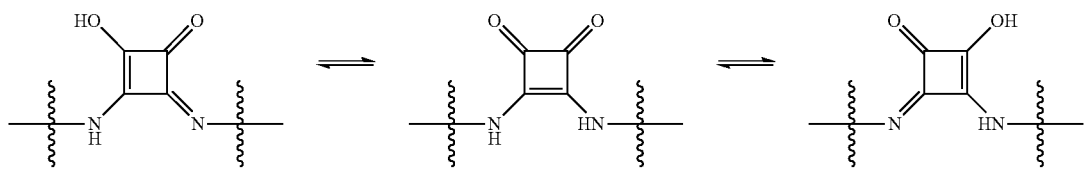 [SMILES: */N=c1/c(N*)c(O)c1=O ; *Nc1c(N*)c(=O)c1=O ; */N=c1/c(N*)c(O)c1=O]

Compounds of the present invention or their pharmaceutically acceptable salts, can be prepared according to the reaction Schemes and Examples disclosed herein below. Unless otherwise indicated, $R_1$, $R_2$, $R_3$, $R_4$, $R_5$, $R_6$, $R_7$, $R_8$, $R_9$, m, n, A, B, X, $R_A$, $R_B$ and $R_C$ in the Schemes are as defined in Formulae (IA) and (IB) of the Summary section above. It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way. Isolation and purification of the products are accomplished by standard procedures known to one of ordinary skill in the art.

Scheme A

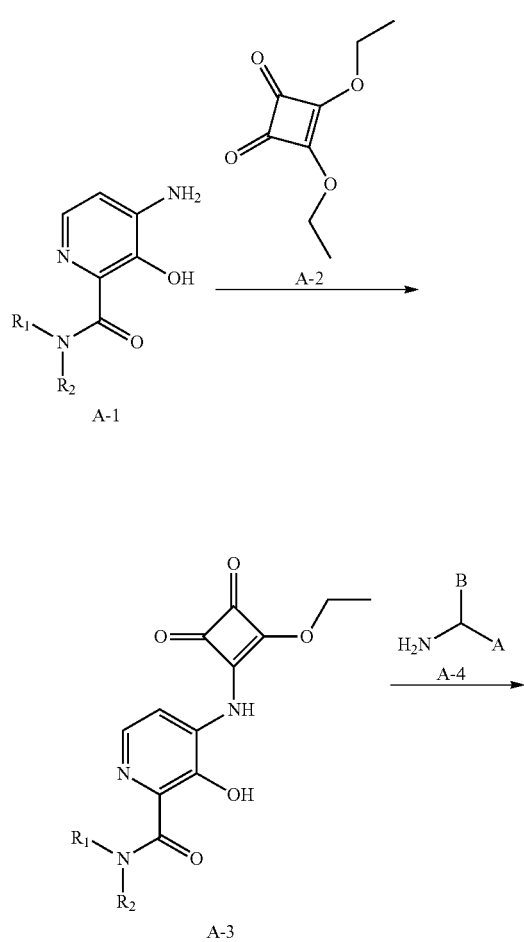

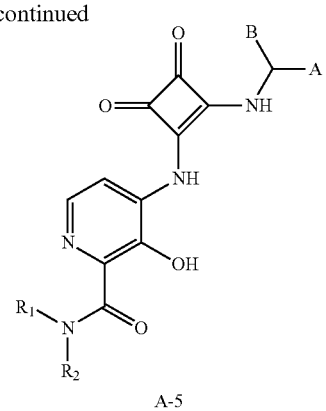

Compounds of Formula (IA) and (IB) can be prepared as described in Scheme A. Nucleophilic aromatic substitution between an amino pyridine A-1 (prepared as described in Scheme B) and commercially available 3,4-diethoxycyclobut-3-ene-1,2-dione (A-2) affords compounds of Formula A-3. A second nucleophilic aromatic substitution between A-3 and an amine A-4 (prepared as described in Schemes C-G) affords compounds of Formula A-5.

Scheme B

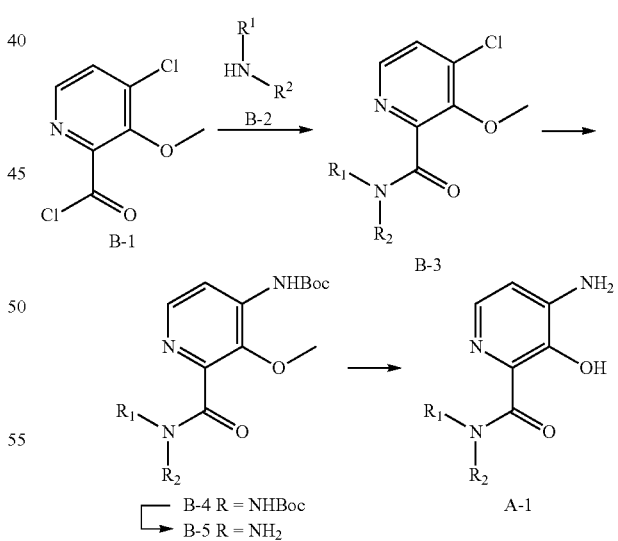

Compounds of formula A-1 employed in Scheme A can be prepared as described in Scheme B. Amidation between commercially available 4-chloro-3-methoxypicolinoyl chloride (B-1) and a commercially available amine B-2 under basic conditions provides compounds of Formula B-3. Buchwald coupling between B-3 and tert-butyl carbamate affords compounds of Formula B-4, which can be subjected to acidic conditions to remove the Boc group and provide compounds of Formula B-5. Demethylation of B-5 leads to compounds of Formula A-1.

HATU-mediated condensation with methoxy methylamine. Metalation of heteroaryl halides C-5 where X is iodine or bromine followed by reaction with D-2 affords ketones of Formula D-3. Reductive amination of D-3 with ammonia in methanol affords compounds of Formula A-4 as a racemic or diastereomeric mixture.

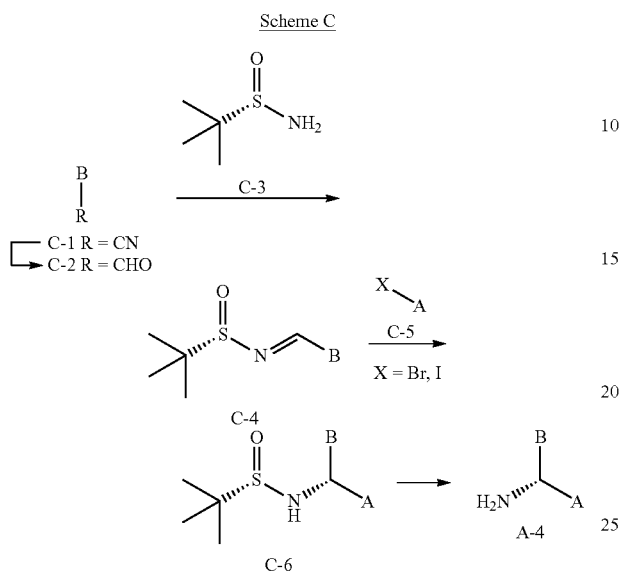

Compounds of Formula A-4 employed in Scheme A where the amines are enantiomerically enriched can be prepared as described in Scheme C. Titanium (IV) ethoxide-mediated condensation of an aldehyde C-2 (either commercially available or obtained via reduction of the corresponding nitrile C-1 commercially available or prepared from methods known in the art) with (S)-2-methylpropane-2-sulfinamide (C-3) provides compounds of Formula C-4. Metalation of heteroaryl halides C-5 where X is iodine or bromine provides a highly diastereoselective addition to C-4 to afford sulfonamides of Formula C-6 as the major diastereomer. Subsequent removal of the chiral auxiliary under acidic conditions leads to compounds of Formula A-4. The absolute stereochemistry of amines A-4 can be established by methods known to those skilled in the art including Mosher's amide analysis and single crystal X-ray crystallography, or derived by analogy to known compounds.

Compounds of Formula A-4 employed in Scheme A where the amines are either racemic mixtures or diastereomeric mixtures can be prepared as described in Scheme D. Carboxylic acids of the formula D-1 (either commercially available or prepared as described herein below) can be converted to the corresponding Weinreb amide D-2 by Alternatively, compounds of Formula A-4 where the Formula (IA) or (IB) variable A is defined as a substituted pyrazole can be prepared from 3-halo-1-alkylpyrazoles E-1 ($R_4$=alkyl and X=Bromo or Iodo) as described in Scheme E. Metalation of E-1 and its addition to either sulfinamine C-4 or Weinreb amide D-2 affords addition products of Formula E-2 or E-4, respectively. Installation of the $R_5$ substituent can be accomplished by either electrophilic aromatic substitution or by the reaction with NIS and then a metal-mediated cross-coupling reaction of the resulting iodide to provide compounds E-3 or E-5. The chiral auxiliary of E-3 can then be removed under acidic conditions to provide compounds of Formula A-4. Reductive amination of E-5 with ammonia in methanol affords compounds of Formula A-4.

Scheme F

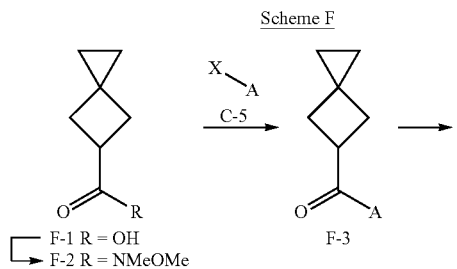

F-1 R = OH
F-2 R = NMeOMe

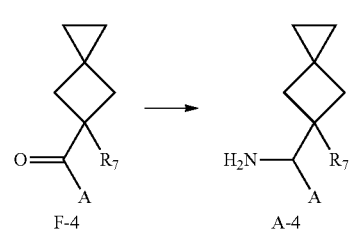

Compounds of Formula A-4 employed in Scheme A where the Formula (IA) or (IB) variable B is defined as 5-methylspiro[2,3]hexan-5-yl can be prepared as described in Scheme F. Commercially available spiro[2,3]hexane-5-carboxylic acid (F-1) can be converted to the corresponding Weinreb amide F-2 by HATU-mediated condensation with methoxy methylamine. Metalation of heteroaryl halides C-5 where X is iodine or bromine followed by reaction with F-2 affords ketones of the Formula F-3. Subsequent alkylation of F-3 employing an alkyl halide (such as iodomethane or iodoethane) and a suitable base followed by reductive amination using ammonia in methanol affords compounds of the Formula A-4 as a racemic mixture.

Scheme G

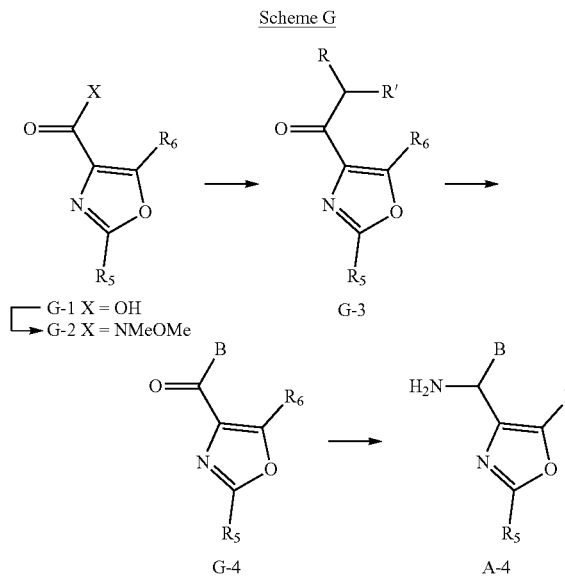

G-1 X = OH
G-2 X = NMeOMe

Compounds of Formula A-4 employed in Scheme A where the Formula (IA) or (IB) variable A is defined as a 2,5-disubstituted oxazole can be prepared as described in Scheme G. Carboxylic acids of Formula G-1, commercially available or prepared from methods known in the art, can be condensed with methoxy methylamine in the presence of HATU to provide Weinreb amides of Formula G-2. Compound G-2 can be reacted with a Grignard reagent (such as isopropyl magnesium bromide or cyclopentyl magnesium bromide) to provide ketones of Formula G-3 where R and R' are methyl or R and R' taken together with the carbon atom that they are attached to form a $C_{3-5}$cycloalkane ring. Subsequent alkylation of G-3 employing an alkyl halide (such as iodomethane or iodoethane) and a suitable base followed by reductive amination using ammonia in methanol affords compounds of Formula A-4 as a racemic mixture.

Scheme H

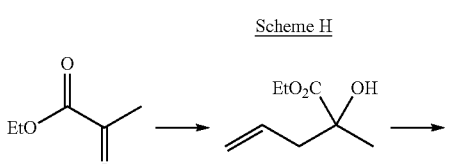

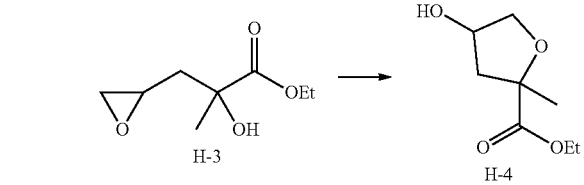

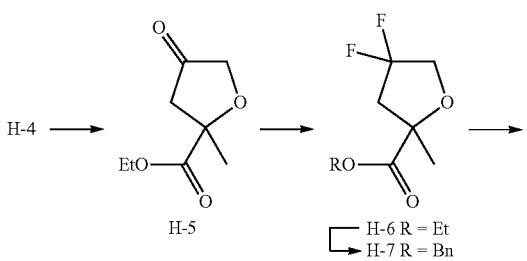

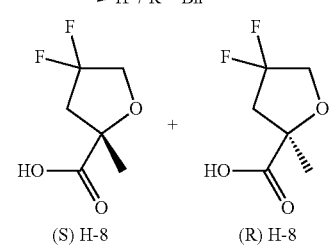

(S) H-8          (R) H-8

The specific carboxylic acid D-1 employed in Scheme D where the Formula (IA) or (IB) variable B is defined as (S) or (R)-4,4-difluoro-2-methyltetrahydrofuran-2-yl can be prepared as described in Scheme H. Titanium (IV) chloride-mediated allylation of commercially available ethyl 2-oxopropanoate (H-1) with allyltrimethylsilane gives ethyl 2-hydroxy-2-methylpent-4-enoate (H-2). Epoxidation of the terminal alkene of H-2 using 3-chloroperbenzoic acid followed by magnesium bromide-mediated intramolecular cyclization provides ethyl 4-hydroxy-2-methyltetrahydrofuran-2-carboxylate (H-4). Subsequent oxidation of the secondary alcohol using pyridinium chlorochromate followed by fluorination using diethylaminosulfur trifluoride affords ethyl 4,4-difluoro-2-methyltetrahydrofuran-2-carboxylate (H-6). Ester H-6 was transesterified to the benzyl ester H-7 which was then resolved using chiral HPLC. Subsequent saponification of the ester affords the individual enantiomers H-8 which can be employed in Scheme D. The absolute stereochemistry of H-8 was established by single crystal X-ray crystallography (see FIG. 3).

Scheme I

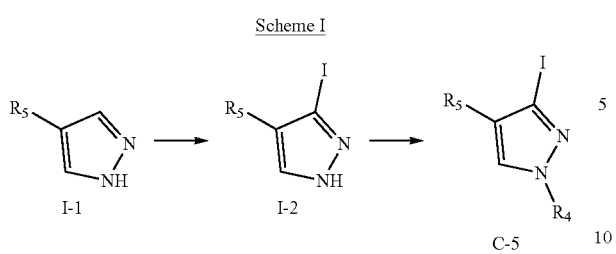

1,4-Disubstituted-3-iodopyrazoles that can be employed in the synthetic methodologies described in Schemes C, D, and F can be prepared as described in Scheme 1. Iodination of commercially available 4-substituted pyrazoles (1-1) using NIS provides compounds of Formula I-2. Subsequent N-alkylation of 1-2 with alkyl halides (e.g. iodomethane, iodoethane) followed by separation of the regioisomers by chromatography affords compounds of Formula C-5 that can be used in the synthetic methodologies described in the above schemes.

Scheme J

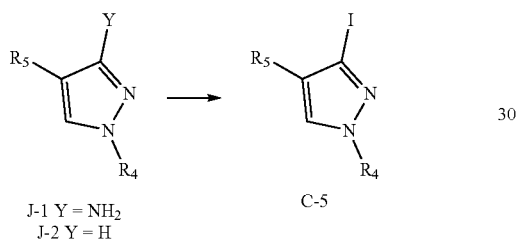

Alternatively, 1,4-disubstituted-3-iodopyrazoles that can be employed in the synthetic methodologies described in Schemes C, D, and F can be prepared as described in Scheme J. 1,4-Disubstituted-3-aminopyrazoles (J-1) may be converted to compounds of Formula C-5 through the Sandmeyer reaction employing sodium nitrite and potassium iodide. Compounds of Formula C-5 can also be prepared via direct iodination of commercially available 1,4-disubstituted pyrazoles J-2 using NIS.

Scheme K

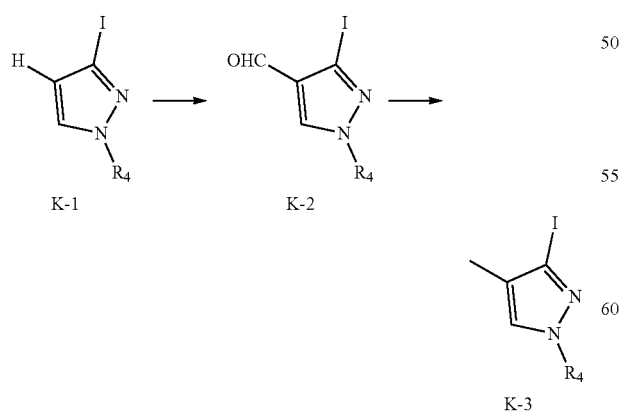

In another variation, 1,4-disubstituted 3-iodopyrazoles employed in Scheme C-D and Scheme F can be prepared as described in Scheme K, specifically were $R_4=R_5=$methyl. 3-Iodo-1-methyl-1H pyrazole, K-1 can be formylated regioselectively with Vilsmeier reagent to give 3-iodo-1-methyl-1H-pyrazole-4-carbaldehyde (K-2), which in turn can be reduced (TFA, triethylsilane) to give 3-iodo-1,4-dimethyl-1H-pyrazole, K-3.

Scheme L

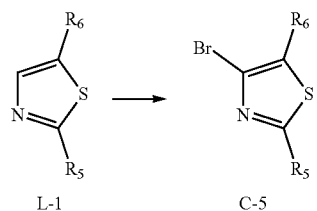

2,5-Disubstituted 4-bromothiazoles employed in Scheme C-D and Scheme F can be prepared as described in Scheme L. Bromination of commercially available 2,5-disubstituted thiazoles L-1 using NBS affords compounds of the Formula C-5.

Scheme M

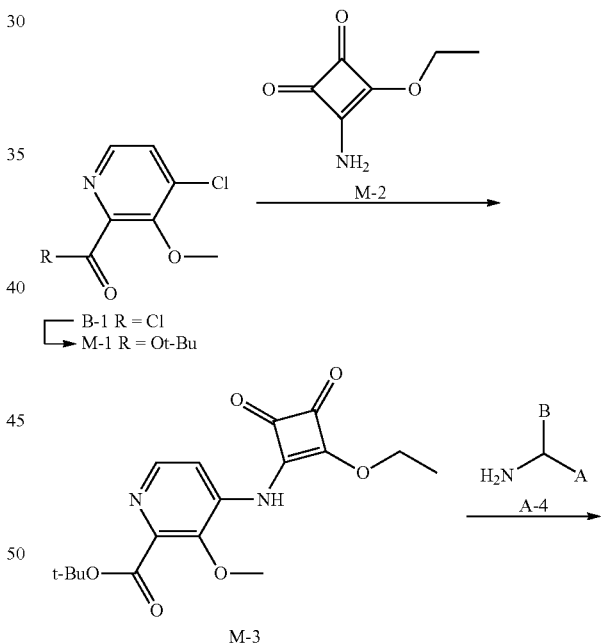

M-4 →

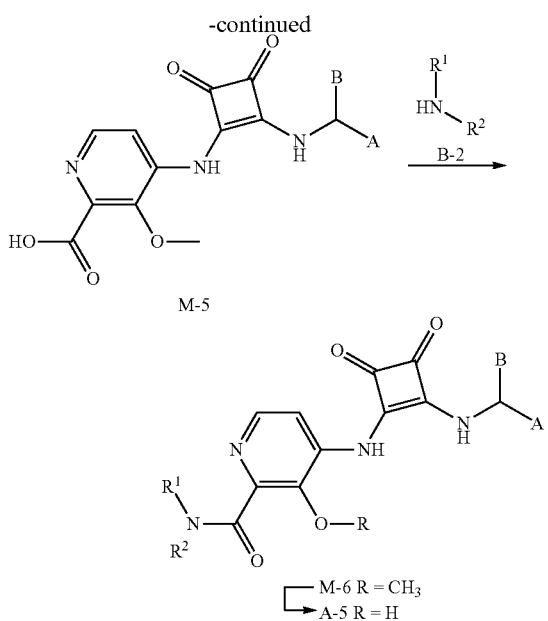

Alternatively, compounds of Formula (IA) and (IB) may be prepared as described in Scheme M. Esterification of commercially available 4-chloro-3-methoxypicolinoyl chloride (B-1) under basic conditions provides tert-butyl 4-chloro-3-methoxypicolinate (M-1). Buchwald coupling between M-1 and commercially available 3-amino-4-ethoxycyclobut-3-ene-1,2-dione (M-2) followed by nucleophilic aromatic substitution with amines A-4 leads to compounds M-4. Ester hydrolysis under acidic conditions followed by HATU-mediated amidation with amines B-2 and O-demethylation using magnesium bromide affords compounds of the formula A-5.

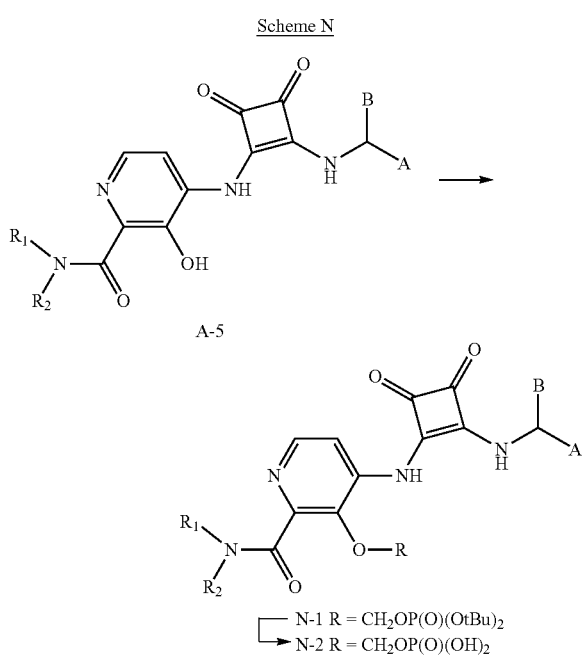

Compounds of Formula (IA) and (IB) where $R_3$ is —$CH_2OP(O)(OH)_2$ may be prepared as described in Scheme N. Alkylation of compounds of the formula A-5 with commercially available di-tert-butyl (chloromethyl) phosphate under basic conditions provides N-1. Subsequent cleavage of tert-butyl ester protecting groups under acid or neutral conditions leads to compound N-2.

EXAMPLES

The present invention will be more readily understood by reference to the following examples, which are included merely for purposes of illustration of certain aspects and embodiments of the present invention, and are not intended to limit the invention. The following illustrate the synthesis of various compounds of the present invention. Additional compounds within the scope of this invention may be prepared using the methods illustrated in these Examples and schemes, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. Coupling constants (J values) are reported in Hertz. For syntheses referencing procedures in other Examples, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate Rfs or retention times (RetT).

Compounds of the present invention were named by Chemdraw Professional version 16.0 or were given names which appeared to be consistent with Chemdraw nomenclature.

The following abbreviations are used herein: DCM: dichloromethane; DAST: (diethylamino)sulfur trifluoride; DEA, diethylamine; DIPEA: diisopropylethylamine; DMF: dimethylformamide; EtOAc: ethyl acetate; EtOH: ethanol; HATU: 1-[bis(dimethylamino)methylene]-1H-1,2,3-triazolo[4,5-b]pyridinium 3-oxide hexafluorophosphate; IPA: isopropyl alcohol; HPLC: high pressure liquid chromatography; LHMDS: lithium hexamethyldisilazide; MeOH: methanol; MTBE: methyl tert-butyl ether; NMM: N-methylmorpholine; NIS: N-iodosuccinimide; PCC: pyridinium chlorochromate; PE: petroleum ether; SFC: super-critical fluid chromatography; TBAI: tetrabutyl ammonium iodide; TEA: triethylamine; TFA: trifluoroacetic acid; and THF: tetrahydrofuran.

The following SFC methods have been employed. SFC method A: Chiral Tech OD-H 250 mm×4.6 mm×5 μm, 5 to 60% 0.2% $NH_4^+$ (7 N in MeOH) in EtOH, 3.0 mL/min. SFC method B: Chiralpak AD-3 50 mm×3 mm×3 μm, 5 to 40% 0.05% DEA in EtOH, 2.5 mL/min, 40° C. SFC method C: Chiralcel OD 250 mm×4.6 mm×5 μm, 5 to 60% 0.2% $NH4^+$ (7 M in MeOH) in EtOH, 3.0 mL/min. SFC method D: Chiralpak AD-3 150 mm×4.6 mm×3 μm, 5 to 40% 0.05% DEA in EtOH, 2.5 mL/min, 40° C. SFC method E: Chiralcel OJ-H 150 mm×4.6 mm×μm, 5 to 40% 0.05% DEA in EtOH, 2.5 mL/min, 40° C. SFC method F: Chiralcel OD-3 100 mm×4.6 mm×3 µm, 5 to 40% 0.05% DEA in EtOH, 2.8 mL/min, 40° C. SFC method G: Chiralpak AD-3 150 mm×4.6 mm×3 µm, 5 to 40% 0.05% DEA in IPA, 2.5 mL/min, 40° C. SFC method H: Chiralcel OD-3 150×4.6 mm I.D. 3 µm, 5 to 40% 0.05% DEA in EtOH, 2.5 mL/min, 40° C.). SFC method I: REGIS (s,s) WHELK-O1 250 mm×30 mm×5 µm 40% 0.05% DEA in EtOH, 2.5 mL/min, 35° C. SFC method J: Chiralpak AS-3 150×4.6 mm×3 µm, 5 to 40% 0.05% DEA in EtOH, 2.5 mL/min, 35° C. SFC method K: Chiralpak AS-3 100×4.6 mm×3 µm, 5 to 40% 0.05% DEA in EtOH, 2.8 mL/min, 40° C. SFC method L. Lux Amylose W-1, 250 mm×4.6 mm, 5 µm, 5 to 60% 0.2% NH$_3$ in EtOH, 3 mL/min. SFC method M. Lux Cellulose, 150 mm×4.6 mm, 3 µm, 5 to 40% MeOH, 2 mL/min. SFC method N: Chiralpak AD-3 150 mm×4.6 mm×3 µm, 5 to 40% 0.1% ethanolamine in EtOH, 2.5 mL/min.

The following HPLC methods have been employed. HPLC method A: Chiralcel OD-RH, 150 mm×4.6 mm×5 µm, 10 to 80% MeCN in 0.069% TFA in H$_2$O, 0.8 mL/min, 30° C. HPLC method B: Chiralpak AS-RH, 150 mm×4.6 mm×5 µm, 10 to 80% MeCN in 0.069% TFA in H$_2$O, 0.8 mL/min, 30° C.

Example 1

(R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide

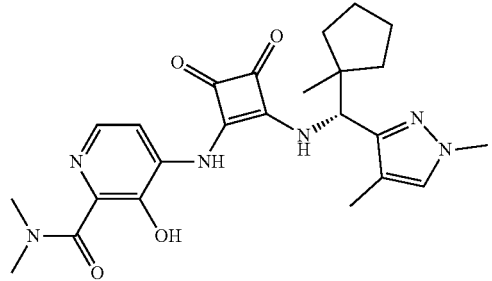

Step 1A. 1-Methylcyclopentane-1-carbonitrile

To a solution of LHMDS (280 mL, 280 mmol, 1 M solution in THF) at −70° C. was added dropwise a solution of cyclopentanecarbonitrile (26.67 g, 280.3 mmol) in THF (20 mL) over 15 min. After stirring for 30 min, iodomethane (59.7 g, 26.2 mL, 420 mmol) was added dropwise, and the reaction was allowed to warm to ambient temperature and stirred for 16 h. The resulting yellow solution was cooled to 0° C. and quenched with saturated aqueous NH$_4$C solution (200 mL) and water (100 mL). The mixture was extracted with MTBE (2.5 L×2), and the combined organic extracts were washed with brine (1 L), dried over Na$_2$SO$_4$, and filtered. The filtrate was concentrated in vacuo. The crude product was purified twice using silica gel column chromatography (100% petroleum ether) to afford 60 g (65%) of the title compound as a yellow oil. $^1$H NMR (400 MHz, CDCl$_3$) δ 2.20-2.10 (m, 2H), 1.90-1.70 (m, 4H), 1.65-1.55 (m, 2H), 1.41 (s, 3H).

Step 1B. 1-Methylcyclopentane-1-carbaldehyde

To a solution of DIBAL-H (824 mL, 824 mmol, 1 M in toluene) at −65° C. was added dropwise a solution of 1-methylcyclopentane-1-carbonitrile (30 g, 275 mmol) in DCM (30 mL). The mixture was stirred at the same temperature for 30 min. The reaction was quenched with saturated aqueous NH$_4$Cl solution (1 L) at −40° C. and stirred vigorously at 25° C. for 10 min. The mixture was diluted with DCM (1 L), and then filtered and the solids were washed with DCM (500 mL×3). The combined filtrate was washed with brine (1 L), dried over Na$_2$SO$_4$, filtered and concentrated in vacuo to give the title compound as a solution in DCM/toluene (3/2, 2 L). The solution was used directly without further purification assuming quantitative yield. $^1$H NMR (400 MHz, CDCl$_3$) δ 9.59 (s, 1H), 2.15-2.01 (m, 2H), 1.80-1.75 (m, 4H), 1.55-1.45 (m, 2H), 1.25 (s, 3H).

Step 1C. (S,E)-2-Methyl-N-((1-methylcyclopentyl)methylene)propane-2-sulfinamide

To a solution of 1-methylcyclopentane-1-carbaldehyde (30.8 g, 275 mmol) in DCM/toluene (3/2, 2.0 L) at 20° C. was added titanium (IV) ethoxide (163 g, 717 mmol). The reaction was stirred for 20 min, and then (S)-2-methylpropane-2-sulfinamide (33.3 g, 275 mmol) was added. The resulting mixture was stirred at ambient temperature for 16 h. The reaction was quenched with water (250 mL). The mixture was filtered and the solids were washed with THF (3 L×3). The combined organic layers were concentrated in vacuo. The crude product was purified by silica gel column chromatography (100% petroleum ether) to afford 44.89 g (38%) of the title compound as a light yellow oil. LCMS m/z 216.3 [M+H]$^+$. $^1$H NMR (400 MHz, CDCl$_3$) δ 7.94 (s, 1H), 1.93-1.85 (m, 2H), 1.80-1.60 (m, 4H), 1.55-1.45 (m, 2H), 1.21 (s, 3H), 1.20 (s, 9H).

Step 1D. 3-Iodo-1,4-dimethyl-1H-pyrazole

Route A

3-Iodo-1,4-dimethyl-1H-pyrazole. To a solution of 1,4-dimethyl-1H-pyrazol-3-amine (1.0 g, 8.6 mmol) in conc. HCl (7.15 mL) at 0° C. was added a solution of sodium nitrite (1.22 g, 17 mmol) in water (1.78 mL) over 5 min. A solution of potassium iodide (3.57 g, 21.5 mmol) in water (3.6 mL) was then added dropwise over 5 min. The mixture was stirred at 0° C. for 30 min, and then warmed to ambient temperature and stirred for 2 h. The reaction mixture was diluted with THF (8 mL) and water (8 mL), and extracted with EtOAc (30 mL×4). The combined organic extracts were washed with saturated aqueous Na$_2$S$_2$O$_3$ solution (30 mL×2) followed by water (30 mL) and brine (30 mL), dried over Na$_2$SO$_4$, filtered and concentrated in vacuo. The crude product was purified by silica gel column chromatography (0 to 60% EtOAc in heptane) to afford 988 mg (52%) of the title compound as a white solid. LCMS m/z 223.0 [M+H]$^+$. $^1$H NMR (400 MHz, CDCl$_3$) δ 7.05 (s, 1H), 3.87 (s, 3H), 1.98 (s, 3H).

Route B

Step 1. 3-Iodo-1-methyl-1H-pyrazole-4-carbaldehyde. POCl$_3$ (45.0 mL, 481 mmol) was added to a solution of 3-iodo-1-methyl-1H-pyrazole (25 g, 120.2 mmol) in DMF (150 mL) at 0° C. After 10 min, the reaction was heated to 65° C. for 18 h. A solution of NaH$_2$PO$_4$ (50 g in 200 mL) was added to the reaction slowly, ensuring the temperature remained between 25-35° C. and pH no greater than 4. After the addition, the reaction was stirred at room temperature for 45 min and then made basic by careful addition of saturated Na$_2$CO$_3$. The aqueous mixture was extracted with EtOAc. The organic layer was washed with brine, dried and filtered. The filtrate was concentrated. The resulting yellow oil was recrystallized from EtOAc/heptane to provided 28.4 g (88%) of the title compound as a tan solid. $^1$H NMR (400 MHz, CDCl$_3$) δ 9.67 (s, 1H), 7.84 (s, 1H), 4.00 (s, 4H).

Step 2. 3-Iodo-1,4-dimethyl-1H-pyrazole. Triethylsilane (5.08 mL, 0.32 mmol) and TFA (1.36 mL, 0.18 mmol) were added to a mixture of 3-iodo-1-methyl-1H-pyrazole-4-carbaldehyde (1.0 g, 0.042 mmol) in chlorobenzene (10 mL). The mixture was heated to 50° C. overnight. The reaction mixture was cooled to room temperature and saturated aqueous NaHCO$_3$ was added. The mixture was extracted with EtOAc. The organic layer was washed with brine, dried (Na$_2$SO$_4$) and filtered. The filtrate was concentrated and the residue was purified by silica gel column chromatography (EtOAc/heptane) to afford 0.64 g (68%) of the title compound. $^1$H NMR (400 MHz, CDCl$_3$) δ 7.08 (s, 1H), 3.90 (s, 3H), 2.01 (s, 3H).

Route C

Step 1: 3-Iodo-4-methyl-1H-pyrazole. NIS (2196.0 g, 9.76 mol) was added in portions to a solution of 4-methyl-1H-pyrazole (800.0 g, 9.76 mol) in DMF (5 L) maintaining the temperature below 25° C. The mixture was stirred at 25° C. for 20 h. Two batches were combined. The combined mixtures were poured into water (20 L) and then extracted with MTBE (5 L×5). The combined organic layers were washed with brine (5 L×3), dried over Na$_2$SO$_4$ and filtered. The filtrate was concentrated in vacuo, and the residue was triturated with petroleum ether/EtOAc (5 L, 10:1). The suspension was stirred at 16° C. for 2 h and then filtered. The resulting solid was dried in vacuo to afford 1280.0 g (32%) of the title compound as alight yellow solid. $^1$H NMR (CDCl$_3$, 400 MHz) δ 7.42 (s, 1H), 2.07 (s, 3H).

Step 2. 3-iodo-1,4-dimethyl-1H-pyrazole. To a suspension of 60% NaH in mineral oil (165.0 g, 4.12 mol) in anhydrous THF (4.5 L) was added a mixture of 3-iodo-4-methyl-1H-pyrazole (710.0 g, 3.41 mol) in anhydrous THF (1.5 L) dropwise at 0° C. The mixture was stirred at 10° C. for 1 h. Iodomethane (496.0 g, 3.49 mol) was added dropwise to the mixture at 0° C. The resulting mixture was stirred at 20° C. for 16 h. The reaction was quenched with water (4.5 L) and extracted with EtOAc (2.5 L×3). The combined organic layers were dried over Na$_2$SO$_4$ and filtered. The filtrate was concentrated in vacuo. The residue was purified by silica gel column chromatography (petroleum ether: EtOAc=10:1 to 1:1) to give two fractions. The first fraction (150 g) was diluted with petroleum ether (200 mL) and stirred at 10° C. for 30 min. The suspension was filtered. The solid was washed with petroleum ether (100 mL) and dried in vacuo to give 100.0 g of the title compound as a white solid. The filtrate was concentrated in vacuo, combined with the second fraction (1300 g), and purified by silica gel column chromatography (petroleum ether: EtOAc=10:1 to 1:1) to afford additional desired compound (500.0 g). This compound was diluted with petroleum ether (800 mL) and stirred at 10° C. for 30 min. The suspension was filtered. The filter cake washed with petroleum ether (500 mL) and dried in vacuo to give 440.0 g of the title compound as a white solid. The total yield was 540 g (35.6%). LCMS m/z 222.8 [M+H]$^+$. $^1$H NMR (CDCl$_3$, 400 MHz) δ 7.04 (s, 1H), 3.86 (s, 3H), 1.97 (s, 3H).

Step 1E. (S)—N—((R)-(1,4-Dimethyl-1H-pyrazol-3-yl)(1-methylcyclopentyl)methyl)-2-methylpropane-2-sulfinamide 3-Iodo-1,4-dimethyl-1H-pyrazole (33 g, 148.6 mmol) in THF (50 mL) was added over 1 h to a solution of 1.0 M iPrMgCl.LiCl in THF (189 mL, 189 mmol) maintaining an internal temperature at 0-5° C. under nitrogen. After 1 h, (S,E)-2-methyl-N-((1-methylcyclopentyl)-methylene)propane-2-sulfinamide (20 g, 92.85 mmol) in THF (50 mL) was added and the mixture stirred at 25° C. for 18 h. The reaction was cooled to 0° C. and 10% acetic acid was added. The organic layer was separated and was partially concentrated. MTBE and water were added. The mixture was stirred for 10 min and the layers separated. The organic layer was concentrated to afford the title compound (66% purity) which was used in the subsequent step without further purification.

Step 1F. (R)-(1,4-Dimethyl-1H-pyrazol-3-yl)(1-methylcyclopentyl)methanamine

The crude (S)—N—((R)-(1,4-dimethyl-1H-pyrazol-3-yl)(1-methylcyclopentyl)methyl)-2-methylpropane-2-sulfinamide (231 g) was suspended in MTBE (300 mL), cooled to 10° C., and conc. HCl (38.4 mL, 2 eq) was added. The mixture was stirred at 10-20° C. for 1 h and then was diluted with water (300 mL). The layers were separated and the organic layer discarded. The aqueous layer was made basic with 20% NaOH to pH 11-13 and extracted with MTBE (2×300 mL). The combined organic layers were concentrated to afford 120 g of the title compound as an oil. The absolute stereochemistry of the title compound was assigned based on the open transition state analysis as described in the literature (Robak, M. T.; Herbage, M. A. Ellman, J. A. *Chem. Rev.* 2010, 110, 3600) and confirmed definitively by Mosher's amide analysis.

Step 1G. (R)-(1,4-Dimethyl-1H-pyrazol-3-yl)(1-methylcyclopentyl)methanamine L-pyroglutamic acid salt L-pyroglutamic acid (77.7 g, 0.6 mol) was added to a solution of (R)-(1,4-dimethyl-1H-pyrazol-3-yl)(1-methylcyclopentyl)methanamine (100 g, 0.48 mol) in THF (1.3 L) at 10-20° C. The mixture was heated to 50° C. and stirred for 2 h, then cooled to 25° C. over 18 h. The solid was filtered and rinsed with THF (890 mL). The solid was dried under vacuum at 45° C. for 6 h to afford 259.6 g (88%) of the title compound. $^1$H NMR (400 MHz, DMSO-d$_6$) δ 7.58 (br. s., 1H), 7.40 (s, 1H), 3.93 (s, 1H), 3.87-3.84 (m, 1H), 3.77 (s, 3H), 2.27-2.14 (m, 1H), 2.12-2.02 (m, 2H), 1.98 (s, 3H), 1.96-1.84 (m, 1H), 1.70-1.48 (m, 6H), 1.42-1.31 (m, 1H), 1.08-1.02 (m, 1H), 0.97 (s, 3H). Chiral SFC (SFC method M) RT=3.81 min, 99% ee.

Step 1H. 4-((2-Ethoxy-3,4-dioxocyclobut-1-en-1-yl)amino)-3-hydroxy-N,N-dimethylpicolinamide 4-((2-Ethoxy-3,4-dioxocyclobut-1-en-1-yl)amino)-3-hydroxy-N,N-dimethylpicolinamide was prepared as described in WO/2010/131145

Step 1I. (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide A mixture of 4-((2-ethoxy-3,4-dioxocyclobut-1-en-1-yl)amino)-3-hydroxy-N,N-dimethylpicolinamide (180 g, 590 mmol), (R)-(1,4-dimethyl-1H-pyrazol-3-yl)(1-methylcyclopentyl)methanamine L-pyroglutamic acid salt (209 g, 625 mmol), EtOH (1 L) and DIPEA (205 mL, 1180 mmol) was stirred at 20-30° C. for 2 h. HOAc (23.8 mL, 416 mmol) was added to adjust the pH to 6-7. The reaction mixture was then concentrated under reduced pressure to about half the volume. The mixture was diluted with water (3.2 L) and stirred for 1.5 hr. The resulting solid was filtered, washed with water and then dried under vacuum at 40-50° C. for 20 h to provide 256 g (93%) of the title compound as a yellow solid. LCMS m/z 467.4 [M+H]$^+$. $^1H$ NMR (400 MHz, DMSO-d$_6$) δ 11.59 (br. s., 1H), 9.92 (br. s., 1H), 9.16 (s, 1H), 8.03-8.00 (m, 2H), 7.43 (s, 1H), 5.33 (d, J=10.0 Hz, 1H), 3.80 (s, 3H), 3.18 (s, 3H), 3.05 (s, 3H), 2.00 (s, 3H), 1.80-1.50 (m, 6H), 1.20-1.15 (m, 1H), 1.14-1.09 (m, 1H), 1.08 (s, 3H). [α]$^{20}_D$=−78.4 (c=1.0, MeOH). Chiral SFC (SFC method N) RT=4.77 min, 98.5% ee. The absolute configuration was established by single crystal X-ray analysis (FIG. 1).

Example 2

(S)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide

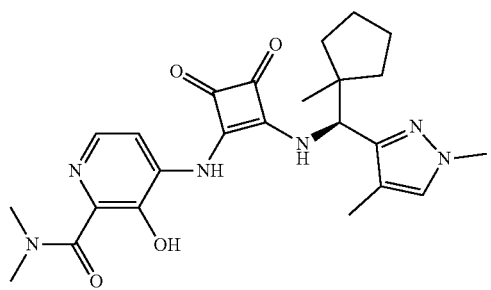

The title compound was prepared analogous to Example 1 employing (R)-2-methylpropane-2-sulfinamide. LCMS m/z 467.4 [M+H]$^+$. $^1$H NMR (400 MHz, DMSO-d$_6$) δ 9.18 (br. s., 1H), 8.12-7.85 (m, 2H), 7.43 (s, 1H), 5.34 (d, J=10.0 Hz, 1H), 3.80 (s, 3H), 3.15 (br. s., 3H), 3.05 (br. s., 3H), 1.98 (s, 3H), 1.74-1.52 (m, 6H), 1.41-1.27 (m, 1H), 1.23-1.15 (m, 1H), 1.08 (s, 3H). [α]$^{29}_D$=+88.49 (c=0.5, MeOH). Chiral SFC (SFC method F) RT=5.45 min, 100% ee.

Example 3

(R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N-isopropyl-N-methylpicolinamide

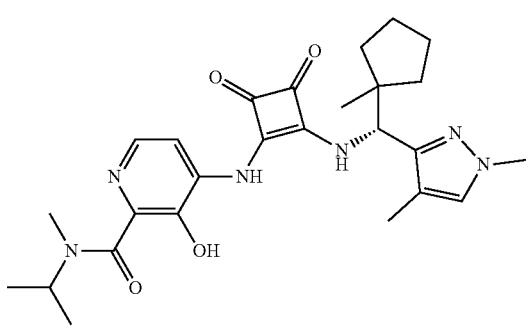 [SMILES: Cc1cn(C)nc1[C@H](Nc1c(Nc2ccnc(C(=O)N(C)C(C)C)c2O)c(=O)c1=O)C1(C)CCCC1]

Step 3A. 4-Chloro-3-methoxypicolinoyl chloride

To a solution of 4-chloro-3-methoxypicolinic acid (5.0 g, 30 mmol) in DCM (59 mL) at 0° C. was added dropwise oxalyl chloride (8.46 g, 5.71 mL, 66.6 mmol). The resulting mixture was warmed to ambient temperature and stirred for 2 h. The reaction was concentrated in vacuo to afford 5.49 g (100%) of the title compound as a light yellow solid. The crude was used directly in the next step without further purification. $^1$H NMR (400 MHz, CDCl$_3$) δ 8.43 (d, J=5.1 Hz, 1H), 7.71-7.51 (m, 1H), 4.01 (s, 3H).

Step 3B. 4-Chloro-N-isopropyl-3-methoxy-N-methylpicolinamide

To a solution of 4-chloro-3-methoxypicolinoyl chloride (175 g, 0.85 mol) in DCM (500 mL) was added Et$_3$N (172 g, 1.7 mol) at 0° C. N-Methylpropan-2-amine (62 g, 0.85 mol) was then added keeping the internal temperature below 10° C. The mixture was stirred at 15° C. for 16 h. Water (500 mL) was added, and the organic layer was separated. The aqueous layer was extracted with DCM (200 mL×2). The combined organic extracts were washed with brine (500 mL), dried over Na$_2$SO$_4$, filtered, and concentrated in vacuo to afford 153 g (74%) of the title compound as a brown oil. The crude product was used directly without further purification.

Step 3C. tert-Butyl (2-(isopropyl(methyl)carbamoyl)-3-methoxypyridin-4-yl)carbamate To a solution of 4-chloro-N-isopropyl-3-methoxy-N-methylpicolinamide (153 g, 0.63 mol) in dioxane (1 L) was added NH$_2$Boc (88.5 g, 0.76 mol) and K$_2$CO$_3$ (130 g, 0.95 mol). The mixture was sparged with N$_2$ and Pd(OAc)$_2$ (11.3 g, 0.05 mol) and xantphos (36.4 g, 0.063 mol) were added. The mixture was heated to 120° C. and stirred for 16 h. The reaction was cooled to 20° C. and filtered through Celite. The filtrate was concentrated in vacuo. The residue was partitioned between EtOAc (500 mL) and water (500 mL). The organic layer was separated and washed with brine (500 mL), dried over Na$_2$SO$_4$, and filtered. The filtrate was concentrated in vacuo, and the crude product was purified by silica gel column chromatography (50 to 66% EtOAc in petroleum ether) to afford 160 g (78%) of the title compound as a yellow solid. $^1$H NMR (400 MHz, CDCl$_3$) δ 8.24-8.20 (m, 1H), 8.07-8.04 (m, 1H), 7.24 (s, 1H), 5.03-5.00 (m, 0.4H), 3.90 (s, 3H), 3.66-3.63 (m, 0.6H), 2.98 (s, 1.7H), 2.69 (s, 1.3H), 1.54 (s, 9H), 1.25-1.20 (m, 3H), 1.16-1.13 (m, 3H).

Step 3D. 4-Amino-N-isopropyl-3-methoxy-N-methylpicolinamide

To a solution of tert-butyl (2-(isopropyl(methyl)carbamoyl)-3-methoxypyridin-4-yl)carbamate (160 g, 0.50 mol) in EtOAc (320 mL) was added HCl/EtOAc (4.0 M, 750 mL). The mixture was stirred at 20° C. for 4 h. The reaction was concentrated in vacuo to afford 150 g (>100%) of the title compound as a brown solid. The crude was used directly without further purification.

Step 3E. 4-Amino-3-hydroxy-N-isopropyl-N-methylpicolinamide

To a solution of 4-amino-N-isopropyl-3-methoxy-N-methylpicolinamide (150 g, 0.67 mol) in DCM (1.5 L) was added TBAI (168 g, 0.47 mol). The mixture was cooled to 0° C. and a solution of BBr$_3$ (420 g, 1.68 mol) in DCM (500 mL) was added dropwise keeping the internal temperature below 10° C. The reaction was stirred at 20° C. for 16 h. The reaction was quenched with saturated aqueous NaHCO$_3$ solution (2.5 L) and adjusted pH to 6-7. The organic layer was separated and washed with water (500 mL). The combined aqueous layers were back-extracted with DCM (1 L×2). The combined organic extracts were concentrated in vacuo, and the residue was treated with DCM:MeOH=10:1 (2 L) for 2 h. The mixture was filtered and the filtrate was concentrated in vacuo. The residue was treated with DCM:MeOH=10:1 (600 mL) for 1 h, and the mixture was filtered. The filtrate was concentrated in vacuo to afford 140 g (99%) of the title compound as a pink solid. The crude was used directly without further purification.

Step 3F. 4-((2-Ethoxy-3,4-dioxocyclobut-1-en-1-yl)amino)-3-hydroxy-N-isopropyl-N-methylpicolinamide To a solution of 4-amino-3-hydroxy-N-isopropyl-N-methylpicolinamide (140 g, 0.67 mol) in EtOH (1.4 L) was added DIPEA (147 g, 1.14 mol) and 3,4-diethoxycyclobut-3-ene-1,2-dione (159 g, 0.94 mol). The mixture was heated to 35° C. and stirred for 16 h. The reaction mixture was filtered and the filtrate was saved for later use. The filter cake was dissolved in water (500 mL) and adjusted pH to 6 with HCl (1.0 M aqueous solution), and extracted with DCM (500 mL×2). The combined DCM extracts were washed with brine (1 L), dried over Na$_2$SO$_4$, filtered and concentrated in vacuo. The residue was triturated with MTBE (500 mL) for 2 h, and then filtered to afford 73 g (33%) of the title compound as a yellow solid. The mother liquor was combined with the filtrate isolated earlier and concentrated in vacuo. The residue was purified by silica gel column chromatography (25 to 50% EtOAc in petroleum ether) to afford additional 30 g (13%) of the title compound as a yellow solid. LCMS m/z 334.2 [M+H]$^+$. $^1$H NMR (400 MHz, CDCl$_3$) δ 13.30 (s, 1H), 8.09 (s, 1H), 8.01-7.90 (m, 2H), 5.85-5.80 (m, 0.5H), 4.95-4.88 (m, 2.5H), 3.50-3.31 (m, 1.5H), 3.03-2.95 (m, 1.5H), 1.55-1.50 (m, 6H), 1.42-1.32 (m, 3H).

Step 3G. (S)—N—((R)-(1,4-Dimethyl-1H-pyrazol-3-yl)(1-methylcyclopentyl)methyl)-2-methylpropane-2-sulfinamide An oven-dried round bottom flask was charged with i-PrMgCl.LiCl (67 mL, 87.1 mmol, 1.3 M solution in THF). The solution was cooled to ° C., and then a solution of 3-Iodo-1,4-dimethyl-1H-pyrazole (15.5 g, 69.7 mmol) in THF (90 mL) was added dropwise over 15 min via addition funnel. The reaction was warmed to ambient temperature and stirred for 1 h. The mixture was cooled back to 0° C., and (S,E)-2-methyl-N-((1-methylcyclopentyl)methylene)-propane-2-sulfinamide (Preparative step 1C) (10.0 g, 46.4 mmol) was added dropwise over 5 min. The mixture was warmed to ambient temperature and stirred for 18 h. The reaction mixture was poured slowly into a saturated aqueous NH$_4$Cl solution (300 mL) at 0° C. The mixture was then extracted with EtOAc (350 mL×2). The combined organic extracts were dried over Na$_2$SO$_4$, filtered and concentrated in vacuo. The crude oil was taken up in MTBE (50 mL) and heptane (100 mL) to give a homogenous solution, which was concentrated in vacuo to give a solid. The solid was suspended in heptane (50 mL) and then concentrated in vacuo. This process was repeated twice, and the final suspension in heptane (50 mL) was cooled to 0° C. to allow more solid to form. The suspension was filtered to afford 11.5 g (80%) of the title compound as a white solid. LCMS m/z 312.2 [M+H]$^+$. $^1$H NMR (500 MHz, DMSO-d$_6$) δ 7.34 (s, 1H), 4.37 (d, J=6.5 Hz, 1H), 4.10 (d, J=6.4 Hz, 1H), 3.72 (s, 3H), 1.96 (s, 3H), 1.72-1.51 (m, 6H), 1.44-1.35 (m, 1H), 1.16-1.03 (m, 1H), 1.01 (d, J=1.8 Hz, 12H).

Step 3H. (R)-(1,4-Dimethyl-1H-pyrazol-3-yl)(1-methylcyclopentyl)methanamine hydrochloride To a solution of (S)—N—((R)-(1,4-dimethyl-1H-pyrazol-3-yl)(1-methylcyclopentyl)methyl)-2-methylpropane-2-sulfinamide (28.7 g, 92.14 mmol) in MeOH (150 mL) at 5° C. was added HCl (50 mL, 200 mmol, 4.0 M in 1,4-dioxane). After stirring for 3 h at 20° C., the solution was concentrated in vacuo to afford the title compound as a mono-HCl salt assuming quantitative yield. The crude product was used directly without further purification. LCMS m/z 191.2 [M-NH$_2$]+. $^1$H NMR (400 MHz, CD$_3$OD) δ 7.39 (s, 1H), 4.25 (s, 1H), 3.86 (s, 3H), 2.07 (s, 3H), 1.75-1.54 (m, 7H), 1.21-1.20 (m, 1H), 1.14 (s, 3H).

Step 3I. (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N-isopropyl-N-methylpicolinamide To a solution of (R)-(1,4-dimethyl-1H-pyrazol-3-yl)(1-methylcyclopentyl)methanamine hydrochloride (3.50 g, 14.36 mmol) in EtOH (50 mL) at 10° C. was added DIEA (3.10 g, 4.31 mL, 24.0 mmol). After stirring for 20 min, a yellow suspension of 4-((2-ethoxy-3,4-dioxocyclobut-1-en-1-yl)amino)-3-hydroxy-N-isopropyl-N-methylpicolinamide (4.0 g, 12.0 mmol) in EtOH (100 mL) was added, and the resulting brown solution was stirred at the same temperature for 16 h. The reaction was concentrated in vacuo. The residue was purified by silica gel column chromatography (80% to 100% EtOAc in petroleum ether). The crude product was azeotroped with EtOH (50 mL×2), and the resulting yellow suspension was concentrated to ~30 mL. Additional EtOH (10 mL) was added and the suspension was stirred at 15° C. for 20 min. The mixture was filtered and the filter cake was washed with EtOH (10 mL). The filter cake was collected and dried to afford 2.62 g (44%) of the title compound as a light yellow solid. LCMS m/z 495.5 [M+H]$^+$. $^1$H NMR (400 MHz, DMSO-d$_6$) δ 11.35 (s, 0.3H), 10.85 (s, 0.7H), 9.88 (s, 1H), 9.11 (d, J=9.8 Hz, 1H), 8.05-7.90 (m, 2H), 7.43 (s, 1H), 5.33 (d, J=10.0 Hz, 1H), 4.81 (s, 0.3H), 4.20 (s, 0.7H), 3.80 (s, 3H), 2.88 (s, 3H), 1.98 (s, 3H), 1.75-1.51 (m, 6H), 1.36-1.32 (m, 1H), 1.25-1.10 (m, 7H), 1.08 (s, 3H). [α]$^{20}_D$=−49.8 (c=0.26, MeOH). Chiral SFC conditions (SFC method D) RT=4.62 min, 100% ee.

Example 4

(R)-4-((2-(((1,4-Dimethyl-1H-pyrazol-3-yl)(1-methylcyclopentyl)methyl)amino)-3,4-dioxocyclobut-1-en-1-yl)amino)-N-ethyl-3-hydroxy-N-methylpicolinamide

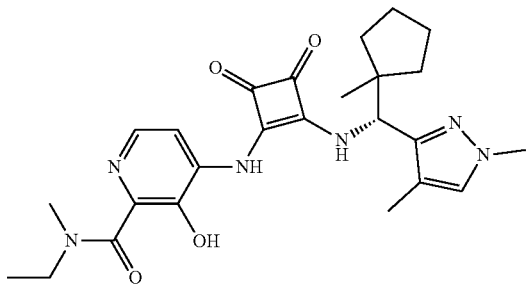 [SMILES: CCN(C)C(=O)c1nccc(Nc2c(N[C@@H](c3nn(C)cc3C)C3(C)CCCC3)c(=O)c2=O)c1O]

Step 4A.
4-Chloro-N-ethyl-3-methoxy-N-methylpicolinamide

N-Methylethanamine (138 g, 233 mmol) and triethylamine (32.3 mL, 233 mmol) were added to a solution of 4-chloro-3-methoxypicolinoyl chloride (Preparative Step 3A) (32 g, 155 mmol) in DCM (150 mL). The mixture was stirred at ambient temperature for 48 h and was then concentrated. The residue was purified by silica gel column chromatography (0 to 100% EtOAc in petroleum ether) to afford 22 g (62%) of the title compound as a yellow oil. $^1$H NMR (400 MHz, CDCl$_3$) δ 8.25 (dd, J=5.3, 6.8 Hz, 1H), 7.35 (d, J=5.3 Hz, 1H), 3.94 (d, J=1.8 Hz, 3H), 3.66-3.55 (m, 1H), 3.23-3.12 (m, 1H), 3.12-2.72 (m, 3H), 1.35-1.05 (m, 3H).

Step 4B. tert-Butyl (2-(ethyl(methyl)carbamoyl)-3-methoxypyridin-4-yl)carbamate To a solution of 4-chloro-N-ethyl-3-methoxy-N-methylpicolinamide (21.3 g, 93 mmol) in dioxane (120 mL) was added NH$_2$Boc (21.8 g, 186 mmol) and K$_2$CO$_3$ (25.7 g, 186 mmol). The mixture was protected under N$_2$ and Pd(OAc)$_2$ (1.05 g, 4.7 mmol) and xantphos (2.7 g, 4.7 mmol) were added. The mixture was heated to 120° C. and stirred for 16 h. The reaction was cooled to 20° C. and filtered through Celite. The filtrate was concentrated in vacuo. The residue was purified by silica gel column chromatography (0 to 100% EtOAc in petroleum ether) to afford 24 g (83%) of the title compound as a yellow solid. $^1$H NMR (400 MHz, CDCl$_3$) δ 8.25 (ddd, J=5.5, 3.8, 0.6 Hz, 1H), 8.09 (dd, J=5.5, 1.6 Hz, 1H), 7.26 (d, J=5.6 Hz, 1H), 3.92 (d, J=1.0 Hz, 3H), 3.64 (q, J=7.2 Hz, 1H), 3.18 (q, J=7.1 Hz, 1H), 3.13 (s, 1.5H), 2.86 (s, 1.5H), 1.56 (s, 9H), 1.28 (t, J=7.2 Hz, 1.5H), 1.13 (t, J=7.1 Hz, 1.5H).

Step 4C.
4-Amino-N-ethyl-3-methoxy-N-methylpicolinamide

A solution of HCl/EtOAc (4.0 M, 40 mL) was added to tert-butyl (2-(ethyl(methyl)-carbamoyl)-3-methoxypyridin-4-yl)carbamate (16 g, 51.7 mmol) and the mixture was stirred at 20° C. for 18 h. The mixture was concentrated in vacuo to afford 12.71 g (100%) of the title compound as a yellow solid. $^1$H NMR (400 MHz, CD$_3$OD) δ 8.00 (dd, J=6.9, 1.5 Hz, 1H), 7.02 (dd, J=6.8, 0.7 Hz, 1H), 3.86 (d, J=2.7 Hz, 3H), 3.35-3.28 (m, 2H), 3.16 (s, 1.5H), 3.00 (s, 1.5), 1.33-1.17 (m, 3H).

Step 4D.
4-Amino-N-ethyl-3-hydroxy-N-methylpicolinamide

To a solution of 4-amino-N-ethyl-3-methoxy-N-methylpicolinamide (5 g, 24 mmol) in DCM (100 mL) was added TBAI (5.7 g, 15.5 mmol). The mixture was cooled to 0° C. and a solution of BBr$_3$ (23.9 g, 95.6 mmol) in DCM (100 mL) was added dropwise keeping the internal temperature below 10° C. The reaction was stirred at 10° C. for 15 h. The reaction was quenched with a solution of aqueous NaOH/MeOH (200 mL MeOH, 11.5 g NaOH, 50 mL water) while keeping the internal temperature at 0° C. The mixture was concentrated in vacuo. The residue was purified by silica gel column chromatography (3 to 9% MeOH in DCM) to afford 3.1 g (78%) of the title compound as a yellow solid. $^1$H NMR (400 MHz, DMSO-d$_6$) δ 7.81 (d, J=6.3 Hz, 1H), 7.39 (br. s., 3H), 6.85 (d, J=6.2 Hz, 1H), 3.52-3.18 (m, 2H), 2.91 (br. s., 3H), 1.37-0.80 (m, 3H).

Step 4E. 4-((2-Ethoxy-3,4-dioxocyclobut-1-en-1-yl)amino)-N-ethyl-3-hydroxy-N-methylpicolinamide To a solution of 4-amino-N-ethyl-3-hydroxy-N-methylpicolinamide (7.01 g, 35.9 mmol) in EtOH (150 mL) was added K$_2$CO$_3$ (4.96 g, 35.9 mmol) and 3,4-diethoxycyclobut-3-ene-1,2-dione (9.17 g, 53.9 mmol). The mixture was heated to 50° C. and stirred for 16 h. The reaction mixture was filtered through Celite and the filtrate was concentrated in vacuo. The residue was purified by silica gel column chromatography (10 to 100% DCM in petroleum ether, 0 to 20% MeOH in DCM) to afford 4.77 g (42%) of the title compound as a brown oil. $^1$H NMR (400 MHz, CDCl$_3$) δ 13.62 (br s, 0.5H), 13.50 (br s, 0.5H), 8.07 (d, J=5.2 Hz, 1H), 7.94 (s, 1H), 7.88 (s, 1H), 4.90 (q, J=7.1 Hz, 2H), 4.16 (br s, 1H), 3.62 (br s, 3H), 3.14 (br s, 1H), 1.55 (t, J=7.1 Hz, 3H), 1.45-1.20 (m, 3H).

Step 4F. (R)-4-((2-(((1,4-Dimethyl-1H-pyrazol-3-yl)(1-methylcyclopentyl)methyl)amino)-3,4-dioxocyclobut-1-en-1-yl)amino)-N-ethyl-3-hydroxy-N-methylpicolinamide A solution of 4-((2-ethoxy-3,4-dioxocyclobut-1-en-1-yl)amino)-N-ethyl-3-hydroxy-N-methylpicolinamide (5.92 g, 18.54 mmol) in EtOH (140 mL) was added to (R)-(1,4-dimethyl-1H-pyrazol-3-yl)(1-methylcyclopentyl)methanamine L-pyroglutamic acid salt (Preparative step 1G) (7.48 g, 22.2 mmol) and DIPEA (4.79 g, 37.1 mmol) in EtOH (50 mL). The reaction was stirred at room temperature for 16 h and then the reaction mixture was concentrated. The residue was purified by silica gel column chromatography (petroleum ether/EtOAc, 1:5 to 0:1) to give 4.4 g (49%) of the title compound as a yellow solid. LCMS m/z 481.1 [M+H]$^+$. $^1$H NMR (400 MHz, CD$_3$OD) δ 8.22 (br. s., 1H), 7.94 (br. s., 1H), 7.28 (s, 1H), 5.44 (s, 1H), 3.83 (s, 3H), 3.65 (br. s., 2H), 3.28-3.06 (m, 3H), 2.09 (s, 3H), 1.92-1.58 (m, 6H), 1.53-1.42 (m, 1H), 1.38-1.21 (m, 4H), 1.17 (s, 3H). [α]$^{26}_D$=−77.88 (c=0.5, MeOH). Chiral SFC (SFC method F) RT=3.52 min, 99% ee.

Example 5

(S)-4-((2-(((1,4-Dimethyl-1H-pyrazol-3-yl)(1-methylcyclopentyl)methyl)amino)-3,4-dioxocyclobut-1-en-1-yl)amino)-N-ethyl-3-hydroxy-N-methylpicolinamide

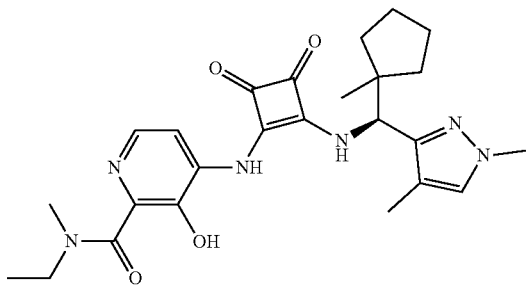 [SMILES: CCN(C)C(=O)c1nccc(Nc2c(N[C@H](c3nn(C)cc3C)C3(C)CCCC3)c(=O)c2=O)c1O]

The title compound was prepared analogous to Example 4 employing (S)-(1,4-dimethyl-1H-pyrazol-3-yl)(1-methylcyclopentyl)methanamine (Example 2). LCMS m/z 481.4 [M+H]$^+$. $^1$H NMR (400 MHz, DMSO-d$_6$) δ 11.70 (br. s., 1H), 9.90 (br. s., 1H), 9.15 (br. s., 1H), 8.00 (br. s., 2H), 7.43 (s, 1H), 5.34 (d, J=10.0 Hz, 1H), 3.80 (s, 3H), 3.54 (br. s., 2H), 3.17 (br. s., 1H), 3.02 (br. s., 2H), 1.98 (s, 3H), 1.75-1.52 (m, 6H), 1.40-1.28 (m, 1H), 1.25-1.10 (4H), 1.08 (s, 3H). [α]$^{29}_D$=+80.8 (c=0.5, MeOH). Chiral SFC (SFC method K) RT=3.11 min, 99% ee.

Example 6

(R)-3-(((1,4-dimethyl-1H-pyrazol-3-yl)(1-methylcyclopentyl)methyl)amino)-4-((3-hydroxy-2-(morpholine-4-carbonyl)pyridin-4-yl)amino)cyclobut-3-ene-1,2-dione

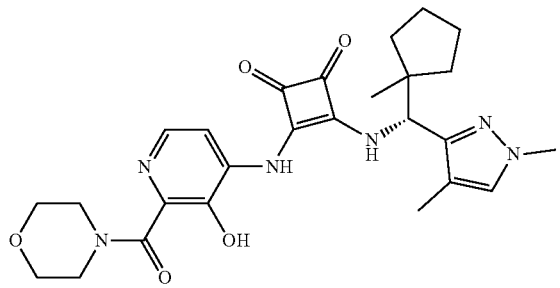 [SMILES: Cc1cn(C)nc1[C@H](Nc1c(Nc2ccnc(C(=O)N3CCOCC3)c2O)c(=O)c1=O)C1(C)CCCC1]

Step 6A. tert-Butyl 4-chloro-3-methoxypicolinate

To a solution of pyridine (7.91 g, 8.05 mL, 100 mmol) and t-BuOH (7.90 g, 10.1 mL, 107 mmol) in DCM (32 mL) at 0° C. was added dropwise a solution of 4-chloro-3-methoxypicolinoyl chloride (Preparative Step 3A) (5.49 g, 26.7 mmol) in DCM (26.7 mL). The reaction was stirred at 0° C. for 15 min, warmed to ambient temperature and then heated at reflux for 4 h. The solvent was removed in vacuo and the residue was taken dissolved in EtOAc. The solution was washed with 1 N aqueous NaOH solution and brine, filtered and concentrated in vacuo. The residue was purified using silica gel column chromatography (0 to 20% EtOAc in DCM) to afford 3.10 g (48%) of the title compound as a liquid. LCMS m/z 188.1 [M-tBu]$^+$. $^1$H NMR (400 MHz, CDC 1) 8.30 (d, J=5.1 Hz, 1H), 7.42 (d, J=5.1 Hz, 1H), 3.98 (s, 3H), 1.65 (s, 9H).

Step 6B. tert-Butyl 4-((2-ethoxy-3,4-dioxocyclobut-1-en-1-yl)amino)-3-methoxypicolinate To the mixture of 3-amino-4-ethoxycyclobut-3-ene-1,2-dione (169.2 g, 1.2 mol) and Na$_2$CO$_3$ (67.84 g, 0.64 mol) in THF (1.8 L) was added tert-butyl 4-chloro-3-methoxypicolinate (97.2 g, 0.4 mol) at 25° C. The mixture was degassed and purged with N$_2$ for 3 times. tBuXPhos-Pd-G$_3$ (15.9 g, 0.02 mol) and tBuXPhos (8.48 g, 0.02 mol) were added. The reaction mixture was degassed and purged with N$_2$ for 3 times. The reaction mixture was heated to 80° C. and stirred for 16 hr. The mixture was cooled to 25° C. and then filtered through Celite. The filtrate was concentrated in vacuo. The residue was purified by silica gel column chromatography (0 to 50% DCM in petroleum ether, then 0 to 2.5% THF in DCM). The resulting oil was triturated with heptane (250 mL) and stirred at 25° C. for 3 h. The mixture was filtered to afford 84.7 g, 60% of the title compound as a light yellow solid. LCMS m/z 349.1 [M+H]$^+$. $^1$H NMR (400 MHz, CDCl$_3$) δ 3 8.38 (d, J=5.4 Hz, 1H), 7.93 (br s, 2H), 4.95 (q, J=7.1 Hz, 2H), 4.01 (s, 3H), 1.68 (s, 9H), 1.59 (t, J=7.2 Hz, 3H).

Step 6C. tert-Butyl (R)-4-((2-(((1,4-dimethyl-1H-pyrazol-3-yl)(1-methylcyclopentyl)methyl)-amino)-3,4-dioxocyclobut-1-en-1-yl)amino)-3-methoxypicolinate DIEA (6.0 g, 46.4 mmol) was added to a solution of (R)-(1,4-dimethyl-1H-pyrazol-3-yl)(1-methylcyclopentyl)methanamine hydrochloride (Preparative step 3H) (4.70 g, 19.3 mmol) in EtOH (70 mL). The mixture was stirred for 10 min, and then tert-butyl 4-((2-ethoxy-3,4-dioxocyclobut-1-en-1-yl)amino)-3-methoxypicolinate (4.0 g, 11.5 mmol) was added. The resulting mixture was stirred at 20° C. for 70 h and then was concentrated in vacuo. The residue was purified by silica gel column chromatography (0 to 80% EtOAc in petroleum ether) to afford 5.85 g (100%) of the title compound as a yellow solid. LCMS m/z 510.1 [M+H]$^+$. $^1$H NMR (400 MHz, DMSO-d$_6$) δ 9.97 (s, 1H), 9.06-9.02 (m, 1H), 8.20-8.18 (m, 1H), 8.09-8.07 (m, 1H), 7.44 (s, 1H), 5.36-5.33 (m, 1H), 3.84 (s, 3H), 3.80 (s, 3H), 1.98 (s, 3H), 1.72-1.53 (m, 15H), 1.35-1.30 (m, 1H), 1.24-1.15 (m, 1H), 1.09 (s, 3H).

Step 6D. (R)-4-((2-(((1,4-Dimethyl-1H-pyrazol-3-yl)(1-methylcyclopentyl)methyl)amino)-3,4-dioxocyclobut-1-en-1-yl)amino)-3-methoxypicolinic acid TFA (25 g, 16.3 mL, 219.3 mmol) was added to a solution of tert-butyl (R)-4-((2-(((1,4-dimethyl-1H-pyrazol-3-yl)(1-methylcyclopentyl)methyl)amino)-3,4-dioxocyclobut-1-en-1-yl)amino)-3-methoxypicolinate (6.60 g, 13.0 mmol) in DCM (50 mL). The resulting solution was stirred at ambient temperature for 44 h. The mixture was concentrated in vacuo, and the pH was adjusted to ~8 using saturated aqueous NaHCO$_3$ solution. The mixture was extracted with DCM (20 mL). The aqueous layer was acidified to pH ~3 with 1 N aqueous HCl solution and then was extracted with DCM (100 mL×5). The combined organic extracts were concentrated in vacuo to afford 5.8 g (99%) of the title compound as a yellow solid. LCMS m/z 454.4 [M+H]$^+$.

Step 6E. (R)-3-(((1,4-Dimethyl-1H-pyrazol-3-yl)(1-methylcyclopentyl)methyl)amino)-4-((3-methoxy-2-(morpholine-4-carbonyl)pyridin-4-yl)amino)cyclobut-3-ene-1,2-dione HATU (377 mg, 0.99 mmol) was added to a solution of (R)-4-((2-(((1,4-dimethyl-1H-pyrazol-3-yl)(1-methylcyclopentyl)methyl)amino)-3,4-dioxocyclobut-1-en-1-yl)amino)-3-methoxypicolinic acid (300 mg, 0.66 mmol), morpholine (57.6 mg, 0.66 mmol) and TEA (134 mg, 1.32 mmol) in DCM (5 mL) at 0° C. The resulting mixture was stirred at 25° C. for 16 h and then was concentrated in vacuo. The residue was dissolved in EtOAc (10 mL) and washed with saturated aqueous KHCO$_2$ solution (10 mL). The aqueous layer was extracted with EtOAc (40 mL×3). The combined organic extracts were dried over Na$_2$SO$_4$, filtered and concentrated in vacuo to afford the title compound as a yellow solid. The crude was used directly without further purification assuming quantitative yield. LCMS m/z 523.2 [M+H]$^+$. $^1$H NMR (400 MHz, CD$_3$OD) δ 8.28-8.26 (m, 1H), 8.21-8.19 (m, 1H), 7.29 (s, 1H), 5.45 (s, 1H), 3.94 (s, 3H), 3.90-3.75 (m, 5H), 3.68-3.64 (m, 2H), 3.01-2.96 (m, 4H), 2.09 (s, 3H), 1.90-1.65 (m, 7H), 1.50-1.42 (m, 1H), 1.18 (s, 3H).

Step 6F. (R)-3-(((1,4-Dimethyl-1H-pyrazol-3-yl)(1-methylcyclopentyl)methyl)amino)-4-((3-hydroxy-2-(morpholine-4-carbonyl)pyridin-4-yl)amino)cyclobut-3-ene-1,2-dione To a solution of (R)-3-(((1,4-dimethyl-1H-pyrazol-3-yl)(1-methylcyclopentyl)methyl)-amino)-4-((3-methoxy-2-(morpholine-4-carbonyl)pyridin-4-yl)amino)cyclobut-3-ene-1,2-dione (600 mg, 1.15 mmol) in 1,4-dioxane (5 mL) at 15° C. was added MgBr$_2$ (634 mg, 3.44 mmol). The mixture was heated at 120° C. for 2 h. The reaction mixture was filtered and the filtrate was concentrated in vacuo. The residue was purified using preparative HPLC (Agela Durashell C18 150 mm×25 mm×5 μm, 30 to 50% MeCN in 0.225% formic acid in water, 25 mL/min, 11 min) to afford 66 mg (11%) of the title compound as a yellow solid. LCMS m/z 509.4 [M+H]$^+$. $^1$H NMR (400 MHz, CD$_3$OD) δ 8.22 (d, J=5.5 Hz, 1H), 7.91 (br s, 1H), 7.28 (s, 1H), 5.44 (s, 1H), 3.90-3.70 (m, 11H), 2.09 (s, 3H), 1.90-1.65 (m, 6H), 1.50-1.43 (m, 1H), 1.35-1.26 (m, 1H), 1.17 (s, 3H). [α]$^{20}_D$=−65.6 (c=0.17, MeOH). Chiral SFC conditions (SFC method K) RT=3.47 min, 100% ee.

Example 7

(R)-3-(((1,4-Dimethyl-1H-pyrazol-3-yl)(1-methylcyclopentyl)methyl)amino)-4-((3-hydroxy-2-(4-methylpiperazine-1-carbonyl)pyridin-4-yl)amino)cyclobut-3-ene-1,2-dione

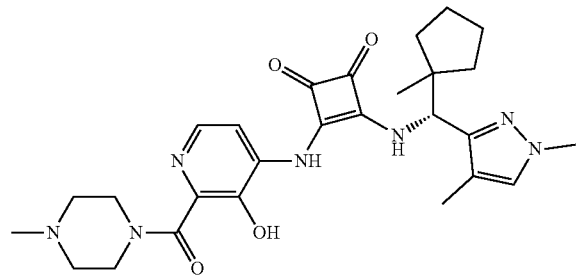

The title compound was prepared following a similar procedure to the preparation of (R)-3-(((1,4-dimethyl-1H-pyrazol-3-yl)(1-methylcyclopentyl)methyl)amino)-4-((3-hydroxy-2-(morpholine-4-carbonyl)pyridin-4-yl)amino)cyclobut-3-ene-1,2-dione (Example 6) employing 1-methylpiperazine to yield 19.7 mg (9%) of the title compound as a yellow solid. LCMS m/z 522.5 [M+H]$^+$. $^1$H NMR (400 MHz, CD$_3$OD) δ 8.35 (s, 1H), 8.24 (d, J=5.6 Hz, 1H), 7.90 (d, J=5.6 Hz, 1H), 7.28 (s, 1H), 5.44 (s, 1H), 3.92 (br s, 4H), 3.82 (s, 3H), 2.80 (br s, 4H), 2.53 (s, 3H), 2.09 (s, 3H), 1.90-1.65 (m, 6H), 1.51-1.42 (m, 1H), 1.35-1.25 (m, 1H), 1.17 (s, 3H). Chiral SFC (SFC method F) RT=3.66 min, 98.6% ee.

Example 8

(R)-4-((2-(((4-Chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide

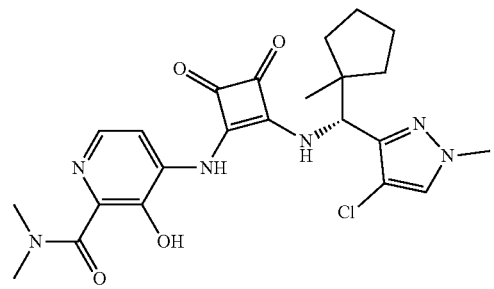

Step 8A. (R)-2-Methyl-N—((R)-(1-methyl-1H-pyrazol-3-yl)(1-methylcyclopentyl)methyl)propane-2-sulfinamide To a solution of i-PrMgCl.LiCl (20.1 mL, 26.2 mmol, 1.3 M solution in THF) at −30° C. was added a solution of 3-iodo-1-methyl-1H-pyrazole (4.35 g, 20.9 mmol) in THF (20 mL). The resulting yellow solution was stirred at 30-40° C. for 2 h. The reaction was cooled to −30° C. and a solution of (S,E)-2-methyl-N-((1-methylcyclopentyl)methylene)propane-2-sulfinamide (Preparactive Step 1C) (3.0 g, 13.93 mmol) in THF (5 mL) was added dropwise. The reaction mixture was warmed to 30° C. and stirred for 16 h. The reaction mixture was poured slowly into a saturated aqueous NH₄Cl solution (100 mL) at 5° C. and diluted with water (20 mL). The mixture was then extracted with EtOAc (50 mL×2). The combined organic extracts were dried over Na₂SO₄, filtered and concentrated in vacuo. The residue was purified by silica gel column chromatography (0 to 80% EtOAc in petroleum ether) to afford 3.48 g (84%) of the title compound as a yellow oil. LCMS m/z 297.9 [M+H]⁺. ¹H NMR (400 MHz, CDCl₃) δ 3 7.26 (d, J=2.1 Hz, 1H), 6.08 (d, J=2.2 Hz, 1H), 4.34 (d, J=3.4 Hz, 1H), 3.86 (s, 3H), 3.59-3.55 (m, 1H), 1.80-1.55 (m, 6H), 1.50-1.43 (s, 1H), 1.18 (s, 9H), 1.18-1.12 (m, 1H), 0.98 (s, 3H).

Step 8B. (R)-(1-Methyl-1H-pyrazol-3-yl)(1-methylcyclopentyl)methanamine

HCl (80 mL, 4.0 M solution in MeOH) was added to a solution of (R)-2-methyl-N—((R)-(1-methyl-1H-pyrazol-3-yl)(1-methylcyclopentyl)methyl)propane-2-sulfinamide (6.59 g, 22.15 mmol) in MeOH (50 mL). The resulting solution was stirred at ambient temperature for 3 h and then concentrated in vacuo. The title compound was isolated as the mono-HCl salt assuming quantitative yield and used directly without further purification. LCMS m/z 193.8 [M+H]⁺. ¹H NMR (400 MHz, CD₃OD) δ 7.63 (d, J=2.3 Hz, 1H), 6.33 (d, J=2.3 Hz, 1H), 4.25 (s, 1H), 3.92 (s, 3H), 1.85-1.65 (m, 6H), 1.60-1.55 (m, 1H), 1.31-1.25 (m, 1H), 1.05 (s, 3H). The absolute stereochemistry of the title compound was assigned by analogy to Preparative Example 1F.

Step 8C. tert-Butyl (R)-((1-methyl-1H-pyrazol-3-yl)(1-methylcyclopentyl)methyl)carbamate To a solution of (R)-(1-methyl-1H-pyrazol-3-yl)(1-methylcyclopentyl)methanamine (5.09 g, 22.2 mmol) in MeOH (150 mL) at 15° C. was added TEA (9.25 mL, 66.5 mmol) and (Boc)₂O (7.25 g, 33.2 mmol). The resulting mixture was stirred for 16 h. The reaction was concentrated in vacuo and the residue was purified by silica gel column chromatography (0 to 20% EtOAc in petroleum ether) to afford 5.72 g (88%) of the title compound as a light yellow oil. LCMS m/z 176.8 [M-BocNH]⁺. ¹H NMR (400 MHz, CDCl₃) δ 7.24 (d, J=2.2 Hz, 1H), 6.07 (d, J=2.2 Hz, 1H), 5.39-5.30 (m, 1H), 4.67 (d, J=9.5 Hz, 1H), 3.87 (s, 3H), 1.79-1.61 (m, 6H), 1.44 (s, 9H), 1.38-1.17 (m, 2H), 0.94 (s, 3H).

Step 8D. tert-Butyl (R)-((4-chloro-1-methyl-1H-pyrazol-3-yl)(1-methylcyclopentyl)methyl)-carbamate NCS (3.12 g, 23.4 mmol) was added portionwise to a solution of tert-butyl (R)-((1-methyl-1H-pyrazol-3-yl)(1-methylcyclopentyl)methyl)carbamate (5.72 g, 19.5 mmol) in DMF (100 mL). The mixture was heated at 50° C. for 16 h. After cooling to ambient temperature, the reaction was poured into a 3% aqueous LiCl solution (150 mL) and then extracted with EtOAc (70 mL×2). The combined organic extracts were concentrated in vacuo. The residue was purified using silica gel column chromatography (0 to 15% EtOAc in petroleum ether) to afford 6.0 g (94%) of the title compound as a pale yellow oil. LCMS m/z 210.7 [M-BocNH]⁺. ¹H NMR (400 MHz, CDCl₃) δ 3 7.25 (s, 1H), 5.32-5.29 (m, 1H), 4.79 (d, J=9.7 Hz, 1H), 3.82 (s, 3H), 1.80-1.55 (m, 6H), 1.42 (s, 9H), 1.40-1.30 (m, 1H), 1.21-1.12 (m, 1H), 1.00 (s, 3H).

Step 8E. (R)-(4-Chloro-1-methyl-1H-pyrazol-3-yl)(1-methylcyclopentyl)methanamine To a mixture of tert-butyl (R)-((4-chloro-1-methyl-1H-pyrazol-3-yl)(1-methylcyclopentyl)methyl)carbamate (6.0 g, 18.3 mmol) in MeOH (20 mL) at 15° C. was added HCl (150 mL, 600 mmol, 4.0 M in MeOH). The mixture was stirred for 5 h and then concentrated in vacuo. The title compound was isolated as the mono-HCl salt assuming quantitative yield and used directly without further purification. LCMS m/z 228.0 [M+H]⁺. ¹H NMR (400 MHz, CD₃OD) δ 7.77 (s, 1H), 4.32 (s, 1H), 3.92 (s, 3H), 1.90-1.55 (m, 7H), 1.30-1.22 (m, 1H), 1.15 (s, 3H).

Figure 2:
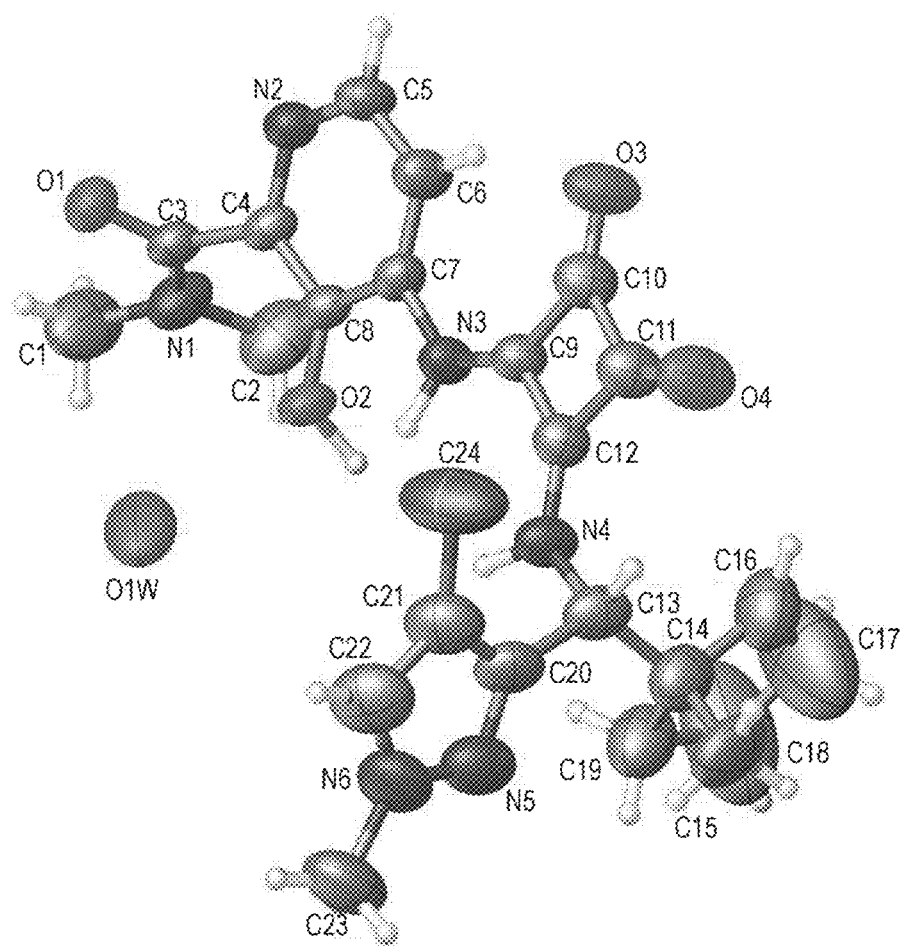
FIG. 2 is an X-ray structure (ORTEP drawing) of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

Step 8F. (R)-4-((2-(((4-Chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide DIEA (5.0 g, 38.7 mmol) was added to a suspension of (R)-(4-chloro-1-methyl-1H-pyrazol-3-yl)(1-methylcyclopentyl)methanamine (5.90 g, 22.3 mmol) in EtOH (100 mL). The mixture was stirred for 30 min, and then 4-((2-ethoxy-3,4-dioxocyclobut-1-en-1-yl)amino)-3-hydroxy-N,N-dimethylpicolinamide (Preparative Step 1H) (5.0 g, 16.4 mmol) was added. The resulting mixture was stirred at 20° C. for 16 h. The reaction mixture was filtered and the solids were washed with EtOH (10 mL×3). The solids were suspended in water (30 mL) and heated at 50° C. for 3 h. The suspension was filtered. The solids were washed with water (10 mL×3) and dried to afford 5.24 g (66%) of the title compound as a yellow solid. LCMS m/z 487.3 [M+H]⁺. ¹H NMR (400 MHz, DMSO-d₆) δ 11.67 (br s, 1H), 9.95 (br s, 1H), 9.18 (s, 1H), 8.01 (s, 2H), 7.95 (s, 1H), 5.44 (d, J=10.0 Hz, 1H), 3.86 (s, 3H), 3.18 (br s, 3H), 3.05 (br s, 3H), 1.78-1.58 (m, 6H), 1.39-1.31 (m, 1H), 1.21-1.10 (m, 1H), 1.07 (s, 3H). [α]²⁴_D=−145.151 (c=0.50, MeOH). Chiral SFC (SFC method F) RT=3.85 min, 100% ee. The absolute configuration was established by single crystal X-ray analysis (FIG. 2).

Example 9

(S)-4-((2-(((4-Chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide

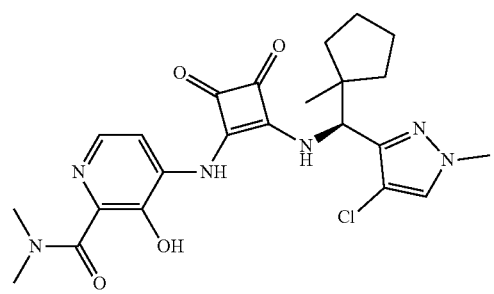

The title compound was prepared analogous to Example 8 employing (R)-2-methylpropane-2-sulfinamide. LCMS m/z 487.4 [M+H]⁺. ¹H NMR (400 MHz, DMSO-$d_6$) δ 11.68 (br. s., 1H), 9.92 (br. s., 1H), 9.16 (br. s., 1H), 8.02-7.98 (m, 2H), 7.94 (s, 1H), 5.37 (d, J=10.2 Hz, 1H), 3.86 (s, 3H), 3.18 (br. s., 3H), 3.05 (br. s., 3H), 1.74-1.55 (m, 6H), 1.37-1.30 (m, 1H), 1.21-1.14 (m, 1H), 1.07 (s, 3H). [α]$^{20}_D$=+107.3 [c=1, MeOH). Chiral SFC (SFC method L) RT=6.28 min, 98% ee.

Example 10

(R)-4-((2-(((4-Chloro-1-methyl-1H-pyrazol-3-yl)(1-methylcyclopentyl)methyl)amino)-3,4-dioxocyclobut-1-en-1-yl)amino)-3-hydroxy-N-isopropyl-N-methylpicolinamide

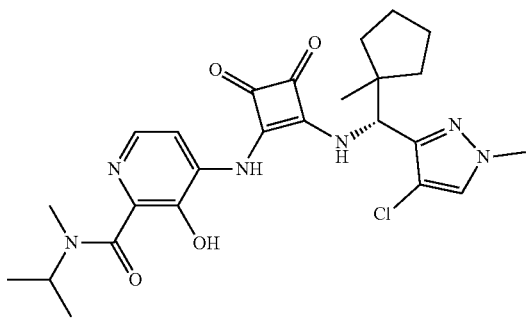 [SMILES: CC(C)N(C)C(=O)c1nccc(Nc2c(N[C@@H](c3nn(C)cc3Cl)C3(C)CCCC3)c(=O)c2=O)c1O]

The title compound was prepared from 4-((2-ethoxy-3,4-dioxocyclobut-1-en-1-yl)amino)-3-hydroxy-N-isopropyl-N-methylpicolinamide (Preparative Step 3F) and (R)-(4-chloro-1-methyl-1H-pyrazol-3-yl)(1-methylcyclopentyl) methanamine (Preparative Step 8E) following the same procedure as the preparation of Example 8. Yellow solid, 64 mg (41%). LCMS m/z 515.3 [M+H]⁺. ¹H NMR (400 MHz, CD₃OD) δ 8.21 (d, J=5.1 Hz, 1H), 7.93 (br s, 1H), 7.64 (s, 1H), 5.55 (s, 1H), 4.70-4.55 (m, 0.4H), 4.40-4.20 (m, 0.6H), 3.88 (s, 3H), 3.01 (s, 3H), 1.95-1.62 (m, 6H), 1.51-1.42 (m, 1H), 1.35-1.20 (m, 7H), 1.18 (s, 3H). [α]$^{20}_D$=−75.5 (c=0.23, MeOH). Chiral SFC (SFC method B) RT=1.59 min, 100% ee.

Example 11

(R)-3-Hydroxy-N-isopropyl-4-((2-(((4-methoxy-1-methyl-1H-pyrazol-3-yl)(1-methyl-cyclopentyl) methyl)amino)-3,4-dioxocyclobut-1-en-1-yl)amino)-N-methylpicolinamide

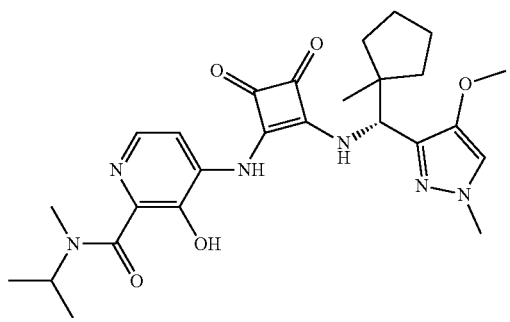 [SMILES: COc1cn(C)nc1[C@H](Nc1c(Nc2ccnc(C(=O)N(C)C(C)C)c2O)c(=O)c1=O)C1(C)CCCC1]

Step 11A. 3-Iodo-4-methoxy-1-methyl-1H-pyrazole

NIS (4.41 g, 19.6 mmol) was added to a solution of 4-methoxy-1-methyl-1H-pyrazole (2.20 g, 19.6 mmol) in DMF (20 mL). The reaction mixture was stirred at ambient temperature for 18 h. The mixture was diluted with water (100 mL) and brine (20 mL), and extracted with EtOAc (50 mL×5). The combined organic extracts were concentrated in vacuo. The residue was purified by silica gel column chromatography (0 to 16% EtOAc in petroleum ether) to afford 310 mg, (7%) of the title compound as a brown solid. LCMS m/z 238.8 [M+H]⁺. ¹H NMR (400 MHz, CDCl₃) δ 6.91 (s, 1H), 3.86 (s, 3H), 3.78 (s, 3H).

Step 11B. (R)—N—((R)-(4-Methoxy-1-methyl-1H-pyrazol-3-yl)(1-methylcyclopentyl)methyl)-2-methylpropane-2-sulfinamide To a solution of 3-iodo-4-methoxy-1-methyl-1H-pyrazole (399 mg, 1.68 mmol) in freshly distilled THF (4 mL) at −40° C. was added i-PrMgCl.LiCl (3 mL, 3.90 mmol, 1.3 M solution in THF). The resulting mixture was stirred at ambient temperature for 2 h, and then cooled to −40° C. A solution of (S,E)-2-methyl-N-((1-methylcyclopentyl)methylene)propane-2-sulfinamide (Preparactive Step 1C) (250 mg, 1.16 mmol) in freshly distilled THF (1 mL) was added. The reaction mixture was warmed to ambient temperature and stirred for 16 h. The reaction was quenched with saturated aqueous NH₄Cl solution (1 mL) at 0° C., and extracted with EtOAc. The combined organic extracts were concentrated in vacuo. The residue was purified by silica gel column chromatography (0 to 100% EtOAc in petroleum ether) to afford 150 mg, 33% of the title compound as a yellow oil. LCMS m/z 327.9 [M+H]⁺. ¹H NMR (400 MHz, CDCl₃) δ 6.95 (s, 1H), 4.31-4.29 (m, 1H), 4.15-4.13 (m, 1H), 3.77 (s, 3H), 3.69 (s, 3H), 1.80-1.70 (m, 2H), 1.70-1.55 (m, 4H), 1.50-1.42 (m, 2H), 1.11 (s, 9H), 1.02 (s, 3H).

Step 11C. (R)-(4-Methoxy-1-methyl-1H-pyrazol-3-yl)(1-methylcyclopentyl)methanamine HCl (2.5 mL, 4.0 M in 1,4-dioxane) was added to a solution of (R)—N—((R)-(4-methoxy-1-methyl-1H-pyrazol-3-yl)(1-methylcyclopentyl)methyl)-2-methylpropane-2-sulfinamide (150 mg, 0.458 mmol) in MeOH (15 mL). The resulting solution was stirred for 4 h and then was concentrated in vacuo. The title compound was isolated as a mono-HCl salt assuming quantitative yield and used directly without further purification. LCMS m/z 207.3 [M-NH₂]+. ¹H NMR (400 MHz, CD₃OD) δ 7.40 (s, 1H), 4.19 (s, 1H), 3.82 (s, 3H), 3.75 (s, 3H), 1.80-1.61 (m, 6H), 1.51-1.45 (m, 1H), 1.25-1.15 (m, 1H), 1.09 (s, 3H). The absolute stereochemistry of the title compound was assigned by analogy to Preparative Example 1F.

Step 11D. (R)-3-Hydroxy-N-isopropyl-4-((2-(((4-methoxy-1-methyl-1H-pyrazol-3-yl)(1-methylcyclopentyl)methyl)amino)-3,4-dioxocyclobut-1-en-1-yl)amino)-N-methylpicolinamide To a suspension of (R)-(4-methoxy-1-methyl-1H-pyrazol-3-yl)(1-methylcyclopentyl)-methanamine (2.43 g, 9.35 mmol) in EtOH (60 mL) at 5° C. was added DIEA (11.8 g, 91.5 mmol). After stirring for 10 min, 4-((2-ethoxy-3,4-dioxocyclobut-1-en-1-yl)amino)-3-hydroxy-N-isopropyl-N-methylpicolinamide (Preparative Step 3F) (3.05 mg, 9.15 mmol) was added. The resulting solution was stirred for 3 d.

The mixture was concentrated in vacuo. The residue was purified by silica gel column chromatography (20 to 100% EtOAc in petroleum ether). The crude product was taken up in EtOH (30 mL) and stirred at 20° C. for 16 h. The slurry was filtered to afford 3.26 g (70%) of the title compound as a yellow solid. LCMS m/z 511.4 [M+H]+. $^1$H NMR (400 MHz, DMSO-$d_6$) δ 11.34 (s, 0.3H), 10.84 (s, 0.7H), 9.94 (s, 1H), 9.13 (d, J=9.8 Hz, 1H), 7.99-7.94 (m, 2H), 7.48 (s, 1H), 5.34 (d, J=10.3 Hz, 1H), 4.82 (br s, 0.3H), 4.18 (br s, 0.7H), 3.78 (s, 3H), 3.67 (s, 3H), 2.95-2.84 (m, 3H), 1.72-1.50 (m, 6H), 1.35-1.24 (m, 1H), 1.21-1.10 (m, 7H), 1.02 (s, 3H). $[α]^{24}_D$=−114.4 (c=0.50, MeOH). Chiral SFC (SFC method B) RT=1.52 min, 100% ee.

Example 12

(R)-3-Hydroxy-4-((2-(((4-methoxy-1-methyl-1H-pyrazol-3-yl)(1-methylcyclopentyl)methyl)amino)-3,4-dioxocyclobut-1-en-1-yl)amino)-N,N-dimethylpicolinamide

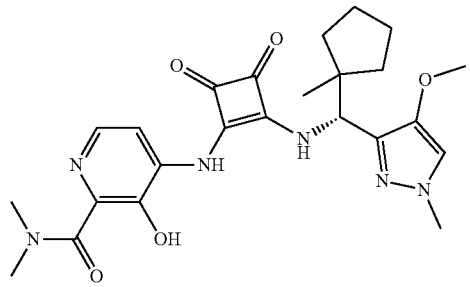

The title compound was prepared from 4-((2-ethoxy-3,4-dioxocyclobut-1-en-1-yl)amino)-3-hydroxy-N,N-dimethylpicolinamide (Preparative Step 1H) and (R)-(4-methoxy-1-methyl-1H-pyrazol-3-yl)(1-methylcyclopentyl)methanamine (Preparative Step 11C) following similar procedure as for the preparation of Example 11. Yellow solid, 45 mg (56%). LCMS m/z 483.4 [M+H]+. $^1$H NMR (400 MHz, CD$_3$OD) δ 8.21 (d, J=5.5 Hz, 1H), 7.90 (d, J=5.5 Hz, 1H), 7.30 (s, 1H), 5.43 (s, 1H), 3.78 (s, 3H), 3.74 (s, 3H), 3.24 (br s, 3H), 3.17 (br s, 3H), 1.91-1.74 (m, 2H), 1.70-1.60 (m, 4H), 1.45-1.35 (m, 1H), 1.30-1.20 (m, 1H), 1.11 (s, 3H). $[α]^{24}_D$=−87.5 (c=0.50, MeOH). Chiral SFC (SFC method F) RT=4.86 min, 97.4% ee.

Example 13

(R)-3-Hydroxy-4-((2-((1-(4-methoxy-1-methyl-1H-pyrazol-3-yl)-2,2-dimethylpropyl)amino)-3,4-dioxocyclobut-1-en-1-yl)amino)-N,N-dimethylpicolinamide

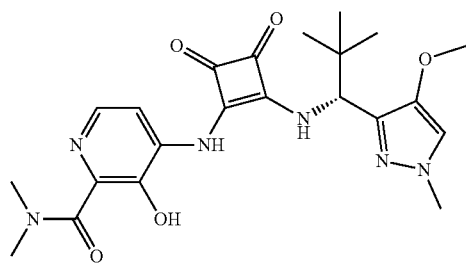

Step 13A. (S,E)-N-(2,2-Dimethylpropylidene)-2-methylpropane-2-sulfinamide

Titanium (IV) ethoxide (68.9 g, 302 mmol) was added to a solution of pivaldehyde (10.0 g, 116 mmol) in DCM (830 mL). The mixture was stirred for 20 min, and then (S)-2-methylpropane-2-sulfinamide (14.1 g, 116 mmol) was added. The resulting mixture was stirred at ambient temperature for 16 h and then was quenched with water (250 mL). The mixture was filtered and the solids were washed with THF (500 mL×2). The combined organic layers were concentrated in vacuo. The residue was purified by silica gel column chromatography (0 to 5% EtOAc in petroleum ether) to afford 24.4 g (75%) of the title compound as a colorless oil. LCMS m/z 190.2 [M+H]+. $^1$H NMR (400 MHz, CDCl$_3$) δ 3 7.92 (s, 1H), 1.20 (s, 9H), 1.16 (s, 9H).

Step 13B. (R)—N—((R)-1-(4-Methoxy-1-methyl-1H-pyrazol-3-yl)-2,2-dimethylpropyl)-2-methylpropane-2-sulfinamide To a solution of 3-iodo-4-methoxy-1-methyl-1H-pyrazole (Preparative Step 11A) (250 mg, 1.05 mmol) in freshly distilled THF (0.7 mL) at −40° C. was added i-PrMgCl.LiCl (1.7 mL, 2.22 mmol, 1.3 M solution in THF). The resulting mixture was stirred at 15° C. for 1 h, and then cooled to −40° C. A solution of (S,E)-N-(2,2-dimethylpropylidene)-2-methylpropane-2-sulfinamide (140 mg, 0.74 mmol) in freshly distilled THF (0.5 mL) was added. The mixture was warmed to 15° C. and stirred for 16 h. The reaction mixture was quenched with saturated aqueous NH$_4$Cl solution (1 mL) at 0° C. and extracted with EtOAc. The combined organic extracts were concentrated in vacuo. The residue was purified by silica gel column chromatography (0 to 100% EtOAc in petroleum ether) to afford 80 mg (36%) of the title compound as a yellow oil. LCMS m/z 301.9 [M+H]+. $^1$H NMR (400 MHz, CDCl$_3$) δ 6.97 (s, 1H), 5.32-5.31 (m, 1H), 4.20-4.15 (m, 1H), 3.83 (s, 3H), 3.71 (s, 3H), 1.11 (s, 9H), 1.01 (s, 9H).

Step 13C. (R)-1-(4-Methoxy-1-methyl-1H-pyrazol-3-yl)-2,2-dimethylpropan-1-amine

HCl (1.2 mL, 4.0 M in MeOH) was added to a solution of (R)—N—((R)-1-(4-methoxy-1-methyl-1H-pyrazol-3-yl)-2,2-dimethylpropyl)-2-methylpropane-2-sulfinamide (80 mg, 0.27 mmol) in MeOH (7 mL). The mixture was stirred at 15° C. for 4 h, and then concentrated in vacuo. The title compound was isolated as a mono-HCl salt assuming quantitative yield and used directly without further purification. LCMS m/z 180.8 [M-NH$_2$]+. $^1$H NMR (400 MHz, CD$_3$OD) δ 7.43 (s, 1H), 4.10 (s, 1H), 3.84 (s, 3H), 3.78 (s, 3H), 1.05 (s, 9H). Chiral SFC (SFC method J) RT=1.85 min, 93.7% ee. The absolute stereochemistry of the title compound was assigned by analogy to Preparative Example 1F.

Step 13D. (R)-3-Hydroxy-4-((2-((1-(4-methoxy-1-methyl-1H-pyrazol-3-yl)-2,2-dimethylpropyl)amino)-3,4-dioxocyclobut-1-en-1-yl)amino)-N,N-dimethylpicolinamide To a solution of (R)-1-(4-methoxy-1-methyl-1H-pyrazol-3-yl)-2,2-dimethylpropan-1-amine (60 mg, 0.26 mmol) in EtOH (3 mL) at 15° C. was added DIEA (63.5 mg, 0.49 mmol). After stirring for 10 min, 4-((2-ethoxy-3,4-dioxocyclobut-1-en-1-yl)amino)-3-hydroxy-N,N-dimethylpicolinamide (Preparative Step 1H) (50 mg, 0.16 mmol) was added.

The resulting mixture was stirred at ambient temperature for 16 h and then was concentrated in vacuo. The residue was purified using preparative HPLC (Agela Durashell C18 150 mm×25 mm×5 μm 14 to 54% CH$_3$CN in 0.225% formic acid in water, 25 mL/min, 11 min) to afford 42.1 mg (56%) of the title compound as a yellow solid. LCMS m/z 457.4 [M+H]$^+$. $^1$H NMR (400 MHz, DMSO-d$_6$) δ 11.64 (br s, 1H), 9.99 (s, 1H), 9.12 (d, J=8.8 Hz, 1H), 8.01 (s, 2H), 7.49 (s, 1H), 5.22 (d, J=10.3 Hz, 1H), 3.79 (s, 3H), 3.67 (s, 3H), 3.19 (br s, 3H), 3.06 (br s, 3H), 0.94 (s, 9H). [α]$^{24}_D$=−110.8 (c=0.33, MeOH). Chiral SFC (SFC method J) RT=3.95 min, 100% ee.

Example 14

(R)-3-Hydroxy-N-isopropyl-4-((2-((1-(4-methoxy-1-methyl-1H-pyrazol-3-yl)-2,2-dimethylpropyl)amino)-3,4-dioxocyclobut-1-en-1-yl)amino)-N-methylpicolinamide

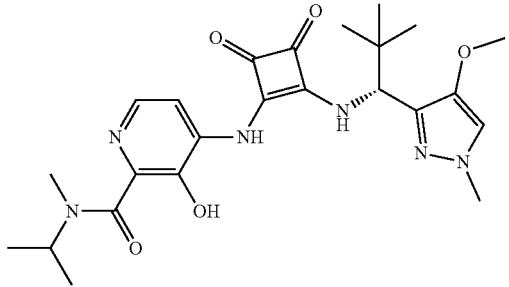 [SMILES: COc1cn(C)nc1[C@H](Nc1c(Nc2ccnc(C(=O)N(C)C(C)C)c2O)c(=O)c1=O)C(C)(C)C]

The title compound was prepared from 4-((2-ethoxy-3,4-dioxocyclobut-1-en-1-yl)amino)-3-hydroxy-N-isopropyl-N-methylpicolinamide (Preparative Step 3F) and (R)-1-(4-methoxy-1-methyl-1H-pyrazol-3-yl)-2,2-dimethylpropan-1-amine (Preparative Step 13C) following similar procedures as the preparation of Example 13. Yellow solid, 18 mg (25%). LCMS m/z 485.4 [M+H]$^+$. $^1$H NMR (400 MHz, CD$_3$OD) δ 8.18 (br s, 1H), 7.94 (br s, 1H), 7.33 (s, 1H), 5.35 (s, 1H), 4.64 (br s, 0.3H), 4.30 (br s, 0.7H), 3.81 (s, 3H), 3.76 (s, 3H), 3.02 (s, 3H), 1.33-1.20 (m, 6H), 1.04 (s, 9H). Chiral SFC (SFC method K) RT=2.78 min, 98.7% ee.

Example 15

(R)-4-((2-(((4-(Difluoromethoxy)-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide

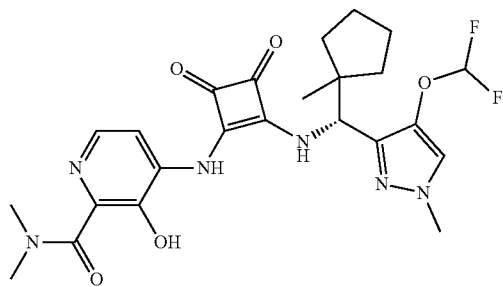 [SMILES: CN(C)C(=O)c1nccc(Nc2c(N[C@@H](c3nn(C)cc3OC(F)F)C3(C)CCCC3)c(=O)c2=O)c1O]

Step 15A.
4-(Difluoromethoxy)-1-methyl-1H-pyrazole

To a solution of 1-methyl-1H-pyrazol-4-ol (1.0 g, 10.2 mmol) in IPA (10 mL) at 15° C. was added KOH (2.86 g, 51.0 mmol) followed by chlorodifluoromethane (8.81 g, 102 mmol). The reaction was exothermic. The mixture was stirred at ambient temperature for 12 h. The reaction mixture was poured into water and extracted with EtOAc. The combined organic extracts were washed with water and brine, dried over MgSO$_4$, filtered and concentrated in vacuo. The residue was purified by silica gel column chromatography (33% EtOAc in petroleum ether) to afford 700 mg (46%) of the title compound as a yellow oil. LCMS m/z 148.9 [M+H]$^+$. $^1$H NMR (400 MHz, CDCl$_3$) δ 7.37 (s, 1H), 7.32 (s, 1H), 6.34 (t, J=73.03 Hz, 1H), 3.98-3.78 (s, 3H). $^{19}$F NMR (376 MHz, CDCl$_3$) δ−83.6.

Step 15B.
4-(Difluoromethoxy)-3-iodo-1-methyl-1H-pyrazole

NIS (6.38 g, 28.4 mmol) was added to a solution of 4-(difluoromethoxy)-1-methyl-1H-pyrazole (1.40 g, 9.45 mmol) in acetonitrile (25 mL). The resulting mixture was heated at 50° C. for 84 h. The reaction was diluted with water (15 mL) and extracted with EtOAc (20 mL×3). The combined organic extracts were washed with saturated aqueous Na$_2$S$_2$O$_3$ solution and brine, dried over Na$_2$SO$_4$, filtered and concentrated in vacuo. The residue was purified using preparative silica gel TLC (50% EtOAc in petroleum ether) to afford 260 mg (10%) of the title compound as a yellow solid. LCMS m/z 275.1 [M+H]$^+$. $^1$H NMR (400 MHz, CDCl$_3$) δ 7.27 (s, 1H), 6.41 (t, J=73.03 Hz, 1H), 3.92 (s, 3H). $^{19}$F NMR (376 MHz, CDCl$_3$) δ−83.6.

Step 15C. (R)—N—((R)-(4-(Difluoromethoxy)-1-methyl-1H-pyrazol-3-yl)(1-methylcyclopentyl)-methyl)-2-methylpropane-2-sulfinamide To a solution of 4-(difluoromethoxy)-3-iodo-1-methyl-1H-pyrazole (66.2 mg, 1.3 mmol) in THF (5 mL) at −40° C. was added dropwise i-PrMgCl.LiCl (0.43 mL, 0. 0.557 mmol, 1.3 M solution in THF). The resulting mixture was stirred at −10° C. for 1 h, and then cooled to −40° C. A solution of (S,E)-2-methyl-N-((1-methylcyclopentyl)methylene)propane-2-sulfinamide (Preparactive Step 1C) (40 mg, 0.19 mmol) in THF (3 mL) was added. The reaction was warmed to 50° C. and stirred overnight. The mixture was quenched with saturated aqueous NH$_4$Cl solution at 10° C. and extracted with EtOAc. The combined organic extracts were concentrated in vacuo. The residue was purified using preparative silica gel TLC (80% EtOAc in petroleum ether) to afford 70 mg (46%) of the title compound as a yellow oil. LCMS m/z 363.9 [M+H]$^+$. $^1$H NMR (400 MHz, CDCl$_3$) δ 7.25 (s, 1H), 6.37 (t, J=73.03 Hz, 1H), 4.33 (d, J=6.8 Hz, 1H), 3.90-3.71 (m, 4H), 1.77-1.55 (m, 6H), 1.54-1.42 (m, 1H), 1.28-1.13 (m, 10H), 1.08-0.98 (m, 3H). $^{19}$F NMR (376 MHz, CDCl$_3$) δ−83.2.

Step 15D. (R)-(4-(Difluoromethoxy)-1-methyl-1H-pyrazol-3-yl)(1-methylcyclopentyl)-methanamine HCl (1 mL, 4.0 M in MeOH) was added to a solution of (R)—N—((R)-(4-(difluoromethoxy)-1-methyl-1H-pyrazol-3-yl)(1-methylcyclopentyl)methyl)-2-methylpropane-2-sulfinamide (35 mg, 0.096 mmol) in MeOH (1 mL) at 5° C. The mixture was stirred at 20° C. for 3 h, and then concentrated in vacuo. The title compound was isolated as a mono-HCl salt assuming quantitative yield and used directly without further purification. The absolute stereochemistry of the title compound was assigned by analogy to Preparative Example 1F. LCMS m/z 242.8 [M-NH$_2$]+.

Step 15E. (R)-4-((2-(((4-(Difluoromethoxy)-1-methyl-1H-pyrazol-3-yl)(1-methylcyclopentyl)-methyl)amino)-3,4-dioxocyclobut-1-en-1-yl)amino)-3-hydroxy-N,N-dimethylpicolinamide To a solution of (R)-(4-(difluoromethoxy)-1-methyl-1H-pyrazol-3-yl)(1-methylcyclopentyl)-methanamine (28 mg, 0.11 mmol) in EtOH (2 mL) at 20° C. was added DIEA (140 mg, 1.08 mmol). After stirring for 5 min, 4-((2-ethoxy-3,4-dioxocyclobut-1-en-1-yl)amino)-3-hydroxy-N,N-dimethylpicolinamide (Preparative Step 1H) (30 mg, 0.108 mmol) was added. The resulting mixture was stirred at 30° C. for 6 h and then was concentrated in vacuo. The residue was purified using preparative HPLC (Xbridge 150 mm×30 mm×10 μm, 15 to 55% CH$_3$CN in 0.225% formic acid in water, 25 mL/min, 10 min) to afford 52 mg (55%) of the title compound as a yellow solid. LCMS m/z 519.3 [M+H]+. $^1$H NMR (400 MHz, CD$_3$OD) δ 8.22 (d, J=5.5 Hz, 1H), 7.92 (br s, 1H), 7.57 (s, 1H), 6.65 (dd, J=75.5, 72.9 Hz, 1H), 5.46 (s, 1H), 3.86 (s, 3H), 3.24 (br s, 3H), 3.17 (br s, 3H), 1.87-1.62 (m, 6H), 1.51-1.43 (m, 1H), 1.33-1.25 (m, 1H), 1.15 (s, 3H). $^{19}$F NMR (376 MHz, CDCl$_3$) δ–85.1. Chiral SFC (SFC method B) RT=1.34 min, 100% ee.

Example 16

(R)-4-((2-(((4-Cyano-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide

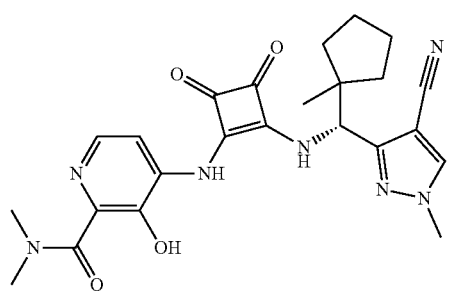 [SMILES: CN(C)C(=O)c1nccc(Nc2c(N[C@@H](c3nn(C)cc3C#N)C3(C)CCCC3)c(=O)c2=O)c1O]

Step 16A.
3-Amino-1-methyl-1H-pyrazole-4-carbonitrile

To a solution of 3-amino-1H-pyrazole-4-carbonitrile (15.0 g, 139 mmol) in DMF (700 mL) at 0° C. was added K$_2$CO$_3$ (23.0 g, 167 mmol). The mixture was stirred for 45 min, and then MeI (23.6 g, 167 mmol) was added. The resulting mixture was heated at 90° C. for 16 h. The reaction mixture was poured into ice water (200 mL) and extracted with EtOAc (400 mL×8). The combined organic extracts were concentrated in vacuo. The residue was purified by silica gel column chromatography (0 to 20% EtOAc in petroleum ether) to afford 3.30 g (20%) of the title compound as a white solid. LCMS m/z 122.8 [M+H]+. $^1$H NMR (400 MHz, DMSO-d$_6$) δ 8.02 (s, 1H), 5.53 (s, 2H), 3.61 (s, 3H).

Step 16B.
3-Iodo-1-methyl-1H-pyrazole-4-carbonitrile

To a stirred solution of 3-amino-1-methyl-1H-pyrazole-4-carbonitrile (1.0 g, 8.19 mmol) and p-TsOH.water (3.55 g, 18.7 mmol) in MeCN (30 mL) at 0° C. was added dropwise a solution of NaNO$_2$ (1.29 g, 18.7 mmol) and KI (3.1 g, 18.7 mmol) in water (4.0 mL). The resulting mixture was stirred at 15° C. for 3 d. The reaction mixture was concentrated in vacuo. The residue was diluted with water (10 mL) and saturated aqueous Na$_2$SO$_3$ solution (20 mL), and then neutralized with NaOH (1.0 N aqueous solution) until pH=8. The mixture was extracted with EtOAc (100 mL×4), and the combined organic extracts were dried over Na$_2$SO$_4$, filtered and concentrated in vacuo. The residue was purified by silica gel column chromatography (0 to 100% EtOAc in petroleum ether) to afford 398 mg (21%) of the title compound as a yellow solid. LCMS m/z 234.1 [M+H]+. $^1$H NMR (400 MHz, CDCl$_3$) δ 8.48 (s, 1H), 3.94 (s, 3H).

Step 16C. (R)—N—((R)-(4-Cyano-1-methyl-1H-pyrazol-3-yl)(1-methylcyclopentyl)methyl)-2-methylpropane-2-sulfinamide To a solution of 3-iodo-1-methyl-1H-pyrazole-4-carbonitrile (398 mg, 1.71 mmol) in freshly distilled THF (12 mL) at –65° C. was added dropwise i-PrMgCl.LiCl (2.60 mL, 3.38 mmol, 1.3 M solution in THF). The resulting mixture was stirred at –40° C. for 1 h, and then cooled to –65° C. A solution of (S,E)-2-methyl-N-((1-methylcyclopentyl)methylene)propane-2-sulfinamide (Preparactive Step 1C) (260 mg, 1.21 mmol) in freshly distilled THF (3 mL) was added dropwise. The mixture was warmed to 15° C. and stirred for 3 d. The reaction mixture was poured into 25% aqueous NH$_4$Cl solution (20 mL) at 15° C., and extracted with EtOAc (50 mL×3). The combined organic extracts were dried over Na$_2$SO$_4$, filtered and concentrated in vacuo. The residue was purified by silica gel column chromatography (0 to 100% EtOAc in petroleum ether) to afford 84 mg (17%) of the title compound as a yellow solid. LCMS m/z 322.9 [M+H]+. $^1$H NMR (400 MHz, CDCl$_3$) δ 3 7.76 (s, 1H), 4.48-4.46 (m, 1H), 3.93 (s, 3H), 3.82-3.75 (m, 1H), 1.85-1.50 (m, 8H), 1.29 (s, 9H), 1.08 (s, 3H).

Step 16D. (R)-3-(Amino(1-methylcyclopentyl)methyl)-1-methyl-1H-pyrazole-4-carbonitrile To a solution of (R)—N—((R)-(4-cyano-1-methyl-1H-pyrazol-3-yl)(1-methylcyclopentyl)-methyl)-2-methylpropane-2-sulfinamide (84 mg, 0.26 mmol) in DCM (6 mL) at 0° C. was added HCl (2 mL, 4.0 M in EtOAc). The mixture was warmed to 15° C. and stirred for 2 h. The reaction mixture was then concentrated in vacuo. The title compound was isolated as a mono-HCl salt assuming quantitative yield and used directly without further purification. LCMS m/z 219.3 [M+H]+. $^1$H NMR (400 MHz, CD$_3$OD) δ 8.31 (s, 1H), 4.40 (s, 1H), 4.00 (s, 3H), 1.90-1.50 (m, 8H), 1.11 (s, 3H). The absolute stereochemistry of the title compound was assigned by analogy to Preparative Example 1F.

Step 16E. (R)-4-((2-(((4-Cyano-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide To a solution of (R)-3-(amino(1-methylcyclopentyl)methyl)-1-methyl-1H-pyrazole-4-carbonitrile (24 mg, 0.094 mmol) in EtOH (3 mL) at 0° C. was added DIEA (59.3 mg, 0.459 mmol) and 4-((2-ethoxy-3,4-dioxocyclobut-1-en-1-yl)amino)-3-hydroxy-N,N-dimethyl-picolinamide (Preparative Step 1H) (28 mg, 0.092 mmol). The resulting solution was stirred at 20° C. for 16 h. The reaction mixture was concentrated in vacuo. The residue was purified using preparative HPLC (Agela Durashell C$_{18\ 150}$ mm×25 mm×5 μm, 18 to 58% MeCN in 0.225% formic acid in water, 25 mL/min, 12 min) to afford 13 mg (18%) of the title compound as a yellow solid. LCMS m/z 478.4 [M+H]$^+$. $^1$H NMR (400 MHz, CD$_3$OD) δ 8.22 (d, J=5.5 Hz, 1H), 8.19 (s, 1H), 7.95-7.85 (m, 1H), 5.52 (s, 1H), 3.95 (s, 3H), 3.24 (br s, 3H), 3.17 (br s, 3H), 1.95-1.65 (m, 6H), 1.55-1.45 (m, 1H), 1.44-1.35 (m, 1H), 1.15 (s, 3H). Chiral HPLC (HPLC method A) RT=8.65 min, 98.0% ee.

Example 17

(R)-4-((2-(((1,4-Dimethyl-1H-pyrazol-3-yl)(5-methylspiro[2.3]hexan-5-yl)methyl)amino)-3,4-dioxocyclobut-1-en-1-yl)amino)-3-hydroxy-N,N-dimethylpicolinamide

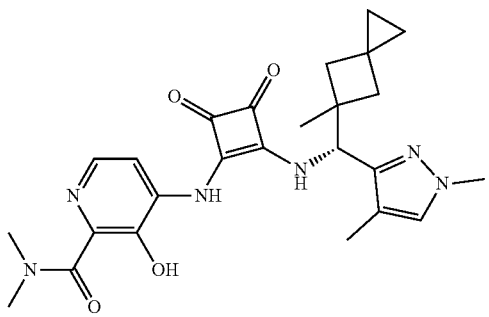

Example 17A. N-Methoxy-N-methylspiro[2.3]hexane-5-carboxamide NMM (1.09 g, 1.18 mL, 10.8 mmol) was added to a solution of N,O-dimethylhydroxyl-amine-HCl (300 mg, 3.07 mmol) in DMF (30.7 mL). The solution was stirred for 5 min, and then spiro[2.3]hexane-5-carboxylic acid (465 mg, 3.69 mmol) and HATU (1.75 g, 4.61 mmol) were added. The resulting mixture was stirred overnight. The reaction mixture was quenched with saturated aqueous NH$_4$Cl solution, and extracted with EtOAc. The combined organic extracts were washed with water (100 mL×2) and brine (100 mL), and concentrated in vacuo. The residue was purified by silica gel column chromatography (0 to 100% EtOAc in heptane) to afford 440 mg (85%) of the title compound as an oil. GCMS m/z 169.1 [M]. $^1$H NMR (400 MHz, CDCl$_3$) δ 3.67 (s, 3H), 3.20 (s, 3H), 2.65-2.42 (m, 2H), 2.26-2.00 (m, 2H), 0.61-0.23 (m, 4H).

Example 17B. (1,4-Dimethyl-1H-pyrazol-3-yl)(spiro[2.3]hexan-5-yl)methanone

To a solution of 3-iodo-1,4-dimethyl-1H-pyrazole (Preparative Step 1D) (304 mg, 1.37 mmol) in THF (2.36 mL) was added dropwise i-PrMgCl.LiCl (1.82 mL, 2.36 mmol, 1.3 M solution in THF). The resulting yellow solution was warmed to ambient temperature and stirred for 1 h. A solution of N-methoxy-N-methylspiro[2.3]hexane-5-carboxamide (200 mg, 1.18 mmol) in THF (1 mL) was then added dropwise, and the mixture was stirred for 16 h. The reaction mixture was poured into a saturated aqueous NH$_4$Cl solution. The mixture was extracted with DCM, and the combined organic extracts were concentrated in vacuo. The residue was purified by silica gel column chromatography (0 to 100% EtOAc in heptane) to afford 220 mg (91%) of the title compound as a solid. LCMS m/z205.2 [M+H]$^+$. $^1$H NMR (400 MHz, CDCl$_3$) δ 7.15 (s, 1H), 4.31 (tt, J=9.2, 7.6 Hz, 1H), 3.89 (s, 3H), 2.67-2.48 (m, 2H), 2.32 (s, 3H), 2.26-2.21 (m, 2H), 0.59-0.28 (m, 4H).

Example 17C. (1,4-Dimethyl-1H-pyrazol-3-yl)(5-methylspiro[2.3]hexan-5-yl)methanone NaH (47.0 mg, 1.17 mmol, 60 wt % in mineral oil) and iodomethane (208 mg, 1.47 mmol) were added to a solution of (1,4-dimethyl-1H-pyrazol-3-yl)(spiro[2.3]hexan-5-yl)methanone (72 mg, 0.37 mmol) in THF (9.79 mL). The resulting mixture was stirred at ambient temperature for 24 h. The reaction mixture was quenched with saturated aqueous NH$_4$C solution, and extracted with EtOAc. The combined organic extracts were dried over Na$_2$SO$_4$, filtered and concentrated in vacuo. The residue was purified by silica gel column chromatography (0 to 100% EtOAc in heptane) to afford 40 mg (19%) of the title compound as a solid. LCMS m/z 219.2 [M+H]$^+$.

Example 17D. (1,4-Dimethyl-1H-pyrazol-3-yl)(5-methylspiro[2.3]hexan-5-yl)methanamine Titanium (IV) ethoxide (157 mg, 0.144 mL, 0.688 mmol) was added to a solution of (1,4-dimethyl-1H-pyrazol-3-yl)(5-methylspiro[2.3]hexan-5-yl)methanone (50 mg, 0.23 mmol) in methanolic NH$_3$ (0.983 mL, 7.0 M in MeOH). The resulting mixture was stirred at 40° C. overnight. The reaction was cooled to ambient temperature, diluted with MeOH (2 mL) and NaBH$_4$ (13 mg, 0.344 mmol) was added. The mixture was stirred for 4 h. The reaction mixture was quenched with saturated aqueous NH$_4$Cl solution and filtered through Celite. The filter cake was washed with 20% MeOH in DCM. The organic layer of the filtrate was separated, and the aqueous layer was acidified to pH 2 using 1.0 M HCl. The aqueous layer was extracted with DCM (30 mL). The aqueous layer was then basified to pH 12 using NaOH, and extracted with DCM (20 mL). The combined organic extracts were dried over Na$_2$SO$_4$, filtered and concentrated in vacuo to afford the title compound and used directly in the next step without further purification assuming quantitative yield.

Example 17E. (R)-4-((2-(((1,4-Dimethyl-1H-pyrazol-3-yl)(5-methylspiro[2.3]hexan-5-yl)methyl)amino)-3,4-dioxocyclobut-1-en-1-yl)amino)-3-hydroxy-N,N-dimethylpicolinamide To a mixture of (1,4-dimethyl-1H-pyrazol-3-yl)(5-methylspiro[2.3]hexan-5-yl)methanamine (52 mg, 0.236 mmol) in EtOH (1.97 mL) at 20° C. was added DIEA (381 mg, 0.529 mL, 2.95 mmol). The resulting solution was stirred for 20 min, and then 4-((2-ethoxy-3,4-dioxocyclobut-1-en-1-yl)amino)-3-hydroxy-N,N-dimethylpicolinamide (Preparative Step 1H) (60 mg, 0.20 mmol) was added. The resulting suspension was stirred at 20° C. for 4 d and then was concentrated in vacuo. The residue was purified employing chiral SFC conditions (Chiral Tech OD-H 21.2×21.2 mm I.D. 5 μm, 45% (0.2% 7N ammonia in MeOH) in EtOH, 80 mL/min). Isolation of the first eluting isomer afforded 21.6 mg (23%) of the title compound and the second eluting isomer afforded the corresponding enantiomer (24 mg, 26%). LCMS m/z 479.8 [MH]+. ¹H NMR (400 MHz, DMSO-d₆) δ 9.93 (brs H, 9.18 (br s, 1H), 8.04-8.00 (m, 2H), 7.44 (s, 1H), 5.53 (d, J=10.1, 1H), 3.79 (s, 3H), 3.20 (br s, 3H), 3.07 (brs, 2.28 (d, J=11.7, 1H), 2.08 (d, J=11.3, 1H), 2.01 (s, 3H), 1.73 (d, J=11.3 Hz, 1H), 1.66 (d, J=10.5 Hz, 1H), 1.35 (s, 3H), 0.45-0.28 (m, 4H). Chiral SFC conditions (Chiral Tech OD-H21.2×21.2 mm I.D. 5 μm, 45% (0.2% 7N ammonia in MeOH) in EtOH, 80 mL/min) RT=5.39 min, 98.8% ee (title compound) and RT=5.98 min, 96% ee (enantiomer).

Preparations 1 to 14

The title compounds in Table 1 were prepared in a similar manner to (R)-(1,4-dimethyl-1H-pyrazol-3-yl)(1-methylcyclopentyl)methanamine (Preparative Step 1F) from the appropriate aldehyde and heteroaryl halide.

TABLE 1

| Prep No | Structure | Chemical Name and Analytical Data |
|---|---|---|
| 1 | 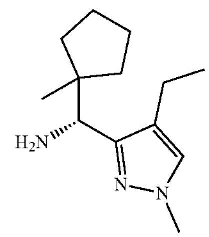 | (R)-(4-Ethyl-1H-pyrazol-3-yl)(1-methylcyclopentyl)methanamine. LCMS m/z 205.4 [M − NH₂]⁺. ¹H NMR (400 MHz, CD₃OD) δ 7.41 (s, 1H), 4.21 (s, 1H), 3.85 (s, 3H), 2.52-2.42 (m, 2H), 1.85-1.48 (m, 8H), 1.24 (t, J = 7.5 Hz, 3H), 1.13 (s, 3H) |
| 2 | 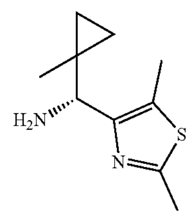 | (R)-(2,5-Dimethylthiazol-4-yl)(1-methylcyclopropyl)-methanamine. LCMS m/z 180.0 [M − NH₂]⁺. ¹H NMR (400 MHz, CD₃OD) δ 4.03 (s, 1H), 2.63 (s, 3H), 2.39 (s, 3H), 1.15 (s, 3H), 0.85-0.77 (m, 1H), 0.66-0.40 (m, 3H) |
| 3 | 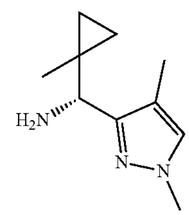 | (R)-(1,4-Dimethyl-1H-pyrazol-3-yl)(1-methylcyclopropyl)-methanamine. LCMS m/z 163.2 [M − NH₂]⁺. ¹H NMR (400 MHz, CD₃OD) δ 7.37 (s, 1H), 3.95 (s, 1H), 3.83 (s, 3H), 2.04 (s, 3H), 1.18 (s, 3H), 0.84-0.82 (m, 1H), 0.65-0.45 (m, 3H) |
| 4 | 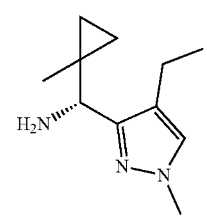 | (R)-(4-Ethyl-1-methyl-1H-pyrazol-3-yl)(1-methylcyclopropyl)-methanamine. LCMS m/z 177.1 [M − NH₂]⁺. ¹H NMR (400 MHz, CD₃OD) δ 7.42 (s, 1H), 3.97 (s, 1H), 3.85 (s, 3H), 2.51-2.42 (m, 2H), 1.25-1.15 (m, 3H), 1.10 (s, 3H), 0.90-0.80 (m, 1H), 0.59-0.50 (m, 3H) |
| 5 | 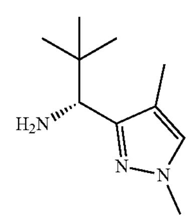 | (R)-1-(1,4-Dimethyl-1H-pyrazol-3-yl)-2,2-dimethylpropan-1-amine. LCMS m/z 165.2 [M − NH₂]⁺. ¹H NMR (400 MHz, CD₃OD) δ 7.38 (s, 1H), 4.13 (s, 1H), 3.86 (s, 3H), 2.07 (s, 3H), 1.08 (s, 9H) |
| 6 | 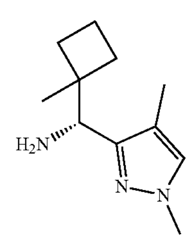 | (R)-(1,4-Dimethyl-1H-pyrazol-3-yl)(1-methylcyclobutyl)-methanamine. LCMS m/z 177.2 [M − NH₂]⁺. ¹H NMR (400 MHz,CD₃OD) δ 7.38 (s, 1H), 4.35 (s, 1H), 3.85 (s, 3H), 2.30-2.15 (m, 2H), 2.09 (s, 3H), 2.05-1.95 (m, 1H), 1.85-1.70 (m, 2H), 1.65-1.55 (m, 1H), 1.17 (s, 3H) |

TABLE 1-continued

| Prep No | Structure | Chemical Name and Analytical Data |
|---|---|---|
| 7 | 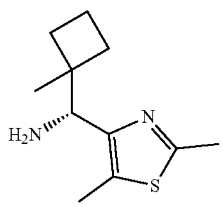 | (R)-(2,5-Dimethylthiazol-4-yl)(1-methylcyclobutyl)methanamine. LCMS m/z 193.9 [M − NH$_2$]$^+$. $^1$H NMR (400 MHz, CDCl$_3$) δ 9.15 (s, 2H), 8.39 (s, 1H), 5.19 (s, 1H), 3.00 (s, 3H), 2.58 (s, 3H), 2.65-2.55 (m, 1H), 2.35-2.26 (m, 1H), 2.15-1.77 (m, 3H), 1.70-1.61 (m, 1H), 1.42 (s, 3H) |
| 8 | 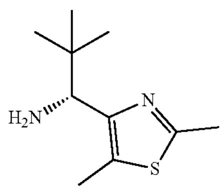 | (R)-1-(2,5-Dimethylthiazol-4-yl)-2,2-dimethylpropan-1-amine. LCMS m/z 181.9 [M − NH$_2$]$^+$ |
| 9 | 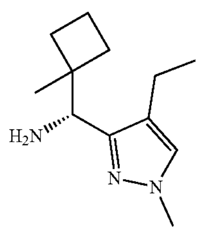 | (R)-(4-Ethyl-1-methyl-1H-pyrazol-3-yl)(1-methylcyclobutyl)-methanamine. LCMS m/z 191.0 [M − NH$_2$]$^+$. $^1$H NMR (400 MHz, CD$_3$OD) δ 7.43 (s, 1H), 4.34 (s, 1H), 3.86 (s, 3H), 2.58-2.47 (m, 2H), 2.21-2.16 (m, 2H), 2.05-1.95 (m, 1H), 1.85-1.70 (m, 2H), 1.64-1.55 (m, 1H), 1.33 (s, 3H), 1.26-1.20 (m, 3H) |
| 10 | 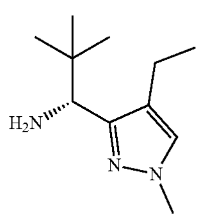 | (R)-1-(4-Ethyl-1-methyl-1H-pyrazol-3-yl)-2,2-dimethylpropan-1-amine. LCMS m/z 179.1 [M − NH$_2$]$^+$. $^1$H NMR (400 MHz, CD$_3$OD) δ 7.44 (s, 1H), 4.13 (s, 1H), 3.88 (s, 3H), 2.52-2.42 (m, 2H), 1.26-1.20 (m, 3H), 1.08 (s, 9H) |
| 11 | 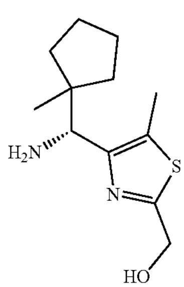 | (R)-(4-(amino(1-methylcyclopentyl)methyl)-5-methylthiazol-2-yl)methanol. LCMS m/z 224.3 [M − NH$_2$]$^+$. $^1$H NMR (400 MHz, CD$_3$OD) δ 4.79 (s, 2H), 4.35 (s, 1H), 2.49 (s, 3H), 1.85-1.65 (m, 6H), 1.56-1.51 (m, 1H), 1.32-1.25 (m, 1H), 1.13 (s, 3H) |
| 12 | 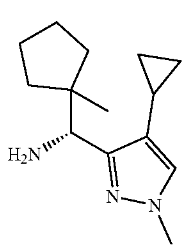 | (R)-(4-Cyclopropyl-1-methyl-1H-pyrazol-3-yl)(1-methylcyclopentyl)methanamine. LCMS m/z 217.3 [M − NH$_2$]$^+$ |

TABLE 1-continued

| Prep No | Structure | Chemical Name and Analytical Data |
|---|---|---|
| 13 | 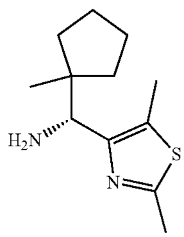 | (R)-(2,5-Dimethylthiazol-4-yl)(1-methylcyclopentyl)-methanamine. LCMS m/z 225.3 [M + H]⁺. $^1$H NMR (400 MHz, CD$_3$OD) δ 4.27 (s, 1H), 2.59 (s, 3H), 2.39 (s, 3H), 1.76-1.41 (m, 7H), 1.25-1.15 (s, 1H), 1.05 (s, 3H) |
| 14 | 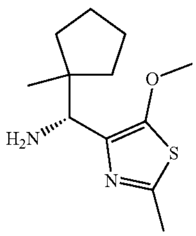 | (R)-(5-Methoxy-2-methylthiazol-4-yl)(1-methylcyclopentyl)-methanamine. LCMS m/z 223.8 [M − NH$_2$]⁺. $^1$H NMR (400 MHz, CD$_3$OD) δ 4.27 (s, 1H), 3.99 (s, 3H), 2.64 (s, 3H), 1.85-1.61 (m, 6H), 1.54-1.45 (m, 1H), 1.30-1.21 (m, 1H), 1.12 (s, 3H) |

Examples 18 to 33

The title compounds in Table 2 were prepared in a similar manner to (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide (Preparative Step 1) from the appropriate amine and a 4-((2-ethoxy-3,4-dioxocyclobut-1-en-1-yl)amino)-3-hydroxy-N,N-dialkylylpicolinamide.

TABLE 2

| Ex. | Structure | Chemical Name and Analytical Data |
|---|---|---|
| 18 | 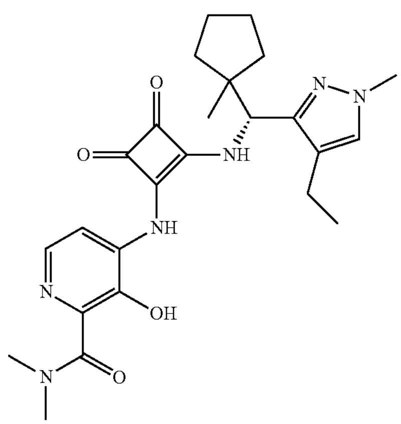 | (R)-4-((2-(((4-Ethyl-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide. Yellow solid, 42.8 mg (34%). LCMS m/z 481.4 [M + H]⁺. $^1$H NMR (400 MHz, CD$_3$OD) δ 8.25-8.22 (m, 1H), 7.95-7.85 (m, 1H), 7.33 (s, 1H), 5.44 (s, 1H), 3.85 (s, 3H), 3.23 (br s, 3H), 3.16 (br s, 3H), 2.65-2.45 (m, 2H), 1.90-1.60 (m, 6H), 1.50-1.40 (m, 1H), 1.40-1.30 (m, 1H), 1.20 (t, J = 7.5 Hz, 3H), 1.17 (s, 3H). [α]$^{24}_D$ = −28.65 (c 1.00, MeOH). RT = 1.56 min, 99.2% ee (SFC method B) |
| 19 | 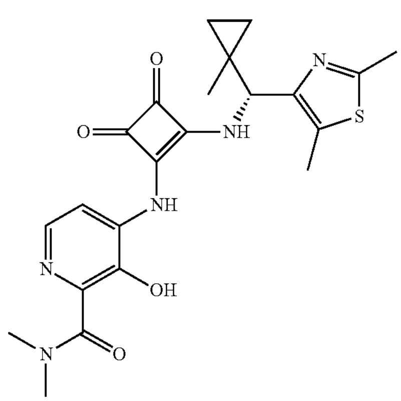 | (R)-4-((2-(((2,5-Dimethylthiazol-4-yl)(1-methylcyclopropyl)-methyl)amino)-3,4-dioxocyclobut-1-en-1-yl)amino)-3-hydroxy-N,N-dimethylpicolinamide. Yellow solid, 75.7 mg (41%). LCMS m/z 456.1 [M + H]⁺. $^1$H NMR (400 MHz, CD$_3$OD) δ 8.21 (d, J = 5.6 Hz, 1H), 7.90 (br s, 1H), 5.32 (s, 1H), 3.21 (br s, 3H), 3.15 (br s, 3H), 2.60 (s, 3H), 2.40 (s, 3H), 1.21 (s, 3H), 0.80-0.75 (m, 1H), 0.50-0.45 (m, 1H), 0.43-0.3 (m, 2H). RT = 4.44 min, 100% ee (SFC method D) |

| Ex. | Structure | Chemical Name and Analytical Data |
|---|---|---|
| 20 | 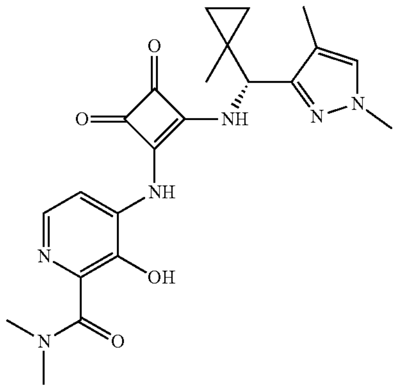 | (R)-4-((2-(((1,4-Dimethyl-1H-pyrazol-3-yl)(1-methylcyclopropyl)methyl)amino)-3,4-dioxocyclobut-1-en-1-yl)amino)-3-hydroxy-N,N-dimethylpicolinamide. Yellow solid, 193 mg (45%). LCMS m/z 439.3 [M + H]$^+$. $^1$H NMR (400 MHz, CD$_3$OD) δ 8.22 (d, J = 5.4 Hz, 1H), 7.92 (br s, 1H), 7.29 (s, 1H), 5.24 (s, 1H), 3.80 (s, 3H), 3.23 (br s, 3H), 3.15 (br s, 3H), 2.06 (s, 3H), 1.21 (s, 3H), 0.82-0.74 (m, 1H), 0.48-0.38 (m, 3H). RT = 3.45 min, 100% ee (SFC method E) |
| 21 | 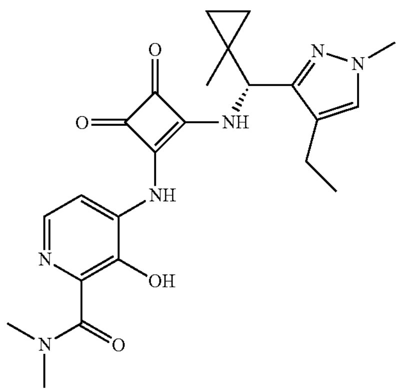 | (R)-4-((2-(((4-Ethyl-1-methyl-1H-pyrazol-3-yl)(1-methylcyclopropyl)methyl)amino)-3,4-dioxocyclobut-1-en-1-yl)amino)-3-hydroxy-N,N-dimethylpicolinamide. Yellow solid, 59 mg, (50%). LCMS m/z 453.3 [M + H]$^+$. $^1$H NMR (400 MHz, CD$_3$OD) δ 8.22 (d, J = 5.5 Hz, 1H), 7.91 (br s, 1H), 7.31 (s, 1H), 5.27 (s, 1H), 3.80 (s, 3H), 3.23 (br s, 3H), 3.15 (br s, 3H), 2.55-2.40 (m, 2H), 1.21 (s, 3H), 1.20 (t, J = 7.6 Hz, 3H), 0.82-0.77 (m, 1H), 0.45-0.37 (m, 3H). RT = 4.49 min, 94.1% ee (SFC method D) |
| 22 | 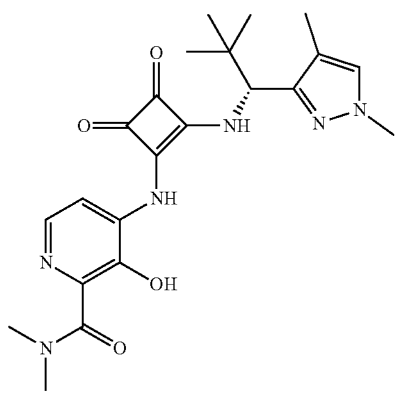 | (R)-4-((2-((1-(1,4-Dimethyl-1H-pyrazol-3-yl)-2,2-dimethylpropyl)amino)-3,4-dioxocyclobut-1-en-1-yl)amino)-3-hydroxy-N,N-dimethylpicolinamide. Yellow solid, 57 mg (44%). LCMS m/z 441.3 [M + H]$^+$. $^1$H NMR (400 MHz, CD$_3$OD) δ 8.20 (d, J = 5.5 Hz, 1H), 7.89 (d, J = 5.5 Hz, 1H), 7.26 (s, 1H), 5.31 (s, 1H), 3.81 (s, 3H), 3.21 (br s, 3H), 3.14 (br s, 3H), 2.06 (s, 3H), 1.05 (s, 9H). RT = 4.13 min, 99.1% ee (SFC method F) |
| 23 | 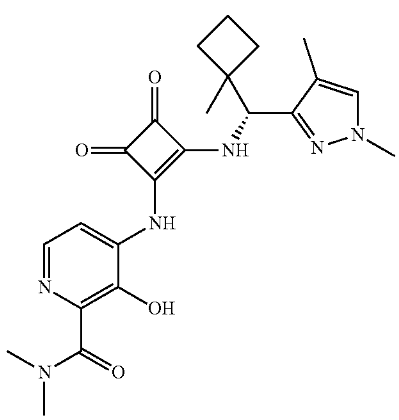 | (R)-4-((2-(((1,4-Dimethyl-1H-pyrazol-3-yl)(1-methylcyclobutyl)methyl)amino)-3,4-dioxocyclobut-1-en-1-yl)amino)-3-hydroxy-N,N-dimethylpicolinamide. Yellow solid, 35 mg (34%). LCMS m/z 453.3 [M + H]$^+$. $^1$H NMR (400 MHz, CD$_3$OD) δ 8.22 (d, 5.5 Hz, 1H), 7.89 (d, J = 5.6 Hz, 1H), 7.29 (s, 1H), 5.45 (s, 1H), 3.82 (s, 3H), 3.22 (br s, 3H), 3.14 (br s, 3H), 2.28-2.17 (m, 2H), 2.07 (s, 3H), 2.02-1.88 (m, 1H), 1.85-1.59 (m, 3H), 1.32 (s, 3H). RT = 4.52 min, 99.7% ee (SFC method D) |

TABLE 2-continued

| Ex. | Structure | Chemical Name and Analytical Data |
|---|---|---|
| 24 | 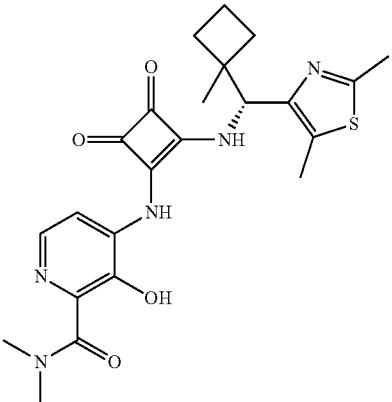 | (R)-4-((2-(((2,5-Dimethylthiazol-4-yl)(1-methylcyclobutyl)-methyl)amino)-3,4-dioxocyclobut-1-en-1-yl)amino)-3-hydroxy-N,N-dimethylpicolinamide. Yellow solid, 140 mg (34%). LCMS m/z 470.3 [M + H]$^+$. $^1$H NMR (400 MHz, DMSO-d$_6$) δ 11.69 (s, 1H), 9.98 (s, 1H), 9.21 (d, J = 9.9 Hz, 1H), 8.01 (s, 2H), 5.46 (d, J = 9.9 Hz, 1H), 3.20 (br s, 3H), 3.06 (br s, 3H), 2.62 (s, 3H), 2.40 (s, 3H), 2.19 (q, J = 9.8 Hz, 1H), 2.04 (q, J = 9.6 Hz, 1H), 1.96-1.83 (m, 1H), 1.80-1.69 (m, 1H), 1.65-1.51 (m, 2H), 1.19 (s, 3H). RT = 3.53 min, 97.2% ee (SFC method F) |
| 25 | 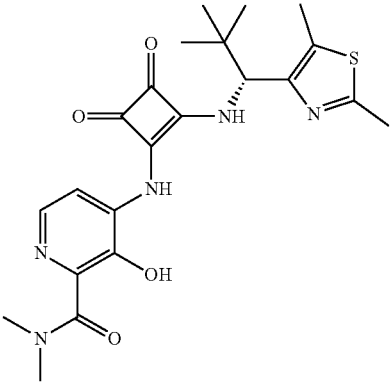 | (R)-4-((2-(((1-(2,5-Dimethylthiazol-4-yl)-2,2-dimethylpropyl)-amino)-3,4-dioxocyclobut-1-en-1-yl)amino)-3-hydroxy-N,N-dimethylpicolinamide. Yellow solid, 71 mg (18%). LCMS m/z 458.3 [M + H]$^+$. $^1$H NMR (400 MHz, DMSO-d$_6$) δ 11.74 (br s, 1H), 10.03 (br s, 1H), 9.23 (s, 1H), 8.10-7.88 (m, 2H), 5.30 (d, J = 10.1 Hz, 1H), 3.18 (s, 3H), 3.05 (s, 3H), 2.63 (s, 3H), 2.37 (s, 3H), 0.97 (s, 9H). RT = 3.23 min, 96.9% ee (SFC method F) |
| 26 | 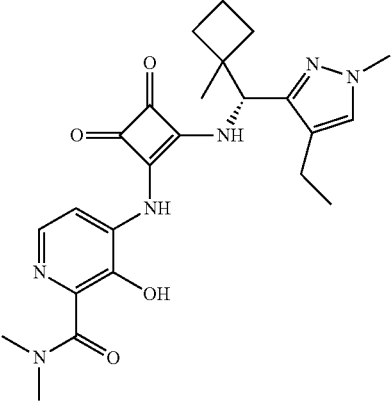 | (R)-4-((2-(((4-Ethyl-1-methyl-1H-pyrazol-3-yl)(1-methylcyclobutyl)methyl)amino)-3,4-dioxocyclobut-1-en-1-yl)amino)-3-hydroxy-N,N-dimethylpicolinamide. Yellow solid, 23.5 mg (44%). LCMS m/z 467.4 [M + H]$^+$. $^1$H NMR (400 MHz, CD$_3$OD) δ 8.22 (d, J 5.6 Hz, 1H), 7.90 (br s, 1H), 7.32 (s, 1H), 5.45 (s, 1H), 3.83 (s, 3H), 3.22 (br s, 3H), 3.15 (br s, 3H), 2.58-2.42 (m, 2H), 2.30-2.15 (m, 2H), 2.01-1.92 (m, 1H), 1.81-1.60 (m, 3H), 1.32 (s, 3H), 1.19 (t, J = 7.5 Hz, 3H). RT = 4.61 min, 100% ee (SFC method F) |
| 27 | 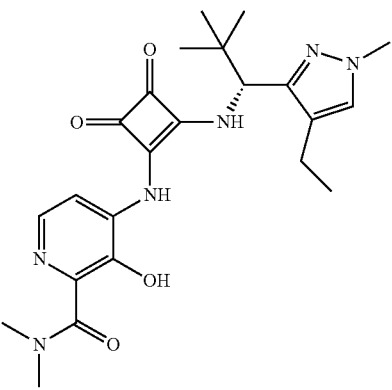 | (R)-4-((2-(((1-(4-Ethyl-1-methyl-1H-pyrazol-3-yl)-2,2-dimethylpropyl)amino)-3,4-dioxocyclobut-1-en-1-yl)amino)-3-hydroxy-N,N-dimethylpicolinamide. Yellow solid, 41.4 mg (35%). LCMS m/z 455.4 [M + H]$^+$. $^1$H NMR (400 MHz, CD$_3$OD) δ 8.21 (d, J = 5.6 Hz, 1H), 7.91 (br s, 1H), 7.33 (s, 1H), 5.33 (s, 1H), 3.86 (s, 3H), 3.22 (br s, 3H), 3.14 (br s, 3H), 2.60-2.42 (m, 2H), 1.18 (t, J = 7.5 Hz, 3H), 1.07 (s, 9H). RT = 4.17 min, 95.7% ee (SFC method G) |

TABLE 2-continued

| Ex. | Structure | Chemical Name and Analytical Data |
|---|---|---|
| 28 | 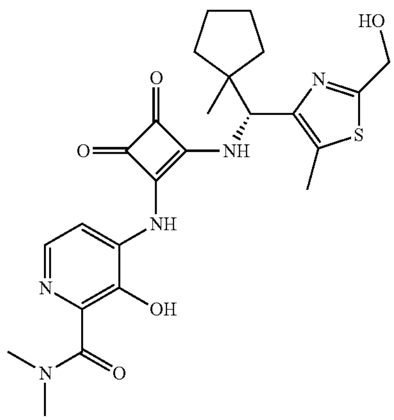 [SMILES: Cc1sc(CO)nc1[C@H](Nc1c(Nc2ccnc(C(=O)N(C)C)c2O)c(=O)c1=O)C1(C)CCCC1] | (R)-3-Hydroxy-4-((2-(((2-(hydroxymethyl)-5-methylthiazol-4-yl)(1-methylcyclopentyl)methyl)amino)-3,4-dioxocyclobut-1-en-1-yl)amino)-N,N-dimethylpicolinamide. Yellow solid, 45.1 mg (46%) LCMS m/z 500.4 [M + H]$^+$. $^1$H NMR (400 MHz, CD$_3$OD) δ 8.21 (d, J = 5.6 Hz, 1H), 7.95-7.85 (m, 1H), 5.51 (s, 1H), 4.79 (s, 2H), 3.21 (br s, 3H), 3.14 (br s, 3H), 2.50 (s, 3H), 1.90-1.76 (m, 2H), 1.75-1.60 (m, 4H), 1.47-1.40 (m, 1H), 1.33-1.25 (m, 1H), 1.14 (s, 3H). RT = 5.15 min, 98.7% ee (SFC method G) |
| 29 | 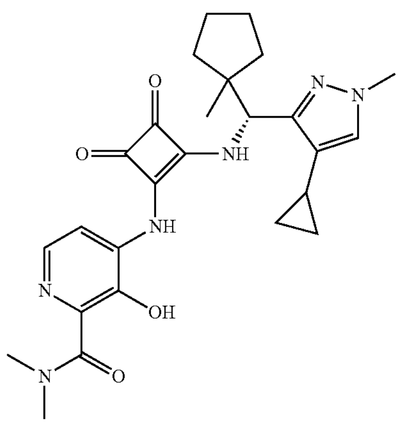 | (R)-4-((2-(((4-Cyclopropyl-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide. Yellow solid, 15.9 mg (33%). LCMS m/z 493.4 [M + H]$^+$. $^1$H NMR (400 MHz, CD$_3$OD) δ 8.22 (d, J = 5.5 Hz, 1H), 7.95-7.85 (m, 1H), 7.14 (s, 1H), 5.63 (s, 1H), 3.81 (s, 3H), 3.32-3.11 (m, 6H), 1.98-1.75 (m, 2H), 1.75-1.60 (m, 5H), 1.53-1.42 (m, 1H), 1.39-1.30 (m, 1H), 1.20 (s, 3H), 0.89-0.86 (m, 2H), 0.54-0.52 (m, 1H), 0.44-0.41 (m, 1H). RT = 4.86 min, 100% ee (SFC method F) |
| 30 | 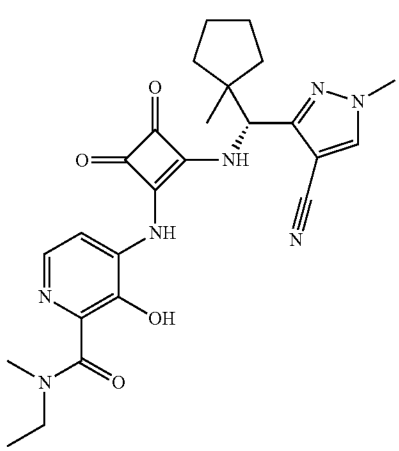 | (R)-4-((2-(((4-Cyano-1-methyl-1H-pyrazol-3-yl)(1-methylcyclopentyl)methyl)amino)-3,4-dioxocyclobut-1-en-1-yl)amino)-N-ethyl-3-hydroxy-N-methylpicolinamide. Yellow solid, 14.3 mg (23%). LCMS m/z 492.5 [M + H]$^+$. $^1$H NMR (400 MHz, CD$_3$OD) δ 8.22 (d, J = 5.5 Hz, 1H), 8.19 (s, 1H), 7.98-7.90 (m, 1H), 5.53 (s, 1H), 3.96 (s, 3H), 3.71-3.60 (m, 2H), 3.23-3.12 (m, 3H), 1.95-1.64 (m, 6H), 1.57-1.49 (m, 1H), 1.42-1.22 (m, 4H), 1.16 (s, 3H). RT = 5.03 min, 98.5% ee (SFC method H) |

TABLE 2-continued

| Ex. | Structure | Chemical Name and Analytical Data |
|---|---|---|
| 31 | 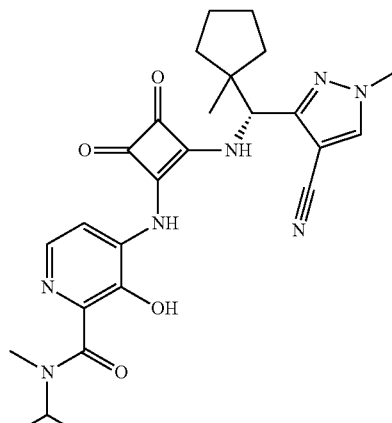 | (R)-4-((2-(((4-cyano-1-methyl-1H-pyrazol-3-yl)(1-methylcyclopentyl)methyl)amino)-3,4-dioxocyclobut-1-en-1-yl)amino)-3-hydroxy-N-isopropyl-N-methylpicolinamide. Yellow solid, 14.8 mg (24%). LCMS m/z 506.4 [M + H]$^+$. $^1$H NMR (400 MHz, CD$_3$OD) δ 8.24-8.20 (m, 1H), 8.19 (s, 1H), 7.93 (br s, 1H), 5.53 (s, 1H), 4.35-4.25 (m, 1H), 3.96 (s, 3H), 3.02 (s, 3H), 1.95-1.65 (m, 6H), 1.60-1.45 (m, 1H), 1.40-1.15 (m, 7H), 1.16 (s, 3H). RT = 4.49 min, 97.6% ee (SFC method J) |
| 32 | 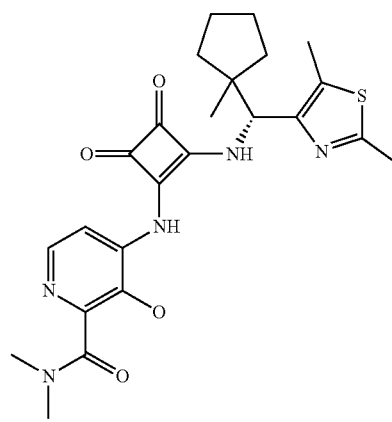 | (R)-4-((2-(((2,5-Dimethylthiazol-4-yl)(1-methylcyclopentyl)methyl)amino)-3,4-dioxocyclobut-1-en-1-yl)amino)-3-hydroxy-N,N-dimethylpicolinamide. Yellow solid, 63 mg (30%). LCMS m/z 484.4 [M + H]$^+$. $^1$H NMR (400 MHz, CD$_3$OD) δ 8.22 (d, J = 5.6 Hz, 1H), 7.92 (br s, 1H), 5.48 (s, 1H), 3.24 (br s, 3H), 3.16 (br s, 3H), 2.62 (s, 3H), 2.45 (s, 3H), 1.90-1.75 (m, 2H), 1.75-1.55 (m, 4H), 1.50-1.40 (m, 1H), 1.40-1.30 (m, 1H), 1.14 (s, 3H). RT = 3.44 min, 98.6% ee (SFC method F) |
| 33 | 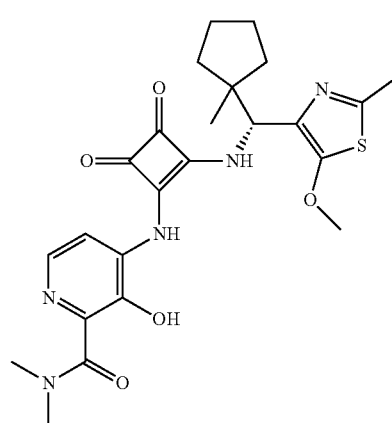 | (R)-3-Hydroxy-4-((2-(((5-methoxy-2-methylthiazol-4-yl)(1-methylcyclopentyl)methyl)amino)-3,4-dioxocyclobut-1-en-1-yl)amino)-N,N-dimethylpicolinamide. Yellow solid, 34.4 mg (42%). LCMS m/z 500.4 [M + H]$^+$. $^1$H NMR (400 MHz, CD$_3$OD) δ 8.22 (d, J = 5.6 Hz, 1H), 7.92 (br s, 1H), 5.46 (s, 1H), 3.94 (s, 3H), 3.22 (br s, 3H), 3.14 (br s, 3H), 2.58 (s, 3H), 1.88-1.76 (m, 2H), 1.70-1.60 (m, 4H), 1.43-1.38 (m, 1H), 1.32-1.25 (m, 1H), 1.12 (s, 3H). RT = 1.46 min, 100% ee (SFC method B) |

Example 34

(R)-4-((2-(((2,5-Dimethyl oxazol-4-yl)(1-methyl cyclopentyl)methyl)amino)-3,4-dioxocyclobut-1-en-1-yl)amino)-3-hydroxy-N,N-dimethylpicolinamide

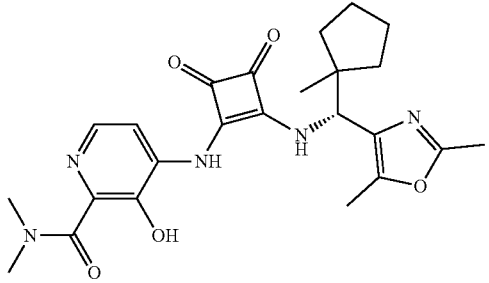

Step 34A. (2,5-Dimethyloxazol-4-yl)(1-methylcyclopentyl)methanamine

The title compound was prepared in a similar manner to (1,4-dimethyl-1H-pyrazol-3-yl)(5-methylspiro[2.3]hexan-5-yl)methanamine (Preparative Step 170) employing 2,5-dimethyloxazole-4-carboxylic acid and cyclopentylmagnesium bromide. LCMS m/z 192.2 [M-NH$_2$]$^+$.

Step 34B. (R)-4-((2-(((2,5-Dimethyloxazol-4-yl)(1-methylcyclopentyl)methyl)amino)-3,4-dioxocyclobut-1-en-1-yl)amino)-3-hydroxy-N,N-dimethylpicolinamide To a solution of (2,5-dimethyloxazol-4-yl)(1-methylcyclopentyl)methanamine (45 mg, 0.22 mmol) in EtOH (1.6 mL) was added 4-((2-ethoxy-3,4-dioxocyclobut-1-en-1-yl)amino)-3-hydroxy-N,N-dimethylpicolinamide (Preparative Step 1H) (50 mg, 0.16 mmol) and DIEA (318 mg, 2.46 mmol). The resulting solution was stirred at 40° C. overnight. The reaction mixture was concentrated in vacuo. The residue was subjected to enantiomer separation employing chiral SFC conditions (Chiralcel OD, 250 mm×21 mm×5 µm, 5 to 60% 0.2% NH$_4$+(7 N in MeOH) in MeOH, 80 mL/min). Isolation of the first eluting isomer afforded 16 mg (21%) of the title compound and the second eluting isomer afforded 23 mg (30%) of the corresponding enantiomer. LCMS m/z 468.6 [M+H]$^+$. $^1$H NMR (400 MHz, DMSO-d$_6$) δ 9.23-9.10 (m, 1H), 7.98-7.97 (m, 1H), 7.91 (br s, 1H), 5.17-5.15 (s, 1H), 3.17 (s, 3H), 3.04 (s, 3H), 2.37 (s, 3H), 2.25 (s, 3H), 1.78-1.47 (m, 7H), 1.37-1.10 (m, 3H), 1.05 (s, 3H). RT=5.58 min, 100% ee (SFC method C)

Example 35

(R)-4-((2-(((1,4-Dimethyl-1H-pyrazol-3-yl)(1-ethyl-cyclobutyl)methyl)amino)-3,4-dioxocyclobut-1-en-1-yl)amino)-3-hydroxy-N,N-dimethylpicolinamide

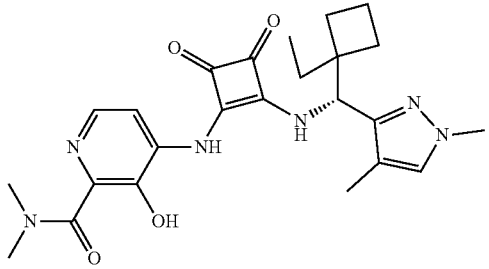

Step 35A. (1,4-Dimethyl-1H-pyrazol-3-yl)(1-ethyl-cyclobutyl)methanamine

The title compound was prepared in a similar manner to (1,4-dimethyl-1H-pyrazol-3-yl)(5-methylspiro[2.3]hexan-5-yl)methanamine (Preparative Step 17D) employing 1-ethylcyclobutane-1-carboxylic acid and 3-iodo-1,4-dimethyl-1H-pyrazole. LCMS m/z 190.8 [M-NH$_2$]$^+$

Step 35B. (R)-4-((2-(((1,4-Dimethyl-1H-pyrazol-3-yl)(1-ethylcyclobutyl)methyl)amino)-3,4-dioxocyclobut-1-en-1-yl)amino)-3-hydroxy-N,N-dimethylpicolinamide To a solution of (1,4-dimethyl-1H-pyrazol-3-yl)(1-ethyl-cyclobutyl)methanamine (800 mg, 3.28 mmol) in EtOH (15 mL) was added 4-((2-ethoxy-3,4-dioxocyclobut-1-en-1-yl)amino)-3-hydroxy-N,N-dimethylpicolinamide (Preparative Step 1H) (120 mg, 0.39 mmol) and DIEA (152 mg, 1.18 mmol). The resulting solution was stirred at 30° C. overnight. The reaction mixture was concentrated in vacuo. The residue was purified using preparative HPLC (Agela Durashell C$_{18\ 150}$ mm×25 mm×5 µm 13 to 53% CH$_3$CN in 0.05% NH$_4$OH in water, 25 mL/min, 11 min) to afford 100 mg of the racemic product. The racemic mixture was subjected to enantiomer separation employing chiral SFC conditions (REGIS (s,s) WHELK-O1 250 mm×30 mm×5 µm 45% 0.1% NH$_4$OH in EtOH, 60 mL/min). Isolation of the first eluting isomer afforded 33 mg (18%) of the title compound as a yellow solid and the second eluting isomer afforded 34 mg (19%) of the corresponding enantiomer as a yellow solid. LCMS m/z 467.4 [M+H]$^+$. $^1$H NMR (400 MHz, CD$_3$OD) δ 8.27 (d, J=5.6 Hz, 1H), 7.94 (d, J=5.7 Hz, 1H), 7.31 (s, 1H), 5.51 (s, 1H), 3.84 (s, 3H), 3.30-3.10 (m, 6H), 2.46-2.38 (m, 1H), 2.15-2.05 (m, 4H), 1.95-1.60 (m, 6H), 1.00 (t, J=7.4, 3H). Chiral SFC (SFC method I) RT=10.44 min, 97.2% ee (title compound) and RT=14.45 min, 91.9% ee (enantiomer).

Example 36

4-((2-(((S)-((S)-4,4-Difluoro-2-methyltetrahydrofuran-2-yl)(1,4-dimethyl-1H-pyrazol-3-yl)methyl)amino)-3,4-dioxocyclobut-1-en-1-yl)amino)-3-hydroxy-N,N-dimethylpicolinamide

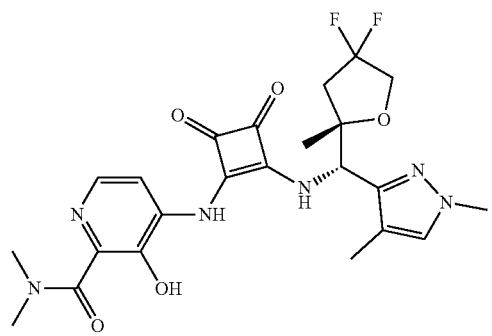

Step 36A. Ethyl 2-hydroxy-2-methylpent-4-enoate

To a solution of ethyl 2-oxopropanoate (76 g, 654.5 mmol) in DCM (380 mL) at −78° C. was added titanium (IV) chloride (124 g, 655 mmol). The resulting mixture was stirred at the same temperature for 30 min as it turned into a yellow suspension. Allyltrimethylsilane (97.2 g, 851 mmol) was then added and the reaction was stirred for 2 h. The reaction was warmed to 0° C. and quenched with saturated aqueous Na$_2$CO$_3$ solution (1.5 L) and extracted with DCM (3.0 L×2). The combined organic extracts were dried over Na$_2$SO$_4$, filtered and concentrated in vacuo. The residue was purified by silica gel column chromatography (5 to 10% EtOAc in petroleum ether) to afford 134 g (63%) of the title compound as a light yellow oil. LCMS m/z 158.8 [M+H]$^+$. $^1$H NMR (400 MHz, CDCl$_3$) δ 5.80-5.70 (m, 1H), 5.12 (s, 1H), 5.10-5.07 (m, 1H), 4.25-4.15 (m, 2H), 3.19 (s, 1H), 2.53-2.45 (m, 1H), 2.41-2.38 (m, 1H), 1.41 (s, 3H), 1.32-1.25 (m, 3H).

Step 36B. Ethyl 2-hydroxy-2-methyl-3-(oxiran-2-yl)propanoate

To a solution of ethyl 2-hydroxy-2-methylpent-4-enoate (46 g, 290.8 mmol) in DCM (1.45 L) at 0° C. was added m-CPBA (81.5 g, 378 mmol, 80% purity) in portions over 20 min. The reaction mixture was stirred at 10° C. for 1 h, and then warmed to 35° C. and stirred for 16 h. The mixture was cooled down to 0° C. and quenched with saturated aqueous Na$_2$S$_2$O$_3$ solution. The organic layer was separated and washed with saturated aqueous Na$_2$CO$_3$ solution, dried over Na$_2$SO$_4$, filtered and concentrated in vacuo. The residue was purified by silica gel column chromatography to give 81 g (80%) of the title compound as a light yellow oil consisting of a diastereomeric mixture. $^1$H NMR (400 MHz, CDCl$_3$) δ 3 4.35-4.20 (m, 2H), 3.50 (s, 0.5H), 3.35 (s, 0.5H), 3.15-3.05 (m, 1H), 2.80-2.70 (m, 1H), 2.50-2.42 (m, 1H), 2.01-1.85 (m, 2H), 1.48 (s, 1.5H), 1.45 (s, 1.5H), 1.35-1.30 (m, 3H).

Step 36C. Ethyl 2-methyl-4-oxotetrahydrofuran-2-carboxylate

Magnesium bromide (12 g, 65.4 mmol) was added to a solution of ethyl 2-hydroxy-2-methyl-3-(oxiran-2-yl)propanoate (76 g, 436 mmol) in THF (957 mL). The mixture was heated at 80° C. for 16 h. The reaction mixture was then concentrated in vacuo. The residue was taken up in water (100 mL) and extracted with DCM (500 mL×2). The combined organic extracts were concentrated in vacuo. The residue was dissolved in DCM (2080 mL) and cooled to 0° C. Silica gel (78.6 g, 1310 mmol) and PCC (122 g, 567 mmol) were added, and the mixture was stirred at 10° C. for 16 h. Additional PCC (18.8 g, 87.3 mmol) was added and the mixture was stirred at 30° C. for 4 h. The reaction mixture was filtered and the solids were washed with DCM (500 mL×2). The organic filtrate was dried over Na$_2$SO$_4$, filtered and concentrated in vacuo. The residue was purified by silica gel column chromatography (10 to 15% EtOAc in petroleum ether) to give 24.3 g (32%) of the title compound as a light yellow oil. $^1$H NMR (400 MHz, CDCl$_3$) δ 4.26-4.20 (m, 2H), 4.14 (s, 2H), 2.90-2.85 (m, 1H), 2.47-2.41 (m, 1H), 1.63 (s, 3H), 1.32-1.28 (m, 3H).

Step 36D. Ethyl 4,4-difluoro-2-methyltetrahydrofuran-2-carboxylate

DAST (37.4 g, 232 mmol) was added dropwise to a neat sample of ethyl 2-methyl-4-oxotetrahydrofuran-2-carboxylate (20.0 g, 116.2 mmol) at 10° C. The resulting mixture was stirred at the same temperature for 15 h. The mixture was then diluted with DCM (50 mL), and poured into a saturated aqueous NaHCO$_3$ solution (500 mL) at 0° C. The mixture was extracted with DCM (500 mL×2), and the combined organic extracts were washed with brine (100 mL), dried over Na$_2$SO$_4$, filtered and concentrated in vacuo to give the title compound as a yellow oil. The crude was used directly without further purification assuming quantitative yield. $^1$H NMR (400 MHz, CDCl$_3$) δ 4.30-4.20 (m, 2H), 4.20-4.05 (m, 2H), 2.95-2.85 (m, 1H), 2.40-2.25 (m, 1H), 1.57 (s, 3H), 1.35-1.25 (m, 3H). $^{19}$F NMR (376 MHz, CD$_3$OD) δ−101, −98.0.

Step 36E. Benzyl (S)-4,4-difluoro-2-methyltetrahydrofuran-2-carboxylate

To a solution of ethyl 4,4-difluoro-2-methyltetrahydrofuran-2-carboxylate (36.5 g, 140 mmol) in THF (1.5 L) at 15° C. was added a 1.0 M aqueous solution of LiOH (214 mL, 214 mmol). The mixture was stirred at 15° C. for 2 h, and then concentrated in vacuo. The residue was acidified with 1.0 M aqueous HCl solution until the solution pH reached 3, and then was extracted with DCM (600 mL×3) and DCM/MeOH (10/1, 600 mL×2). The combined organic extracts were dried over Na$_2$SO$_4$, filtered and concentrated in vacuo. The residue was dissolved in acetonitrile (500 mL) and K$_2$CO$_3$ (25 g, 181 mmol) was added in portions. Benzyl bromide (25 g, 146 mmol) was then added dropwise. The resulting suspension was stirred at 60° C. for 16 h. The reaction mixture was quenched with water (500 mL) and extracted with EtOAc (500 mL×3). The combined organic extracts were concentrated in vacuo. The residue was purified by silica gel column chromatography (0 to 25% EtOAc in petroleum ether) to give the racemic product as a yellow oil (24.7 g, 80%). A portion of the racemic product (5.0 g) was subjected to chiral resolution employing normal phase chiral chromatography conditions (Phenomenex Lux 10 μm Cellulose-3 45% EtOH in hexanes, 20 mL/min, 12 min). Isolation of the second eluting peak afforded 2.56 g of the title compound as a colorless oil. LCMS m/z 274.2 [M+water]. $^1$H NMR (400 MHz, CDCl$_3$) δ 3 7.39-7.34 (m, 5H), 5.21 (s, 2H), 4.15-4.04 (m, 2H), 2.96-2.84 (m, 1H), 2.40-2.24 (m, 1H), 1.59 (s, 3H). $^{19}$F NMR (376 MHz, CDCl$_3$) δ−101, −98.0.

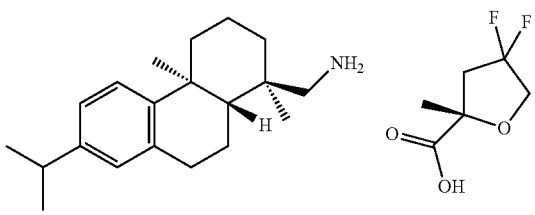 [SMILES: CC(C)c1ccc2c(c1)CC[C@H]1[C@](C)(CN)CCC[C@]21C ; C[C@@]1(C(=O)O)CC(F)(F)CO1]

Figure 3:
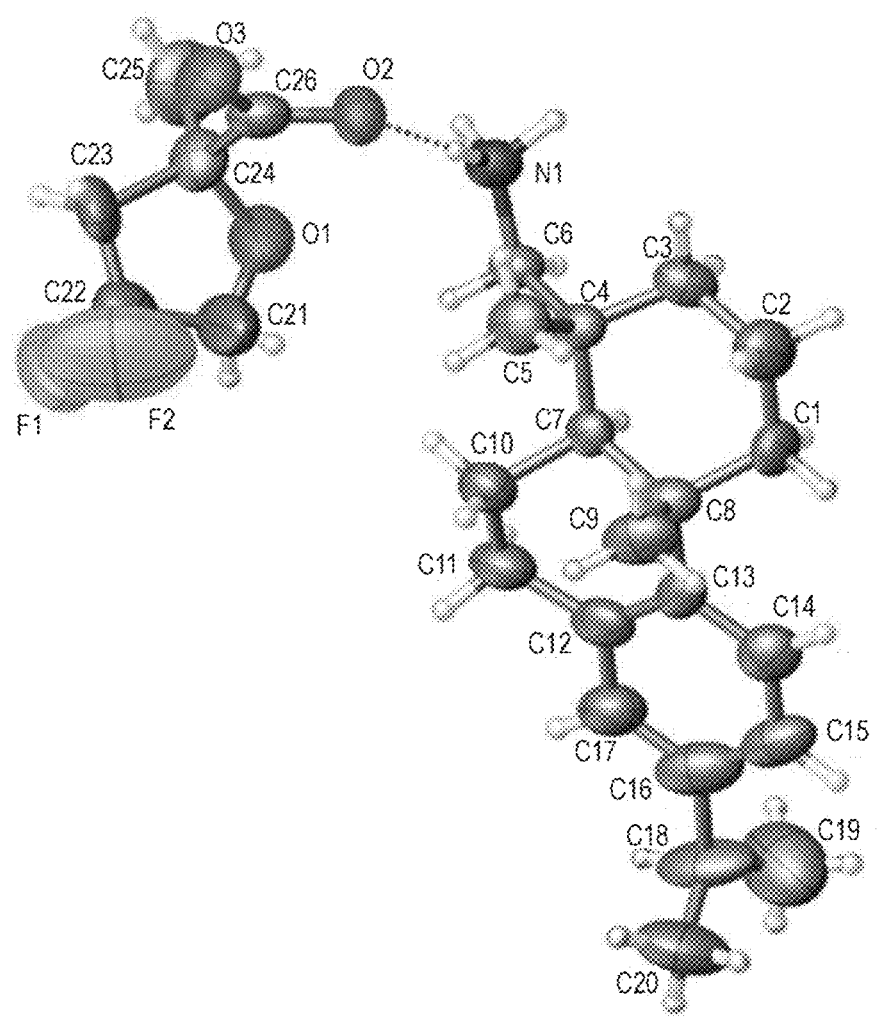
FIG. 3 is an X-ray structure (ORTEP drawing) of crystalline (S)-4,4-difluoro-2-methyltetrahydrofuran-2-carboxylic acid ((1R,4aS,10aR)-7-isopropyl-1,4a-dimethyl-1,2,3,4,4a,9,10,10a-octahydrophenanthren-1-yl)methanamine salt (Example 36F).

Step 36F. (S)-4,4-difluoro-2-methyltetrahydrofuran-2-carboxylic acid ((1R,4aS,10aR)-7-isopropyl-1,4a-dimethyl-1,2,3,4,4a,9,10,10a-octahydrophenanthren-1-yl)methanamine salt The absolute stereochemistry of the title compound was determined by single crystal X-ray crystallography (FIG. 3). Benzyl (S)-4,4-difluoro-2-methyltetrahydrofuran-2-carboxylate was hydrolyzed to the corresponding acid and crystallized with ((1R,4aS,10aR)-7-isopropyl-1,4a-dimethyl-1,2,3,4,4a,9,10,10a-octahydrophenanthren-1-yl)methanamine from ethanol.

Step 36G. (S)-(4,4-Difluoro-2-methyltetrahydrofuran-2-yl)(1,4-dimethyl-1H-pyrazol-3-yl)methanone To a solution of 3-iodo-1,4-dimethyl-1H-pyrazole (Preparative Step 1D) (394 mg, 1.77 mmol) in THF (3.23 mL) at 0° C. was added dropwise i-PrMgCl.LiCl (1.37 mL, 1.77 mmol, 1.3 M solution in THF). The resulting yellow solution was stirred at the same temperature for 2 h, and then warmed to ambient temperature and stirred for 30 min. The mixture was cooled to 0° C., and benzyl (S)-4,4-difluoro-2-methyltetrahydrofuran-2-carboxylate (413 mg, 1.61 mmol) was added. The mixture was stirred at 0° C. for 30 min, and then warmed to ambient temperature and stirred for >12 h. The reaction mixture was quenched with a saturated aqueous $NH_4Cl$ solution and the mixture was extracted with DCM. The combined organic extracts were dried over $Na_2SO_4$, filtered and concentrated in vacuo. The residue was purified by silica gel column chromatography (0 to 100% EtOAc in DCM) to afford 351 mg (89%) of the title compound as an oil. LCMS m/z 245.3 [M+H]$^+$. $^1$H NMR (400 MHz, CDCl$_3$) δ 7.16 (s, 1H), 4.20-4.05 (m, 2H), 3.90 (s, 3H), 3.34-3.23 (m, 1H), 2.62-2.51 (m, 1H), 2.29 (s, 3H), 1.78 (s, 3H).

Step 36H. (S,R)—((S)-4,4-Difluoro-2-methyltetrahydrofuran-2-yl)(1,4-dimethyl-1H-pyrazol-3-yl)methanamine To a solution of (S)-(4,4-difluoro-2-methyltetrahydrofuran-2-yl)(1,4-dimethyl-1H-pyrazol-3-yl)methanone (352 mg, 1.44 mmol) in methanolic ammonia (1.23 g, 10.3 mL, 72.1 mmol, 7.0 M in MeOH) was added titanium (IV) ethoxide (1.97 g, 1.81 mL, 8.65 mmol). The resulting suspension was sealed and stirred at 60° C. overnight. The reaction was cooled down to 0° C., and NaBH$_4$ (224 mg, 5.91 mmol) was added. The mixture was stirred at 0° C. for 30 min, and then at ambient temperature for 1 h. The reaction mixture was concentrated in vacuo. HCl (1.0 N aqueous solution) was added to the residue until the mixture was acidic, and then was extracted with Et$_2$O. The aqueous layer was neutralized with NaOH (1.0 N aqueous solution), and then extracted with DCM (×2). The combined organic extracts were dried over Na$_2$SO$_4$, filtered and concentrated in vacuo. The residue was dissolved in DCM (2 mL) and HCl (4 mL, 4.0 M in MeOH) was added. The solution was stirred for 10 min and then concentrated in vacuo to afford the title compound as a white solid as a mono-HCl salt. The product was isolated as a mixture of two diastereomers and used directly without further purification.

Step 36I. 4-((2-(((S)-((S)-4,4-difluoro-2-methyltetrahydrofuran-2-yl)(1,4-dimethyl-1H-pyrazol-3-yl)methyl)amino)-3,4-dioxocyclobut-1-en-1-yl)amino)-3-hydroxy-N,N-dimethylpicolinamide DIEA (131 mg, 1.02 mmol) and (S,R)—((S)-4,4-difluoro-2-methyltetrahydrofuran-2-yl)(1,4-dimethyl-1H-pyrazol-3-yl)methanamine (292 mg, 1.19 mmol) was added to 4-((2-ethoxy-3,4-dioxocyclobut-1-en-1-yl)amino)-3-hydroxy-N,N-dimethylpicolinamide (Preparative Step 1G) (330 mg, 1.08 mmol) in EtOH (1.9 mL). The mixture was stirred at room temperature for 18 h and then concentrated in vacuo. The residue was purified by silica gel column chromatography (0 to 10% MeOH in DCM). The resulting diastereomeric mixture was separated by chiral SFC chromatography (Chiral Tech OD-H, 250 mm×30 mm, 5 μm, 25% ethanol containing 0.2% 7N ammonia in methanol, 80 mL/min). Isolation of the first eluting peak afforded 299 mg (55%) of the title compound as a yellow solid. LCMS m/z 505.4 [M+H]$^+$. $^1$H NMR (600 MHz, DMSO-d$_6$) δ 10.48 (br s, 2H), 9.23 (br s, 1H), 7.99 (d, J=5.3 Hz, 1H), 7.91 (br. s., 1H), 7.49 (s, 1H), 5.56 (d, J=8.4 Hz, 1H), 4.10-3.96 (m, 1H), 3.93-3.82 (m, 1H), 3.80 (s, 3H), 3.14 (br s, 3H), 3.03 (br s, 3H), 2.55-2.45 (m, 1H), 2.34-2.22 (m, 1H), 1.99 (s, 3H), 1.49 (s, 3H). Chiral SFC (SFC method A) RT=5.26 min, 100% ee.

Examples 37 to 38

The title compounds in Table 3 were prepared in a similar manner to 4-((2-(((S)—((S)-4,4-difluoro-2-methyltetrahydrofuran-2-yl)(1,4-dimethyl-1H-pyrazol-3-yl)methyl)amino)-3,4-dioxocyclobut-1-en-1-yl)amino)-3-hydroxy-N,N-dimethylpicolinamide (Example 36) employing the appropriate heteroaryl halide.

TABLE 3

| Ex. | Structure | Chemical Name and Analytical Data |
|---|---|---|
| 37 | 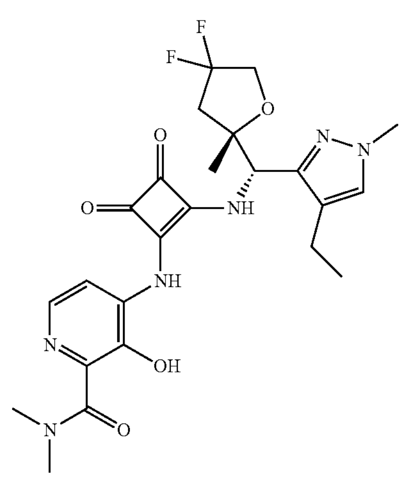 | 4-((2-(((S)-((S)-4,4-Difluoro-2-methyltetrahydrofuran-2-yl)(4-ethyl-1-methyl-1H-pyrazol-3-yl)methyl)amino)-3,4-dioxocyclobut-1-en-1-yl)amino)-3-hydroxy-N,N-dimethylpicolinamide. Yellow solid, 21.5 mg (15%). LCMS m/z 519.3 [M + H]$^+$. $^1$H NMR (400 MHz, CD$_3$OD) δ 8.24 (d, J = 5.6 Hz, 1H), 7.95-7.90 (m, 1H), 7.38 (s, 1H), 5.68 (s, 1H), 4.10-3.88 (m, 2H), 3.86 (s, 3H), 3.23 (br s, 3H), 3.16 (br s, 3H), 2.75-2.65 (m, 1H), 2.60-2.45 (m, 2H), 2.35-2.20 (m, 1H), 1.60 (s, 3H), 1.20 (t, J = 7.5 Hz, 3H). $^{19}$F NMR (376 MHz, CD$_3$OD) δ −104, −98.0. RT = 3.86 min, 100% ee (SFC method D) |

TABLE 3-continued

| Ex. | Structure | Chemical Name and Analytical Data |
|---|---|---|
| 38 | (structure) | 4-((2-(((S)-((S)-4,4-Difluoro-2-methyltetrahydrofuran-2-yl)(2,5-dimethylthiazol-4-yl)methyl)amino)-3,4-dioxocyclobut-1-en-1-yl)amino)-3-hydroxy-N,N-dimethylpicolinamide. Yellow solid, 22.9 mg (9%). LCMS m/z 522.3 [M + H]$^+$. $^1$H NMR (400 MHz,bCD$_3$OD) δ 8.24 (d, J = 5.5 Hz, 1H), 7.92 (d, J = 5.5 Hz, 1H), 5.71 (s, 1H), 4.02 (q, J = 10.9 Hz, 1H), 3.86 (dt, J = 18.6, 10.3 Hz, 1H), 3.23 (br s, 3H), 3.16 (br s, 3H), 2.85-2.70 (m, 1H), 2.64 (s, 3H), 2.47 (s, 3H), 2.26 (ddd, J = 17.7, 14.4, 8.0 Hz, 1H), 1.54 (s, 3H). $^{19}$F NMR (376 MHz, CD$_3$OD) δ −104, −98. RT = 4.14 min, 100.0% ee (SFC method H) |

Example 39

(R)-3-hydroxy-N,N-dimethyl-4-((2-(((1-methyl-4-(methyl-d$_3$)-1H-pyrazol-3-yl)(1-methylcyclopentyl)methyl)amino)-3,4-dioxocyclobut-1-en-1-yl)amino)picolinamide

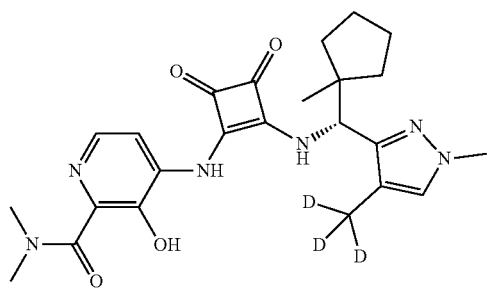

Step 39A. 4,4,5,5-Tetramethyl-2-(methyl-d$_3$)-1,3,2-dioxaborolane

To a dried and nitrogen filled flask equipped with a condenser and addition funnel was added Mg metal (1.26 g, 51.7 mmol) and a flake of iodine. The bottom of flask was heated with a heat gun until purple gas spread onto the Mg surface. Et$_2$O (5 mL) was added. The solution was stirred until the iodine color disappeared. Once the solution turned colorless, a solution of iodomethane-d$_3$ (5.0 g, 34.49 mmol) in Et$_2$O (45 mL) was added slowly. After the addition was complete, the reaction was heated to reflux for 20 min. The formed Grignard reagent was added dropwise to a solution of 2-methoxy-4,4,5,5-tetramethyl-1,3,2-dioxaborolane (5.45 g, 5.65 mL, 34.5 mmol) in Et$_2$O (20 mL) at −60° C. The reaction was then allowed to warm to 20° C. and stirred for 1 h. The reaction mixture was quenched with saturated NH$_4$Cl and the layers separated. The organic layer was dried (Na$_2$SO$_4$) and filtered. The filtrate was concentrated to afford the title compound, which was used without further purification.

Step 39B. N-Methoxy-N,1-dimethylcyclopentane-1-carboxamide

To a solution of 1-methylcyclopentane-1-carboxylic acid (60 g, 470 mmol) in DCM (1.5 L) was added HN(Me)(OMe)·HCl (50.2 g, 515 mmol), TEA (194 g, 1.92 mol) and HATU (267 g, 702 mmol) at 0° C. The mixture was stirred at 25° C. for 15 h and then concentrated. The residue was added to saturated aqueous Na$_2$CO$_3$ (1 L) and extracted with EtOAc (2×1 L). The combined organic extracts were dried (Na$_2$SO$_4$) and filtered. The filtrate was concentrated and the residue was purified by distillation to afford 62.1 g (77%) of the title compound as a colorless oil. LCMS 193.2 [M+H]$^+$. $^1$H NMR (400 MHz, CDCl$_3$) δ 3.69 (s, 3H), 3.20 (s, 3H), 2.15-2.01 (m, 2H), 1.73-1.54 (m, 6H), 1.26 (s, 3H).

Step 39C. (1-Methyl-1H-pyrazol-3-yl)(1-methylcyclopentyl)methanone

3-Iodo-1-methyl-1H-pyrazole (2.19 g, 10.5 mmol) was added dropwise to iPrMgCl·LiCl (10.8 mL, 14.0 mmol, 1.3 M THF solution) and THF (14 mL) cooled to 0° C. under a nitrogen atmosphere. The mixture was allowed to stir at room temperature for 1 h. N-Methoxy-N,1-dimethylcyclopentane-1-carboxamide (1.2 g, 7.0 mmol) was then added dropwise. The mixture was stirred at room temperature for 18 h and then was quenched with saturated aqueous NH$_4$Cl. The reaction mixture was extracted with EtOAc. The organic extract was dried (Na$_2$SO$_4$) and filtered. The filtrate was concentrated and the residue was purified by silica gel column chromatography (10-50% EtOAc/heptane) to afford 992 mg (74%) of the title compound. LCMS 172.4 [M+H]$^+$. $^1$H NMR (400 MHz, CDCl$_3$) δ 7.34 (d, J=2.3 Hz, 1H), 6.81 (d, J=2.3 Hz, 1H), 3.98 (s, 3H), 2.46-2.33 (m, 2H), 1.79-1.63 (m, 6H), 1.49 (s, 3H).

Step 39D. (4-Iodo-1-methyl-1H-pyrazol-3-yl)(1-methylcyclopentyl)methanone

NIS (702 mg, 3.12 mmol) was added to a solution of (1-methyl-1H-pyrazol-3-yl)(1-methylcyclopentyl)methanone (400 mg, 2.08 mmol) in acetic acid (4.2 mL) and the mixture was stirred at room temperature for 18 h. The reaction mixture was concentrated and the residue was purified by silica gel column chromatography (0-20% EtOAc/heptane) to afford 595 mg (90%) of the title compound as a white solid. $^1$H NMR (400 MHz, CDCl$_3$) δ 7.47 (s, 1H), 3.98 (s, 3H), 2.43-2.32 (m, 2H), 1.80-1.60 (m, 6H), 1.47 (s, 3H).

Step 39E. (1-Methyl-4-(methyl-d$_3$)-1H-pyrazol-3-yl)(1-methylcyclopentyl)methanone A vial containing (4-iodo-1-methyl-1H-pyrazol-3-yl)(1-methylcyclopentyl)methanone (532 mg, 1.67 mmol), 4,4,5,5-tetramethyl-2-(methyl-d$_3$)-1,3,2-dioxaborolane (1.7 g, 11.7 mmol), dioxane (8 mL) and aqueous K$_3$PO$_4$ (3.55 g, 16.7 mmol, 8.36 mL, 2.0M) was purged with argon gas for 5 min. P(tBu)$_3$ Pd-G2 (177 mg, 0.33 mmol) was added and the mixture was heated to 100° C. for 4 h. The reaction mixture was partitioned with EtOAc. The organic layer was dried (Na$_2$SO$_4$) and filtered. The filtrate was concentrated and the residue was purified by silica gel column chromatography (50% DCM/heptane) to afford 185 mg (53%) of the title compound. 1H NMR (400 MHz, CDCl$_3$) δ 7.14 (s, 1H), 3.90 (s, 3H), 2.43-2.32 (m, 2H), 1.78-1.61, (m, 6H), 1.49 (s, 3H).

Step 39F. (1-Methyl-4-(methyl-d)-1H-pyrazol-3-yl)(1-methylcyclopentyl)methanone oxime A vial containing NaOAc (129 mg, 1.58 mmol), hydroxylamine hydrochloride (219 mg, 3.15 mmol), (1-methyl-4-(methyl-d$_3$)-1H-pyrazol-3-yl)(1-methylcyclopentyl)methanone (165 mg, 0.788 mmol), and EtOH (3.94 mL) was heated at 95° C. for 2 h and then cooled to room temperature. The solvent was removed and the residue was partitioned between DCM and saturated aqueous NaCl. The layers were separated and the aqueous layer was extracted with DCM (2×20 mL). The combined organic extracts were dried (Na$_2$SO$_4$) and filtered. The filtrate was concentrated to afford 212 mg of the title compound as a solid. LCMS m/z 225.2 [M+H]$^+$. $^1$H NMR (400 MHz, CDCl$_3$) δ 7.21 (s, 1H), 3.89 (s, 3H), 2.11-1.99 (m, 2H), 1.77-1.60 (m, 4H), 1.53-1.40 (m, 2H), 1.25 (s, 3H).

Step 39G. (1-Methyl-4-(methyl-d)-1H-pyrazol-3-yl)(1-methylcyclopentyl)methanamine HOAc (3 mL), followed by Zn (311 mg, 4.76 mmol) were added to a flask containing (1-methyl-4-(methyl-d$_3$)-1H-pyrazol-3-yl)(1-methylcyclopentyl)methanone oxime (178 mg, 0.79 mmol). The mixture was heated at 60° C. overnight. After cooling to room temperature, the reaction mixture was filtered through Celite and washed with HOAc. The filtrate was concentrated and azeotroped with toluene (3 times). The residue was diluted with DCM and Et$_2$O and pH was adjusted to pH-14 with 50% aqueous NaOH. The layers were separated and the aqueous layer extracted twice with DCM/Et$_2$O (2:8). The combined organic extracts were dried (Na$_2$SO$_4$) and filtered. The filtrate was concentrated to afford 145 mg (87%) of the title compound. LCMS m/z 194.2 [M-NH$_2$]+. $^1$H NMR (400 MHz, CDCl$_3$) δ 3 7.05 (s, 1H), 3.81 (s, 3H), 3.55-3.47 (m, 1H), 1.81-1.14 (m, 8H), 1.05 (s, 3H).

Step 39H. (R)-3-Hydroxy-N,N-dimethyl-4-((2-(((1-methyl-4-(methyl-d$_3$)-1H-pyrazol-3-yl)(1-methylcyclopentyl)methyl)amino)-3,4-dioxocyclobut-1-en-1-yl)amino)picolinamide EtOH (3.0 mL), 4-((2-ethoxy-3,4-dioxocyclobut-1-en-1-yl)amino)-3-hydroxy-N,N-dimethylpicolinamide (Preparative Step 1H) (842 mg, 0.7 mmol) and DIEA (267 mg, 0.36 mL, 2.07 mmol) were added to a flask containing (1-methyl-4-(methyl-d$_3$)-1H-pyrazol-3-yl)(1-methylcyclopentyl)methanamine (145 mg, 0.69 mmol). The mixture was stirred at room temperature overnight. The reaction mixture was filtered and the filtrate was concentrated. The residue was purified by silica gel column chromatography (6% MeOH/DCM) to afford the racemic product. The racemate was resolved by chiral SFC chromatography (Chiralcel OD, 250 mm×30 mm, 5 μm, 80 mL/min, 25% MeOH containing 0.2% 7N ammonia/MeOH). Isolation of the first eluting enantiomer afforded 70 mg of the title compound. LCMS m/z 470.5 [M+H]$^+$. $^1$H NMR (400 MHz, DMSO-d$_6$) δ 11.70 (s, 1H), 9.92 (s, 1H), 9.13 (d, J=10.1 Hz, 1H), 8.02 (s, 2H), 7.44 (s, 1H), 5.35 (d, J=10.1 Hz, 1H), 3.81 (s, 3H), 3.22-3.07 (m, 6H), 1.72-1.60 (m, 6H), 1.39-1.12 (m, 2H), 1.10 (s, 3H). The second eluting enantiomer was isolated to afford 70 mg of the corresponding (S)-enantiomer.

Example 40

4-((2-(((1R)-(1,4-dimethyl-1H-pyrazol-3-yl)(1-methylcyclopentyl-3,4-d$_2$)methyl)amino)-3,4-dioxocyclobut-1-en-1-yl)amino)-3-hydroxy-N,N-dimethylpicolinamide

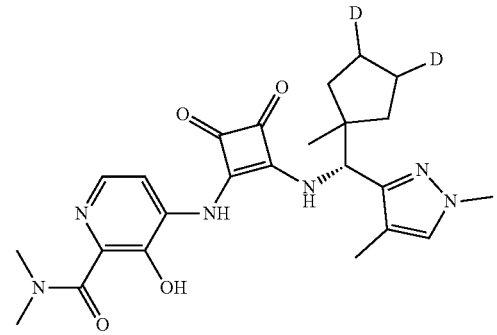

Step 40A. Cyclopent-3-ene-1-carboxylic acid

To a solution of methyl 1-methylcyclopent-3-ene-1-carboxylate (50 g, 396 mmol) in THF:H$_2$O (500 mL:125 mL) at 25° C. was added LiOH (19 g, 793 mmol). After 15 h, the reaction mixture was extracted with EtOAc. The aqueous layer was then acidified to pH=3 with 1N HCl and extracted with EtOAc (3×1 L). The combined organic extracts were combined, dried (Na$_2$SO$_4$) and filtered. The filtrate was concentrated to afford 40 g (90%) of the title compound as a yellow oil. $^1$H NMR (400 MHz, CDCl$_3$) δ 5.68 (s, 2H), 3.29-3.03 (m, 1H), 2.82-2.53 (m, 4H).

Step 40B. 1-Methylcyclopent-3-ene-1-carboxylic acid

To a solution of LDA (2M in THF/heptane/ethyl benzene, 446 mL) in THF (800 mL) was added dropwise a solution of cyclopent-3-ene-1-carboxylic acid (40 g, 357 mmol) in THF (200 mL) maintaining a temperature of −30° C. The mixture was warmed to 25° C. and stirred for 15 h. The mixture was then cooled to −30° C. and iodomethane (50.6 g, 22.2 mL, 357 mmol) was added. After 2 h at 25° C., the mixture was quenched with 3M HCl and extracted with EtOAc (3×1 L). The combined organic extracts were dried (Na$_2$SO$_4$) and filtered. The filtrate was concentrated under reduced pressure and the residue was purified by silica gel column chromatography (EtOAc) to afford 45 g (100%) of the title compound as an oil. $^1$H NMR (400 MHz, CDCl$_3$) δ 5.64 (s, 2H), 2.98 (d, J=14.7 Hz, 2H), 2.28 (d, J=14.7 Hz, 2H), 1.36 (s, 3H).

Step 40C. N-Methoxy-N,1-dimethylcyclopent-3-ene-1-carboxamide

To a solution of 1-methylcyclopent-3-ene-1-carboxylic acid (45 g, 357 mmol) in DCM (1 L) at 0° C. was added HN(Me)(OMe)·HCl (38.3 g, 392 mmol), TEA (148 g, 1.46 mol) and HATU (203 g, 535 mmol). After stirring at room temperature for 24 h, the reaction mixture was concentrated under reduced pressure. The residue was diluted with EtOAc (1 L) and washed with saturated aqueous Na$_2$CO$_3$. The aqueous layer was further extracted with EtOAc (1 L). The combined organic extracts were dried (Na$_2$SO$_4$) and filtered. The filtrate was concentrated under reduced pressure and the residue was purified by silica gel column chromatography (PE:EtOAc, 20:1 to 5:1) to afford 23.4 g (39%) of the title compound as a light yellow oil. LC/MS m/z 170.3 [M+H]$^+$; $^1$H NMR (400 MHz, CDCl$_3$) δ 5.59 (s, 2H), 3.69 (s, 3H), 3.20 (s, 3H), 2.88 (d, J=15.1 Hz, 2H), 2.23 (d, J=15.1 Hz, 2H), 1.27 (s, 3H).

Step 40D. (1,4-Dimethyl-1H-pyrazol-3-yl)(1-methylcyclopent-3-en-1-yl)methanone A 125 mL round bottomed flask with stir bar and fitted with a septum was backfilled with nitrogen three times, after which THF (7.0 mL) was added followed by 3-iodo-1,4-dimethyl-1H-pyrazole (Preparative Step 1D) (917 mg, 4.13 mmol). To this solution was added dropwise a 1.3 M solution of iPrMgCl·LiC in THF (5.45 mL) and the mixture was stirred for 1 h at room temperature. N-Methoxy-N,1-dimethylcyclopent-3-ene-1-carboxamide (600 mg, 3.55 mmol) in THF (5 mL) was added dropwise. After stirring for 2 h, the reaction mixture was quenched with saturated aqueous NH$_4$Cl (20 mL) and extracted with DCM (3×25 mL). The combined extracts were dried (Na$_2$SO$_4$) and filtered. The filtrate was concentrated under reduced pressure. The residue was purified by silica gel column chromatography (EtOAc in heptane, 0-100%) to afford 500 mg (69%) of the title compound as a colorless oil. $^1$H NMR (400 MHz, CDCl$_3$) δ 7.14 (s, 1H), 5.70-5.64 (m, 2H), 3.90 (s, 3H), 3.20-3.12 (m, 2H), 2.44-2.36 (m, 2H), 2.30 (s, 3H), 1.52 (s, 3H).

Step 40E. N-((1,4-Dimethyl-1H-pyrazol-3-yl)(1-methylcyclopent-3-en-1-yl)methyl)formamide Formamide (10.5 mL) and formic acid (6 mL) was added to a flask containing (1,4-dimethyl-1H-pyrazol-3-yl)(1-methylcyclopent-3-en-1-yl)methanone (1.1 g, 5.4 mmol). The mixture was heated at 135° C. for 20 h and then cooled to room temperature. Water (60 mL) was added and the mixture was extracted with MTBE (3×50 mL). The combined organic extracts were dried (Na$_2$SO$_4$) and filtered. The filtrate was concentrated to afford the title compound, which was used in next step without purification. LC/MS m/z=234.0 [M+H]$^+$.

Step 40F. (1,4-Dimethyl-1H-pyrazol-3-yl)(1-methylcyclopent-3-en-1-yl)methanamine Aqueous 1N HCl (24 mL) was added to a flask containing N-((1,4-dimethyl-1H-pyrazol-3-yl)(1-methylcyclopent-3-en-1-yl)methyl)formamide (1.26 g, 5.4 mmol). The mixture was heated at 100° C. for 2 h and then cooled to room temperature. The pH of the solution was adjusted to pH ~11 with solid NaOH. The mixture was extracted with MTBE (3×30 mL). The combined organic extracts were dried (Na$_2$SO$_4$) and filtered. The filtrate was concentrated to afford 1.1 g (100%) of the title compound. LCMS m/z 189.1 [M-NH$_2$]$^+$. $^1$H NMR (400 MHz, CD$_3$OD) δ 7.27 (s, 1H), 5.66-5.58 (m, 2H), 3.86 (s, 1H), 3.82 (s, 3H), 2.67-2.51 (m, 2H), 2.09-1.97 (m, 4H), 1.93-1.83 (m, 1H), 1.10 (s, 3H).

Step 40G. 4-((2-(((R)-(1,4-Dimethyl-1H-pyrazol-3-yl)(1-methylcyclopent-3-en-1-yl)methyl)amino)-3,4-dioxocyclobut-1-en-1-yl)amino)-3-hydroxy-N,N-dimethylpicolinamide A mixture of 4-((2-ethoxy-3,4-dioxocyclobut-1-en-1-yl)amino)-3-hydroxy-N,N-dimethylpicolinamide (Preparative Step 1H) (300 mg, 0.983 mmol), (1,4-dimethyl-1H-pyrazol-3-yl)(1-methylcyclopent-3-en-1-yl)methanamine (242 mg, 1.18 mmol), ethanol (9.83 mL) and diisopropylethylamine (2.65 mL, 14.7 mmol) was stirred at 40° C. overnight. The reaction mixture was concentrated under reduced pressure. The residue was purified by silica gel column chromatography (0-20% MeOH in DCM) to afford 450 mg of racemic product. The enantiomers were resolved by chiral SFC (Chiral Tech OD-H, 250 mm×21.2 mm, 5 μm, 22.5% methanol containing 0.2% 7N ammonia/MeOH, 80 mL/min). Isolation of the first eluting enantiomer afforded 80 mg of the title compound. LCMS m/z 465.4 [M+H]$^+$. $^1$H NMR (400 MHz, CDCl$_3$) δ 12.84 (br. s., 1H), 8.27 (br. s., 1H), 8.02 (d, J=5.1 Hz, 1H), 7.97 (br. s., 1H), 7.22 (br. s., 1H), 7.11 (br. s., 1H), 5.63 (br. s., 2H), 5.50 (br. s., 1H), 3.81 (s, 3H), 3.61 (br. s., 3H), 3.19 (br. s., 3H), 2.78-2.64 (m, 2H), 2.15-2.02 (m, 5H), 1.21 (s, 3H). The second eluting enantiomer was isolated to afford 100 mg of the corresponding (S)-enantiomer.

Step 40H. 4-((2-(((1R)-(1,4-dimethyl-1H-pyrazol-3-yl)(1-methylcyclopentyl-3,4-d$_2$)methyl)amino)-3,4-dioxocyclobut-1-en-1-yl)amino)-3-hydroxy-N,N-dimethylpicolinamide To a Parr reactor with stir bar was added 4-((2-(((R)-(1,4-dimethyl-1H-pyrazol-3-yl)(1-methylcyclopent-3-en-1-yl)methyl)amino)-3,4-dioxocyclobut-1-en-1-yl)amino)-3-hydroxy-N,N-dimethylpicolinamide (20 mg, 0.043 mmol), 10% Pd/C (6.05 mg) and MeOH (10 mL). The reactor was degassed with nitrogen and then charged with D$_2$ gas to 10 psi. The reaction mixture was stirred for 16 h and then filtered through celite. The filtrate was concentrated under reduced pressure and the residue was purified by silica gel column chromatography (0-20% MeOH/DCM) to afford 16 mg (80%) of the title compound as a yellow solid. LCMS m/z 469.4 [M+H]$^+$. $^1$H NMR (400 MHz, DMSO d$_6$) δ 11.75 (br. s., 1H), 9.96 (br. s., 1H), 9.17 (br. s., 1H), 8.05-7.89 (m, 2H), 7.44 (s, 1H), 5.35 (d, J=10.2 Hz, 1H), 3.81 (s, 3H), 3.20 (br. s., 3H), 3.07 (br. s., 3H), 2.00 (s, 3H), 1.72-1.55 (m, 4H), 1.37-1.31 (m, 1H), 1.25-1.19 (m, 1H), 1.10 (s, 3H).

Example 41

(R)-((4-((2-(((1,4-Dimethyl-1H-pyrazol-3-yl)(1-methylcyclopentyl)methyl)amino)-3,4-dioxocyclobut-1-en-1-yl)amino)-2-(dimethylcarbamoyl)pyridin-3-yl)oxy)methyl dihydrogen phosphate

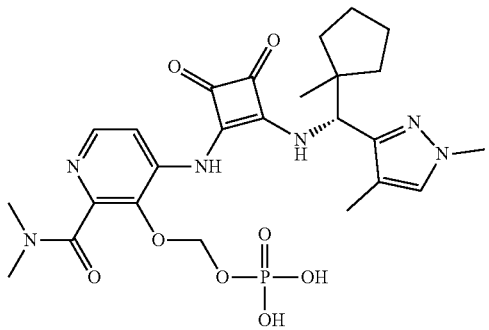

Step 41A. (R)-Di-tert-butyl(((4-((2-(((1,4-dimethyl-1H-pyrazol-3-yl)(1-methylcyclopentyl)methyl)-amino)-3,4-dioxocyclobut-1-en-1-yl)amino)-2-(dimethylcarbamoyl)pyridin-3-yl)oxy)methyl) phosphate $K_2CO_3$ (89 mg, 0.643 mmol), TBAI (119 mg, 0.322 mmol) and di-tert-butyl (chloromethyl) phosphate (0.65 mL, 0.75 mmol) were added to a room temperature solution of (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide (Example 1) (250 mg, 0.536 mmol)) in DMF. The reaction mixture was stirred at room temperature for 2 d and then toluene:$H_2O$ (4 mL:2 mL) was added. The layers were separated and the organic layer washed with brine, $H_3PO_4$ (1 M solution) and 10% $Na_2CO_3$. The organic layer was concentrated. The residue was taken up in toluene:MTBE (1 mL:20 mL) and placed in a refrigerator. The solid precipitate was collected and the filtrate concentrated. Heptane was added to the filtrate to effect precipitation of a solid, which was filtered, collected and dried on high vacuum to afford 140 mg (38%) of the title compound. LCMS 689.3 [M+H]$^+$. $^1$H NMR (400 MHz, $CDCl_3$) δ 10.08 (s, 1H), 8.43-8.08 (m, 3H), 6.95 (s, 1H), 5.57 (s, 2H), 5.39 (d, J=10.2 Hz, 1H), 3.68 (s, 3H), 3.06 (s, 3H), 2.75 (s, 3H), 2.00 (s, 3H), 1.82-1.53 (m, 6H), 1.45 (s, 9H), 1.43 (s, 9H), 1.41-1.18 (m, 2H), 1.09 (s, 3H).

Step 41B. (R)-((4-((2-(((1,4-Dimethyl-1H-pyrazol-3-yl)(1-methylcyclopentyl)methyl)amino)-3,4-dioxocyclobut-1-en-1-yl)amino)-2-(dimethylcarbamoyl)pyridin-3-yl)oxy)methyl dihydrogen phosphate To a solution of (R)-di-tert-butyl(((4-((2-(((1,4-dimethyl-1H-pyrazol-3-yl)(1-methylcyclopentyl)methyl)amino)-3,4-dioxocyclobut-1-en-1-yl)amino)-2-(dimethylcarbamoyl)-pyridin-3-yl)oxy)methyl) phosphate (80 mg, 0.12 mmol) in dioxane (1 mL) was added 4N HCl in dioxane (3 mL). After stirring for 45 h, the solvent was removed to afford 73 mg (100%) of the title compound as the HCl salt. LCMS 577.5 [M+H]$^+$. $^1$H NMR (400 MHz, $CD_3OD$) δ 8.86 (d, J=7.0 Hz, 1H), 8.49 (d, J=6.6 Hz, 1H), 7.78 (s, 1H), 5.75-5.63 (m, 1H), 5.52-5.40 (m, 2H), 4.01 (s, 3H), 3.22 (s, 3H), 3.04 (s, 3H), 2.23 (s, 3H), 1.84-1.74 (m, 6H), 1.66-1.60 (m, 1H), 1.50-1.41 (m, 1H), 1.22 (s, 3H).

Example 42

(R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate

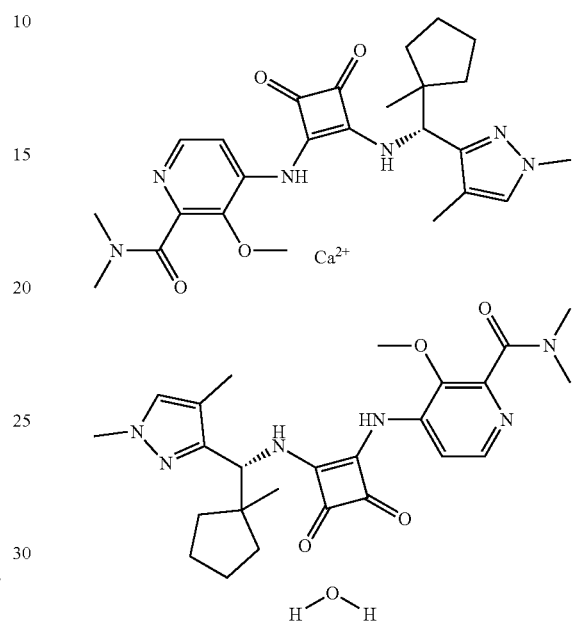

Method A. Calcium hydroxide (7.94 mg, 0.107 mmol) was added to a 7 mL vial with stir bar containing (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide (Example 1) (100 mg, 0.214 mmol) and MeOH (0.75 mL). The mixture was heated at 55° C. for 2 h and then cooled to room temperature and stirred for 72 h. The resulting suspension was filtered to afford the title compound as yellow crystals having a PXRD pattern consistent with that described in FIG. 12. When the desired PXRD pattern was not obtained, the resulting salt was taken up in MeOH (1 g material/10 mL MeOH) and slurried until a PXRD pattern consistent with that described in FIG. 12 was observed.

Method B. (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide (Example 1) (6.0 g, 12.86 mmol), MeOH (45 mL), and water (3.6 mL) followed by calcium hydroxide (476 mg, 6.43 mmol) were added to a 250 mL round bottomed flask with stir bar. The suspension was stirred at 45° C. for 4 h and then at room temperature for 4 d. The suspension was filtered. The solids were then added to a 125 mL round bottomed flask with stir bar and suspended in MeOH (50 mL). The mixture was seeded with ~1 mg of the title compound having a PXRD pattern consistent with that described in FIG. 12. The mixture was stirred at room temperature for 20 h and then was filtered to afford 4.21 g of the title compound as a slightly yellow solid that was determined to have the PXRD pattern in FIG. 12. LCMS m/z 467.5 [M+H]$^+$. $^1$H NMR (400 MHz, DMSO-$d_6$) δ 9.19 (br. d, J=8.2 Hz, 1H), 7.66 (d, J=4.7 Hz, 1H), 7.40 (s, 1H), 7.35 (m, 1H), 5.37 (d, J=9.8 Hz, 1H), 3.77 (s, 3H), 3.06 (s, 3H), 2.00 (s, 3H), 1.99 (s, 3H), 1.72-1.59 (m, 6H), 1.22-1.20 (m, 1H), 1.19-1.18 (m, 1H), 1.09 (s, 3H).

Single Crystal X-Ray Analysis of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate A crystal suitable for X-ray analysis was prepared by recrystallization from ethanol.

Data collection was performed on a Bruker D8 Venture diffractometer at room temperature. Data collection consisted of omega and phi scans. The structure was solved by intrinsic phasing using SHELX software suite in the Tetragonal class space group P4(3). The structure was subsequently refined by the full-matrix least squares method. All non-hydrogen atoms were found and refined using anisotropic displacement parameters. The hydrogen atoms located on nitrogen and oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft 2008) was performed using PLATON (Spek 2010). Assuming the sample submitted is enantiopure, the results indicate that the absolute structure has been correctly assigned. The final R-index was 4.3%. A final difference Fourier revealed no missing or misplaced electron density.

FIG. 1 is the obtained X-ray structure (ORTEP drawing) of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate. The crystal structure data is summarized in Table 4.

TABLE 4

| Crystal data and structure refinement. | |
|---|---|
| Empirical formula | C24 H32 N6 O5 |
| Formula weight | 484.55 |
| Temperature | 296(2) K |
| Wavelength | 1.54178 Å |
| Crystal system | Tetragonal |
| Space group | P43 |
| Unit cell dimensions | a = 10.6580(2) Å   α = 90°. |
|  | b = 10.6580(2) Å   β = 90°. |
|  | c = 22.9487(6) Å   γ = 90°. |
| Volume | 2606.81(12) Å$^3$ |
| Z | 4 |
| Density (calculated) | 1.235 Mg/m$^3$ |
| Absorption coefficient | 0.727 mm$^{-1}$ |
| F(000) | 1032 |
| Crystal size | 0.140 × 0.080 × 0.040 mm$^3$ |
| Theta range for data collection | 5.871 to 70.212°. |
| Index ranges | −12 <= h <= 12, |
|  | −12 <= k <= 12, |
|  | −28 <= l <= 25 |
| Reflections collected | 72157 |
| Independent reflections | 4856 [R(int) = 0.0500] |
| Completeness to theta = 67.679° | 99.3% |
| Absorption correction | Empirical |
| Refinement method | Full-matrix least-squares on F$^2$ |
| Data/restraints/parameters | 4856/6/336 |
| Goodness-of-fit on F2 | 1.200 |
| Final R indices [I > 2sigma(I)] | R1 = 0.0426, wR2 = 0.1240 |
| R indices (all data) | R1 = 0.0445, wR2 = 0.1259 |

TABLE 4-continued

| Crystal data and structure refinement. | |
|---|---|
| Extinction coefficient | n/a |
| Largest diff. peak and hole | 0.254 and −0.280 e.Å$^{-3}$ |

Single Crystal X-Ray Analysis of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate A crystal suitable for X-ray analysis was grown from a mixture of heptane, ethyl acetate, acetone and DCM via slow evaporation over 48 hours.

Data collection was performed on a Bruker D8 Venture diffractometer at room temperature. Data collection consisted of omega and phi scans. The structure was solved by intrinsic phasing using SHELX software suite in the Tetragonal class space group P43. The structure was subsequently refined by the full-matrix least squares method. All non-hydrogen atoms were found and refined using anisotropic displacement parameters. Water was found from the difference map during refinement, modeled with 0.33 occupancy. The hydrogen atoms bonded to water were not included in the refinement. The hydrogen atoms located on nitrogen and oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft 2008) was performed using PLATON (Spek 2010). Assuming the sample submitted is enantiopure, the results indicate that the absolute structure has been correctly assigned. The final R-index was 6.4%. A final difference Fourier revealed no missing or misplaced electron density.

FIG. 2 is the obtained X-ray structure (ORTEP drawing) of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate. The crystal structure data is summarized in Table 5.

TABLE 5

| Crystal data and structure refinement. | |
|---|---|
| Empirical formula | C23 H26.67 Cl N6 O |
| Formula weight | 438.62 |
| Temperature | 296(2) K |
| Wavelength | 1.54178 Å |
| Crystal system | Tetragonal |
| Space group | P43 |
| Unit cell dimensions | a = 10.5851(2) Å   α = 90°. |
|  | b = 10.5851(2) Å   β = 90°. |
|  | c = 22.9584(5) Å   γ = 90°. |
| Volume | 2572.36(11) Å$^3$ |
| Z | 4 |
| Density (calculated) | 1.133 Mg/m$^3$ |
| Absorption coefficient | 1.503 mm$^{-1}$ |
| F(000) | 927 |
| Crystal size | 0.140 × 0.040 × 0.020 mm$^3$ |
| Theta range for data collection | 4.600 to 65.219°. |
| Index ranges | −12 <= h <= 12, |
|  | −12 <= k <= 10, |
|  | −24 <= l <= 27 |
| Reflections collected | 20312 |
| Independent reflections | 4250 [R(int) = 0.0845] |
| Completeness to theta = 65.219° | 99.2% |

TABLE 5-continued

Crystal data and structure refinement.

| | |
|---|---|
| Absorption correction | None |
| Refinement method | Full-matrix least-squares on $F^2$ |
| Data/restraints/parameters | 4250/214/329 |
| Goodness-of-fit on F2 | 1.045 |
| Final R indices [I > 2sigma(I)] | R1 = 0.0637, wR2 = 0.1550 |
| R indices (all data) | R1 = 0.0872, wR2 = 0.1686 |
| Extinction coefficient | n/a |
| Largest diff. peak and hole | 0.238 and −0.261 e.Å$^{-3}$ |

Single Crystal X-Ray Analysis of crystalline (S)-4,4-difluoro-2-methyltetrahydrofuran-2-carboxylic acid ((1R,4aS,10aR)-7-isopropyl-1,4a-dimethyl-1,2,3,4,4a,9,10,10a-octahydrophenanthren-1-yl)methanamine salt (Example 36F)

A crystal suitable for X-ray analysis was prepared by recrystallization from ethanol.

Data collection was performed on a Bruker D8 Venture diffractometer at room temperature. Data collection consisted of omega and phi scans. The structure was solved by intrinsic phasing using SHELX software suite in the Monoclinic class space group P21. The structure was subsequently refined by the full-matrix least squares method. All non-hydrogen atoms were found and refined using anisotropic displacement parameters. The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms.

Stereochemistry was based on the known chiral configurations from centers C4(-R), C7(-R), and C8(-S) of the base. The final R-index was 7.6%. A final difference Fourier revealed no missing or misplaced electron density.

FIG. 3 is the obtained X-ray structure (ORTEP drawing) of crystalline (S)-4,4-difluoro-2-methyltetrahydrofuran-2-carboxylic acid ((1R,4aS,10aR)-7-isopropyl-1,4a-dimethyl-1,2,3,4,4a,9,10,10a-octahydrophenanthren-1-yl)methanamine salt. The crystal structure data is summarized in Table 6.

TABLE 6

Crystal data and structure refinement.

| | |
|---|---|
| Empirical formula | C52 H78 F4 N2 O6 |
| Formula weight | 903.16 |
| Temperature | 296(2) K |
| Wavelength | 1.54178 Å |
| Crystal system | Monoclinic |
| Space group | P21 |
| Unit cell dimensions | a = 10.8650(6) Å  α = 90°. |
| | b = 6.0384(4) Å  β = 91.899(5)°. |
| | c = 37.758(3) Å  γ = 90°. |
| Volume | 2475.8(3) Å$^3$ |
| Z | 2 |
| Density (calculated) | 1.211 Mg/m$^3$ |
| Absorption coefficient | 0.718 mm$^{-1}$ |
| F(000) | 976 |
| Crystal size | 0.280 × 0.060 × 0.020 mm$^3$ |
| Theta range for data collection | 3.513 to 70.682°. |
| Index ranges | −11 <= h <= 13, |
| | −6 <= k <= 6, |
| | −46 <= l <= 39 |
| Reflections collected | 22232 |
| Independent reflections | 7301 [R(int) = 0.0683] |
| Completeness to theta = 67.679° | 88.6% |
| Absorption correction | Empirical |

TABLE 6-continued

Crystal data and structure refinement.

| | |
|---|---|
| Refinement method | Full-matrix least-squares on $F^2$ |
| Data/restraints/parameters | 7301/7/607 |
| Goodness-of-fit on F2 | 1.038 |
| Final R indices [I > 2sigma(I)] | R1 = 0.0762, wR2 = 0.1915 |
| R indices (all data) | R1 = 0.1089, wR2 = 0.2102 |
| Absolute structure parameter | 0.04(15) |
| Extinction coefficient | 0.0032(8) |
| Largest diff. peak and hole | 0.253 and −0.209 e.Å$^{-3}$ |

Powder X-ray diffraction analysis of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate Powder X-ray diffraction analysis was conducted using a Bruker AXS D8 Advance diffractometer equipped with a Cu radiation source. Diffracted radiation was detected by a LYNXEYE_EX detector with motorized slits. Both primary and secondary detectors were equipped with 2.5 soller slits. The X-ray tube voltage and amperage were set at 40 kV and 40 mA, respectively. Data was collected in the Theta-Theta goniometer in a locked couple scan at Cu K-alpha wavelength from 3.0 to 40.0 degrees 2-Theta with an increment of 0.01 degrees, using a scan speed of 1.0 seconds per step. Samples were prepared by placement in a silicon low background sample holder (Bruker part number: C79298A3244B261). Data were collected and analyzed using Bruker DIFFRAC Plus software and analysis was performed by EVA Diffrac Plus software (v 4.2.1.10). Generally a threshold value of 1 and a Width value of 0.3 were used to make preliminary peak assignments. To ensure validity, adjustments were manually made; the output of automated assignments was visually checked and peak positions were adjusted to the peak maximum. Peaks with relative intensity of 3% were generally chosen. The peaks which were not resolved or were consistent with noise were not selected. A typical error associated with the peak position of crystalline material, from PXRD, stated in USP, is up to +/−0.2° 2-Theta (USP-941).

FIG. 4 is the obtained powder X-ray diffraction pattern for crystalline (R)-4-((2-(((1,4-dimethyl-1H-pyrazol-3-yl)-methylcyclopentyl)methyl)amino)-3,4-dioxocyclobut-1-en-1-yl)amino)-3-hydroxy-N,N-dimethylpicolinamide monohydrate and Table 7 lists the diffraction peaks in terms of 2-theta values.

TABLE 7

| Angle 2-Theta (degrees) | Relative Intensity (%) |
|---|---|
| 8.3 | 7.8 |
| 8.4 | 9.4 |
| 9.3 | 6.8 |
| 11.4 | 19.9 |
| 12.4 | 31.2 |
| 15.5 | 23.3 |
| 16.7 | 12.9 |
| 17.1 | 6.5 |
| 17.6 | 25.4 |
| 18.4 | 46.7 |
| 18.7 | 82.4 |
| 19.1 | 78.3 |
| 19.5 | 5.2 |

TABLE 7-continued

| Angle 2-Theta (degrees) | Relative Intensity (%) |
| --- | --- |
| 20.2 | 100.0 |
| 21.1 | 7.3 |
| 22.0 | 10.2 |
| 22.8 | 6.5 |
| 23.7 | 16.9 |
| 24.0 | 7.4 |
| 24.3 | 32.4 |
| 24.9 | 13.2 |
| 26.4 | 21.9 |
| 26.8 | 20.2 |
| 27.0 | 17.4 |
| 27.6 | 7.5 |
| 28.5 | 9.4 |
| 28.8 | 7.7 |
| 29.0 | 3.2 |
| 29.7 | 13.2 |
| 30.0 | 10.5 |
| 30.3 | 10.8 |
| 30.5 | 26.8 |
| 30.8 | 6.0 |
| 31.3 | 4.8 |
| 32.5 | 10.5 |
| 33.0 | 5.0 |
| 33.2 | 3.9 |
| 33.7 | 4.7 |
| 34.2 | 5.6 |
| 34.5 | 6.0 |
| 34.8 | 7.5 |
| 34.9 | 8.4 |
| 35.6 | 13.1 |
| 36.2 | 8.7 |
| 36.6 | 7.0 |
| 37.2 | 3.5 |
| 38.0 | 11.9 |
| 38.3 | 7.0 |
| 38.6 | 9.9 |

Differential scanning calorimeter analysis of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate Differential scanning calorimeter (DSC) measurements were performed with a Discovery DSC (TA instruments) equipped with a refrigerated cooling accessory. All the experiments were performed in standard/Tzero aluminum pans. The cell constant was determined using indium and temperature calibration was performed using indium and tin as standards. All the measurements were done under continuous dry nitrogen purge (50 mL/min). Approximately 1-5 mg of solid sample was weighed into a Tzero aluminum pan, sealed non-hermetically and heated from 25° C. to at least 250° C. at a 10° C./min heating rate. The experimental data were analyzed using commercially available software (TA Universal Analysis 2000/Trios software, TA Instruments).

FIG. 5 is the obtained differential scanning calorimeter analysis for crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

Thermogravimetric analysis of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate Thermogravimetric analysis was conducted using a Discovery TGA (TA instruments) thermogravimetric analyzer. Samples of approximately 10 mg were weighed into aluminum pans and heated from ambient to at least 250° C. at a 10° C./minute heating rate under nitrogen purge (10 mL/min for both sample chamber and balance).

FIG. 6 is the obtained thermogravimetric analysis for crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

Powder X-ray diffraction analysis of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate Powder X-ray diffraction analysis was conducted as described above. FIG. 7 is the obtained powder X-ray diffraction pattern for crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate and Table 8 lists the diffraction peaks in terms of 2-theta values.

TABLE 8

| Angle 2-Theta (degrees) | Relative Intensity (%) |
| --- | --- |
| 8.4 | 71.2 |
| 9.3 | 24.1 |
| 11.5 | 52.0 |
| 12.5 | 36.7 |
| 15.5 | 7.9 |
| 16.8 | 11.1 |
| 17.6 | 13.6 |
| 18.5 | 39.8 |
| 18.8 | 100.0 |
| 19.2 | 65.3 |
| 20.4 | 68.8 |
| 21.1 | 5.3 |
| 22.2 | 7.4 |
| 23.9 | 9.7 |
| 24.2 | 6.8 |
| 24.5 | 16.8 |
| 25.1 | 16.0 |
| 26.6 | 13.5 |
| 26.7 | 17.8 |
| 27.0 | 14.0 |
| 27.9 | 4.9 |
| 29.8 | 3.3 |
| 30.6 | 3.2 |
| 30.8 | 12.4 |
| 31.0 | 3.0 |
| 32.8 | 7.7 |
| 35.1 | 3.1 |
| 36.0 | 3.1 |
| 36.4 | 3.3 |

Differential scanning calorimeter analysis of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate DSC measurements were performed as described above. FIG. 8 is the obtained differential scanning calorimeter analysis for crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

Thermogravimetric analysis of crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate Thermogravimetric analysis was performed as described above.

FIG. 9 is the obtained thermogravimetric analysis for crystalline (R)-4-((2-(((4-chloro-1-methyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate.

Single Crystal X-Ray Analysis of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate Solid calcium hydroxide (0.978 mg, 0.0132 mmol, 0.50 eq) was added to an HPLC vial with a stir bar. A solution of (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide (Example 1) (0.504 mL, 0.0265 mmol, 1.00 eq, 25.4 mg/mL) in methanol was pipetted into the vial. The mixture was stirred at 60° C. for 3 h. During this time, a yellow solid formed. The stirring was turned off and the mixture slowly cooled to 21° C. at a rate of −0.1° C./min. A yellow solid (powder) was still present after cooling to 21° C. The solid was allowed to sit in the mother liquor for several weeks at room temperature until suitable crystals formed.

Data collection was performed on a Bruker APEX diffractometer at room temperature. Data collection consisted of omega and phi scans. The structure was solved by intrinsic phasing using SHELX software suite in the space group P21212. The structure was subsequently refined by the full-matrix least squares method. All non-hydrogen atoms were found and refined using anisotropic displacement parameters. The hydrogen atoms located on nitrogen and oxygen were found from the Fourier difference map and refined with distances restrained. The remaining hydrogen atoms were placed in calculated positions and were allowed to ride on their carrier atoms. The final refinement included riding isotropic displacement parameters for all hydrogen atoms.

Analysis of the absolute structure using likelihood methods (Hooft 2008) was performed using PLATON (Spek 2010). Assuming the sample submitted is enantiopure, the results indicate that the absolute structure has been correctly assigned. The final R-index was 6.92%. A final difference Fourier revealed no missing or misplaced electron density.

Figure 10:
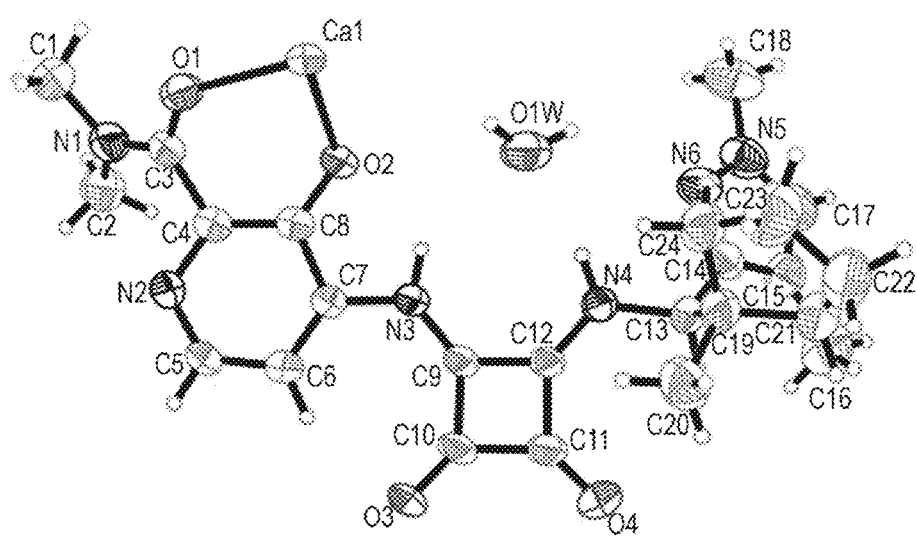
FIG. 10 is an X-ray structure (ORTEP drawing) of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate.
Figure 11:
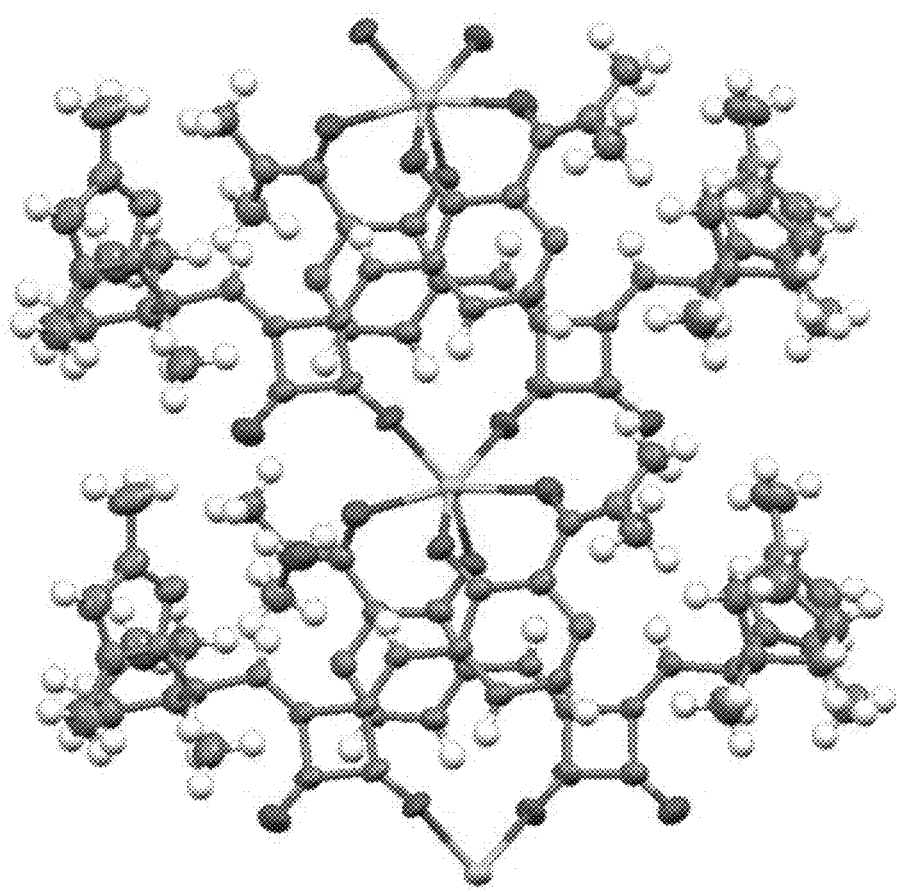
FIG. 11 is an X-ray structure (ORTEP drawing) for the unit cell of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate.

FIG. 10 is the obtained X-ray structure (ORTEP drawing) of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate. FIG. 11 is the X-ray structure (ORTEP drawing) of the corresponding unit cell. The crystal structure data is summarized in Table 9.

TABLE 9

Crystal data and structure refinement.

| | |
|---|---|
| Empirical formula | C48 H62 Ca N12 O10 |
| Formula weight | 1007.17 |
| Temperature | 296(2) K |
| Wavelength | 1.54178 Å |
| Crystal system | Orthorhombic |
| Space group | P21212 |
| Unit cell dimensions | a = 13.2412(15)   α = 90°. |
| | b = 22.094(3)   β = 90°. |
| | c = 8.7809(9)   γ = 90°. |
| Volume | 2568.8(5) Å$^3$ |
| Z | 2 |
| Density (calculated) | 1.302 Mg/m$^3$ |
| Absorption coefficient | 1.617 mm$^{-1}$ |
| F(000) | 1068 |
| Crystal size | 0.205 × 0.127 × 0.046 mm$^3$ |
| Theta range for data collection | 3.892 to 51.384°. |
| Index ranges | −9 <= h <= 13, |
| | −21 <= k <= 22, |
| | −8 <= l <= 8 |
| Reflections collected | 10761 |
| Independent reflections | 2654 [R(int) = 0.0553] |
| Completeness to theta = 51.384° | 95.3% |
| Absorption correction | multi-scan |
| Max. and min. transmission | 0.7533 and 0.5516 |
| Refinement method | Full-matrix least-squares on F2 |
| Data/restraints/parameters | 2654/299/338 |
| Goodness-of-fit on F2 | 1.218 |
| Final R indices [I > 2sigma(I)] | R1 = 0.0697, wR2 = 0.1588 |
| R indices (all data) | R1 = 0.0828, wR2 = 0.1644 |
| Absolute structure parameter | 0.183(12) |
| Largest diff. peak and hole | 0.330 and −0.254 e.Å$^{-3}$ |

Powder X-ray diffraction analysis of crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate Powder X-ray diffraction analysis was conducted using a Bruker AXS D4 Endeavor diffractometer equipped with a Cu radiation source. The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu (k-alpha average) from 3.0 to 40.0 degrees 2-Theta using a step size of 0.01 degrees and a time per step of 1.0 seconds. Samples were prepared by placing them in a silicon low background sample holder and rotated during collection. Data were collected using Bruker DIFFRAC Plus XRD Commander (version 2.6.1) and analysis was performed by EVA diffract plus software (version 3.1). The PXRD data file was not processed prior to peak searching. Using the peak search algorithm in the EVA software, peaks selected with a threshold value of 1 were used to make preliminary peak assignments. To ensure validity, adjustments were manually made. The output of automated assignments was visually checked and peak positions were adjusted to the peak maximum. Peaks with relative intensity of 3% were generally chosen. The peaks which were not resolved or were consistent with noise were not selected. A typical error associated with the peak position of crystalline material, from PXRD, stated in USP, is up to +/−0.2° 2-Theta (USP-941).

FIG. 12 is the obtained powder X-ray diffraction pattern for crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, 0.5 calcium salt, monohydrate and Table 10 lists the diffraction peaks in terms of 2-theta values.

TABLE 10

| Angle 2-Theta (degrees) | Relative Intensity (%) |
|---|---|
| 7.7 | 43.0 |
| 7.8 | 100.0 |
| 10.3 | 35.3 |
| 10.7 | 22.2 |
| 11.9 | 18.6 |
| 12.6 | 8.6 |
| 13.2 | 11.0 |
| 13.6 | 26.0 |
| 14.4 | 11.8 |
| 15.5 | 24.2 |
| 16.6 | 25.3 |
| 17.0 | 52.5 |
| 18.4 | 15.1 |
| 20.0 | 11.2 |
| 20.5 | 25.7 |
| 20.8 | 43.1 |
| 21.0 | 47.9 |
| 21.5 | 3.8 |
| 22.3 | 43.4 |
| 22.6 | 9.3 |
| 23.3 | 15.9 |
| 24.0 | 61.2 |
| 24.5 | 10.2 |
| 24.9 | 21.7 |
| 25.6 | 34.4 |
| 26.1 | 24.6 |
| 27.0 | 10.4 |
| 27.6 | 13.3 |
| 28.4 | 15.5 |
| 28.9 | 13.5 |
| 29.3 | 14.6 |
| 29.6 | 6.5 |
| 30.2 | 8.1 |
| 31.3 | 22.6 |
| 31.4 | 22.2 |
| 32.2 | 5.5 |
| 32.9 | 12.0 |
| 34.3 | 14.3 |
| 35.0 | 13.8 |
| 35.5 | 5.6 |
| 35.9 | 3.6 |
| 36.3 | 7.2 |
| 37.6 | 5.1 |
| 38.9 | 2.7 |
| 39.6 | 5.7 |

Biological Data

CCR6+ T Cell Chemotaxis Assay

Human CD4+CCR6+CXCR3-T cells were isolated from leukopak from healthy donors using EasySep™ Human Th17 Cell Enrichment Kit. (StemCell Technologies, 18162). To obtain large quantities of cells, CCR6+ T cells were activated with Dynabeads Human T-activator (catalog no. 11132D, Gibco) at a density of 1×10⁶ cell/mL in growth media (RPM11640 media with 10% serum, 4 ng/mL IL-2) with a 1:1.5 cell to bead ratio. Day 4 post activation, Dynabeads were removed from the culture. The activated T cells were maintained at 1-2×10⁶ cells/mL for 15 days by feeding fresh growth media when needed.

The CCR6+ T cell chemotaxis assay was carried out on day 12 to 15 post T cell activation using 96 well ChemoTx® Disposable Chemotaxis System (Neuroprobe 101-5) according to the manufacturer's protocol. After one wash with assay buffer (1×HBSS containing 20 mM HEPES and 0.25% BSA), cells were incubated with test compounds for 30 min at room temperature prior to initiation of chemotaxis. For $IC_{50}$ determination, the top and bottom of the chemotaxis chamber contained the same concentration of compound. DMSO was kept constant at 0.1% (v/v) in all wells. The final concentration of CCL20 (Peprotech 300-29A) in the bottom chamber is 0.5 nM. The fully assembled chemotaxis plate was placed in a cell culture incubator at 37° C., 5% $CO_2$ for 1 h. After incubation, the top filter was removed, followed by a quick freeze of the bottom chamber at −80° C. for 1 h. The migrated cells in the bottom chamber were stained with CyQUANT dye (Life Technologies, C7026) for cell number determination.

$IC_{50}$ values for compounds of the present invention (Table 11) were determined by the non-linear regression analysis of dose response curves.

TABLE 11

| Example | $IC_{50}$ (nM) |
|---|---|
| 1 | 5.8 |
| 2 | 186 |
| 3 | 2.3 |
| 4 | 6.3 |
| 5 | 922 |
| 6 | 11.6 |
| 7 | 29.8 |
| 8 | 3.0 |
| 9 | 59.7 |
| 10 | 8.7 |
| 11 | 1.9 |
| 12 | 1.7 |
| 13 | 5.4 |
| 14 | 12.5 |
| 15 | 10.6 |
| 16 | 41.7 |
| 17 | 5.9 |
| 18 | 3.3 |
| 19 | 70.6 |
| 20 | 271 |
| 21 | 102 |
| 22 | 7.4 |
| 23 | 16.5 |
| 24 | 3.1 |
| 25 | 1.2 |
| 26 | 3.3 |
| 27 | 13.2 |
| 28 | 36.7 |
| 29 | 12.0 |
| 30 | 96.1 |
| 31 | 45.4 |
| 32 | 2.7 |
| 33 | 4.4 |
| 34 | 24.0 |
| 35 | 30.0 |
| 36 | 32.3 |
| 37 | 5.2 |
| 38 | 12.6 |
| 39 | 6.5 |
| 40 | ND* |

*No Data

Human Neutrophil Chemotaxis Assay

Human neutrophils were purified from freshly drawn human whole blood by immune-magnetic negative selection using the EasySep™ Direct Human Neutrophil Isolation Kit (StemCell Technologies, #19666) according to manufacturer's instructions.

Human neutrophil chemotaxis assay was carried out with Corning FluoroBlok 96 well cell insert system (Corning #351164). Purified neutrophils were resuspended in chemotaxis buffer (1×HBSS containing 25 mM HEPES, pH 7.4 and 0.25% BSA) to a working concentration of 2×10⁶ cells/mL and incubated for 30 min at 37° C. with calcein-AM for cell staining. After 30 min, the labeled neutrophils were washed twice in chemotaxis buffer, resuspended as before and used immediately. For the assay, test compounds were tested in a dose-response format to determine $IC_{50}$. Labeled neutrophils (50 µL) were pre-incubated with diluted test compound (50 µL) for 30 min in a 96-well plate (Greiner). Next, 100 µL of diluted compound was mixed with 100 µL of GROα (Peprotech #300-11, 2 nM) in the bottom portion of the chemotaxis chamber. The top portion (insert) of the chemotaxis system containing the FluoroBlok porous membrane was then assembled together. 50 µL of the pre-incubated neutrophils were added to the FluoroBlok insert (top portion) and chemotaxis measured by the neutrophils ability to migrate through the membrane towards the specific CXCR2 ligand, GROα. The Envision multilabel reader (Perkin Elmer) and/or the Typhoon Fluorescent Imager (GE) was used to evaluate changes in fluorescent signal (calcein-AM fluorophore) at 485/535 nm generated by the labeled neutrophils that passed through the porous membrane.

$IC_{50}$ values for compounds of the present invention (Table 12) were determined by the non-linear regression analysis of dose response curves. Navarixin ((R)-2-hydroxy-N,N-dimethyl-3-((2-((1-(5-methylfuran-2-yl)propyl)amino)-3,4-dioxocyclobut-1-en-1-yl)amino)benzamide) was used as a reference control in the assay ($IC_{50}$=16.8, n=52).

TABLE 12

| Example | $IC_{50}$ (nM) |
| --- | --- |
| 1 | 524 |
| 2 | 7,310 |
| 3 | 1,530 |
| 4 | 886 |
| 5 | ND* |
| 6 | 586 |
| 7 | 2,160 |
| 8 | 103 |
| 9 | 2,750 |
| 10 | 175 |
| 11 | 210 |
| 12 | 107 |
| 13 | 328 |
| 14 | 272 |
| 15 | 735 |
| 16 | 4,350 |
| 17 | 3,160 |
| 18 | 1,010 |
| 19 | 197 |
| 20 | 167 |
| 21 | 293 |
| 22 | 141 |
| 23 | 248 |
| 24 | 1,010 |
| 25 | 355 |
| 26 | 142 |
| 27 | 52.6 |
| 28 | 2,190 |
| 29 | 4,410 |
| 30 | 4,030 |
| 31 | 2,750 |
| 32 | 332 |
| 33 | 69.9 |
| 34 | 2,510 |
| 35 | 255 |
| 36 | 7,130 |
| 37 | 3,630 |
| 38 | 3,460 |
| 39 | 502 |
| 40 | ND* |

*No Data

Mouse in Vivo Model of IL-23-induced Psoriasis-like Skin Inflammation

Efficacy of a CCR6 antagonist of the present invention is evaluated in a mouse in vivo model of psoriasis-like skin inflammation. Recombinant mouse IL-23 is administered via intradermal injections into the left ears of female 8-10 weeks old $C_{57}BL/6$ mice. This leads to increased psoriasis-like disease symptoms including thickening and erythema in the skin of the left ears. Mice given IL-23 are treated from Day 0 to Day 11 with either daily (QD) oral doses of a CCR6 antagonist or twice daily (BID) doses of a CCR6 antagonist. Additionally, a group of mice are treated with an anti-IL-17 Ab as a positive efficacy control. Representative dosing groups for the study consist of the following:

a group dosed orally twice daily (BID) with vehicle, negative control group, a group dosed by intraperitoneal injection twice weekly with an anti-IL-17 Ab (5 mg/kg), positive control group, a group dosed orally with Compound A at 3-100 mg/kg either once a day (QD) or twice a day (BID), an untreated, naive control group.

Ten mice are enrolled per treatment group with the exception of the naïve control group, which contains five mice. Study day 0 is designated as the first treatment day, and ear thickness measurements are taken daily by an engineer's micrometer (Mitutoyo, Aurora, Ill., USA). Ear swelling measurements for each mouse was compared to baseline and expressed in microns.

The compounds of the present invention selectively inhibit T cell chemotaxis compared to neutrophil chemotaxis (see Table 13). This selectivity renders the compounds of the present invention as viable therapeutic agents for treating inflammatory, immune, autoimmune, neurodegenerative and neuroinflammatory diseases, conditions, or disorders in humans with reduced risk of neutropenia.

TABLE 13

| Example | T Cell Chemotaxis Selectivity |
| --- | --- |
| 1 | 90 |
| 2 | 39 |
| 3 | 665 |
| 4 | 140 |
| 5 | ND* |
| 6 | 51 |
| 7 | 72 |
| 8 | 34 |
| 9 | 46 |
| 10 | 20 |
| 11 | 110 |
| 12 | 63 |
| 13 | 60 |
| 14 | 22 |
| 15 | 69 |
| 16 | 104 |
| 17 | 535 |
| 18 | 306 |
| 19 | 3 |
| 20 | NS** |
| 21 | 3 |
| 22 | 19 |
| 23 | 15 |
| 24 | 325 |
| 25 | 296 |
| 26 | 43 |
| 27 | 4 |
| 28 | 60 |
| 29 | 367 |
| 30 | 42 |

TABLE 13-continued

| Example | T Cell Chemotaxis Selectivity |
|---|---|
| 31 | 60 |
| 32 | 123 |
| 33 | 16 |
| 34 | 104 |
| 35 | 8 |
| 36 | 220 |
| 37 | 698 |
| 38 | 274 |
| 39 | 77 |
| 40 | ND* |

*No Data
**Not selective for T cell chemotaxis compared to neutrophil chemotaxis Applicant discovered unexpectedly that T cell chemotaxis inhibition versus neutrophil chemotaxis inhibition was enhanced by replacing hydrogen with a methyl group alpha to the point of attachment of the heteroaryl "A" ring (see Table 14).

Comparator Data

WO 2010/131145 discloses Examples 112 and 120.

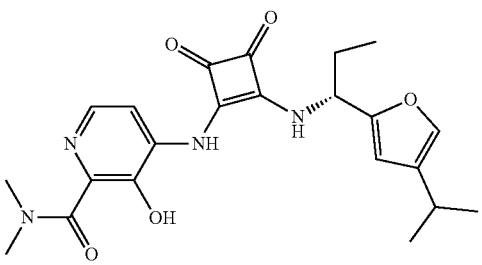

Example 112

TABLE 14

| Compound of the Present Invention | R = H, IC$_{50}$ (nM) | | | R = CH$_3$, IC$_{50}$ (nM) | | |
|---|---|---|---|---|---|---|
| | CCR6 T cell, CCL20 Chemotaxis | CXCR2 Neutrophil, GROα Chemotaxis | T Cell Chemotaxis Selectivity | CCR6 T cell, CCL20 Chemotaxis | CXCR2 Neutrophil, GROα Chemotaxis | T Cell Chemotaxis Selectivity |
| [pyrazole structure] | 19.2 | 42.1 | 2.2 | 5.8 | 524 | 90.3 |
| [thiazole structure] | 32.1 | 346 | 10.8 | 2.7 | 332 | 123 |
| [oxazole structure] | 64.5 | 12.2 | NS* | 24.0 | 2510 | 104 |

*Not selective for T cell chemotaxis compared to neutrophil chemotaxis

-continued

Example 120

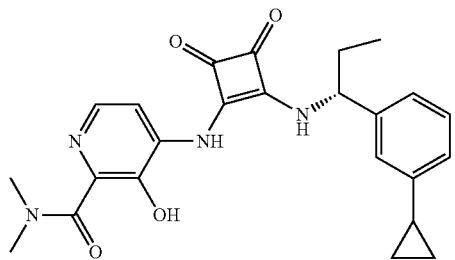

Applicant provides comparative chemotaxis data in Table 15 for the WO 2010/131145 compounds. The data in Table 15 demonstrates that Examples 112 and 120 are more potent at inhibiting neutrophil migration than the compounds of the present invention and less potent at inhibiting T cell migration than the compounds of the present invention. The WO 2010/131145 compounds are functionally selective for CXCR2 compared to CCR6 in opposite to the compounds of the present invention. This data suggests that the WO 2010/131145 compounds are less attractive as agents for treating diseases, conditions, or disorders ameliorated by reducing T cell chemotaxis via CCR6 inhibition and that the WO 2010/131145 compounds also have a greater neutropenia risk to patients compared to the compounds of the present invention.

TABLE 15

| | IC$_{50}$ (nM) | | |
| Example | CCR6 T cell, CCL20 Chemotaxis | CXCR2 Neutrophil, GROα Chemotaxis | T Cell Chemotaxis Selectivity |
| --- | --- | --- | --- |
| 112 | 267 | 23.2 | NS* |
| 120 | 388 | 5.7 | NS* |

*Not selective for T cell chemotaxis compared to neutrophil chemotaxis

WO 2013/061005 discloses Examples 22, 50 and 53 and provides CXCR2 and CCR6 functional data for each compound which is reproduced from WO 2013/061005 in Table 16 below. CXCR2 antagonist activity was determined via inhibition of β-arrestin recruitment following activation with CXCL8 in Path-Hunter HEK293 cells. CCR6 antagonist activity was determined via inhibition of Ca$^{2+}$ flux in cells following activation of CCR6 in the FLIPR TETRA® platform. The CCR6 activating agent was not reported.

Example 22

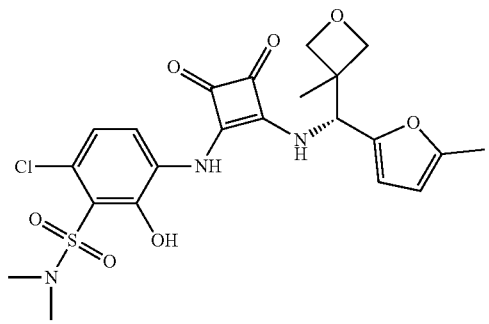

Example 50

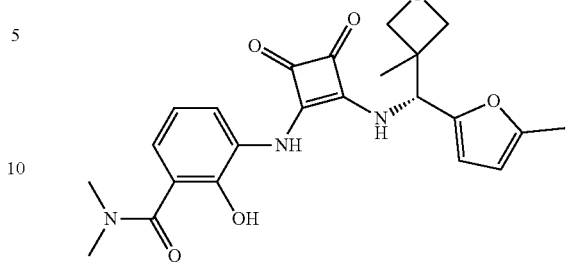

Example 53

TABLE 16

| Compound | CXCR2 IC$_{50}$ (nM) | CCR6 IC$_{50}$ (nM) |
| --- | --- | --- |
| 22 | 31 | 3.4 |
| 50 | 72 | 1.4 |
| 53 | 30 | 1.9 |

*Data disclosed in WO 2013/061005

Applicant provides the following comparative chemotaxis data in Table 17 for the WO 2013/061005 compounds. The data in Table 17 demonstrates that Example 22 is potent at both the inhibition of T cell and neutrophil chemotaxis with a slightly greater potency (1.5x) for inhibition of CCR6. The high affinity for both receptors combined with the poor selectivity for CCR6 renders this compound less attractive as an anti-inflammatory agent with reduced potential for neutropenia than the compounds of the present invention. Example 50 has low affinity for CCR6 and inhibits neutrophil chemotaxis better than T cell chemotaxis. Example 50's chemotaxis profile is less attractive for development as an anti-inflammatory agent than the compounds of the present invention. Example 53 is not a potent inhibitor of T cell chemotaxis nor neutrophil chemotaxis. The lack of functional potency at CCR6 renders Example 53 less attractive for treating inflammatory diseases than the compounds of the present invention.

TABLE 17

| | IC$_{50}$ (nM) | | |
| Example | CCR6 T cell, CCL20 Chemotaxis | CXCR2 Neutrophil, GROα Chemotaxis | T Cell Chemotaxis Selectivity |
| --- | --- | --- | --- |
| 22 | 22.6 | 35.2 | 1.5 |
| 50 | 330 | 121 | NS* |
| 53 | 390 | 1143 | 3 |

*Not selective for T cell chemotaxis compared to neutrophil chemotaxis

We claim:

1. A pharmaceutical composition comprising a compound of Formula (IA) or (IB)

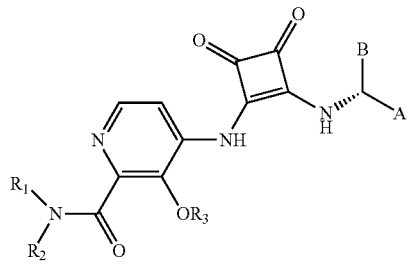

Formula (IA)

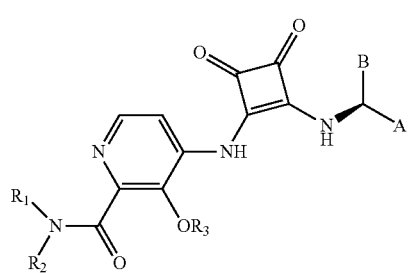

Formula (IB)

or a pharmaceutically acceptable salt or hydrate thereof, wherein
$R_1$ is methyl;
$R_2$ is methyl, ethyl, or isopropyl
or $R_1$ and $R_2$ taken together with the nitrogen atom to which they are attached form morpholine or 4-methylpiperazine;
$R_3$ is H or —$CH_2OP(=O)(OH)_2$;
A is

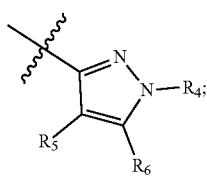

$R_4$ is methyl;
$R_5$ is methyl, ethyl, methoxy, Cl, difluoromethoxy, cyano, or cyclopropyl;
$R_6$ is H;
B is

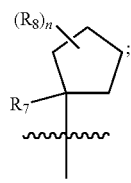

$R_7$ is methyl; and
n is 0,
and at least one pharmaceutically acceptable excipient, diluent, or carrier.

2. The pharmaceutical composition according to claim 1 wherein the composition comprises the compound of Formula (IIA)

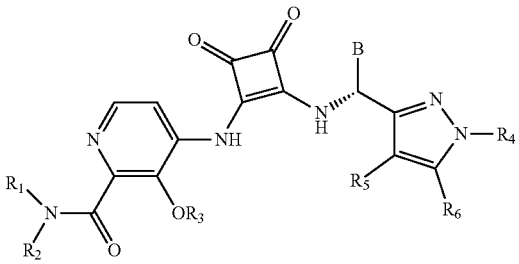

Formula (IIA)

or a pharmaceutically acceptable salt or hydrate thereof, wherein
$R_1$ is methyl;
$R_2$ is methyl, ethyl, or isopropyl;
or $R_1$ and $R_2$ taken together with the nitrogen atom to which they are attached form morpholine or 4-methylpiperazine;
$R_3$ is H or —$CH_2OP(=O)(OH)_2$;
$R_4$ is methyl;
$R_5$ is methyl, ethyl, methoxy, Cl, difluoromethoxy, cyano, or cyclopropyl;
$R_6$ is H;
B is

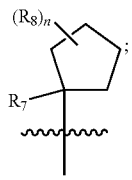

$R_7$ is methyl; and
n is 0,
and at least one pharmaceutically acceptable excipient, diluent, or carrier.

3. The pharmaceutical composition according to claim 2, wherein the composition comprises the compound of Formula (IIA) or a pharmaceutically acceptable salt or hydrate thereof, wherein $R_1$ and $R_2$ taken together with the nitrogen atom to which they are attached form morpholine or 4-methylpiperazine,
and at least one pharmaceutically acceptable excipient, diluent, or carrier.

4. The pharmaceutical composition according to claim 1 wherein the composition comprises a compound selected from the group consisting of
(R)-4-((2-(((4-Chloro-1-methyl-1H-pyrazol-3-yl)(1-methylcyclopentyl)methyl) amino)-3,4-dioxocyclobut-1-en-1-yl)amino)-3-hydroxy-N,N-dimethylpicolinamide,
(R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N-isopropyl-N-methylpicolinamide,
(S)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide,
(R)-4-((2-(((1,4-Dimethyl-1H-pyrazol-3-yl)(1-methylcyclopentyl)methyl)amino)-3,4-dioxocyclobut-1-en-1-yl)amino)-N-ethyl-3-hydroxy-N-methylpicolinamide, (S)-4-((2-(((1,4-Dimethyl-1H-pyrazol-3-yl)(1-methylcyclopentyl)methyl)amino)-3,4-dioxocyclobut-1-en-1-yl)amino)-N-ethyl-3-hydroxy-N-methylpicolinamide, (R)-3-(((1,4-dimethyl-1H-pyrazol-3-yl)(1-methylcyclopentyl)methyl)amino)-4-((3-hydroxy-2-(morpholine-4-carbonyl)pyridin-4-yl)amino)cyclobut-3-ene-1,2-dione, (R)-3-(((1,4-Dimethyl-1H-pyrazol-3-yl)(1-methylcyclopentyl)methyl)amino)-4-((3-hydroxy-2-(4-methylpiperazine-1-carbonyl)pyridin-4-yl)amino)cyclobut-3-ene-1,2-dione, (S)-4-((2-(((4-Chloro-1-methyl-1H-pyrazol-3-yl)(1-methylcyclopentyl)methyl) amino)-3,4-dioxocyclobut-1-en-1-yl)amino)-3-hydroxy-N,N-dimethylpicolinamide, (R)-4-((2-(((4-Chloro-1-methyl-1H-pyrazol-3-yl)(1-methylcyclopentyl)methyl) amino)-3,4-dioxocyclobut-1-en-1-yl)amino)-3-hydroxy-N-isopropyl-N-methylpicolinamide, (R)-3-Hydroxy-N-isopropyl-4-((2-(((4-methoxy-1-methyl-1H-pyrazol-3-yl)(1-methylcyclopentyl)methyl) amino)-3,4-dioxocyclobut-1-en-1-yl)amino)-N-methylpicolinamide, (R)-3-Hydroxy-4-((2-(((4-m ethoxy-1-methyl-1H-pyrazol-3-yl)(1-methylcyclopentyl)methyl)amino)-3,4-dioxocyclobut-1-en-1-yl)amino)-N,N-dimethylpicolinamide, (R)-4-((2-(((4-(Difluoromethoxy)-1-methyl-1H-pyrazol-3-yl)(1-methylcyclopentyl) methyl)amino)-3,4-dioxocyclobut-1-en-1-yl)amino)-3-hydroxy-N,N-dimethylpicolinamide, (R)-4-((2-(((4-Cyano-1-methyl-1H-pyrazol-3-yl)(1-methylcyclopentyl)methyl) amino)-3,4-dioxocyclobut-1-en-1-yl)amino)-3-hydroxy-N,N-dimethylpicolinamide, (R)-4-((2-(((4-Cyclopropyl-1-methyl-1H-pyrazol-3-yl)(1-methylcyclopentyl)methyl) amino)-3,4-dioxocyclobut-1-en-1-yl)amino)-3-hydroxy-N,N-dimethylpicolinamide, (R)-4-((2-(((4-Cyano-1-methyl-1H-pyrazol-3-yl)(1-methylcyclopentyl)methyl) amino)-3,4-dioxocyclobut-1-en-1-yl)amino)-N-ethyl-3-hydroxy-N-methylpicolinamide, and (R)-4-((2-(((4-cyano-1-methyl-1H-pyrazol-3-yl)(1-methylcyclopentyl)methyl) amino)-3,4-dioxocyclobut-1-en-1-yl)amino)-3-hydroxy-N-isopropyl-N-methylpicolinamide, or a pharmaceutically acceptable salt or hydrate thereof, and at least one pharmaceutically acceptable excipient, diluent, or carrier.

5. A pharmaceutical composition comprising the compound (R)-4-((2-(((1,4-Dimethyl-1H-pyrazol-3-yl)(1-methylcyclopentyl)methyl)amino)-3,4-dioxocyclobut-1-en-1-yl)amino)-3-hydroxy-N,N-dimethylpicolinamide or a pharmaceutically acceptable salt or hydrate thereof, and at least one pharmaceutically acceptable excipient, diluent, or carrier.

6. The pharmaceutical composition according to claim 5 wherein the composition comprises a compound of structure

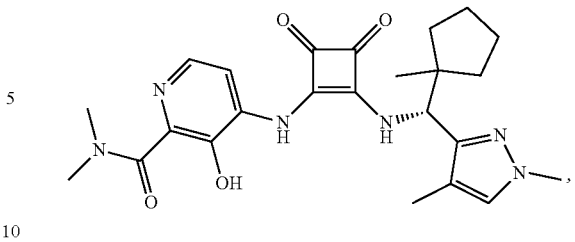

and at least one pharmaceutically acceptable excipient, diluent, or carrier.

7. A pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide, and at least one pharmaceutically acceptable excipient, diluent, or carrier.

8. A pharmaceutical composition comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate, and at least one pharmaceutically acceptable excipient, diluent, or carrier.

9. The pharmaceutical composition of claim 8 comprising crystalline (R)-4-((2-(((1,4-dimethyl-1H-pyrazol-3-yl)(1-methylcyclopentyl)methyl)amino)-3,4-dioxocyclobut-1-en-1-yl)amino)-3-hydroxy-N,N-dimethylpicolinamide monohydrate having an X-ray powder diffraction pattern comprising diffraction peaks 18.7±0.2, 19.1±0.2, and 20.2±0.2 degrees two theta, and at least one pharmaceutically acceptable excipient, diluent, or carrier.

10. The pharmaceutical composition of claim 8 comprising crystalline (R)-4-((2-(((1,4-dimethyl-1H-pyrazol-3-yl) (1-methylcyclopentyl) methyl)amino)-3,4-dioxocyclobut-1-en-1-yl)amino)-3-hydroxy-N,N-dimethylpicolinamide monohydrate having an X-ray powder diffraction pattern comprising diffraction peaks 17.6±0.2, 18.4±0.2, 18.7±0.2, 19.1±0.2, and 20.2±0.2 degrees two theta, and at least one pharmaceutically acceptable excipient, diluent, or carrier.

11. The pharmaceutical composition of claim 8 comprising crystalline (R)-4-((2-(((1,4-dimethyl-1H-pyrazol-3-yl) (1-methylcyclopentyl) methyl)amino)-3,4-dioxocyclobut-1-en-1-yl)amino)-3-hydroxy-N,N-dimethylpicolinamide monohydrate having an X-ray powder diffraction pattern comprising diffraction peaks 11.4±0.2, 15.5±0.2, 17.6±0.2, 18.4±0.2, 18.7±0.2, 19.1±0.2, 20.2±0.2, and 24.3±0.2 degrees two theta, and at least one pharmaceutically acceptable excipient, diluent, or carrier.

12. The pharmaceutical composition of claim 8 comprising crystalline (R)-4-((2-(((1,4-dimethyl-1H-pyrazol-3-yl) (1-methylcyclopentyl) methyl)amino)-3,4-dioxocyclobut-1-en-1-yl)amino)-3-hydroxy-N,N-dimethylpicolinamide monohydrate having an X-ray powder diffraction pattern as depicted in FIG. 4, and at least one pharmaceutically acceptable excipient, diluent, or carrier.

13. The pharmaceutical composition of claim 1 comprising (R)-((4-((2-(((1,4-Dimethyl-1H-pyrazol-3-yl)(1-methylcyclopentyl)methyl)amino)-3,4-dioxocyclobut-1-en-1-yl) amino)-2-(dimethylcarbamoyl)pyridin-3-yl)oxy)methyl dihydrogen phosphate or a pharmaceutically acceptable salt thereof, and at least one pharmaceutically acceptable excipient, diluent, or carrier.

14. The pharmaceutical composition of claim 13 comprising a compound of structure

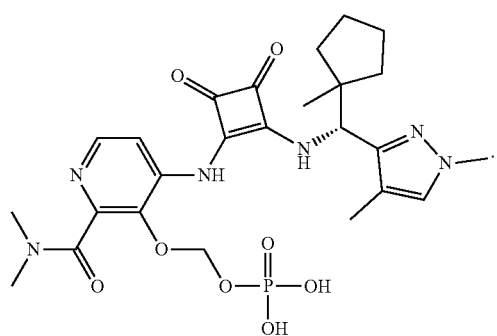

15. A method of treating a disorder selected from the group consisting of rheumatoid arthritis, juvenile arthritis, juvenile rheumatoid arthritis, systemic onset rheumatoid arthritis, pauciarticular rheumatoid arthritis, pauciarticular juvenile rheumatoid arthritis, polyarticular rheumatoid arthritis, enteropathic arthritis, juvenile Reiter's Syndrome, ankylosing spondylitis, juvenile ankylosing spondylitis, SEA Syndrome, reactive arthritis (reactive arthropathy), psoriatic arthropathy, juvenile enteropathic arthritis, polymyalgia rheumatica, enteropathic spondylitis, juvenile idiopathic arthritis (JIA), juvenile psoriatic arthritis, juvenile rheumatoid arthritis, systemic onset juvenile rheumatoid arthritis, giant cell arteritis, and secondary osteoarthritis from inflammatory diseases in a human comprising administering to the human in need of such treatment a therapeutically effective amount of a pharmaceutical composition according to any one of claims 1, 2 and 3 to 14.

16. A method of treating a disorder selected from the group consisting of inflammatory bowel disease, Crohn's disease, and ulcerative colitis in a human comprising administering to the human in need of such treatment a therapeutically effective amount of a pharmaceutical composition according to any one of claims 1, 2 and 3 to 14.

* * * * *